(12) United States Patent
van Santen et al.

(10) Patent No.: US 10,772,953 B2
(45) Date of Patent: Sep. 15, 2020

(54) RECOMBINANT SPIKE ECTODOMAIN PROTEINS, COMPOSITIONS, VECTORS, KITS, AND METHODS FOR IMMUNIZING AGAINST AVIAN INFECTIOUS BRONCHITIS VIRUS

(71) Applicant: Auburn University, Auburn, AL (US)

(72) Inventors: Vicky L. van Santen, Auburn, AL (US); Haroldo E. Toro, Auburn, AL (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 16/059,803

(22) Filed: Aug. 9, 2018

(65) Prior Publication Data
US 2019/0046634 A1 Feb. 14, 2019

Related U.S. Application Data

(60) Provisional application No. 62/543,142, filed on Aug. 9, 2017.

(51) Int. Cl.
| | |
|---|---|
| *A61K 39/215* | (2006.01) |
| *C07K 14/165* | (2006.01) |
| *A61P 31/14* | (2006.01) |
| *C07K 14/005* | (2006.01) |
| *A61K 39/12* | (2006.01) |
| *A61K 39/00* | (2006.01) |

(52) U.S. Cl.
CPC ............ *A61K 39/215* (2013.01); *A61K 39/12* (2013.01); *A61P 31/14* (2018.01); *C07K 14/005* (2013.01); *C07K 14/165* (2013.01); *A61K 2039/552* (2013.01); *C12N 2770/20022* (2013.01); *C12N 2770/20034* (2013.01)

(58) Field of Classification Search
None
See application file for complete search history.

(56) References Cited

U.S. PATENT DOCUMENTS

| 8,541,003 B2 * | 9/2013 | Anderson | ............ | A61K 39/215 424/199.1 |
| 2014/0127264 A1 * | 5/2014 | Verheije | ................ | C07K 14/005 424/222.1 |

OTHER PUBLICATIONS

Santen et al. Avian Pathology 2008 vol. 37(3), pp. 293-306). (Year: 2008).*
Feb. 28, 2019 SEQ ID# 91 Comparison Sheet (Year: 2019).*
Feb. 28, 2019 SEQ ID# 93 Comparison Sheet (Year: 2019).*
Morris et al., Veterinary Immunology and Immunopathology vol. 126 (2008) pp. 373-376 (Year: 2008).*
Belouzard S, Millet JK, Licitra BN, Whittaker GR. Mechanisms of coronavirus cell entry mediated by the viral spike protein. Viruses 2012;4:1011-33.
Ben Arousa J, Devillea S, Palb J, Baksib S, Bertranda F, Dupuisa L. Reduction of Newcastle disease vaccine dose using a novel adjuvant for cellular immune response in poultry. Procedia in Vaccinology 2013;7:28-33.
Bosch BJ, van der Zee R, de Haan CA, Rottier PJ. The coronavirus spike protein is a class I virus fusion protein: Structural and functional characterization of the fusion core complex. J Virol 2003;77:8801-11.
Bukreyev, A., Collins, P.L., 2008. Newcastle disease virus as a vaccine vector for humans. Current Opinion in Molecular Therapeutics 10, 46-55.
Bukreyev, A., Huang, Z., Yang, L., Elankumaran, S., St Claire, M., Murphy, B.R., Samal, S.K., Collins, P.L., 2005. Recombinant newcastle disease virus expressing a foreign viral antigen is attenuated and highly immunogenic in primates. J. Virol. 79, 13275-13284.
Callison SA, Hilt DA, Boynton TO, Sample BF, Robison R, Swayne DE, Jackwood MW. Development and evaluation of a real-time taqman RT-PCR assay for the detection of infectious bronchitis virus from infected chickens. J Virol Methods 2006;138:60-5.
Cavanagh, D., 1981. Structural polypeptides of coronavirus IBV. J. Gen. Virol. 53, 93-103.
Cavanagh, D., 1983. Coronavirus IBV: structural characterization of the spike protein. J. Gen. Virol. 64, 2577-2583.
Cavanagh, D., 1984. Structural characterization of IBV glycoproteins. Adv. Exp. Med. Biol. 173, 95-108.
Cavanagh D. Coronavirus avian infectious bronchitis virus. Vet Res 2007;38:281-97.
Cavanagh, D., et al. Coronavirus IBV: removal of spike glycopolypeptide S1 by urea abolishes infectivity and haemagglutination but not attachment to cells. J. Gen. Virol. 1986 67, 1443-1448.
Cavanagh D, et al. Coronavirus IBV: Virus retaining spike glycopolypeptide S2 but not S1 is unable to induce virus-neutralizing or haemagglutination-inhibiting antibody, or induce chicken tracheal protection. J Gen Virol 1986;67:1435-42.
Cavanagh D, Davis PJ, Mockett AP. Amino acids within hypervariable region 1 of avian coronavirus IBV (Massachusetts serotype) spike glycoprotein are associated with neutralization epitopes. Virus Res 1988; 11: 141-150.
DiNapoli, J.M., Kotelkin, A., Yang, L., Elankumaran, S., Murphy, B.R., Samal, S.K., Collins, P.L., Bukreyev, A., 2007. Newcastle disease virus, a host range-restricted virus, as a vaccine vector for intranasal immunization against emerging pathogens. PNASU.S.A. 104, 9788-9793.

(Continued)

*Primary Examiner* — Shanon A. Foley
*Assistant Examiner* — Myron G Hill
(74) *Attorney, Agent, or Firm* — Quarles & Brady LLP

(57) ABSTRACT

Disclosed are recombinant spike ectodomain proteins, compositions, vectors, kits, and methods for inducing an immune response against avian infectious bronchitis virus (IBV). In particular, the recombinant proteins, compositions, vectors, kits, and methods relate to, include, and/or utilize a soluble, multimerized form of the (IBV) spike (S) protein ectodomain. The recombinant proteins, compositions, vectors, kits, and methods may be utilized to immunize poultry against disease associated with IBV infection or to protect poultry from IBV infection.

17 Claims, 7 Drawing Sheets

Specification includes a Sequence Listing.

(56) References Cited

OTHER PUBLICATIONS

DiNapoli, J.M., Ward, J.M., Cheng, L., Yang, L., Elankumaran, S., Murphy, B.R., Samal, S.K., Collins, P.L., Bukreyev, A., 2009. Delivery to the lower respiratory tract is required for effective immunization with Newcastle disease virus-vectored vaccines intended for humans. Vaccine 27, 1530-1539.

Eldemery F, Joiner KS, Toro H, van Santen VL. Protection against infectious bronchitis virus by spike ectodomain subunit vaccine. Vaccine 2017;35:5864-71.

Enjuanes, L., Nidovirales, in: Virus taxonomy. Classification and nomenclature of viruses Academic Press, New York, N.Y., (2000) pp. 827-834.

Enjuanes, L., et al. Coronaviridae, in: Virus taxonomy. Classification and nomenclature of viruses. Academic Press, New York, N.Y., (2000) pp. 835-849.

Gallardo RA, Hoerr FJ, Berry WD, van Santen VL, Toro H. Infectious bronchitis virus in testicles and venereal transmission. Avian Dis 2011;55:255-8.

Gallardo RA, van Santen VL, Toro H. Host intraspatial selection of infectious bronchitis virus populations. Avian Dis 2010;54:807-13.

Ge, J., Deng, G., Wen, Z., Tian, G., Wang, Y., Shi, J., Wang, X., Li, Y., Hu, S., Jiang, Y., Yang, C., Yu, K., Bu, Z., Chen, H., 2007. Newcastle disease virus-based live attenuated vaccine completely protects chickens and mice from lethal challenge of homologous and heterologous II5N1 avian influenza viruses. J. Virol. 81, 150-158.

Ge, J., Tian, G., Zeng, X., Jiang, Y., Chen, H., Bua, Z., 2010. Generation and evaluation of a Newcastle disease virus-based H9 avian influenza live vaccine. Avian Dis. 54, 294-296.

Heald-Sargent T, Gallagher T. Ready, set, fuse! The coronavirus spike protein and acquisition of fusion competence. Viruses 2012;4:557-80.

Huang, Z., Elankumaran, S., Panda, A., Samal, S.K., 2003a. Recombinant Newcastle disease virus as a vaccine vector. Poultry Science 82, 899-906.

Huang, Z., Krishnamurthy, S., Panda, A., Samal, S.K., 2003b. Newcastle disease virus V protein is associated with viral pathogenesis and functions as an alpha interferon antagonist. J. Virol. 77, 8676-8685.

Huang, Z., Panda, A., Elankumaran, S., Govindarajan, D., Rockemann, D.D., Samal, S.K., 2004. The hemagglutinin-neuraminidase protein of Newcastle disease virus determines tropism and virulence. J. Virol. 78, 4176-4184.

Ignjatovic J, Galli L. The S1 glycoprotein but not the N or M proteins of avian infectious bronchitis virus induces protection in vaccinated chickens. Arch Virol 1994;138:117-34.

Ignjatovic J, Sapats S. Identification of previously unknown antigenic epitopes on the S and N proteins of avian infectious bronchitis virus. Arch Virol 2005;150:1813-31.

Jackwood, M., 2012. Review of Infectious bronchitis virus around the world. Avian Dis. 56, 634-641.

Jackwood, M.W., Hilt, D.A., Lee, C.W., Kwon, H.M., Callison, S.A., Moore, K.M., Moscoso, H., Sellers, H., Thayer, S., 2005. Data from 11 years of molecular typing infectious bronchitis virus field isolates. Avian Dis. 49, 614-618.

Jang SI, Kim DK, Lillehoj HS, Lee SH, Lee KW, Bertrand F, Dupuis L, Deville S, Ben Arous J, Lillehoj EP. Evaluation of Montanide ISA 71 VG adjuvant during profilin vaccination against experimental coccidiosis. PLoS One 2013;8:e59786.

Jang SI, Lillehoj HS, Lee SH, Lee KW, Lillehoj EP, Bertrand F, Dupuis L, Deville S. Montanide ISA 71 VG adjuvant enhances antibody and cell-mediated immune responses to profilin subunit antigen vaccination and promotes protection against Eimeria acervulina and Eimeria tenella. Exp Parasitol 2011;127:178-83.

Kant A, Koch G, van Roozelaar DJ, Kusters JG, Poelwijk FA, van der Zeijst BA. Location of antigenic sites defined by neutralizing monoclonal antibodies on the S1 avian infectious bronchitis virus glycopolypeptide. J Gen Virol 1992;73:591-6.

Karaca K, Naqi S, Gelb J. Production and characterization of monoclonal antibodies to three infectious bronchitis virus serotypes. Avian Dis 1992;36:903-15.

Keeler C, Reed KL, Nix W, Gelb J. Serotype identification of avian infectious bronchitis virus by RT-PCR of the peplomer (S-1) gene. Avian Dis 1998;42:275-84.

Kirchdoerfer RN, Cottrell CA, Wang N, Pallesen J, Yassine HM, Turner HL, Corbett KS, Graham BS, McLellan JS, Ward AB. Pre-fusion structure of a human coronavirus spike protein. Nature 2016;531:118-21.

Koch, G., Hartog, L., Kant, A., van Roozelaar, D.J., 1990. Antigenic domains on the peplomer protein of avian infectious bronchitis virus: correlation with biological functions. J. Gen. Virol. 71, 1929-1935.

Koch, G., Kant, A., 1990. Binding of antibodies that strongly neutralise infectious bronchitis virus is dependent on the glycosylation of the viral peplomer protein. Adv. Exp. Med. Biol. 276, 143-150.

Kusters JG, Jager EJ, Lenstra JA, Koch G, Posthumus WP, Meloen RH, van der Zeijst BA. Analysis of an immunodominant region of infectious bronchitis virus. J Immunol 1989;143:2692-8.

Kusters JG, Niesters HG, Bleumink-Pluym NM, Davelaar FG, Horzinek MC, Van der Zeijst BA. Molecular epidemiology of infectious bronchitis virus in the Netherlands. J Gen Virol 1987;68:343-52.

Kusters JG, Niesters HG, Lenstra JA, Horzinek MC, van der Zeijst BA. Phylogeny of antigenic variants of avian coronavirus IBV. Virology 1989;169:217-21.

Lai, M.M.C., Cavanagh, D., 1997. The molecular biology of coronaviruses. Adv. Vir. Res. 48, 1-100.

Lai, M.M.C., Holmes, K.V., 2001. Coronaviridae: The viruses and their replication, in: Knipe, D.M., Howley, P.M. (Eds.), Fundamental Virology, 4th ed. Lippincott Williams & Wilkins, Philadelphia, pp. 641-663.

Lenstra JA, Kusters JG, Koch G, van der Zeijst BA. Antigenicity of the peplomer protein of infectious bronchitis virus. Mol Immunol 1989;26:7-15.

McKinley ET, Hilt DA, Jackwood MW. Avian coronavirus infectious bronchitis attenuated live vaccines undergo selection of subpopulations and mutations following vaccination. Vaccine 2008;26:1274-84.

Mockett, A.P., Cavanagh, D., Brown, T.D., 1984. Monoclonal antibodies to the S1 spike and membrane proteins of avian infectious bronchitis coronavirus strain Massachusetts M41. J. Gen. Virol. 65, 2281-2286.

Moore KM, Jackwood MW, Hilt DA. Identification of amino acids involved in a serotype and neutralization specific epitope within the s1 subunit of avian infectious bronchitis virus. Arch Virol 1997;142:2249-56.

Mork AK, Hesse M, Abd El Rahman S, Rautenschlein S, Herrler G, Winter C. Differences in the tissue tropism to chicken oviduct epithelial cells between avian coronavirus IBV strains QX and B1648 are not related to the sialic acid binding properties of their spike proteins. Vet Res 2014;45:67.

Nakaya, T., Cros, J., Park, M.S., Nakaya, Y., Zheng, H., Sagrera, A., Villar, E., Garcia-Sastre, A., Palese, P., 2001. Recombinant Newcastle disease virus as a vaccine vector. J. Virol. 75, 11868-11873.

Nayak, B., Rout, S.N., Kumar, S., Khalil, M.S., Fouda, M.M., Ahmed, L.E., Earhart, K.C., Perez, D.R., Collins, P.L., Samal, S.K., 2009. Immunization of chickens with Newcastle disease virus expressing H5 hemagglutinin protects against highly pathogenic H5N1 avian influenza viruses. PloS one 4, e6509.

Ndegwa EN, Joiner KS, Toro H, van Ginkel FW, van Santen VL. The proportion of specific viral subpopulations in attenuated Arkansas Delmarva poultry industry infectious bronchitis vaccines influences vaccination outcome. Avian Dis 2012;56:642-53.

Nix, W.A., Troeber, D.S., Kingham, B.F., Keeler, C.L., Jr., Gelb, J., Jr., 2000. Emergence of subtype strains of the Arkansas serotype of infectious bronchitis virus in Delmarva broiler chickens. Avian Dis. 44, 568-581.

Orr-Burks N, Gulley SL, Toro H, van Ginkel FW. Immunoglobulin A as an early humoral responder after mucosal avian coronavirus vaccination. Avian Dis 2014;58:279-86.

(56) References Cited

OTHER PUBLICATIONS

Park, M.S., Steel, J., Garcia-Sastre, A., Swayne, D., Palese, P., 2006. Engineered viral vaccine constructs with dual specificity: avian influenza and Newcastle disease. PNAS U.S.A. 103, 8203-8208.
Promkuntod N, van Eijndhoven RE, de Vrieze G, Grone A, Verheije MH. Mapping of the receptor-binding domain and amino acids critical for attachment in the spike protein of avian coronavirus infectious bronchitis virus. Virology 2014;448:26-32.
Promkuntod N, Wickramasinghe IN, de Vrieze G, Grone A, Verheije MH. Contributions of the S2 spike ectodomain to attachment and host range of infectious bronchitis virus. Virus Res 2013;177:127-37.
Shahwan K, Hesse M, Mork AK, Herrler G, Winter C. Sialic acid binding properties of soluble coronavirus spike (S1) proteins: Differences between infectious bronchitis virus and transmissible gastroenteritis virus. Viruses 2013;5:1924-33.
Song CS, Lee YJ, Lee CW, Sung HW, Kim JH, Mo IP, Izumiya Y, Jang HK, Mikami T. Induction of protective immunity in chickens vaccinated with infectious bronchitis virus S1 glycoprotein expressed by a recombinant baculovirus. J Gen Virol 1998;79:719-23.
Stadler, K., Masignani, V., Eickmann, M., Becker, S., Abrignani, S., Klenk, H.-D., Rappuoli, R., 2003. Comparison of coronavirus genome structures. Nature Rev. Microbiol. 1, 209-218.
Swayne, D.E., Suarez, D.L., Schultz-Cherry, S., Tumpey, T.M., King, D.J., Nakaya, T., Palese, P., Garcia-Sastre, A., 2003. Recombinant paramyxovirus type 1-avian influenza-H7 virus as a vaccine for protection of chickens against influenza and Newcastle disease. Avian Dis. 47, 1047-1050.
Toro, H., et al, Protection induced by distinct IBV Ark-DPI S1 expressed from rAdenovirus, in: VII. International Symposium on Avian Corona- and Pneumoviruses and Complicating Pathogens. World Veterinary Poultry Association, Rauischholzhausen, Germany, 2012. pp. 225-229.
Toro H, et al. Genetic diversity and selection regulates evolution of infectious bronchitis virus. Avian Dis 2012; 56: 449-55.
Toro H, et al. Infectious bronchitis virus subpopulations in vaccinated chickens after challenge. Avian Dis 2012; 56: 501-8.
Toro, H., et al., 2007. RCA-free recombinant adenovirus-vectored vaccine for mass immunization of poultry against avian influenza, 2007 AAAP/AVMA Annual Meeting, Washington DC.
Toro, H., Tang, D.C., Suarez, D.L., Zhang, J., Shi, Z., 2008. Protection of chickens against avian influenza with non-replicating adenovirus-vectored vaccine. Vaccine 26, 2640-2646.
Toro H, et al. Epidemiological and experimental evidence for immunodeficiency affecting avian infectious bronchitis. Avian Pathol 2006; 35: 455-464.
Toro H, Zhao W, Breedlove C, Zhang Z, Yu Q, van Santen V. Infectious bronchitis virus S2 expressed from recombinant virus confers broad protection against challenge. Avian Dis 2014; 58: 83-89.
Van Santen VL, Toro H. Rapid selection in chickens of subpopulations within ArkDPI-derived infectious bronchitis virus vaccines. Avian Pathol 2008;37:293-306.
Walls AC, Tortorici MA, Bosch BJ, Frenz B, Rottier PJ, DiMaio F, Rey FA, Veesler D. Cryo-electron microscopy structure of a coronavirus spike glycoprotein trimer. Nature 2016;531:114-7.
Wickramasinghe IN, de Vries RP, Grone A, de Haan CA, Verheije MH. Binding of avian coronavirus spike proteins to host factors reflects virus tropism and pathogenicity. J Virol 2011;85:8903-12.
Wickramasinghe IN, van Beurden SJ, Weerts EA, Verheije MH. The avian coronavirus spike protein. Virus Res 2014;194:37-48.
Wickramasinghe IN, Verheije MH. Protein histochemistry using coronaviral spike proteins: Studying binding profiles and sialic acid requirements for attachment to tissues. Methods Mol Biol 2015;1282:155-63.
Yin L, Zeng Y, Wang W, Wei Y, Xue C, Cao Y. Immunogenicity and protective efficacy of recombinant fusion proteins containing spike protein of infectious bronchitis virus and hemagglutinin of H3N2 influenza virus in chickens. Virus Res 2016;223:206-12.
Yu Q, Spatz S, Li Y, Yang J, Zhao W, Zhang Z, Wen G, Garcia M, Zsak L. Newcastle disease virus vectored infectious laryngotracheitis vaccines protect commercial broiler chickens in the presence of maternally derived antibodies. Vaccine 2017;35:789-95.
Zhao W, Spatz S, Zhang Z, Wen G, Garcia M, Zsak L, Yu Q. Newcastle disease virus (NDV) recombinants expressing infectious laryngotracheitis virus (ILTV) glycoproteins gB and gD protect chickens against ILTV and NDV challenges. J Virol 2014;88:8397-406.
Andoh, K., et al. (2015). Decreased neutralizing antigenicity in IBV S1 protein expressed from mammalian cells. Virus Res, 208, 164-170.
Cavanagh, D., et al. (1984). Induction of humoral neutralising and haemagglutination-inhibiting antibody by the spike protein of avian infectious bronchitis virus. Avian Pathol, 13, 573-583.
Chen, H. W., et al. (2016). Synthetic virus-like particles prepared via protein corona formation enable effective vaccination in an avian model of coronavirus infection. Biomaterials, 106, 111-118.
Chen, H. Y., et al. (2010). Construction and immunogenicity of a recombinant fowlpox vaccine coexpressing S1 glycoprotein of infectious bronchitis virus and chicken IL-18. Vaccine, 28, 8112-8119.
Falchieri, M., et al. (2013). Avian metapneumoviruses expressing infectious bronchitis virus genes are stable and induce protection. Vaccine, 31, 2565-2571.
Guo, Z., et al. (2010). Priming with a DNA vaccine and boosting with an inactivated vaccine enhance the immune response against infectious bronchitis virus. J Virol Methods, 167, 84-89.
Jiao, H., et al. (2011). Oral and nasal DNA vaccines delivered by attenuated Salmonella enterica serovar Typhimurium induce a protective immune response against infectious bronchitis in chickens. Clin Vaccine Immunol, 18, 1041-1045.
Johnson, M. A., et al. (2003). A recombinant fowl adenovirus expressing the S1 gene of infectious bronchitis virus protects against challenge with infectious bronchitis virus. Vaccine, 21, 2730-2736.
Kapczynski, D. R., et al. (2003). Protection of chickens from infectious bronchitis by in ovo and intramuscular vaccination with a DNA vaccine expressing the S1 glycoprotein. Avian Dis, 47, 272-285.
Li, H., et al. (2016). Recombinant duck enteritis viruses expressing major structural proteins of the infectious bronchitis virus provide protection against infectious bronchitis in chickens. Antiviral Res, 130, 19-26.
Liu, G., et al. (2013). Assembly and immunogenicity of coronavirus-like particles carrying infectious bronchitis virus M and S proteins. Vaccine, 31, 5524-5530.
Lv, L., et al. (2014). Production and immunogenicity of chimeric virus-like particles containing the spike glycoprotein of Infectious bronchitis virus. J Vet Sci, 15, 209-216.
Meir, R., et al. (2012). Immune responses to mucosal vaccination by the recombinant S1 and N proteins of infectious bronchitis virus. Viral Immunol, 25, 55-62.
Mockett, A. P. (1985). Envelope proteins of avian infectious bronchitis virus: Purification and biological properties. J Virol Methods, 12, 271-278.
Shi, X. M., et al. (2011). Evaluation of recombinant fowlpox virus expressing infectious bronchitis virus S1 gene and chicken interferon-gamma gene for immune protection against heterologous strains. Vaccine, 29, 1576-1582.
Shil, P. K., et al. (2011). Development and immunogenicity of recombinant GapA(+) Mycoplasma gallisepticum vaccine strain ts-11 expressing infectious bronchitis virus-S1 glycoprotein and chicken interleukin-6. Vaccine, 29, 3197-3205.
Tan, B., et al. (2009). Coadministration of chicken GM-CSF with a DNA vaccine expressing infectious bronchitis virus (IBV) S1 glycoprotein enhances the specific immune response and protects against IBV infection. Arch Virol, 154, 1117-1124.
Tian, L., et al. (2008). The immunoreactivity of a chimeric multi-epitope DNA vaccine against IBV in chickens. Biochem Biophys Res Commun, 377, 221-225.

(56) References Cited

OTHER PUBLICATIONS

Tomley, F. M., et al. (1987). Expression of the infectious bronchitis virus spike protein by recombinant vaccinia virus and induction of neutralizing antibodies in vaccinated mice. J Gen Virol, 68, 2291-2298.

Toro, H., et al. (2014). S1 of distinct IBV population expressed from recombinant adenovirus confers protection against challenge. Avian Dis, 58, 211-215.

Wang, X., et al. (2002). Construction and immunogenicity studies of recombinant fowl poxvirus containing the S1 gene of Massachusetts 41 strain of infectious bronchitis virus. Avian Dis, 46, 831-838.

Wang, Y. F., et al. (2009). Protection of chickens against infectious bronchitis by a recombinant fowlpox virus co-expressing IBV-S1 and chicken IFNgamma. Vaccine, 27, 7046-7052.

Xu, P. W., et al. (2016). Assembly and immunogenicity of baculovirus-derived infectious bronchitis virus-like particles carrying membrane, envelope and the recombinant spike proteins. Biotechnol Lett, 38, 299-304.

Yan, F., et al. (2013). Protection of chickens against infectious bronchitis virus with a multivalent DNA vaccine and boosting with an inactivated vaccine. J Vet Sci, 14, 53-60.

Yang, T., et al. (2009). Multivalent DNA vaccine enhanced protection efficacy against infectious bronchitis virus in chickens. J Vet Med Sci, 71, 1585-1590.

Zeshan, B., et al. (2011). Protective immune responses induced by in ovo immunization with recombinant adenoviruses expressing spike (S1) glycoprotein of infectious bronchitis virus fused/co-administered with granulocyte-macrophage colony stimulating factor. Vet Microbiol, 148, 8-17.

Zeshan, B., et al. (2010). Immunogenicity and protective efficacy of a replication-defective infectious bronchitis virus vaccine using an adenovirus vector and administered in ovo. J Virol Methods, 166, 54-59.

Zhang, J., et al. (2014). BacMam virus-based surface display of the infectious bronchitis virus (IBV) S1 glycoprotein confers strong protection against virulent IBV challenge in chickens. Vaccine, 32, 664-670.

Zhang, X., et al. (2012). Protection conferred by a recombinant Marek's disease virus that expresses the spike protein from infectious bronchitis virus in specific pathogen-free chicken. Virol J, 9, 85.

Zhao, R., et al. (2017). Recombinant Newcastle disease virus expressing the infectious bronchitis virus S1 gene protects chickens against Newcastle disease virus and infectious bronchitis virus challenge. Vaccine, 35, 2435-2442.

Zhou, J. Y., et al. (2004). Generation of the transgenic potato expressing full-length spike protein of infectious bronchitis virus. J Biotechnol, 111, 121-130.

Zhou, J. Y., et al. (2003). Expression of immunogenic S1 glycoprotein of infectious bronchitis virus in transgenic potatoes. J Virol, 77, 9090-9093.

* cited by examiner

A IBV RNA in tears

B IBV RNA in tracheas

FIG. 6

IBV RNA in tears

RECOMBINANT SPIKE ECTODOMAIN PROTEINS, COMPOSITIONS, VECTORS, KITS, AND METHODS FOR IMMUNIZING AGAINST AVIAN INFECTIOUS BRONCHITIS VIRUS

CROSS-REFERENCE TO RELATED APPLICATIONS

This application claims the benefit under 35 U.S.C. § 119(e) to U.S. Provisional Application No. 62/543,142, filed on Aug. 9, 2017, the content of which is incorporated herein by reference in its entirety.

STATEMENT REGARDING FEDERALLY SPONSORED RESEARCH OR DEVELOPMENT

This invention was made with government support under Grant/Contract No. 2015-68004-23131 awarded by the National Institute of Food & Agriculture (NIFA). The government has certain rights in the invention.

BACKGROUND

The present invention relates generally to the field of recombinant proteins, compositions, vectors, kits, and methods for immunizing against coronaviruses. In particular, the invention relates to recombinant infectious bronchitis virus (IBV) spike ectodomain proteins, compositions, vectors, kits, and methods for immunizing avian species against infection by IBV.

In the poultry industry avian infectious bronchitis virus (IBV) continues to be the most common contributor to respiratory disease in chicken populations despite worldwide extensive vaccination with a multiplicity of type-specific vaccines. IBV replicates primarily in the upper respiratory tract causing respiratory disease in large chicken populations. IBV's surface spike (S) glycoprotein is post-translationally cleaved into an S1 subunit (~550 amino acids) and an S2 subunit (~600 amino acids) (Lai and Holmes, 2001). Like other coronaviruses, the S1 subunit of the S glycoprotein is responsible for viral attachment to host cells and is important for host protective immune responses as it induces virus neutralizing-antibodies (Cavanagh, 1981, 1983, 1984; Cavanagh and Davis, 1986; Koch et al., 1990; Koch and Kant, 1990; Mockett et al., 1984). Because of the relevance of S1 for the first step of replication (i.e., attachment to cells) and immunological escape, the extensive variation exhibited by The S1 glycoprotein among IBV coronaviruses (Kusters et al., 1987; Kusters et al., 1989b) is likely the most relevant phenotypic characteristic for this virus's "adaptation" and evolutionary success (Toro et al., 2012b). Genetic diversity among coronaviruses is achieved by high mutation frequency and recombination events (Enjuanes et al., 2000a; Enjuanes et al., 2000b; Lai and Cavanagh, 1997; Stadler et al., 2003). Selection acting on diverse populations results in rapid evolution of the virus and the emergence of antigenically different strains (Toro et al., 2012b). More than 30 different IBV types have been identified during the last 5 decades in the U.S. alone. According to a 2012 review, over 30 different genotypes of IBV are currently affecting chicken populations worldwide (Jackwood, 2012). These have recently been grouped into 6 genotypes divided into 32 lineages (Valastro, V., E. C. Holmes, P. Britton, A. Fusaro, M. W. Jackwood, G. Cattoli, and I. Monne. S1 gene-based phylogeny of infectious bronchitis virus: An attempt to harmonize virus classification. Infect Genet Evol 39:349-364. 2016). Multiple surveillance studies performed in the U.S. have demonstrated that serotypes/genotypes Arkansas (Ark), Massachusetts (Mass), Connecticut (Conn), DE072, and Georgia variants GAV and GA98 are the most prevalent (Jackwood et al., 2005; Nix et al., 2000; Toro et al., 2006). The scientific literature states that the amino acid sequences of the S1 subunit of different IBVs can have as little as 50% amino acid sequence identity (Valastro et al., 2016). However IBV S1 amino acid sequences with even less (~45%) amino acid sequence identity can be found in GenBank. The amino acid sequences of IBV S2 subunits are more conserved than those of S1 subunits; nevertheless considerable variation is found. One report indicated that IBV S2 subunits exhibited as little as 74% amino acid identity (Toro et al., 2014). A more recent analysis of IBV S2 ectodomain amino acid sequences in GenBank showed some with as little as 70% amino acid sequence identity.

Because IBV exists as multiple different serotypes that do not provide for cross-protection after host exposure or vaccination, a multiplicity of serotype-specific IBV vaccines have been developed worldwide. For example, vaccination programs in the U.S. currently comprise mono- or polyvalent vaccines including Mass, Conn, GA98, DE072, and Ark serotypes. In Europe, IBV vaccines commonly include strains belonging to serotypes Mass, UK4/91, D274, and D-1466. However, IBV's high ability to evolve allows it to consistently circulate in commercial poultry and cause outbreaks of disease in spite of extensive vaccination. In addition, accumulating evidence indicates that attenuated IBV vaccines may also be contributing to the emergence and circulation of vaccine-like viruses in host populations (Toro et al., 2012b; Toro et al., 2012c). Indeed, viral sub-populations differing from the predominant live vaccine population have been shown to emerge during a single passage of attenuated IBV vaccine in chickens (McKinley et al., 2008; van Santen and Toro, 2008).

In an effort to understand the mechanisms underlying the emergence of vaccine-like viruses, S1 gene sequences of virus populations of all four IBV Ark-serotype attenuated vaccines commercially available in the U.S. were analyzed before and after replication in chickens (Gallardo et al., 2010; van Santen and Toro, 2008). The results from these analyses demonstrated different degrees of genetic heterogeneity among Ark-derived vaccines prior to inoculation into chickens, ranging from no apparent heterogeneity to heterogeneity in 20 positions in the S gene. In all except one position, nucleotide differences resulted in different amino acids encoded and therefore in phenotypic differences among subpopulations present in the vaccines. Significantly, it has been observed that specific minor subpopulations present in each of the vaccines were rapidly "selected" during a single passage in chickens. Indeed, by 3-days post-ocular vaccination, viral populations with S gene sequences distinct from the vaccine major consensus sequence at 5 to 11 codons were found to predominate in chickens (Gallardo et al., 2010; McKinley et al., 2008; van Santen and Toro, 2008). Thus, the use of attenuated coronavirus vaccines may be contributing to the problem of antigenic variation, and the development of a novel vaccine technology to increase the resistance of chicken populations to IBV and reduce economic losses is essential for the poultry industry.

The currently most effective and most widely used IBV vaccination program for broilers utilizes live-attenuated vaccines of various serotypes generated by extensive serial passage in embryonated chicken eggs, applied by eyedrop or spray in the hatchery and often a second time by spray or drinking water in chicken houses at 14-18 days of age. Disadvantages of this type of vaccine include the long time required to produce attenuated vaccine strains of emerging serotypes and the risk of increase in virulence as the vaccine strain circulates among inadequately vaccinated chickens in a flock.

The vast majority of efforts to generate vectored vaccines or recombinant subunit vaccines against IBV to overcome the disadvantages of live-attenuated vaccines have utilized sequences encoding the amino terminal portion (S1) of the spike protein. However, here, the inventors have shown that immunization with a larger portion of the spike protein, including the entire ectodomain, provides more effective protection against IBV infection than the S1 domain alone. Importantly, the recombinant proteins disclosed herein may be derived and prepared from any IBV strain in order to generate a more effective antigen for inducing a protective immune response.

SUMMARY

Disclosed are recombinant spike ectodomain proteins, compositions, vectors, kits, and methods for inducing an immune response against avian infectious bronchitis virus (IBV). In particular, the recombinant proteins, compositions, vectors, kits, and methods may be utilized to immunize poultry against disease associated with IBV infection or to protect poultry from IBV infection.

One aspect of the subject matter of this disclosure is a recombinant protein of IBV which may be referred to as a recombinant S protein of IBV that includes the ectodomain portion (S ectodomain) of the native S protein from which the recombinant S protein is derived and that typically does not include any of the non-ectodomain portion of the native S protein. The disclosed recombinant protein may include in succession from N-terminus to C-terminus an amino acid sequence represented by the formula "$N_{ter}$-S1-S2$_{ecto}$-MD-$C_{ter}$" where "$N_{ter}$" represents the N-terminus of the protein, "S1" represents the S1 domain of a spike protein (S) of IBV (or a variant amino acid sequence thereof), "S2$_{ecto}$" represents the ecto-subdomain portion of the S2 domain of the S protein (or a variant amino acid sequence thereof), "MD" represents a multimerization domain (e.g., a trimerization domain) which is not present in the ectodomain of the S protein, and "$C_{ter}$" represents the C-terminus of the protein. Optionally, the disclosed recombinant protein may include in succession from N-terminus to C-terminus an amino acid sequence represented by the formula "$N_{ter}$-S1-Spacer-S2$_{ecto}$-MD-$C_{ter}$" where "Spacer" represents a spacer sequence of amino acids between S1 and S2$_{ecto}$ which typically does not comprise the amino acid sequence Arg-X-(Arg/Lys)-Arg, which is the consensus cleavage recognition sequence for the furin endoprotease.

Optionally, the disclosed recombinant proteins may include an N-terminal leader sequence that facilitates translocation of the protein into the endoplasmic reticulum and may otherwise be referred to as a "signal peptide" (SP). For example, the recombinant proteins may be described as having a formula $N_{ter}$-SP-S1-Spacer-S2$_{ecto}$-MD-$C_t$—, where SP is a signal peptide.

Optionally, the disclosed recombinant proteins further may comprise a tag for identifying and/or purifying the recombinant proteins. In some embodiments, the tag is present at the C-terminus and the recombinant protein may be described as having a formula $N_{ter}$-SP-S1-Spacer-S2$_{ecto}$-MD-Tag-$C_{ter}$.

Optionally, the recombinant protein may include one or more additional spacer sequences. In some embodiments, the recombinant protein includes an additional spacer between S2$_{ecto}$ and MD and the recombinant protein may be described as having a formula $N_{ter}$-SP-S1-Spacer1-S2$_{ecto}$-Spacer2-MD-$C_{ter}$.

Also disclosed herein are vectors that express the disclosed recombinant protein. For example, the disclosed vectors may comprise a polynucleotide encoding the amino acid sequence of the disclosed recombinant proteins operably linked to a promoter for expressing the polynucleotide and recombinant protein in a suitable cell line or in an animal (e.g. a chicken). Suitable vectors may include, but are not limited to, viral vectors.

Also disclosed herein are methods for making the disclosed recombinant proteins. The disclosed methods may include expressing the recombinant proteins in a cell line, for example, via a vector that optionally is a viral vector. The recombinant proteins thus made optionally may be purified, for example, via a protein tag, and further processed or formulated for use (e.g., as part of a vaccine composition).

Also disclosed herein are methods for vaccinating a subject against infection by IBV. In some embodiments, the methods include administering to the subject (e.g., a chicken) a composition comprising the recombinant proteins as disclosed herein and a suitable carrier. In other embodiments, the methods include administering to the subject (e.g., a chicken) a composition comprising a vector that expresses the recombinant proteins as disclosed herein and a suitable carrier.

BRIEF DESCRIPTION OF THE DRAWINGS

Figure 1:
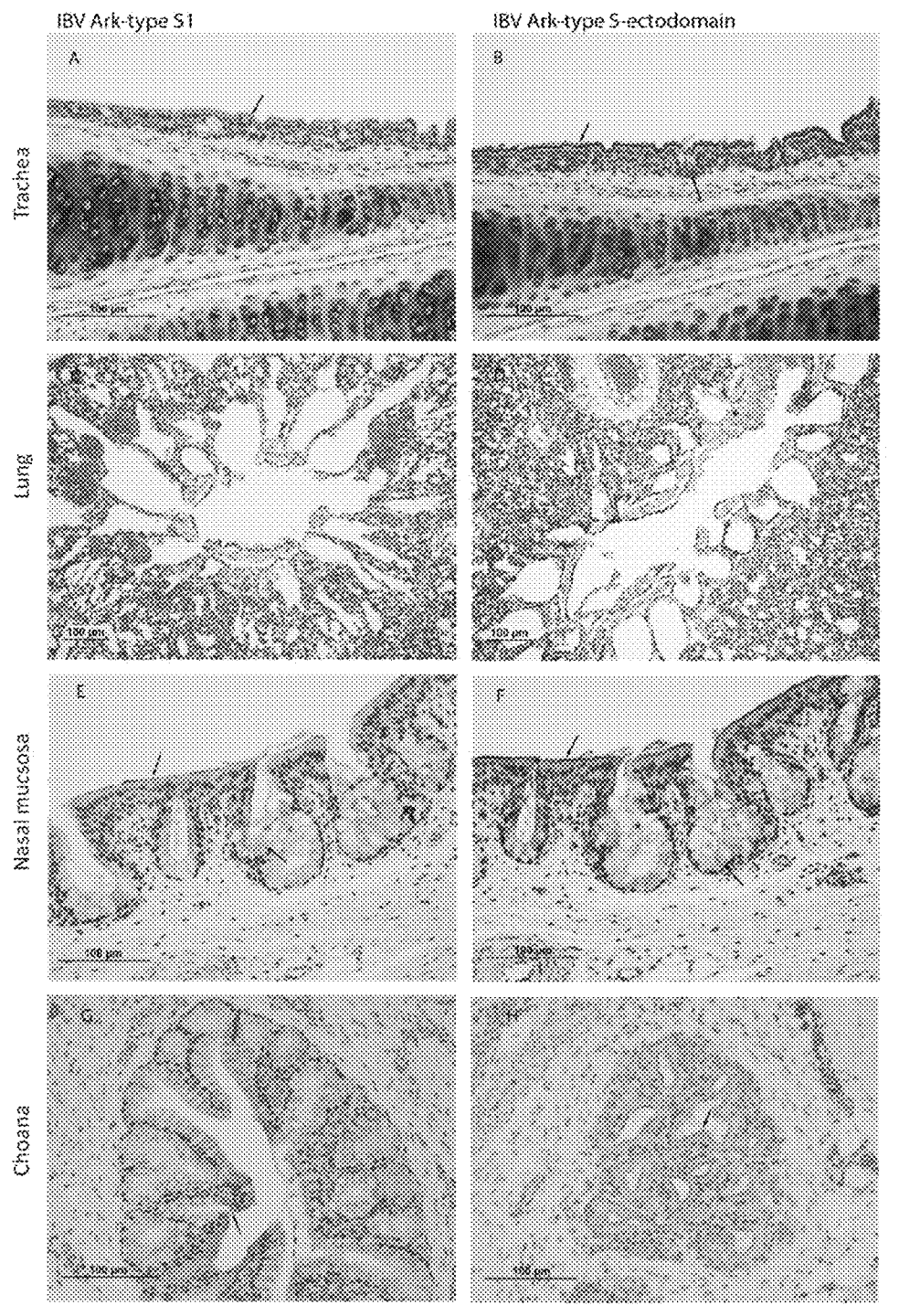
Figure 1:
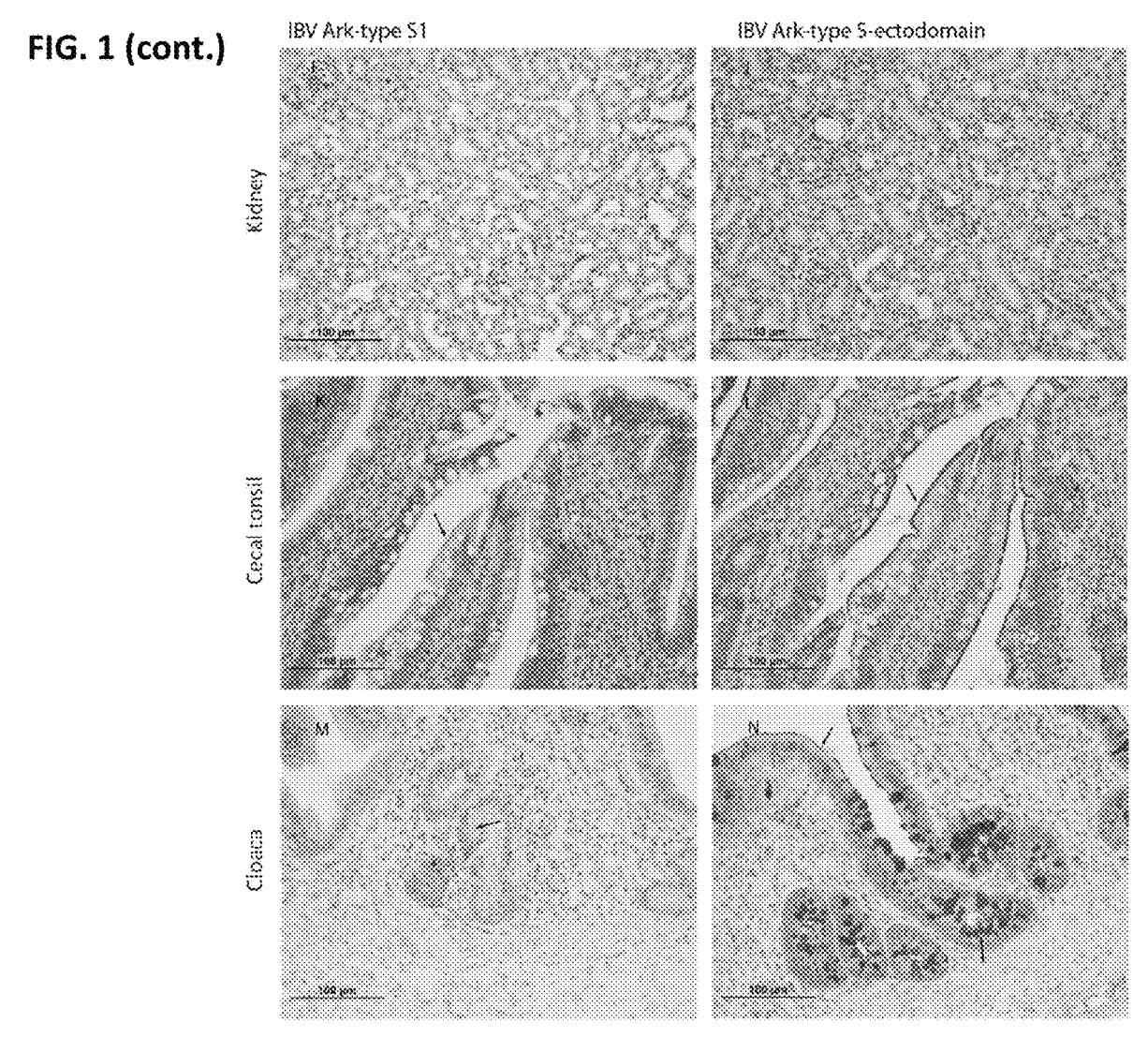

FIG. 1. Protein histochemistry demonstrating recombinant IBV Ark-type S1 and S-ectodomain binding in various chicken tissues. AEC+ chromogenic substrate was used to identify bound spike protein as indicated by red staining (arrows). (A) S1 binds to the apical surface of the tracheal epithelium, while S-ectodomain (B) binds to the cilia, tracheal epithelium, and the mucin-containing goblet cell secretory vesicles. (C) S1 protein binding was not identified in the lung. (D) S-ectodomain binding was recognized in the epithelium lining the pulmonary parabronchi and atria. (E) Minimal staining at the apical surface of the nasal mucosal epithelium and mucus glands with S1 protein was observed, whereas S-ectodomain (F) exhibited enhanced staining of the nasal mucosal epithelium and mucus glands. (G) Sparse punctate S1 binding occurred along the apical surface of the choanal submucosal glandular epithelium. (H) Intense S-ectodomain binding of the epithelial apical surface and secretory product in the choanal glands was recognized. (I and J) S-ectodomain binding was detected on the epithelial apex of scattered renal tubules; however, S1 binding was not observed. (K) Multifocal, weak staining at the apical surface of the cecal tonsil intestinal epithelium with S1 protein was observed, whereas S-ectodomain (L) exhibited diffuse enhanced staining of the epithelium. (M and N) There was diffuse, strong staining of the cloacal glands with S-ectodomain, and only scattered, weak staining with the S1 protein. Although recombinant S-ectodomain is twice the molecular weight of recombinant S1 protein, it was used at half the µg/ml concentration. Thus the molar concentration of S-ectodomain was one-fourth that of S1. Thus, the increased binding affinity of S-ectodomain compared to S1 is even greater than it appears.

FIG. 2. Relative IBV RNA in (A) tears and (B) trachea of chickens primed at day 12 of age with adjuvanted trimeric recombinant S1, or S-ectodomain (Se), boosted 21 days later, and challenged with virulent Ark-type IBV 21 days post-boost. Nv/C=non-vaccinated (chickens primed and boosted with the adjuvant with PBS)/challenged. Nv/Nc=non-vaccinated/non-challenged. Relative IBV RNA levels determined 5 days post-challenge by qRT-PCR. Lines indicate median $\log_{10}$ relative RNA copy numbers, boxes indicate $25^{th}$ to $75^{th}$ percentile, and whiskers indicate minimum and maximum values. Different letters indicate significant differences (P<0.05). Nv/Nc were assigned $\log_{10}$ values of 0 to be included in the graphs with log scale Y axes.

FIG. 6. Relative IBV RNA levels in tears 5 days-post challenge with virulent Ark-type IBV. Chickens (NDV.Se/C; N=12/group) were vaccinated with recombinant LaSota NDV expressing IBV Ark-type S-ectodomain protein at 1 and 14 days of age and challenged with virulent Ark-type IBV 18 days later. A non-vaccinated/challenged (NvC) control group was mock-vaccinated with LaSota NDV and challenged. A non-vaccinated/non-challenged (Nv/Nc) control group was mock-vaccinated with LaSota NDV and not challenged. Lines indicate median $\log_{10}$ relative RNA copy numbers, boxes indicate 25th to 75th percentile, and whiskers indicate minimum and maximum values. Nv/Nc samples, which had no detectable IBV RNA, were assigned $\log_{10}$ values of 0. Different letters indicate significant differences (One-way ANOVA and Tukey's multiple comparison test; P<0.05).

DETAILED DESCRIPTION

Figure 3:
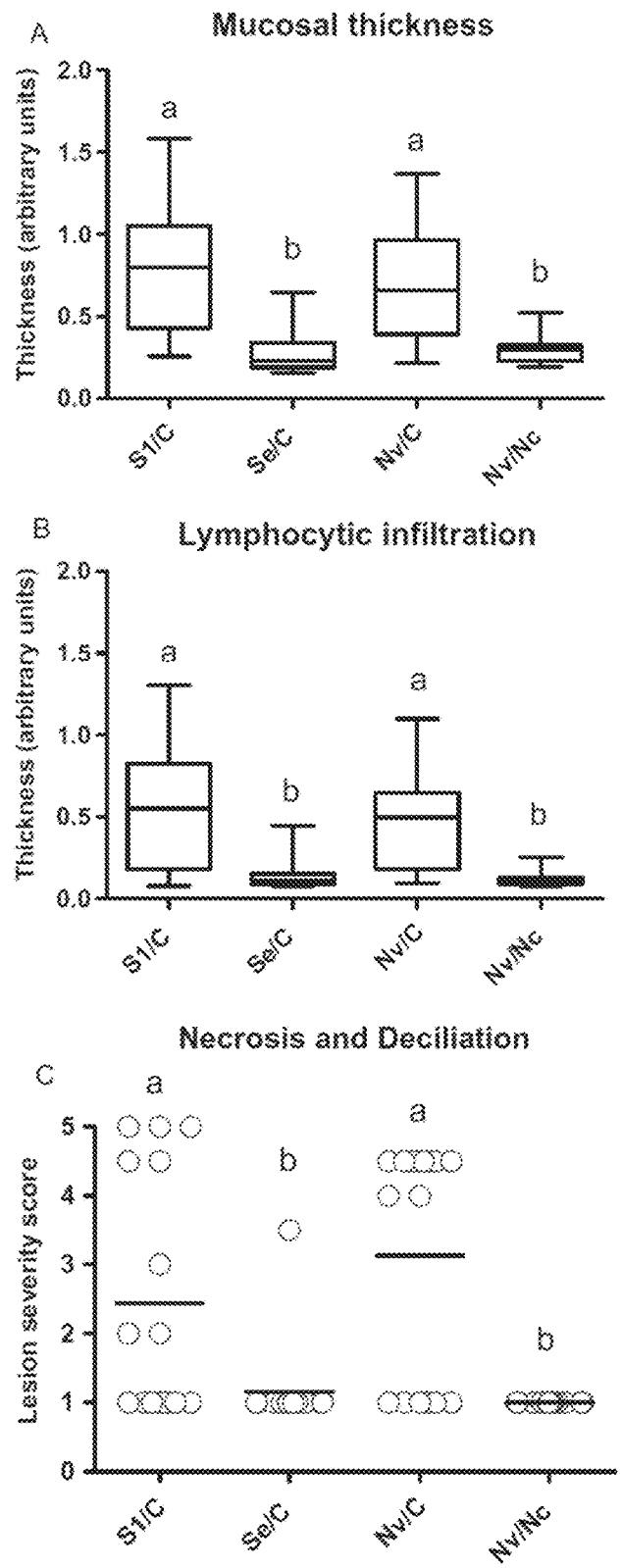
FIG. 3. Tracheal histomorphometry and histopathology 5 days after virulent IBV Ark challenge in chickens primed with adjuvanted trimeric recombinant S1, or S-ectodomain (Se), boosted 21 days later, and challenged with virulent Ark-type IBV 21 days post-boost. (A) Mucosal thickness and (B) thickness of lymphocytic infiltration by tracheal histomorphometry. (C) Severity of tracheal mucosal necrosis and deciliation scored blindly (1=normal, 2=mild, 3=moderate, 4=marked, 5=severe) for each chicken. In box and whisker plots (A and B), lines indicate the median thickness, the boxes indicate the $25^{th}$ and $75^{th}$ percentiles, and the whiskers indicate minimum and maximum values. In the scatter plot (C), each point indicates the lesion score for an individual chicken and the lines indicate mean scores for each group. Nv/C=non-vaccinated (chickens primed and boosted with the adjuvant with PBS)/challenged. Nv/Nc=non-vaccinated/non-challenged. Different letters indicate significant differences (P<0.05).

Disclosed are recombinant IBV spike ectodomain proteins, compositions, vectors, kits, and methods for inducing an immune response against avian infectious bronchitis virus (IBV) which may be described herein using definitions as set forth below and throughout the application.

Unless otherwise specified or indicated by context, the terms "a," "an," and "the," mean "one or more." For example, "protein" or "domain" should be interpreted to mean "one or more proteins" and "one or more domains," respectively.

As used herein, "about", "approximately," "substantially," and "significantly" will be understood by persons of ordinary skill in the art and will vary to some extent depending on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

As used herein, the terms "subject," "host," or "individual" typically refer to an animal at risk for acquiring an infection by infectious bronchitis virus (IBV), such as an avian species. The terms "subject," "host," or "individual" may be used interchangeably. Suitable avian species for the disclosed vaccine may include poultry such as members of the order Galliformes, and in particular the species *Gallus gallus* or the subspecies *Gallus gallus domesticus*.

Infectious Bronchitis Virus (IBV)

As used herein infectious bronchitis virus (IBV) refers to an avian bronchitis virus, which is a coronavirus that infects chicken among other avian species and causes the associated disease infectious bronchitis "IB." As a coronavirus, IBV is an enveloped virus with a positive-sense, single-strand RNA genome having a size of ~27.6 kb. The name "coronavirus" is derived from the Latin word "corona" meaning crown or halo, and refers to the characteristic appearance of the virus under electron microscopy, where the virus includes a fringe of large, bulbous surface projections creating an image reminiscent of a crown or halo. This coronal morphology is created by the viral spike protein (S), which is present on the surface of the virus and determines the host tropism for the virus. The S protein comprises an S1 domain and an S2 domain. The S protein of IBV is expressed and cleaved by the endopeptidase furin to generate the S1 subunit and S2 subunit. The S2 subunit transverses the viral membrane and includes an N-terminal ectodomain, a transmembrane domain, and a cytosolic C-terminus. The S1 subunit associates non-covalently with the ectodomain of the S2 subunit. Preferably, the recombinant S proteins disclosed herein include the ectodomain portion of the S protein (i.e., the S1 subunit and the ectodomain portion of the S2 subunit) and do not include the non-ectodomain portion of the S protein (i.e., the non-ectodomain portion of the S2 subunit).

The term "IBV" is meant to encompass numerous serotypes and strains of IBV that have been isolated and will be isolated in the future throughout the United States and the world and characterized, including but not limited to: B/D207/84; B/D274/84; B/UK167/84; B/UK142/86; E/D3896/84; E/UK123/82; Brazil/BR1/USP-73/09; 793B/4-91/91; FR/CR88121/88; China/Q1/98; China/LDL971/97; LX4; CAV/CAV9437/95; CAV/CAV1686/95; CAV/CAV56b/91; PA/Wolgemuth/98; PA/171/99; CA/557/03 S1; JAA/04 S1 vaccine; HN99 S1; N1/62/S1; GA08; Ark/ArkDPI/81 S1; Ark/Ark99/73; CAL99; CAL99/CAL99/99 S1; CAL99/NE15172/95 S1; Holte/Holte/54; JMK/JMK/64; Gray/Gray/60; Iowa/Iowa609/56; Ca/1737/04; DMA/5642/06 S1; GA07/GA07/07; QX/QXIBV/99; Mass/H52; Mass/H120; Mass/Mass41/41; Conn/Conn46/51 vaccine; FL/FL18288/71; DE/DE072/92 vaccine; Georgia 98; GA98/0470/98; GA-08; GA-13; and Dutch/D1466/81. The complete genomic sequences of many strains of IBV have been reported. (See Ammayappan et al., Virology Journal 2008, 5:157, reporting the genomic sequence of Ark/ArkDPI/81; which is incorporated herein by reference in its entirety). Live attenuated strains of IBV are available commercially as vaccines and may include Mass/Mass41/41 S1 and Ark/ArkDPI/81 S1.

Polypeptide, Proteins, and Peptides

As used herein, polypeptide, proteins, and peptides comprise polymers of amino acids, otherwise referred to as "amino acid sequences." A polypeptide or protein is typically of length >100 amino acids (Garrett & Grisham, Biochemistry, $2^{nd}$ edition, 1999, Brooks/Cole, 110). A peptide is defined as a short polymer of amino acids, of a length typically of 20 or less amino acids, and more typically of a length of 12 or less amino acids (Garrett & Grisham, Biochemistry, $2^{nd}$ edition, 1999, Brooks/Cole, 110). However, the terms "polypeptide," "protein," and "peptide" may be used interchangeably herein.

As contemplated herein, a polypeptide, protein, or peptide may be further modified to include non-amino acid moieties. Modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, or glycosylation (e.g., the addition of a glycosyl group to either asparagine, hydroxylysine, serine, or threonine, resulting in a glycoprotein). Additional modifications may include, but are not limited to polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine). In particular, the S protein of IBV generated in eukaryotic cells is heavily glycosylated. In some embodiments, the disclosed recombinant proteins of IBV may be modified to include a non-naturally occurring N-terminal modification such as an acetylation. In some embodiments, the disclosed recombinant proteins of IBV may be modified to include a non-naturally occurring C-terminal modification such as an amidation.

The amino acid sequences contemplated herein may include one or more amino acid substitutions relative to a reference amino acid sequence (e.g., relative to any of SEQ ID NOs:1-119). In some cases, these substitutions may be conservative amino acid substitutions relative to the reference amino acid sequence. For example, a variant, mutant, or derivative polypeptide may include conservative amino acid substitutions and/or non-conservative amino acid substitutions relative to a reference polypeptide, which may include but is not limited to any of SEQ ID NOs:1-119. "Conservative amino acid substitutions" are those substitutions that are predicted to interfere least with the properties of the reference polypeptide. In other words, conservative amino acid substitutions substantially conserve the structure and the function of the reference protein. Table 1 provides a list of exemplary conservative amino acid substitutions.

TABLE 1

| Original Residue | Conservative Substitution |
| --- | --- |
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain. In contrast, non-conservative amino acid substitutions generally disrupt and/or alter (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

A "deletion" refers to a change in a reference amino acid sequence (e.g., any of SEQ ID NOs:1-119) that results in the absence of one or more amino acid residues. A deletion removes at least 1, 2, 3, 4, 5, 10, 20, 50, 100, or 200 amino acids residues or a range of amino acid residues bounded by any of these values (e.g., a deletion of 5-10 amino acids). A deletion may include an internal deletion or a terminal deletion (e.g., an N-terminal truncation or a C-terminal truncation of a reference polypeptide). A "variant" of a reference polypeptide sequence may include a deletion relative to the reference polypeptide sequence. For example, SEQ ID NO:3 (amino acids 18-532) and SEQ ID NO:5 (amino acids 538-1091) include N-terminal deletions and C-terminal deletions relative to reference sequence SEQ ID NO:1 (amino acids 1-1162).

The disclosed recombinant IBV S protein may include an N-terminal methionine residue that does not occur naturally in the native amino acid of the protein. For example, the amino acid sequence of recombinant IBV S proteins contemplated herein may include an N-terminal deletion relative to the amino acid sequence of the full-length S protein, and further, may be modified to include an N-terminal methionine residue that is not present in the amino acid sequence of the full-length S protein. For example a recombinant IBV S protein may include a deletion of amino acids 1-17 which are replaced with an N-terminal methionine.

The words "insertion" and "addition" refer to changes in an amino acid sequence resulting in the addition of one or more amino acid residues. An insertion or addition may refer to 1, 2, 3, 4, 5, 10, 20, 30, 40, 50, 60, 70, 80, 90, 100, 150, or 200 amino acid residues or a range of amino acid residues bounded by any of these values (e.g., an insertion or addition of 5-10 amino acids). A "variant" of a reference polypeptide sequence may include an insertion or addition relative to the reference polypeptide sequence.

A "fusion polypeptide" refers to a polypeptide comprising at the N-terminus, the C-terminus, or at both termini of its amino acid sequence a heterologous amino acid sequence, for example, a heterologous amino acid sequence that extends the half-life of the fusion polypeptide in serum. A "variant" of a reference polypeptide sequence may include a fusion polypeptide comprising the reference polypeptide. In some embodiments, the disclosed recombinant S IBV proteins may be defined as fusion polypeptides that include IBV amino acid sequences optionally fused to non-IBV amino acid sequences heterologous amino acid sequences (i.e., heterologous amino acid sequences).

A "fragment" is a portion of an amino acid sequence that is identical in sequence to but shorter in length than a reference sequence (e.g., any of SEQ ID NOs:1-191). A fragment may comprise up to the entire length of the reference sequence, minus at least one amino acid residue. For example, a fragment may comprise from 5 to 1000 contiguous amino acid residues of a reference polypeptide. In some embodiments, a fragment may comprise at least 5, 10, 15, 20, 25, 30, 40, 50, 60, 70, 80, 90, 100, 150, 250, 300, 350, 400, 450, 500, 550, 600, 650, 700, 750, 800, 850, 900, 950, or 1000 contiguous amino acid residues of a reference polypeptide; or a fragment may comprise no more than 5, 10, 15, 20, 25, 30, 40, 50, 60, 70, 80, 90, 100, 150, 250, 300, 350, 400, 450, 500, 550, 600, 650, 700, 750, 800, 850, 900, 950, or 1000 contiguous amino acid residues of a reference polypeptide; or a fragment may comprise a range of contiguous amino acid residues of a reference polypeptide bounded by any of these values (e.g., 400-600 contiguous amino acid residues). Fragments may be preferentially selected from certain regions of a molecule. The term "at least a fragment" encompasses the full-length polypeptide. A "variant" of a reference polypeptide sequence may include a fragment of the reference polypeptide sequence. For example, SEQ ID NO:3 (amino acids 18-532) and SEQ ID NO:5 (amino acids 538-1091) comprise fragments of reference sequence SEQ ID NO:1 (amino acids 1-1162).

"Homology" refers to sequence similarity or, interchangeably, sequence identity, between two or more polypeptide sequences. Homology, sequence similarity, and percentage sequence identity may be determined using methods in the art and described herein.

The phrases "percent identity" and "% identity," as applied to polypeptide sequences, refer to the percentage of amino acid residue matches between at least two polypeptide sequences aligned using a standardized algorithm. Methods of polypeptide sequence alignment are well-known. Some alignment methods take into account conservative amino acid substitutions, non-conservative amino acid substitutions, deletions, and/or insertions. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastp," which is used to align a known amino acid sequence with other amino acids sequences from a variety of databases.

Percent identity may be measured over the length of an entire defined polypeptide sequence, for example, as defined by a particular SEQ ID number, or may be measured over a shorter length, for example, over the length of a fragment taken from a larger, defined polypeptide sequence as defined by a particular SEQ ID number, for instance, a fragment of at least 15, at least 20, at least 30, at least 40, at least 50, at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, or at least 1000 contiguous amino acid residues of any of SEQ ID NOs:1-119; or a fragment of no more than 15, 20, 30, 40, 50, 100, 150, 200, 250, 300, 350, 400, 450, 500, 550, 600, 650, at least 700, at least 750, at least 800, at least 850, at least 900, at least 950, or at least 1000 contiguous amino acid residues of any of SEQ ID NOs:1-119; or over a range bounded by any of these values (e.g., a range of 500-600 amino acid residues). Such lengths are exemplary only, and it is understood that any fragment length supported by the sequences shown herein, in the tables, figures or Sequence Listing, may be used to describe a length over which percentage identity may be measured.

In some embodiments, a "variant" of a particular polypeptide sequence may be defined as a polypeptide sequence having at least 20% sequence identity to the particular polypeptide sequence over a certain length of one of the polypeptide sequences using blastp with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). In other embodiments, a pair of polypeptides may show, for example, at least 20%, at least 30%, at least 40%, at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, or at least 99% or greater sequence identity over a certain defined length of one of the polypeptides, or range of percentage identity bounded by any of these values (e.g., range of percentage identity of 80-99%).

The disclosed variants and mutants of a reference polypeptide may possess one or more biological activities associated with the reference polypeptide, or alternatively, the disclosed variants and mutants of a reference polypeptide may lack one or more biological activities associated with the reference polypeptide. For example, the disclosed recombinant IBV spike proteins may possess one or more biological activities associated with the wild-type IBV spike protein, or the disclosed recombinant IBV spike proteins may lack one or more biological activities associated with the wild-type IBV spike protein.

Polynucleotides, Nucleic Acid, and Nucleic Acid Sequences

The terms "polynucleotide," "nucleic acid" and "nucleic acid sequence" refer to a polymer of DNA or RNA nucleotide of genomic or synthetic origin (which may be single-stranded or double-stranded and may represent the sense or the antisense strand). The polynucleotides contemplated herein may encode and may be utilized to express one or more IBV polypeptides such as the disclosed recombinant spike ectodomain proteins of IBV.

The terms "nucleic acid" and "oligonucleotide," as used herein, refer to polydeoxyribonucleotides (containing 2-deoxy-ribose), polyribonucleotides (containing ribose), and to any other type of polynucleotide that is an N glycoside of a purine or pyrimidine base. As used herein, the terms "A," "T," "C", "G" and "U" refer to adenine, thymine, cytosine, guanine, uracil as a nucleotide base, respectively. There is no intended distinction in length between the terms "nucleic acid," "oligonucleotide," and "polynucleotide," and these terms will be used interchangeably. These terms refer only to the primary structure of the molecule. Thus, these terms include double- and single-stranded DNA, as well as double- and single-stranded RNA. For use in the present invention, an oligonucleotide also can comprise nucleotide analogs in which the base, sugar or phosphate backbone is modified as well as non-purine or non-pyrimidine nucleotide analogs.

A "fragment" of a polynucleotide is a portion of a polynucleotide sequence which is identical in sequence to but shorter in length than a reference sequence. A fragment may comprise up to the entire length of the reference sequence, minus at least one nucleotide. For example, a fragment may comprise from 5 to 1000 contiguous nucleotides of a reference polynucleotide. In some embodiments, a fragment may comprise at least 5, 10, 15, 20, 25, 30, 40, 50, 60, 70, 80, 90, 100, 150, 250, or 500 contiguous nucleotides of a reference polynucleotide; in other embodiments a fragment may comprise no more than 5, 10, 15, 20, 25, 30, 40, 50, 60, 70, 80, 90, 100, 150, 250, or 500 contiguous nucleotides of a reference polynucleotide; in further embodiments a fragment may comprise a range of contiguous nucleotides of a reference polynucleotide bounded by any of the foregoing values (e.g. a fragment comprising 20-50 contiguous nucleotides of a reference polynucleotide). Fragments may be preferentially selected from certain regions of a molecule. The term "at least a fragment" encompasses the full-length polynucleotide. A "variant," "mutant," or "derivative" of a reference polynucleotide sequence may include a fragment of the reference polynucleotide sequence.

Regarding polynucleotide sequences, percent identity may be measured over the length of an entire defined polynucleotide sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Regarding polynucleotide sequences, "variant," "mutant," or "derivative" may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of nucleic acids may show, for example, at least 20%, at least 30%, at least 40%, at least 50%, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length.

A "recombinant nucleic acid" is a sequence that is not naturally occurring or has a sequence that is made by an artificial combination of two or more otherwise separated segments of sequence. This artificial combination is often accomplished by chemical synthesis or by the artificial manipulation of isolated segments of nucleic acids, e.g., by genetic engineering techniques known in the art. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

The term "promoter" as used herein refers to a cis-acting DNA sequence that directs RNA polymerase and other trans-acting transcription factors to initiate RNA transcription from the DNA or RNA (in an RNA virus) template that includes the cis-acting DNA of RNA sequence. A promoter may be "operably linked" to a coding sequence meaning that the promoter promotes transcription of the coding sequence, for example, as part of a vector.

Spike Protein of Infectious Bronchitis Virus

Referring now to the spike protein (S) of Infectious Bronchitis Virus (IBV), the S protein is expressed as a polypeptide having a length which typically is ~1160-1170 amino acids depending on the particular variant of IBV. The S protein is expressed as a type I membrane protein. (See, e.g., Shen et al., Virology, 326 (2004) 288-298; and Winter et al., J. Virol., March 2008, p. 2765-2771; the contents of which are incorporate herein by reference in their entireties). The N-terminal amino sequence of the S protein (i.e., about amino acids 1-17) functions as a leader sequence, which directs the nascent S protein into the lumen of the endoplasmic reticulum (ER) and as such functions as a signal peptide. The signal peptide of the S protein is subsequently cleaved from the S protein to provide the N-terminus of the S1 domain (i.e., between amino acids 17 and 18). The S protein is cleaved again by furin endoprotease at a recognition site (RFRR/S) at about amino acid positions 534-538 to provide the C-terminus for the S1 subunit and to provide the N-terminus of the S2 subunit (i.e., between amino acids 537 and 538 in this example). The S2 subunit of the S protein includes a membrane anchor sequence at about amino acid positions 1096-1115 and a cytosolic portion from about amino acid positions 1116 to the C-terminus (i.e., to about amino acid position 1160-1170). The S1 subunit and the S2 subunit in the lumen of the ER associate together non-covalently to form the mature S protein. The mature S protein comprising the non-covalently associated S1 subunit and S2 subunit self-associates to form a multimeric structure, typically a trimeric structure (i.e., 3×(S1/S2). Subsequently, the S protein is transported to the surface of the cell where the S1 subunits and the N-terminal portions of the S2 subunits are expressed extracellularly and otherwise are referred to as the "ectodomain." The membrane anchor sequences of the S2 subunits anchor the S protein in the cell membrane whereas and the C-terminal portions of the S2 subunits are expressed intracellularly.

As discussed herein and as known in the art, most serotypes of IBV are related to antigenic determinants in the S1 subunit. However, because the S1 subunit and the S2 subunit associate naturally in IBV, it is thought that the S2 subunit may be important in order for the S1 subunit to be presented in its natural state where it can function as a surface protein for recognizing the cellular receptor for IBV.

The present inventors have hypothesized that the presence of the S2 domain and the association of the S1 domain with the S2 domain may be important for creating a recombinant antigenic S protein that best mimics the natural, mature S protein to generate a protective immune response against IBV. However, the S1 domain and the S2 domain are not covalently associated in the natural, mature S protein. Furthermore, ideally, an antigenic protein for use in vaccination method against IBV will be soluble in aqueous solution. However, the natural, mature S protein is a membrane-bound protein. Finally, because the natural, mature S protein is multimeric, the present inventors have hypothesized that it may be important that a recombinant antigenic S protein adopt a multimeric structure in order to generate neutralizing antibodies that are an important part of a protective immune response. The presently disclosed recombinant proteins were designed to address these issues.

Pharmaceutical Compositions and Vaccines

The compositions disclosed herein may include pharmaceutical compositions such as vaccine compositions comprising the presently disclosed recombinant proteins and/or vectors for expressing the presently disclosed recombinant protein, which are formulated for administration to a subject in need thereof. Such compositions can be formulated and/or administered in dosages and by techniques well known to those skilled in the medical arts taking into consideration such factors as the age of the particular subjects and the route of administration.

The disclosed compositions may include additional components such as carriers, diluents, excipients, and surfactants, as known in the art. Further, the compositions may include preservatives (e.g., anti-microbial or anti-bacterial agents such as benzalkonium chloride). The compositions also may include buffering agents (e.g., in order to maintain the pH of the composition between 6.5 and 7.5).

The disclosed compositions may be administered as a vaccine in an amount sufficient to induce an immune response for protecting against infection. Inducing a protective response may include inducing sterilizing immunity against a pathogen (e.g., against IBV), or reducing the effects of the pathogen.

The compositions disclosed herein may be delivered via a variety of routes. Typical delivery routes include parenteral administration (e.g., intradermal, intramuscular, intraperitoneal, or subcutaneous delivery), intranasal, oral, and ocular (via eyedrop). Another route of administration may include in ovo administration (e.g., in ovo vaccination). Formulations of the pharmaceutical compositions may include liquids (e.g., solutions and emulsions), sprays, and aerosols.

The compositions disclosed herein may be co-administered or sequentially administered with other immunological, antigenic or vaccine or therapeutic compositions, including an adjuvant, or a chemical or biological agent given in combination with an antigen to enhance immunogenicity of the antigen.

Adjuvants. The compositions disclosed herein optionally include an adjuvant. The term "adjuvant" refers to a compound or mixture that enhances an immune response. An adjuvant can serve as a tissue depot that slowly releases the antigen and also as a lymphoid system activator that non-specifically enhances the immune response. Examples of adjuvants that may be utilized in the disclosed compositions include but are not limited to, co-polymer adjuvants (e.g., Pluronic L121® brand poloxamer 401, CRL1005, or a low molecular weight co-polymer adjuvant such as Polygen® adjuvant), poly (I:C), R-848 (a Th1-like adjuvant), resiquimod, imiquimod, PAM3CYS, aluminum phosphates (e.g., $AlPO_4$), loxoribine, potentially useful human adjuvants such as BCG (Bacille Calmette-Guerin) and *Corynebacterium parvum*, CpG oligodeoxynucleotides (ODN), cholera toxin derived antigens (e.g., CTA1-DD), lipopolysaccharide adjuvants, complete Freund's adjuvant, incomplete Freund's adjuvant, saponin (e.g., Quil-A), mineral gels such as aluminum hydroxide, surface active substances such as lysolecithin, pluronic polyols, polyanions, peptides, oil or hydrocarbon emulsions in water (e.g., MF59 available from Novartis Vaccines, Montanide ISA 720, or Montanide ISA 71 VG), keyhole limpet hemocyanins, and dinitrophenol.

Prime-Boost Vaccination Regimen

As used herein, a "prime-boost vaccination regimen" refers to a regimen in which a subject is administered a first composition and then after a determined period of time (e.g., after about 2, 3, 4, 5, or 6 weeks), the subject is administered a second composition, which may be the same or different than the first composition. The first composition (and the second composition) may be administered one or more times. The disclosed methods may include priming a subject with a first composition by administering the first composition at least one time, allowing a predetermined length of time to pass (e.g., at least about 2, 3, 4, 5, or 6 weeks), and then boosting by administering the same composition or a second, different composition.

For example, the methods may include administering a first pharmaceutical composition and optionally may include administering a second pharmaceutical composition to augment or boost an immunogenic response induced by the first pharmaceutical composition. The first and second pharmaceutical compositions may be the same or different. The optionally administered second pharmaceutical composition may be administered prior to, concurrently with, or after administering the first pharmaceutical composition. In some embodiments, the first composition is administered and then the second composition is administered after waiting at least about 2, 3, 4, 5, or 6 weeks. The first composition (and the second composition) may be administered one or more times.

Characterization of the Immune Response in Vaccinated Subjects

The pharmaceutical compositions disclosed herein may be delivered to subjects at risk for acquiring an infection by IBV. In order to assess the efficacy of an administered immunogenic composition or vaccine, the immune response can be assessed by measuring the induction of antibodies to particular epitopes of IBV and/or cell-mediated responses against IBV. Antibody responses may be measured by assays known in the art such as ELISA. Immune responses also may be characterized by physiological responses. (See Li et al., Vaccine 28 (2010) 1598-1605; and Stemke-Hale et al., Vaccine 2005 Apr. 27; 23(23):3016-25, the content of which are incorporated herein by reference in their entireties.) Immune response also may be measured by reduction in pathological responses such as respiratory signs after challenge with IBV, or reduction in titer or load as measured using methods in the art including methods that detect nucleic acid of the pathogen. (See, e.g., U.S. Pat. No. 7,252,937, the content of which is incorporated by reference in its entirety). Immune response also may be measured by reduction in pathological responses such as a pathological response for an organ of the animal (e.g., the trachea) after challenge with IBV.

As used herein, an "immune response" may include an antibody response (i.e., a humoral response), where an immunized individual is induced to produce antibodies against an administered antigen (e.g., IgG (IgY), IgA, IgM, or other antibody isotypes). As used herein, an "immune response" also may include a cell-mediated response, for example, a cytotoxic T-cell response against cells expressing foreign peptides derived from an administered antigen in the context of a major histocompatibility complex (MHC) class I molecule.

As used herein, "potentiating" or "enhancing" an immune response means increasing the magnitude and/or the breadth of the immune response. For example, the number of cells that recognize a particular epitope may be increased ("magnitude") and/or the numbers of epitopes that are recognized may be increased ("breadth").

As used herein, "viral load" is the amount of virus present in a sample from a subject infected with the virus. Viral load is also referred to as viral titer or viremia. Viral load can be measured in variety of standard ways including copy Equivalents of the viral RNA (vRNA) genome per milliliter individual sample (vRNA copy Eq/ml). This quantity may be determined by standard methods that include RT-PCR.

Antigens and Dose

The compositions disclosed herein optionally may include an antigen (e.g., a recombinant spike ectodomain of IBV) or a plurality of antigens (e.g., different recombinant spike ectodomains of different strains of IBV). A "plurality" or antigens as used herein means "more than one" and may mean more than 1, 2, 3, 4, 5, 10, 25, 50, or 100 antigens.

The composition, kits, and methods contain or utilize a protein, polypeptide, peptide, or plurality thereof as an antigen. The compositions, kits, and methods may be utilized to induce an antibody response and/or a cell-mediated response against infection by IBV.

Conventional vaccines and methods typically involve administering at least about 3 μg of an antigen per dose to a subject. (See, e.g., Scheifele et al. 2005, Hum. Vaccin. 1:180-186; Evans et al. 2001, Vaccine 19:2080-2091; and Kenney et al., N. Engl. J. Med. 351:2295-2301, the contents of which are incorporated herein by reference in their entireties). However, a dose as low as 1 μg of an antigen per dose to a subject also has been proposed. (See U.S. Pat. No. 6,372,223, the content of which is incorporated herein by reference in its entirety). In some embodiments, the vaccines and methods disclosed herein may include or utilize at least about 1, 2, 3, 4, 5, 10, 15, 20, 25, or 30 μg of an antigen per dose to a subject.

Suitable antigens may include polypeptides, peptides, or panels thereof that comprise one or more epitopes of a protein expressed by a pathogen associated with a disease. For example suitable polypeptides, peptides, or panels thereof may comprise one or more epitopes of a protein associated with a pathogen. Suitable polypeptides may comprise the full-length amino acid sequence of a corresponding protein of a pathogen or a fragment thereof. For example, suitable fragments may include 5-2000 amino acids (or from 5-1000, 5-100, 5-50, 5-25, 5-15, 10-2000, 10-1000, 10-50, 10-25, or 10-15 amino acids) and include at least one epitope of the protein from which the fragment is derived. Suitable antigens for the compositions, kits, and methods may include a plurality of peptides derived from a protein of a pathogen. For example, a suitable antigen may comprise a plurality of at least 2, 3, 4, 5, 10, 25, 50, 100, or more different peptides comprising at least about a 10-20 amino acid sequence from a protein of a pathogen. The different peptide antigens may overlap at the N-terminus, the C-terminus, or both termini with at least one other peptide antigen of the composition, for example, by at least about 1, 2, 3, 4, 5, 6, 7, 8, 9, or 10 amino acids.

Vectors

The term "vector" refers to some means by which DNA or RNA can be introduced into a host. There are various types of vectors including virus, plasmid, bacteriophages, cosmids, and bacteria. As used herein, a "viral vector" refers to recombinant viral nucleic acid that has been engineered to express a heterologous polypeptide (e.g., a recombinant IBV S protein as disclosed herein). The recombinant viral nucleic acid typically includes cis-acting elements for expression of the heterologous polypeptide. The recombinant viral nucleic acid typically is capable of being packaged into a virus that is capable of infecting a host cell. For example, the recombinant viral nucleic acid may include cis-acting elements for packaging. Preferably, the viral vector is not replication competent, is attenuated, or at least does not cause disease. The viral vector may naturally be non-pathogenic to the host. Alternatively the viral vector may be genetically altered by modern molecular biological methods (e.g., restriction endonuclease and ligase treatment, and rendered less virulent than wild type), typically by deletion of specific genes. For example, the recombinant viral nucleic acid may lack a gene essential for production of infectious or virulent virus.

The recombinant viral nucleic acid may function as a vector for the immunogenic IBV S protein by virtue of the recombinant viral nucleic acid containing foreign DNA or RNA. The recombinant viral nucleic acid, packaged in a virus may be introduced into a vaccinee by standard methods for vaccination with live vaccines. A live vaccine of the invention can be administered at, for example, about $10^4$ to $10^8$ viruses/dose, or $10^6$ to $10^9$ pfu/dose. Actual dosages of such a vaccine can be readily determined by one of ordinary skill in the field of vaccine technology.

Numerous virus species can be used as the recombinant virus vectors for the composition disclosed herein. A preferred recombinant virus vector for a viral vaccine may include a recombinant paramyxovirus. (See, e.g., Bukreyev and Collins, 2008; Bukreyev et al., 2005; DiNapoli et al., 2007; DiNapoli et al., 2009; Ge et al., 2007; Ge et al., 2010; Huang et al., 2003a; Huang et al., 2004; Nakaya et al., 2001; Nayak et al., 2009; Park et al., 2006; Swayne et al., 2003). Other suitable viral vectors may include recombinant adenovirus, herpesvirus, retrovirus, or poxvirus vectors. Coronavirus and influenza virus transgenes have been expressed from replication-defective recombinant adenovirus, and the recombinant adenoviruses have proven to be stable and to induce strong immune responses (Toro et al., 2012a; Toro et al., 2012c; Toro et al., 2007; Toro et al., 2008).

Suitable virus species for vectors may include virus species or strains that naturally are not virulent for chickens. Preferred virus species for vectors include lentogenic Newcastle disease strains. Such strains are naturally not virulent, pathogenic, or exhibit only low pathogenicity for chickens. Other vectors used in the poultry industry to vaccinate chickens include herpesvirus of turkeys (HVT). These viruses also are not naturally virulent for chickens and do not need to be modified further in order to reduce their virulence. In particular, a HVT vector vaccine may be utilized for in ovo administration. (See, e.g., Roh et al., Poult. Sci. 2016 May; 95(5):1020-4; the content of which is incorporated herein by reference in its entirety).

Codon Optimization

The transgene expressed in the vectors disclosed herein may have the native polynucleotide sequence of an IBV gene or may have a polynucleotide sequence that has been modified. For example, the presently disclosed vectors may express polypeptides from polynucleotides that encode the polypeptides where the polynucleotides contain codons that are optimized for expression in a particular host. For example, presently disclosed vectors may include one or more polypeptides from IBV where the encoding polynucleotide sequence is optimized to include codons that are most prevalent in an avian such as a chicken. Codon usage for the chicken genome has been reported. (See Rao et al., DNA Res. 2011 December, 18(6):499-512, which is incorporated herein by reference). Accordingly, a polynucleotide encoding the amino acid sequence of a recombinant protein with the segments $N_{ter}$-S1-Spacer-$S2_{ecto}$-MD-$C_{ter}$ is contemplated herein wherein the polynucleotide's nucleic acid sequence has been codon-optimized for expressing these protein segments listed as SEQ ID NOs: 3, 5, 11, 13, 19, 21, 27, 29, 35, 37, 43, 45, 51, 53, 59, 61, 67, 69, 75, 77, 83, 85, 91, 93, 97, 99, 101, 106, 107, 110, 111, 114, 115, 118, 119, or variants thereof in chicken (i.e., codon-optimized based on codon usage for the chicken genome).

Recombinant Proteins, Compositions, Vectors, Kits, and Methods for Immunizing Against Avian Infectious Bronchitis Virus Disclosed are recombinant IBV spike ectodomain proteins, compositions, vectors, kits, and methods for inducing an immune response against avian infectious bronchitis virus (IBV). In particular, the compositions, vectors, kits, and methods may be utilized to immunize poultry against disease associated with IBV infection or to protect poultry from IBV infection.

One aspect of the subject matter of this disclosure is a recombinant protein of IBV that may be referred to as a recombinant S protein of IBV that includes ectodomain portions of the native S protein from which the recombinant S protein is derived. The disclosed recombinant protein may include in succession from N-terminus to C-terminus an amino acid sequence represented by the formula $N_{ter}$-S1-Spacer-$S2_{ecto}$-MD-$C_{ter}$ or optionally represented by the formula $N_{ter}$-S1-$S2_{ecto}$-MD-$C_{ter}$.

In the disclosed formula, "$N_{ter}$" represents the N-terminus of the protein and "$C_{ter}$" represents the C-terminus of the protein. As discussed herein, the N-terminus of the protein may be modified to include a non-naturally occurring moiety, such as an N-terminal acetyl group, and the C-terminus of the protein may be modified to include a non-naturally occurring moiety, such as an amide group.

In the disclosed formula, "S1" represents the S1 domain of a spike protein (S) of IBV or a variant thereof. In some embodiments, S1 comprises an amino acid sequence of any of SEQ ID NOs:3, 11, 19, 27, 35, 43, 51, 59, 67, 75, 83, 91, 99, 106, 110, 114, and 118 or an amino acid sequence having at least about 40%, 45%, 50%, 55%, 60%, 65%, 70%, 75%, 80%, 85%, 90%, 95%, 96%, 97%, 98%, or 99% sequence identity to any of SEQ ID NOs:3, 11, 19, 27, 35, 43, 51, 59, 67, 75, 83, 91, 99, 106, 110, 114, and 118.

In the disclosed formula, "$S2_{ecto}$" represents the ectosubdomain portion of the S2 domain of the spike protein (S) or a variant thereof (i.e., the extracellular portion of the S2 domain or a variant thereof). In some embodiments, $S2_{ecto}$ comprises an amino acid sequence of any of SEQ ID NOs:5, 13, 21, 29, 37, 45, 53, 61, 69, 77, 85, 93, 101, 107, 111, 115, and 119 or an amino acid sequence having at least about 40%, 45%, 50%, 55%, 60%, 65%, 70%, 75%, 80%, 85%, 90%, 95%, 96%, 97%, 98%, or 99% sequence identity to any of SEQ ID NOs:5, 13, 21, 29, 37, 45, 53, 61, 69, 77, 85, 93, 101, 107, 111, 115, and 119.

In the disclosed formula, "Spacer" represents a spacer sequence of amino acids between S1 and $S2_{ecto}$. The Spacer typically does not comprise the amino acid sequence Arg-X-(Arg/Lys)-Arg. The amino acid sequence Arg-X-(Arg/Lys)-Arg-Ser is the recognition sequence for the furin endoprotease which cleaves between the arginine and serine residues where the serine residue provides the N-terminus for the S2 subunit. The amino acid sequence Arg-X-(Arg/Lys)-Arg-Ser is normally present in the native amino acid sequence of the S protein between the S1 domain and the S2 domain at about amino acid numbers 534-537 and is cleaved by the furin endoprotease during natural maturation of the S protein as discussed herein. Because the amino acid sequence Arg-X-(Arg/Lys)-Arg is not present in the Spacer of the recombinant protein, S1 and S2 remain covalently linked by the Spacer in the recombinant S protein. In the disclosed recombinant proteins, the native spacer between the S1 domain and the S2 domain may be replaced and/or mutated so as not to contain the amino acid sequence Arg-X-(Arg/Lys)-Arg.

In some IBV strains, the S2 ectodomain includes an additional recognition sequence for the furin endoprotease at about amino acid numbers 687-691 (e.g., Arg-Arg-Lys-Arg-Ser). (See, e.g., Yamada et al., J. Virol., September 2009, p. 8744-8758; the content of which is incorporated herein by reference in its entirety). Therefore, preferably in the disclosed recombinant proteins, the recombinant protein does not include the sequence Arg-X-(Arg/Lys)-Arg anywhere in the amino acid sequence of the recombinant protein. For recombinant S proteins derived from strains of IBV that include the additional recognition sequence for the furin endoprotease at about amino acid numbers 687-691, the amino acid sequence of the S2 ectodomain here may be replaced and/or mutated so as not to contain the amino acid sequence Arg-X-(Arg/Lys)-Arg.

In some embodiments of the disclosed recombinant proteins, the Spacer sequence may be relatively flexible, for example, so as to permit S1 and $S2_{ecto}$ to mimic their natural interaction in the S protein. In some embodiments, the Spacer sequence is of sufficient length to permit the domains to mimic their natural interaction in the S protein. Suitable spacer sequences may include, but are not limited to, amino acid sequences of 3, 4, 5, 6, 7, 8, 9, 10, 11, 12, 13, 14, 15, 20, 25, 30, 35, 40, 45, or 50 amino acids or more, or a range bounded by any of these values (e.g., a spacer of 3-15 amino acids). In some embodiments, the Spacer sequence includes amino acids that provide flexibility to the Spacer and/or are small, neutral amino acids. In some embodiments, the spacer sequence comprises only glycine and/or serine residues or is rich in glycine and/or serine residues. For example, in some embodiments, the spacer sequence comprises at least about 50% glycine and/or serine residues, or at least about 55%, 60%, 65%, 70%, 75%, 80%, 85%, 90%, 95%, 96%, 97%, 98%, or 99% glycine and/or serine residues.

In the disclosed formula, "MD" represents a multimerization domain that is not present in the ectodomain of the S protein. As such, MD is a heterologous sequence with respect to the S protein. The multimerization domain is an amino acid sequence that self-associates. In some embodiments, the multimerization domain comprises a trimerization motif as known in the art and the recombinant protein forms trimers in aqueous solution. (See, e.g., Kammerer et al., PNAS USA, Sep. 27, 2005, vol. 102, no. 39, pages 13891-13896; Kammerer et al., PLoSONE, August 2012, Volume 7, Issue 8, e43603; Sliepen et al., J. Biol. Chem., Volume 290, Number 12, Mar. 20, 2015, 7436-7442; Alvarez-Cienfuegos et al., Scientific Reports, 6:28643, 1-14; the content of which is incorporated by reference in its entirety).

Optionally, the recombinant protein may include one or more additional spacer sequences. In some embodiments, the recombinant protein includes an additional Spacer between $S2_{ecto}$ and MD and the recombinant protein may be described as having a formula $N_{ter}$-SP-S1-Spacer1-$S2_{ecto}$-Spacer2-MD-$C_{ter}$, where Spacer1 and Spacer2 may be the same or different.

The disclosed recombinant proteins typically comprise the ectodomain portion of S or a variant thereof. The disclosed recombinant proteins typically do not comprise the transmembrane anchoring domain of the S protein. Similarly, the disclosed recombinant proteins typically do not comprise the cytoplasmic domain of the S protein.

The disclosed recombinant proteins typically are not membrane proteins. The disclosed recombinant proteins preferably are soluble in aqueous solution.

The disclosed recombinant proteins may include an N-terminal leader sequence that facilitates translocation of the protein into the endoplasmic reticulum and may otherwise be referred to as a "signal peptide." For example, the recombinant proteins may be described as having a formula $N_{ter}$-SP-S1-Spacer-$S2_{ecto}$-MD-$C_{ter}$, where SP is a signal peptide.

In the disclosed formula, SP may comprise the native signal peptide of the S protein or a variant thereof. In some embodiments, SP comprises an amino acid sequence of any of SEQ ID NOs:2, 10, 18, 26, 34, 42, 50, 58, 66, 74, 82, 90, 105, 109, 113, or 117 or an amino acid sequence having at least about 50%, 60%, 70%, 80%, 90%, or 95% sequence identity to any of SEQ ID NOs: 2, 10, 18, 26, 34, 42, 50, 58, 66, 74, 82, 90, 105, 109, 113, or 117.

In the disclosed formula, SP may comprise a non-native signal peptide of the S protein (i.e., a heterologous signal peptide relative to the S protein). Signal peptides are known in the art. The core of the signal peptide contains a long stretch of hydrophobic amino acids (about 5-16 residues long) that has a tendency to form a single alpha-helix and is also referred to as the "h-region." Signal peptides may begin with a short positively charged stretch of amino acids, which may help to enforce proper topology of the polypeptide during translocation by what is known as the positive-inside rule. Because of its close location to the N-terminus this short positively charged stretch of amino acid is called the "n-region." At the end of the signal peptide there is typically a stretch of amino acids that is recognized and cleaved by signal peptidase and therefore named the "cleavage site." A database of signal peptides is provided at Signal Peptide Website.

The disclosed recombinant proteins further may comprise a tag for identifying and/or purifying the recombinant proteins. In some embodiments, the tag is present at the C-terminus and the recombinant protein may be described as having a formula $N_{ter}$-SP-S1-Spacer-$S2_{ecto}$-MD-Tag-$C_{ter}$. Suitable tags may include but are not limited to Streptag (i.e., a sequence comprising SEQ ID NO:102), for example where the recombinant protein may be described as having a formula $N_{ter}$-SP-S1-Spacer-$S2_{ecto}$-MD-Streptag-$C_{ter}$. Other suitable amino acid tag sequences may include, but are not limited to, a strep tag, poly(His) tag comprising 5-10 histidine residues, chitin binding protein (CBP), maltose binding protein (MBP), and glutathione-S-transferase (GST).

Also disclosed herein are polynucleotides that encode the disclosed recombinant proteins. The polynucleotides may include a coding sequence for the recombinant proteins that has been optimized for expression in an avian such as a chicken.

Also disclosed herein are vectors that express the disclosed recombinant proteins. For example, the disclosed vectors may comprise a polynucleotide encoding the amino acid sequence of the disclosed recombinant proteins operably linked to a promoter for expressing the polynucleotide and recombinant protein in a suitable cell line. As discussed herein, suitable vectors may include, but are not limited to, viral vectors.

Also disclosed herein are methods for making the disclosed recombinant proteins. The disclosed methods may include expressing the recombinant proteins in a cell line, for example, via a vector which optionally is a viral vector, or in a unicellular eukaryotic host. The recombinant proteins thus made optionally may be purified, for example, via a protein tag, and further processed or formulated for use (e.g., as part of a vaccine composition).

Also disclosed herein are methods for vaccinating a subject against infection by IBV. In some embodiments, the methods include administering to the subject (e.g., a chicken) a composition comprising the recombinant proteins as disclosed herein and a suitable carrier. In other embodiment, the methods include administering to the subject (e.g., a chicken) a composition comprising a vector that expresses the recombinant proteins as disclosed herein and a suitable carrier. The disclosed methods for vaccinating a subject may include a prime-boost vaccination regimen as known in the art.

EXAMPLES

The following examples are illustrative and are not intended to limit the disclosed subject matter.

Example 1

Title—Protection Against Infectious Bronchitis Virus by Spike Ectodomain Subunit Vaccine Reference is made to the manuscript: Fatma Eldemery, Kellye S. Joiner, Haroldo Toro, and Vicky L. van Santen, "Protection against infectious bronchitis virus by spike ectodomain subunit vaccine," Vaccine 35 (2017), 5864-5871; the content of which is incorporated herein by reference in its entirety.

Abstract

The avian coronavirus infectious bronchitis virus (IBV) S1 subunit of the spike (S) glycoprotein mediates viral attachment to host cells and the S2 subunit is responsible for membrane fusion. Using IBV Arkansas-type (Ark) S protein histochemistry, we show that extension of S1 with the S2 ectodomain improves binding to chicken tissues. Although the S1 subunit is the major inducer of neutralizing antibodies, vaccination with S1 protein has been shown to confer inadequate protection against challenge. The demonstrated contribution of S2 ectodomain to binding to chicken tissues suggests that vaccination with the ectodomain might improve protection compared to vaccination with S1 alone. Therefore, we immunized chickens with recombinant trimeric soluble IBV Ark-type S1 or S-ectodomain protein produced from codon-optimized constructs in mammalian cells. Chickens were primed at 12 days of age with water-in-oil emulsified S1 or S-ectodomain proteins, and then boosted 21 days later. Challenge was performed with virulent Ark IBV 21 days after boost. Chickens immunized with recombinant S-ectodomain protein showed statistically significantly ($P<0.05$) reduced viral loads 5 days post-challenge in both tears and tracheas compared to chickens immunized with recombinant S1 protein. Consistent with viral loads, significantly reduced ($P<0.05$) tracheal mucosal thickness and tracheal lesion scores revealed that recombinant S-ectodomain protein provided improved protection of tracheal integrity compared to S1 protein. These results indicate that the S2 domain has an important role in inducing protective immunity. Thus, including the S2 domain with S1 might be promising for better viral vectored and/or subunit vaccine strategies.

1. Introduction

Infectious bronchitis virus (IBV) is a highly prevalent coronavirus of chickens that causes economic losses worldwide despite extensive vaccination. Continuous emergence of new virus serotypes results from mutation and recombination followed by selection [1]. Routinely used live-attenuated IBV vaccines, which are affected by the same evolutionary processes, not only result in vaccine-like viruses with increased virulence and persistence [2, 3], but may also contribute genetic material for recombination with other vaccine or wild virus populations. We previously identified five minor vaccine virus subpopulations selected in chickens from Arkansas-Delmarva Poultry Industry (ArkDPI)-derived IBV vaccines, designated components (C) 1-5 [3, 4]. The selection of these viral subpopulations within 3 days post-vaccination suggests they replicate better in chickens than the predominant virus population in the vaccine prior to inoculation [3, 4].

The spike (S) protein of IBV mediates viral entry into host cells [5, 6]. Its S1 subunit mediates viral attachment to host cells and induces virus-neutralizing antibodies that are important for host protective immune responses [7-9]. However, the S1 subunit shows extensive amino acid sequence variability among IBV strains, which leads to the virus's immunological escape [1, 10, 11]. The S2 subunit of S, responsible for membrane fusion, is more conserved among IBV strains [12]. The N-terminal portion of S2 contains immunodominant regions and a neutralizing epitope and therefore the S2 protein has been suggested for vaccine development [12, 13].

Previous studies indicated that the S1 protein alone does not induce effective protection against IBV challenge. For instance, at least four immunizations with purified S1 glycoprotein were required to induce protection against nephropathogenic N1/62 strain challenge [14]. Similarly, three immunizations with KM91 S1 protein expressed by a recombinant baculovirus produced only 50% protection against virulent nephropathogenic KM91 strain challenge [15].

The S1 subunit of IBV is sufficient for attachment [5, 16-19] and the S2 portion of coronavirus spike proteins has traditionally been considered to play a role only in subsequent entry [20, 21]. However, a role for the S2 ectodomain in binding to cells has been demonstrated for spike proteins of Massachusetts serotype IBVs, i.e. the highly-attenuated Beaudette strain and the virulent M41 strain [22, 23]. In the current study, we evaluated binding of trimeric Ark S-ectodomain compared to trimeric S1 subunit alone to multiple relevant chicken tissues. After confirming improved binding of Ark S-ectodomain, which might be explained by the presence of the S2 ectodomain altering the conformation of S1 and thus increasing its affinity for receptors, or by S2 directly contributing to interaction with receptors or co-receptors, we tested the hypothesis that immunization with recombinant soluble trimeric S-ectodomain provides more effective protection than immunization with trimeric S1 subunit alone.

2. Materials and Methods 2.1. Genes and Expression Vectors

The amino acid sequence of S proteins representing an IBV ArkDPI vaccine subpopulation previously designated C2 (GenBank accession ABY66333) was chosen to produce recombinant proteins. C2 was strongly selected in chickens after vaccination with an ArkDPI-derived attenuated vaccine [3, 4]. Its S1 is almost identical to that of the unattenuated parent ArkDPI isolate [24] and represents the consensus sequence of vaccine subpopulations rapidly positively selected in chickens after vaccination with ArkDPI-derived attenuated vaccines [2-4, 25, 26]. To generate recombinant S1 protein, a human codon-optimized sequence encoding C2 S1 [amino acids (AA) 19-538] was synthesized (GeneArt, Regensburg, Germany) and cloned into the pCD5 vector. To generate recombinant S-ectodomain, a human-codon optimized sequence encoding the C2 S2 ectodomain (S AA 544-1097) was cloned into the pCD5 vector already containing the S1 domain as described [22]. At the S1/S2 border, the furin cleavage site sequence RRSRR was replaced by GGGVP to avoid cleavage of the full length S-ectodomain [22]. These S1 and S-ectodomain-coding sequences were flanked by sequences encoding an N-terminal CD5 signal sequence and sequences encoding C-terminal artificial GCN4 trimerization motif and Strep-tag II for purification and detection of proteins, as described [16].

2.2. Recombinant S Protein Production and Purification

Soluble trimeric recombinant S1 and S-ectodomain proteins were produced in human embryonic kidney (HEK) 293T cells as described [16, 22, 27]. In brief, the expression vectors encoding S1 or S-ectodomain were transfected into HEK293T cells and recombinant proteins purified from tissue culture supernatants 6 days post-transfection using Strep-Tactin® Sepharose columns according to the manufacturer's instructions (IBA GmbH, Göttingen, Germany). The concentration of purified proteins was determined by Qubit® 2.0 fluorometer (Invitrogen, Carlsbad, Calif.). The purified proteins were confirmed and concentrations normalized by electrophoresis in Mini-PROTEAN®TGX Stain-Free™ Precast Gels (Bio-Rad, Hercules, Calif.).

2.3. Binding to Tissues by Protein Histochemistry

The binding efficiency of S1 and S-ectodomain proteins to tissue sections prepared from healthy specific pathogen free (SPF) 40-day old white leghorn chickens was assessed by protein histochemistry as described [22, 27] with minor modifications: antigen retrieval was conducted at 80° C. for 30 min, Tris buffers were substituted for phosphate buffers, slides were blocked with universal negative serum (Biocare, Pacheco, Calif.) instead of 10% goat serum, and the addition of most reagents and washing steps were performed by an intelliPATH FLX automated slide stainer (Biocare, Pacheco, Calif.). S proteins and 3-amino-9-ethyl-carbazole (AEC+; Dako, Carpinteria, Calif.) were added manually. Briefly, S proteins (100 μg/ml for S1 and 50 μg/ml for S-ectodomain) pre-complexed with Strep-Tactin-HRP (IBA GmbH, Göttingen, Germany) were incubated with deparaffinized and rehydrated tissue sections overnight at 4° C. Bound S protein was visualized with AEC+chromogenic substrate. The tissues were counterstained with hematoxylin and mounted with Lerner AquaMount (Covance, Princeton, N.J.). Images were captured from an Olympus BX41 microscope with an Olympus DP71 12 mp camera.

2.4. Protection Trial 2.4.1. Chickens

White leghorn chickens hatched from SPF eggs (Charles River, North Franklin, Conn.) were maintained in Horsfall-type isolators in biosafety level 2 facilities. Experimental procedures and animal care were performed in compliance with all applicable federal and institutional animal guidelines. Auburn University College of Veterinary Medicine is an Association for Assessment and Accreditation of Laboratory Animal Care-accredited institution.

2.4.2. Experimental Design

Four groups of chickens (each n=16-17) were used. Chickens were primed at 12 days of age (DOA) by subcutaneous injection in the neck region of 0.2 ml containing 10 μg of S1 (group A) or 20 μg of S-ectodomain protein (group B) emulsified in Montanide™ ISA 71 VG adjuvant (Seppic, Paris, France). Twice the amount of S-ectodomain protein was used because recombinant S-ectodomain is 1.96-times the molecular weight of recombinant S1. Thus, approximately equimolar amounts of protein were administered. Chickens in groups A and B were subsequently boosted with the same adjuvanted protein 21 days later. Control group C (non-vaccinated) was primed and boosted with PBS and the adjuvant, and group D was the unvaccinated/unchallenged control group. Chickens in groups A, B and C were challenged 21 days after boost by ocular and nasal instillation of $10^5$ 50% embryo infective doses ($EID_{50}$) of a virulent IBV Ark-type strain (GenBank accession JN861120) previously characterized [28]. Protection was evaluated 5 days post-challenge (DPC) by viral load in tears and tracheas, tracheal histomorphometry, and tracheal histopathology lesion scoring. In addition, antibodies in sera specific for IBV or S protein were determined by ELISA before prime (11 DOA), three weeks after prime (32 DOA), two weeks after boost (45 DOA) and 5 days post-challenge.

2.4.3. Viral Load by qRT-PCR

Relative IBV RNA levels in tears and tracheas were determined by quantitative reverse transcription polymerase chain reaction (qRT-PCR). Viral RNA was extracted from individual tear samples using the QIAmp viral RNA mini kit (Qiagen, Valencia, Calif.), and from homogenized tracheas with TriReagent® RNA/DNA/protein isolation reagent (Molecular Research Center, Cincinnati, Ohio) following the manufacturers' protocols. Relative viral RNA concentrations in tear and tracheal samples were determined by TaqMan® qRT-PCR as described [29]. Data were analyzed by one-way analysis of variance (ANOVA) followed by Tukey's multiple comparisons post-test.

2.4.4. Tracheal Histomorphometry and Histopathology

Histomorphometry of the tracheal mucosa was evaluated blindly as described [30]. Briefly, formalin-fixed sections of trachea collected from challenged and control birds at 5 days post-challenge were processed, embedded in paraffin, sectioned at 4-6 μm and stained with hematoxylin and eosin for histopathological examination. The tracheal mucosal thickness and the thickness of lymphocytic infiltration were measured using ImageJ, and the average of five measurements for each chicken calculated. The severity of lesions (tracheal deciliation and epithelial necrosis) was scored (1=normal, 2=mild, 3=moderate, 4=marked, 5=severe) and the average of the two scores determined as a lesion score for each chicken. Histomorphometric data were analyzed by one-way ANOVA followed by Tukey's multiple comparisons post-test. Lesion scores were analyzed by Kruskal-Wallis test followed by Dunn's multiple comparisons post-test.

2.4.5. Antibodies Measured by ELISA

IBV-Specific ELISA.

IBV-specific ELISA was performed as previously described [31]. Briefly, ELISA plates (Nunc MaxiSorp Immuno Plates; Thermo Scientific) were coated with heat-inactivated IBV (ArkDPI vaccine strain; S AA sequence GenBank # ABY66334) purified as described [31]. Individual chicken sera diluted 1:100 were loaded and plates incubated at 4° C. overnight. IBV-specific IgG was detected using biotinylated monoclonal mouse-anti chicken IgG [(clone G-1) Southern Biotechnology Associates, Inc., Birmingham, Ala.], streptavidin-conjugated HRP (Southern Biotechnology Associates, Inc.) and tetramethylbenzidine (TMB; Invitrogen Corp., Frederick, Md.) HRP substrate. Absorbance at 450 nm was measured with a Powerwave XS (BioTek Instruments, Inc., Winooski, Vt.).

S1 and S-Ectodomain Protein-Specific ELISA.

ELISA plates (Nunc MaxiSorp Immuno Plates; Thermo Scientific) were coated with 100 μl of 0.25 μg/ml of either recombinant S1 protein or S-ectodomain protein at 4° C. overnight. Plates were drained and blocked with 200 μl of 1% bovine serum albumin and 0.05% Tween 20 in PBS for 1 h at room temperature. Plates were drained and individual chicken sera (diluted 1:100) were loaded and incubated 30 min at room temperature. Plates were washed and antibodies detected using reagents in a commercial IBV ELISA kit (Idexx Laboratories, Inc., Westbrook, Me.) following instructions in the kit. Absorbance at 650 nm was measured with a Powerwave XS. Statistical analyses were performed using one-way ANOVA followed by Tukey's multiple comparisons test.

3. Results 3.1. S Binding to Tissues

The binding affinity of recombinant S-ectodomain to relevant chicken tissues was compared to that of recombinant S1 protein using protein histochemistry. As seen in FIG. 1, the S1 protein bound weakly to the epithelium of trachea, nasal mucosa, choana (not shown), cecal tonsils, and cloaca, and to secretory cells of trachea, nasal mucosa, and choana, while binding was not detected in the lung and kidney. Extension of S1 with S2 subunit ectodomain (S-ectodomain) increased binding affinity to trachea, choana, nasal mucosa, cloaca, and cecal tonsils and enabled binding to lung and kidney. It should be noted that the molar concentration of S-ectodomain used for spike histochemistry was approximately one-fourth that of S1, indicating that the binding affinity of S-ectodomain is much greater than that of S1.

3.2. Viral Load

Figure 2:
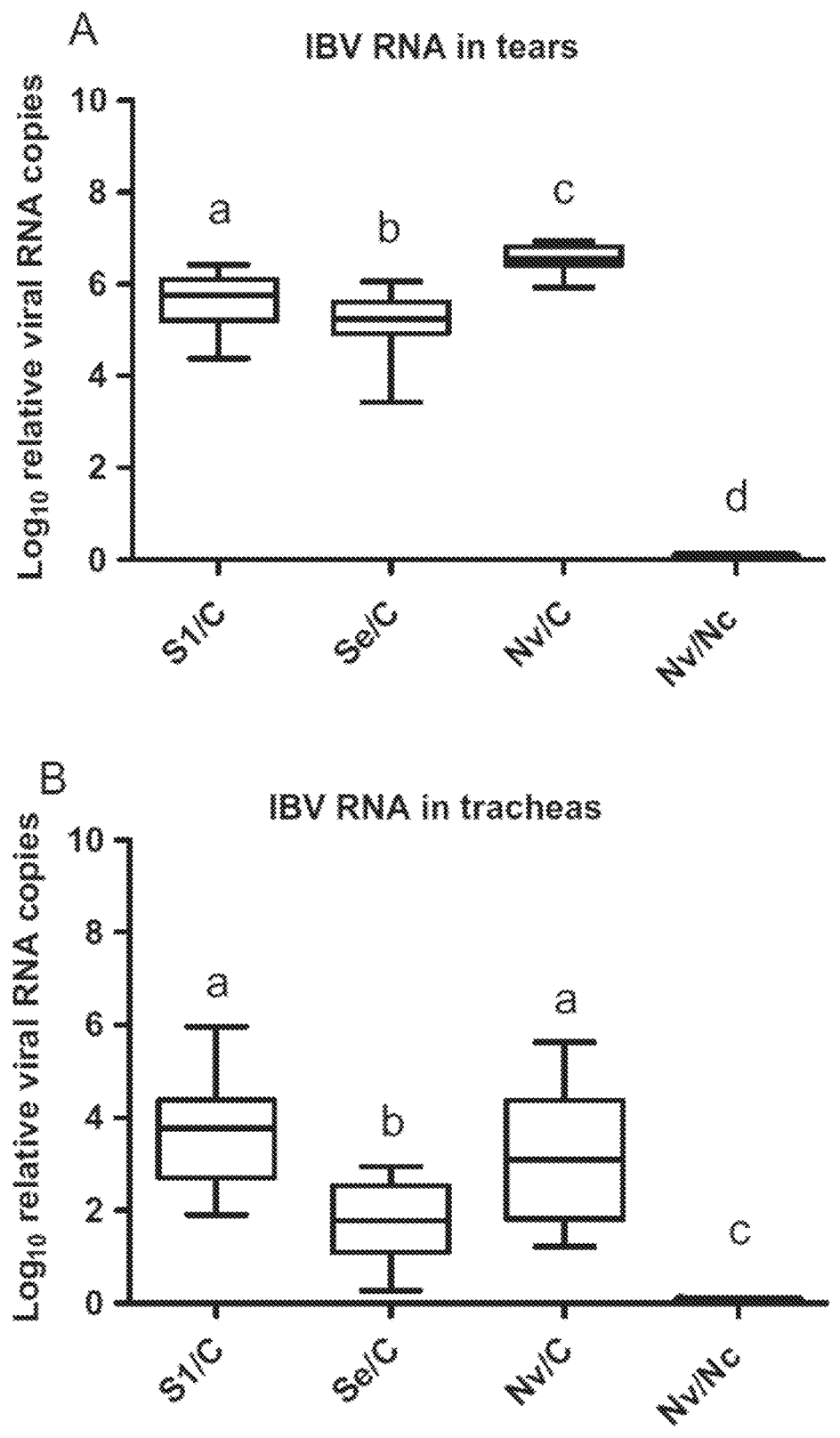

Chickens immunized with recombinant S-ectodomain protein showed statistically significant (P<0.05) reductions of viral RNA both in tears and tracheas 5 days post-challenge compared to chickens immunized with recombinant S1 protein or adjuvant alone (FIG. 2). A significant (P<0.05) reduction of the viral RNA in the S1-immunized group compared to mock-vaccinated chickens was detected only in tears. S1-protein immunization did not significantly reduce viral RNA levels in trachea.

3.3. Tracheal Histomorphometry and Histopathology

Consistent with the viral load results, the S-ectodomain-immunized chickens showed a significant reduction ($P<0.05$) of tracheal mucosal thickness, lymphocyte infiltration, and lesion severity (tracheal deciliation and epithelial necrosis) 5 days post-challenge compared to recombinant S1 protein alone-immunized and adjuvant-only chickens (FIG. 3). In contrast, no significant differences ($P<0.05$) were detected between recombinant S1 protein-immunized and adjuvant-only groups. Remarkably, no significant differences in any of the tested tracheal histopathology parameters were detected between chickens immunized with S-ectodomain protein and unvaccinated/unchallenged controls, indicating that immunization with recombinant S-ectodomain protein provided complete protection of tracheal integrity.

3.4. Antibodies

Figure 4:
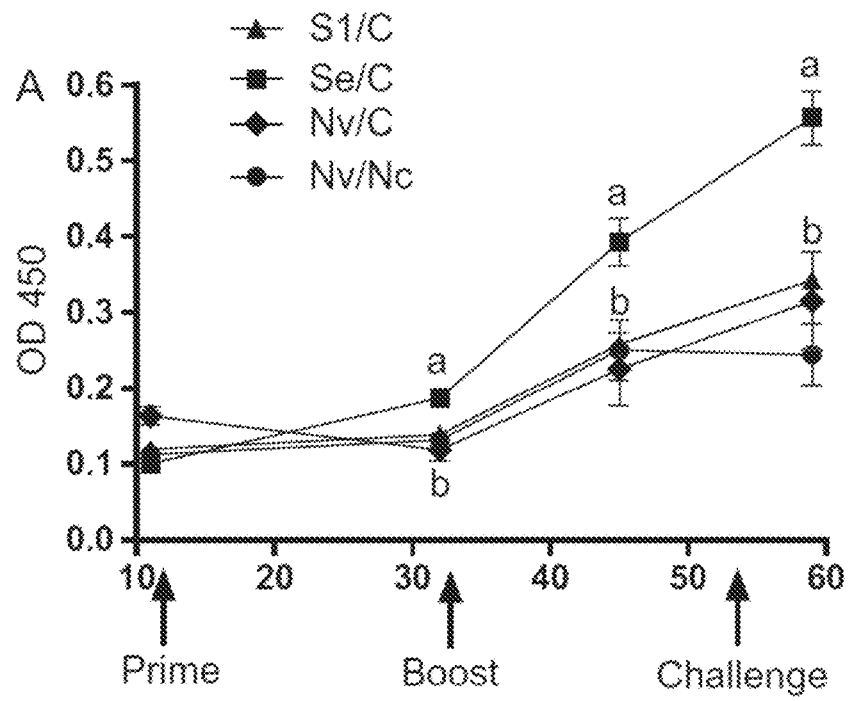
FIG. 4. IBV antibodies in chicken sera before prime [11 days of age (DOA)], 3 weeks after prime (32 DOA), 2 weeks after boost (45 DOA) and 5 days post-challenge (59 DOA) determined by ELISA. IBV-specific ELISA (A), and S-ectodomain protein-specific ELISA (B) of chickens primed with recombinant S1, S-ectodomain (Se), boosted 21 days later, and challenged 21 days post-boost. Nv/C=non-vaccinated (chickens primed and boosted with the adjuvant with PBS)/challenged. Nv/Nc=non-vaccinated/non-challenged. Mean absorbance values and SEM are shown. In (B) the error bars are so small that they are obscured by the symbols. The S-ectodomain-immunized group showed significantly higher antibody levels (as measured by optical density) than the S1 protein-immunized, adjuvant only, and non-vaccinated non-challenged groups (P<0.05). Statistically significant differences for each time-point post-vaccination indicated by letters.
Figure 4:
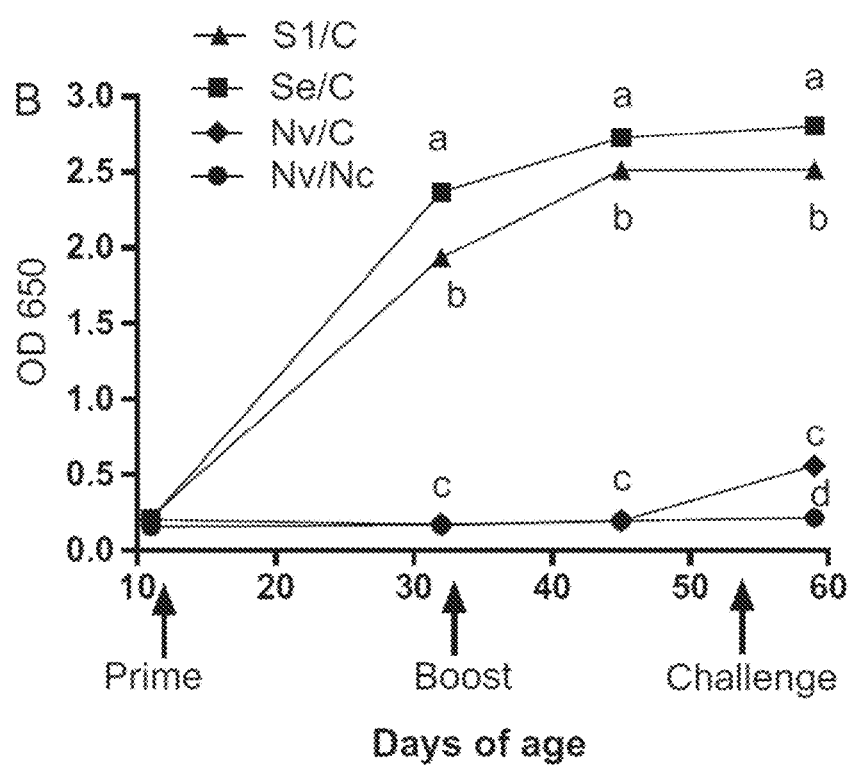

Chickens immunized with S-ectodomain protein showed significant ($P<0.05$) increases in IBV-specific antibodies in sera compared to those immunized with S1 protein alone and the non-vaccinated controls before challenge at 32 and 45 DOA, as well as 5 DPC (FIG. 4A). However, no significant differences were detected between S1 protein-immunized chickens and non-vaccinated controls. Consistent with IBV-specific antibodies, S-ectodomain protein-specific ELISA also revealed significant differences between the S-ectodomain protein-immunized group and the S1 protein-immunized group at all times post-immunization (FIG. 4B). S1 protein-specific ELISA did not indicate any significant differences between the chickens immunized with S-ectodomain protein compared to chickens immunized with S1 protein alone (not shown). Collectively, these results indicate the presence of antibodies directed against S2 and/or 5-ectodomain-specific conformational epitope(s) in chickens immunized with S-ectodomain protein.

4. Discussion

The evolutionary success of IBV and the problems associated with use of live-attenuated vaccines indicate an urgent need to develop novel vaccines. Alternative approaches such as subunit vaccines or viral-vectored vaccines expressing specific proteins would eliminate emergence of vaccine subpopulations and facilitate the rapid development of effective vaccines against new serotypes. We have demonstrated that trimeric S-ectodomain provides more effective protection than trimeric S1 protein.

Comparing the binding of recombinant S1 and S-ectodomain proteins of IBV Ark-type strain revealed that S-ectodomain shows increased binding affinity to chicken tissues including trachea, choana, nasal mucosa, cecal tonsils and cloaca. Interestingly, S1 protein was unable to bind to lung and kidney tissues, which are also target organs for IBV, and required the S2 ectodomain to bind. These results are consistent with reports by others, showing that while the S1 subunit of the embryo- and cell-culture-adapted Beaudette strain is unable to bind to chorioallantoic membrane, the Beaudette S-ectodomain binds efficiently [22]. Furthermore, the extension of the M41 S1 with the M41 S2 ectodomain domain increased binding to chicken trachea [23]. The M41 S1 shows only 77% amino acid sequence identity with the ArkDPI S1 used herein. Thus, the current results confirm these findings for another IBV serotype and additional tissues. Using chimeric S-ectodomain proteins, Promunktod et al. concluded that S2 does not contain an additional independent receptor binding site that would explain its contribution to the affinity of S for receptors [22]. Another possible explanation for improved tissue binding of S-ectodomain is that the S2 subunit is necessary for the S1 protein to adopt a conformation optimal for binding. Structures of trimeric S-ectodomains of other coronaviruses determined by cryo-electron microscopy, e.g. [32, 33], suggest that the trimeric structure is important for the conformation of S1, because the S1 domains of the monomers are interwoven in the trimer. In the recombinant S1 protein used in this study, the artificial trimerization domain immediately follows the S1 domain and could thus artificially constrain the trimeric S1 in a suboptimal conformation. When the S2 ectodomain is included between S1 and the trimerization domain, the trimers might be closer to their normal conformation. However, our unpublished results indicate that a single amino acid change in the S2 domain can reduce the binding of the S-ectodomain (S. Farjana et al., unpublished results). Thus, S2 may influence the conformation of S1 in a more specific way.

Most IBV neutralizing antibodies recognize conformational epitopes in S1 [8, 34-36]. Thus, if the S2 ectodomain allows S1 to adopt a conformation optimal for attachment, antibodies generated against this conformation might more effectively neutralize virus than antibodies generated against the suboptimal conformation of S1 adopted in the absence of S2. Therefore, we considered the possibility that extension of recombinant S1 protein with the S2 ectodomain would improve the protection afforded by a subunit vaccine. Indeed, our protection trial results indicated that immunization with trimeric S-ectodomain protein significantly reduces viral loads in tears and trachea, as well as tracheal damage, compared to immunization with trimeric S1 protein. Moreover, there were no significant differences in tracheal damage between chickens immunized with S-ectodomain protein and unvaccinated/unchallenged control chickens, indicating complete protection. Conversely, no significant differences were observed between chickens immunized with S1 protein and the mock-immunized group except for the viral load in tears. This limited protection conferred by S1 protein is in agreement with results of others [14] who found that at least four immunizations with the purified S1 glycoprotein of nephropathogenic N1/62 strain of IBV were necessary to induce protection, even though they used a considerably larger amount of purified S1 antigen (50 µg) for immunization.

One possible explanation for improved protection following immunization with S-ectodomain, as already mentioned, is that antibodies produced to S1 in the ectodomain conformation neutralize the challenge virus more effectively than antibodies produced to S1 protein alone. Alternatively, the conserved immunodominant linear neutralizing epitope within S2 [13] might also contribute to improved protection. Although we did not attempt to demonstrate neutralizing antibodies, our ELISA results using both purified IBV and S-ectodomain protein showed a significant increase of antibody level in chickens immunized with S-ectodomain protein compared to those immunized with S1 protein alone, indicating that antibodies to S2 epitopes were generated. Furthermore, a peptide near the amino terminal end of S2 has been shown to induce a protective cell-mediated response [37]. The adjuvant used has been reported to stimulate both antibody and cell-mediated immune responses [38-40]. The addition of the HA2 domain of the influenza hemagglutinin has also been demonstrated to increase the immunogenicity and protective capacity of IBV S1, possibly by increasing thermo stability [41].

The findings that recombinant S-ectodomain protein shows improved binding to cell receptors and elicits improved protection against challenge suggests that the S2 domain has an important role in inducing protective immunity. Thus, including the S2 ectodomain with S1 provides a promising option for a subunit vaccine and expands options for better viral vectored vaccines.

Example 2

Title—Protection Against Infectious Bronchitis Virus by Spike Ectodomain Protein Expressed from Recombinant Newcastle Disease Virus Vector Abstract We previously demonstrated protection against infectious bronchitis virus (IBV) infection in chickens following subcutaneous vaccination with recombinant soluble trimeric recombinant spike (S)-ectodomain (e) protein. We now demonstrate proof-of-principle that vaccination with this recombinant protein delivered by a recombinant viral vector can also protect chickens against IBV infection. A recombinant LaSota strain Newcastle disease virus (NDV.Se) encoding Ark-type IBV S-ectodomain protein was generated and used to vaccinate chickens at one and again at 14 days of age. Vaccinated chickens challenged with virulent Ark-type IBV 18 days after the second vaccination exhibited a lower incidence of respiratory signs and lower viral loads in tears five days post challenge than chickens unvaccinated chickens mock-vaccinated with LaSota NDV not expressing the recombinant protein.

Materials and Methods

Construction and Characterization of Recombinant LaSota NDV Expressing Soluble Trimeric IBV Ark-Type S-Ectodomain Protein.

A chicken-codon-optimized synthetic gene encoding the same recombinant S-ectodomain protein used for previous vaccination experiments described above 1731 was inserted into a full-length LaSota cDNA clone between the phosphoprotein (P) and matrix (M) genes as an additional transcription unit as previously described [12]. The recombinant protein encoded includes an N-terminal CD5 signal sequence, a C-terminal artificial GCN4 trimerization motif, and a C-terminal Strep-tag II for detection of the expressed protein. At the S1/S2 border, the furin cleavage site sequence RRSRR was replaced by GGGVP to avoid cleavage of the full length S-ectodomain [22]. Recombinant virus NDV.Se was rescued, propagated, and characterized as previously described [12].

Vaccination and Challenge.

White leghorn chickens hatched from specific-pathogen-free (SPF) eggs were divided into three groups of twelve chickens each and maintained in Horsfall-type isolators in biosafety level 2 facilities. Experimental procedures and animal care were performed in compliance with all applicable federal and institutional animal guidelines. Auburn University College of Veterinary Medicine is an Association for Assessment and Accreditation of Laboratory Animal Care-accredited institution. At one day of age one group of chickens (vaccinated group) was vaccinated ocularly with $10^5$ 50% embryo infective doses ($EID_{50}$) recombinant NDV.Se. The other two groups, unvaccinated/challenged and unvaccinated/non-challenged control groups, were mock-vaccinated with LaSota NDV lacking the recombinant IBV S-ectodomain gene. At 14 days of age, vaccinated chickens were boosted ocularly with the same dose of NDV.Se and the control groups were mock-boosted with LaSota NDV. Nineteen days after boosting, chickens in the vaccinated and unvaccinated/challenged group were challenged by ocular and nasal instillation of $10^6$ 50% embryo infective doses ($EID_{50}$) of a virulent IBV Ark-type strain (GenBank accession JN861120) previously characterized [28].

Evaluation of Protection.

Protection was assessed five days after challenge by respiratory signs and viral load in tears. The presence or absence of tracheal and/or nasal rales was determined for each individual bird without knowledge of treatment group by bringing the head of the bird near the examiner's ear and listening. RNA was isolated from tears collected five days post challenge from each individual bird and relative number of IBV RNA copy numbers determined as described above Statistical Analysis.

The significance of differences in numbers of chickens in each group exhibiting respiratory signs was evaluated using Fisher's exact test. The significance of differences in relative viral RNA copy numbers in tears among groups was evaluated using $\log_{10}$ relative copy numbers by one-way ANOVA followed by Tukey's multiple comparison test. Differences with $P<0.05$ were considered statistically significant.

Results

Properties of Recombinant LaSota NDV Expressing Recombinant Soluble Trimeric IBV S-Ectodomain Protein.

Recombinant virus NDV.S had an intracerebral pathogenicity index (ICPI) in day-old chickens of 0.0 and exhibited mean death time in embryonating eggs >150 hours, indicating even lower pathogenicity than the already low pathogenicity of the parental LaSota virus. Expression of the recombinant S protein in NDV.S-infected cells in vitro was confirmed by indirect immunofluorescence using sera both from chickens vaccinated with Ark-type live vaccine and chickens vaccinated with recombinant Ark-type S-ectodomain protein (results not shown). Chickens immunized with the recombinant NDV.Se or LaSota NDV did not exhibit any clinical signs.

Clinical Signs.

Figure 5:
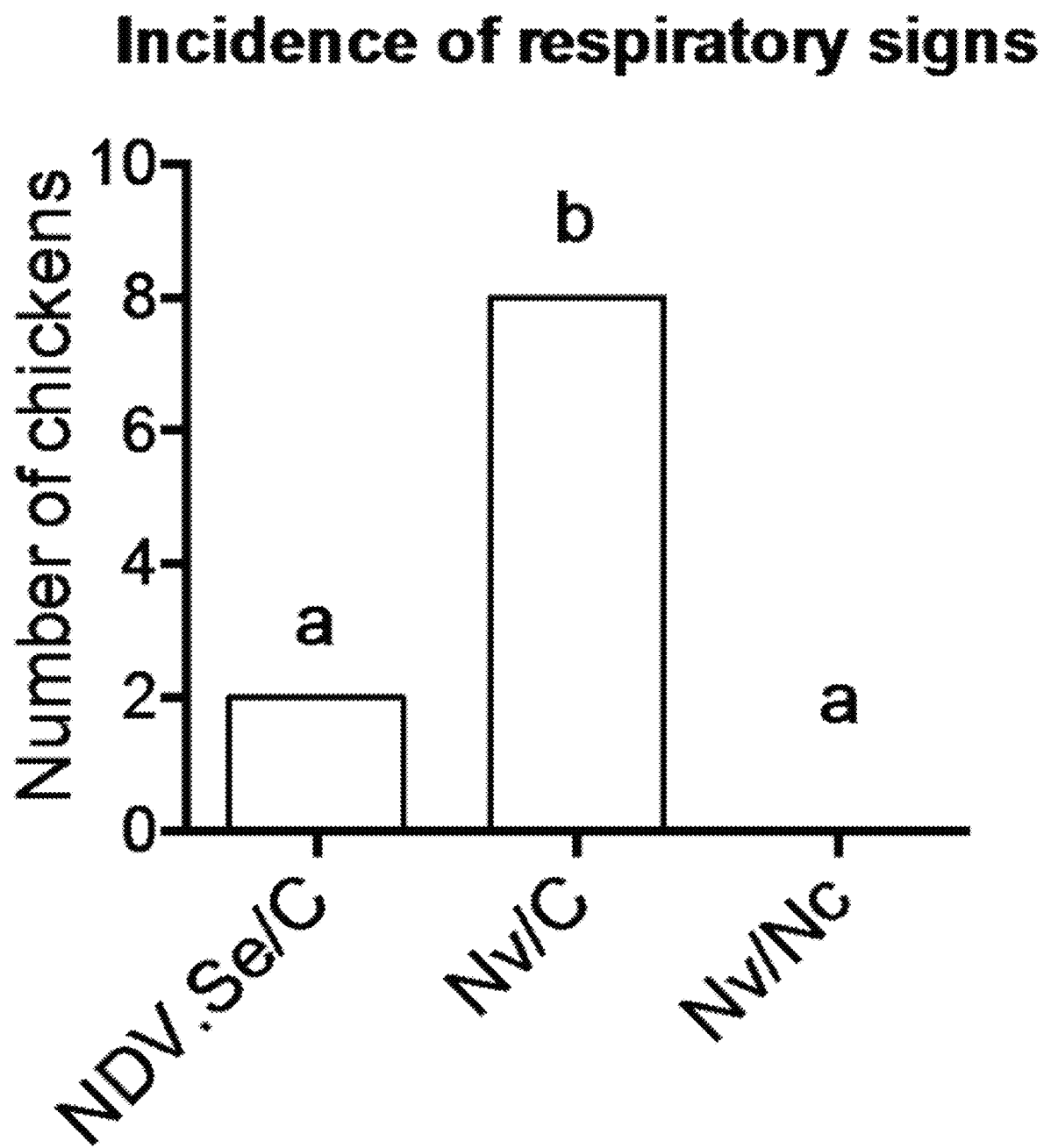
FIG. 5. Incidence of respiratory signs 5 days-post challenge with virulent Ark-type IBV. Chickens (NDV.Se/C; N=12/group) were vaccinated with recombinant LaSota NDV expressing IBV Ark-type S-ectodomain protein at 1 and 14 days of age and challenged with virulent Ark-type IBV 18 days later. A non-vaccinated/challenged (NvC) control group was mock-vaccinated with LaSota NDV and challenged. A non-vaccinated/non-challenged (Nv/Nc) control group was mock-vaccinated with LaSota NDV and not challenged. Statistically significant differences (Fisher's exact test; P<0.05) are indicated by different letters over the bars.

Only two of twelve chickens vaccinated with NDV.Se exhibited respiratory and/or nasal rales five days post-challenge with virulent IBV, compared to eight of twelve chickens mock-vaccinated with LaSota NDV (FIG. 5). Fisher's exact test indicated that this difference in incidence of respiratory signs was statistically significant ($P<0.05$). No chickens in the unvaccinated/non-challenged control group exhibited respiratory signs.

Viral Load in Tears.

Figure 6:
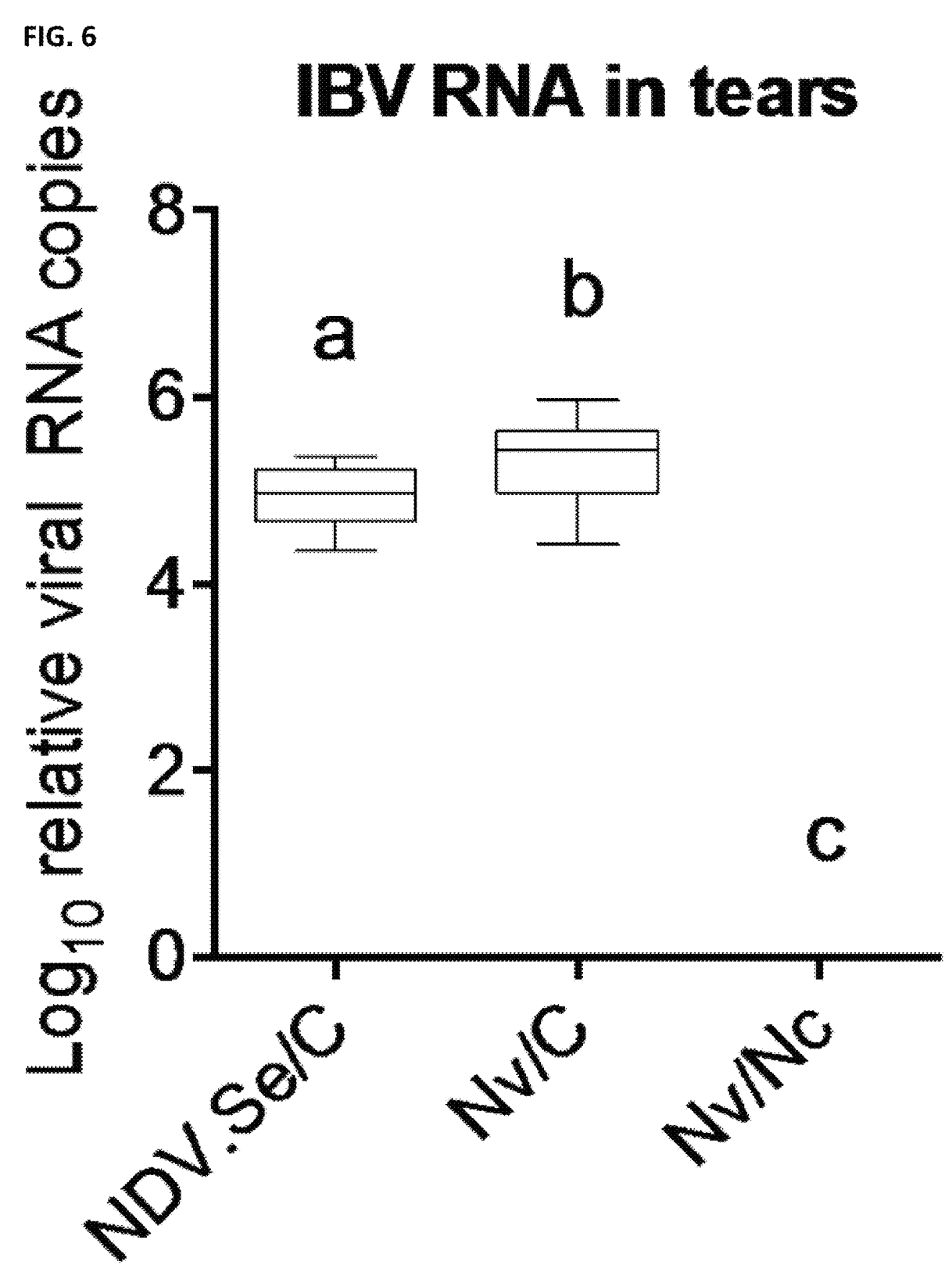

The relative viral loads in tears five days post challenge, as reflected in relative IBV RNA copy numbers, were significantly lower ($P<0.05$) in chickens vaccinated with NDV.Se compared to control chickens that had been mock-vaccinated with LaSota NDV and challenged (FIG. 6). IBV RNA was not detected in unvaccinated/non-challenged control chickens.

Discussion

Our results indicate that it is possible to protect chickens from IBV infection by vaccination with soluble trimeric S-ectodomain protein delivered by a recombinant virus. In this initial experiment, the protection parameters assessed show statistically significant, but modest, protection. It should be noted that this experiment used a ten-fold lower dose of recombinant NDV vaccine virus than used in other vaccination-challenge studies in chickens using LaSota NDV-vectored recombinant vaccines (e.g. [12, 74, 75]). Furthermore, our experiment used a ten-fold higher dose of virulent IBV challenge virus than was used in our study demonstrating remarkable protection following immunization with recombinant S-ectodomain protein administered subcutaneously [73]. Thus there is potential for substantial improvement in degree of protection demonstrated by increasing the dose of recombinant vaccine virus and/or decreasing the challenge virus dose.

REFERENCES

[1] Toro H, Jackwood M W, van Santen V L. Genetic diversity and selection regulates evolution of infectious bronchitis virus. Avian Dis 2012; 56:449-55.
[2] Toro H, Pennington D, Gallardo R A, van Santen V L, van Ginkel F W, Zhang J, Joiner K S. Infectious bronchitis virus subpopulations in vaccinated chickens after challenge. Avian Dis 2012; 56:501-8.
[3] van Santen V L, Toro H. Rapid selection in chickens of subpopulations within ArkDPI-derived infectious bronchitis virus vaccines. Avian Pathol 2008; 37:293-306.
[4] Gallardo R A, van Santen V L, Toro H. Host intraspatial selection of infectious bronchitis virus populations. Avian Dis 2010; 54:807-13.
[5] Cavanagh D. Coronavirus avian infectious bronchitis virus. Vet Res 2007; 38:281-97.
[6] Belouzard S, Millet J K, Licitra B N, Whittaker G R. Mechanisms of coronavirus cell entry mediated by the viral spike protein. Viruses 2012; 4:1011-33.
[7] Cavanagh D, Davis P J, Darbyshire J H, Peters R W. Coronavirus IBV: Virus retaining spike glycopolypeptide S2 but not S1 is unable to induce virus-neutralizing or haemagglutination-inhibiting antibody, or induce chicken tracheal protection. J Gen Virol 1986; 67:1435-42.
[8] Cavanagh D, Davis P J, Mockett A P. Amino acids within hypervariable region 1 of avian coronavirus IBV (Massachusetts serotype) spike glycoprotein are associated with neutralization epitopes. Virus Res 1988; 11:141-50.
[9] Moore K M, Jackwood M W, Hilt D A. Identification of amino acids involved in a serotype and neutralization specific epitope within the s 1 subunit of avian infectious bronchitis virus. Arch Virol 1997; 142:2249-56.
[10] Kusters J G, Niesters H G, Bleumink-Pluym N M, Davelaar F G, Horzinek M C, Van der Zeijst B A. Molecular epidemiology of infectious bronchitis virus in the Netherlands. J Gen Virol 1987; 68:343-52.
[11] Kusters J G, Niesters H G, Lenstra J A, Horzinek M C, van der Zeijst B A. Phylogeny of antigenic variants of avian coronavirus IBV. Virology 1989; 169:217-21.
[12] Toro H, Zhao W, Breedlove C, Zhang Z, Yu Q, van Santen V. Infectious bronchitis virus S2 expressed from recombinant virus confers broad protection against challenge. Avian Dis 2014; 58:83-9.
[13] Lenstra J A, Kusters J G, Koch G, van der Zeijst B A. Antigenicity of the peplomer protein of infectious bronchitis virus. Mol Immunol 1989; 26:7-15.
[14] Ignjatovic J, Galli L. The S1 glycoprotein but not the N or M proteins of avian infectious bronchitis virus induces protection in vaccinated chickens. Arch Virol 1994; 138: 117-34.
[15] Song C S, Lee Y J, Lee C W, Sung H W, Kim J H, Mo I P, Izumiya Y, Jang H K, Mikami T. Induction of protective immunity in chickens vaccinated with infectious bronchitis virus S1 glycoprotein expressed by a recombinant baculovirus. J Gen Virol 1998; 79:719-23.
[16] Wickramasinghe I N, de Vries R P, Grone A, de Haan C A, Verheije M H. Binding of avian coronavirus spike proteins to host factors reflects virus tropism and pathogenicity. J Virol 2011; 85:8903-12.
[17] Promkuntod N, van Eijndhoven R E, de Vrieze G, Grone A, Verheije M H. Mapping of the receptor-binding domain and amino acids critical for attachment in the spike protein of avian coronavirus infectious bronchitis virus. Virology 2014; 448:26-32.
[18] Mork A K, Hesse M, Abd El Rahman S, Rautenschlein S, Herrler G, Winter C. Differences in the tissue tropism to chicken oviduct epithelial cells between avian coronavirus IBV strains QX and B1648 are not related to the sialic acid binding properties of their spike proteins. Vet Res 2014; 45:67.
[19] Shahwan K, Hesse M, Mork A K, Herrler G, Winter C. Sialic acid binding properties of soluble coronavirus spike (S1) proteins: Differences between infectious bronchitis virus and transmissible gastroenteritis virus. Viruses 2013; 5:1924-33.
[20] Bosch B J, van der Zee R, de Haan C A, Rottier P J. The coronavirus spike protein is a class I virus fusion protein: Structural and functional characterization of the fusion core complex. J Virol 2003; 77:8801-11.
[21] Heald-Sargent T, Gallagher T. Ready, set, fuse! The coronavirus spike protein and acquisition of fusion competence. Viruses 2012; 4:557-80.
[22] Promkuntod N, Wickramasinghe I N, de Vrieze G, Grone A, Verheije M H. Contributions of the S2 spike ectodomain to attachment and host range of infectious bronchitis virus. Virus Res 2013; 177:127-37.
[23] Wickramasinghe I N, van Beurden S J, Weerts E A, Verheije M H. The avian coronavirus spike protein. Virus Res 2014; 194:37-48.
[24] Keeler C, Reed K L, Nix W, Gelb J. Serotype identification of avian infectious bronchitis virus by R T-PCR of the peplomer (S-1) gene. Avian Dis 1998; 42:275-84.
[25] McKinley E T, Hilt D A, Jackwood M W. Avian coronavirus infectious bronchitis attenuated live vaccines undergo selection of subpopulations and mutations following vaccination. Vaccine 2008; 26:1274-84.
[26] Ndegwa E N, Joiner K S, Toro H, van Ginkel F W, van Santen V L. The proportion of specific viral subpopulations in attenuated Arkansas Delmarva poultry industry infectious bronchitis vaccines influences vaccination outcome. Avian Dis 2012; 56:642-53.
[27] Wickramasinghe I N, Verheije M H. Protein histochemistry using coronaviral spike proteins: Studying binding profiles and sialic acid requirements for attachment to tissues. Methods Mol Biol 2015; 1282:155-63.
[28] Gallardo R A, Hoerr F J, Berry W D, van Santen V L, Toro H. Infectious bronchitis virus in testicles and venereal transmission. Avian Dis 2011; 55:255-8.
[29] Callison S A, Hilt D A, Boynton T O, Sample B F, Robison R, Swayne D E, Jackwood M W. Development and evaluation of a real-time taqman R T-PCR assay for the detection of infectious bronchitis virus from infected chickens. J Virol Methods 2006; 138:60-5.
[30] Toro H, van Santen V L, Li L, Lockaby S B, van Santen E, Hoerr F J. Epidemiological and experimental evidence for immunodeficiency affecting avian infectious bronchitis. Avian Pathol 2006; 35:455-64.
[31] Orr-Burks N, Gulley S L, Toro H, van Ginkel F W. Immunoglobulin A as an early humoral responder after mucosal avian coronavirus vaccination. Avian Dis 2014; 58:279-86.
[32] Kirchdoerfer R N, Cottrell C A, Wang N, Pallesen J, Yassine H M, Turner H L, Corbett K S, Graham B S, McLellan J S, Ward A B. Pre-fusion structure of a human coronavirus spike protein. Nature 2016; 531:118-21.

[33] Walls A C, Tortorici M A, Bosch B J, Frenz B, Rottier P J, DiMaio F, Rey F A, Veesler D. Cryo-electron microscopy structure of a coronavirus spike glycoprotein trimer. Nature 2016; 531:114-7.

[34] Kant A, Koch G, van Roozelaar D J, Kusters J G, Poelwijk F A, van der Zeijst B A. Location of antigenic sites defined by neutralizing monoclonal antibodies on the S1 avian infectious bronchitis virus glycopolypeptide. J Gen Virol 1992; 73:591-6.

[35] Karaca K, Naqi S, Gelb J. Production and characterization of monoclonal antibodies to three infectious bronchitis virus serotypes. Avian Dis 1992; 36:903-15.

[36] Kusters J G, Jager E J, Lenstra J A, Koch G, Posthumus W P, Meloen R H, van der Zeijst B A. Analysis of an immunodominant region of infectious bronchitis virus. J Immunol 1989; 143:2692-8.

[37] Ignjatovic J, Sapats S. Identification of previously unknown antigenic epitopes on the S and N proteins of avian infectious bronchitis virus. Arch Virol 2005; 150: 1813-31.

[38] Jang S I, Kim D K, Lillehoj H S, Lee S H, Lee K W, Bertrand F, Dupuis L, Deville S, Ben Arous J, Lillehoj E P. Evaluation of Montanide ISA 71 V G adjuvant during profilin vaccination against experimental coccidiosis. PLoS One 2013; 8:e59786.

[39] Jang S I, Lillehoj H S, Lee S H, Lee K W, Lillehoj E P, Bertrand F, Dupuis L, Deville S. Montanide ISA 71 V G adjuvant enhances antibody and cell-mediated immune responses to profilin subunit antigen vaccination and promotes protection against *Eimeria acervulina* and *Eimeria tenella*. Exp Parasitol 2011; 127:178-83.

[40] Ben Arousa J, Devillea S, Palb J, Baksib S, Bertranda F, Dupuisa L. Reduction of Newcastle disease vaccine dose using a novel adjuvant for cellular immune response in poultry. Procedia in Vaccinology 2013; 7:28-33.

[41] Yin L, Zeng Y, Wang W, Wei Y, Xue C, Cao Y. Immunogenicity and protective efficacy of recombinant fusion proteins containing spike protein of infectious bronchitis virus and hemagglutinin of H3N2 influenza virus in chickens. Virus Res 2016; 223:206-12.

[42] Lai, M. M. C., Cavanagh, D., 1997. The molecular biology of coronaviruses. Adv. Vir. Res. 48, 1-100.

[43] Lai, M. M. C., Holmes, K. V., 2001. Coronaviridae: The viruses and their replication, in: Knipe, D. M., Howley, P. M. (Eds.), Fundamental Virology, 4th ed. Lippincott Williams & Wilkins, Philadelphia, pp. 641-663.

[44] Bukreyev, A., Collins, P. L., 2008. Newcastle disease virus as a vaccine vector for humans. Current Opinion in Molecular Therapeutics 10, 46-55.

[45] Bukreyev, A., Huang, Z., Yang, L., Elankumaran, S., St Claire, M., Murphy, B. R., Samal, S. K., Collins, P. L., 2005. Recombinant newcastle disease virus expressing a foreign viral antigen is attenuated and highly immunogenic in primates. J. Virol. 79, 13275-13284.

[46] Cavanagh, D., 1981. Structural polypeptides of coronavirus IBV. J. Gen. Virol. 53, 93-103.

[47] Cavanagh, D., 1983. Coronavirus IBV: structural characterization of the spike protein. J. Gen. Virol. 64, 2577-2583.

[48] Cavanagh, D., 1984. Structural characterization of IBV glycoproteins. Adv. Exp. Med. Biol. 173, 95-108.

[49] Cavanagh, D., Davis, P. J., 1986. Coronavirus IBV: removal of spike glycopolypeptide S1 by urea abolishes infectivity and haemagglutination but not attachment to cells. J. Gen. Virol. 67, 1443-1448.

[50] DiNapoli, J. M., Kotelkin, A., Yang, L., Elankumaran, S., Murphy, B. R., Samal, S. K., Collins, P. L., Bukreyev, A., 2007. Newcastle disease virus, a host range-restricted virus, as a vaccine vector for intranasal immunization against emerging pathogens. PNAS U.S.A. 104, 9788-9793.

[51] DiNapoli, J. M., Ward, J. M., Cheng, L., Yang, L., Elankumaran, S., Murphy, B. R., Samal, S. K., Collins, P. L., Bukreyev, A., 2009. Delivery to the lower respiratory tract is required for effective immunization with Newcastle disease virus-vectored vaccines intended for humans. Vaccine 27, 1530-1539.

[52] Enjuanes, L., Brian, D., Cavanagh, D., Holmes, K., Lai, M. M. C., Laude, H., Masters, P., Rottier, P., Siddell, S. G., Spaan, W. J. M., Taguchi, F., Talbot, P., 2000a. Coronaviridae, in: van Regenmortel, M. H. V., Fauquet, C. M., Bishop, D. H. L., Carstens, E. B., Estes, M. K., Lemon, S., Maniloff, J., Mayo, M., McGeoch, D. J., Pringle, C. R., Wickner, R. B. (Eds.), Virus taxonomy. Classification and nomenclature of viruses. Academic Press, New York, N.Y., pp. 835-849.

[53] Enjuanes, L., Spaan, W. J., Snijder, E. J., Cavanagh, D., 2000b. Nidovirales, in: Regenmortel, M. H. V. v., Fauquet, C. M., Bishop, D. H. L., Carsten, E. B., Estes, M. K., Lemon, S. M., McGeoch, D. J., Maniloff, J., Mayo, M. A., Pringle, C. R., Wickner, R. B. (Eds.), Virus taxonomy. Classification and nomenclature of viruses Academic Press, New York, N.Y., pp. 827-834.

[54] Ge, J., Deng, G., Wen, Z., Tian, G., Wang, Y., Shi, J., Wang, X., Li, Y., Hu, S., Jiang, Y., Yang, C., Yu, K., Bu, Z., Chen, H., 2007. Newcastle disease virus-based live attenuated vaccine completely protects chickens and mice from lethal challenge of homologous and heterologous H5N1 avian influenza viruses. J. Virol. 81, 150-158.

[55] Ge, J., Tian, G., Zeng, X., Jiang, Y., Chen, H., Bua, Z., 2010. Generation and evaluation of a Newcastle disease virus-based H9 avian influenza live vaccine. Avian Dis. 54, 294-296.

[56] Huang, Z., Elankumaran, S., Panda, A., Samal, S. K., 2003a. Recombinant Newcastle disease virus as a vaccine vector. Poultry Science 82, 899-906.

[57] Huang, Z., Krishnamurthy, S., Panda, A., Samal, S. K., 2003b. Newcastle disease virus V protein is associated with viral pathogenesis and functions as an alpha interferon antagonist. J. Virol. 77, 8676-8685.

[58] Huang, Z., Panda, A., Elankumaran, S., Govindarajan, D., Rockemann, D. D., Samal, S. K., 2004. The hemagglutinin-neuraminidase protein of Newcastle disease virus determines tropism and virulence. J. Virol. 78, 4176-4184.

[59] Jackwood, M., 2012. Review of Infectious bronchitis virus around the world. Avian Dis. 56, 634-641.

[60] Jackwood, M. W., Hilt, D. A., Lee, C. W., Kwon, H. M., Callison, S. A., Moore, K. M., Moscoso, H., Sellers, H., Thayer, S., 2005. Data from 11 years of molecular typing infectious bronchitis virus field isolates. Avian Dis. 49, 614-618.

[61] Koch, G., Hartog, L., Kant, A., van Roozelaar, D. J., 1990. Antigenic domains on the peplomer protein of avian infectious bronchitis virus: correlation with biological functions. J. Gen. Virol. 71, 1929-1935.

[62] Koch, G., Kant, A., 1990. Binding of antibodies that strongly neutralise infectious bronchitis virus is dependent on the glycosylation of the viral peplomer protein. Adv. Exp. Med. Biol. 276, 143-150.

[63] Mockett, A. P., Cavanagh, D., Brown, T. D., 1984. Monoclonal antibodies to the S1 spike and membrane proteins of avian infectious bronchitis coronavirus strain Massachusetts M41. J. Gen. Virol. 65, 2281-2286.

[64] Nakaya, T., Cros, J., Park, M. S., Nakaya, Y., Zheng, H., Sagrera, A., Villar, E., Garcia-Sastre, A., Palese, P., 2001. Recombinant Newcastle disease virus as a vaccine vector. J. Virol. 75, 11868-11873.

[65] Nayak, B., Rout, S. N., Kumar, S., Khalil, M. S., Fouda, M. M., Ahmed, L. E., Earhart, K. C., Perez, D. R., Collins, P. L., Samal, S. K., 2009. Immunization of chickens with Newcastle disease virus expressing H5 hemagglutinin protects against highly pathogenic H5N1 avian influenza viruses. PloS one 4, e6509.

[66] Nix, W. A., Troeber, D. S., Kingham, B. F., Keeler, C. L., Jr., Gelb, J., Jr., 2000. Emergence of subtype strains of the Arkansas serotype of infectious bronchitis virus in Delmarva broiler chickens. Avian Dis. 44, 568-581.

[67] Park, M. S., Steel, J., Garcia-Sastre, A., Swayne, D., Palese, P., 2006. Engineered viral vaccine constructs with dual specificity: avian influenza and Newcastle disease. PNAS U.S.A. 103, 8203-8208.

[68] Stadler, K., Masignani, V., Eickmann, M., Becker, S., Abrignani, S., Klenk, H.-D., Rappuoli, R., 2003. Comparison of coronavirus genome structures. Nature Rev. Microbiol. 1, 209-218.

[69] Swayne, D. E., Suarez, D. L., Schultz-Cherry, S., Tumpey, T. M., King, D. J., Nakaya, T., Palese, P., Garcia-Sastre, A., 2003. Recombinant paramyxovirus type 1-avian influenza-H7 virus as a vaccine for protection of chickens against influenza and Newcastle disease. Avian Dis. 47, 1047-1050.

[70] Toro, H., Gallardo, R. A., Santen, V. L. v., Zhang, J. F., Joiner, K. S., 2012a. Protection induced by distinct IBV Ark-DPI S1 expressed from rAdenovirus, in: Lierz, M., Heffels-Redmann, U., Kaleta, E. F. (Eds.), VII. International Symposium on Avian Corona- and Pneumoviruses and Complicating Pathogens. World Veterinary Poultry Association, Rauischolzhausen, Germany, pp. 225-229.

[71] Toro, H., Suarez, D. L., Tang, D., Ginkel, F. v., Shi, Z., 2007. RCA-free recombinant adenovirus-vectored vaccine for mass immunization of poultry against avian influenza, 2007 AAAP/AVMA Annual Meeting, Washington D.C.

[72] Toro, H., Tang, D. C., Suarez, D. L., Zhang, J., Shi, Z., 2008. Protection of chickens against avian influenza with non-replicating adenovirus-vectored vaccine. Vaccine 26, 2640-2646.

[73] Eldemery F, Joiner K S, Toro H, van Santen V L. Protection against infectious bronchitis virus by spike ectodomain subunit vaccine. Vaccine 2017; 35:5864-71.

[74] Zhao W, Spatz S, Zhang Z, Wen G, Garcia M, Zsak L, Yu Q. Newcastle disease virus (NDV) recombinants expressing infectious laryngotracheitis virus (ILTV) glycoproteins gB and gD protect chickens against ILTV and NDV challenges. J Virol 2014; 88:8397-406.

[75] Yu Q, Spatz S, Li Y, Yang J, Zhao W, Zhang Z, Wen G, Garcia M, Zsak L. Newcastle disease virus vectored infectious laryngotracheitis vaccines protect commercial broiler chickens in the presence of maternally derived antibodies. Vaccine 2017; 35:789-95.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method for vaccinating chickens against infection by a virulent infectious bronchitis virus (IBV), the method comprising administering to the chickens a composition comprising:
   (a) a vector that expresses a multimeric recombinant protein, the multimeric recombinant protein comprising an amino acid sequence represented by $N_{ter}$-S1-Spacer-S2$_{ecto}$-MD-C$_{ter}$, wherein
      (i) S1 is the S1 domain of a spike protein (S) of the IBV or a variant thereof;
      (ii) S2$_{ecto}$ is the ectodomain of the S2 domain of the IBV or a variant thereof;
      (iii) MD is a heterologous multimerization domain; and
      (iv) Spacer is a spacer sequence that does not comprise the amino acid sequence Arg-X-(Arg/Lys)-Arg; and
   (b) a suitable carrier;
wherein chickens vaccinated by the method exhibit protection against challenge by the virulent IBV relative to chickens not vaccinated by the method.

2. The method of claim 1, wherein the multimeric recombinant protein that is expressed by the vector further comprises a signal peptide (SP) at the N-terminus of the recombinant protein and the multimeric recombinant protein is represented by the formula $N_{ter}$-SP-S1-Spacer-S2$_{ecto}$-MD-C$_{ter}$.

3. The method of claim 2, wherein the signal peptide of the multimeric recombinant protein that is expressed by the vector is the native signal peptide of the spike protein (S) of the IBV.

4. The method of claim 2, wherein the signal peptide of the multimeric recombinant protein that is expressed by the vector is not the native signal peptide of the spike protein (S) of the IBV.

5. The method of claim 1, wherein the vector is a viral vector.

6. The method of claim 1, wherein the spacer sequence of the recombinant protein is glycine rich and comprises >50% glycine residues.

7. The method of claim 1, wherein the multimeric recombinant protein does not comprise the amino acid sequence Arg-X-(Arg/Lys)-Arg.

8. The method of claim 1, wherein MD of the multimeric recombinant protein comprises a trimerization motif and the multimeric recombinant protein forms soluble trimers in aqueous solution.

9. The method of claim 1, wherein the multimeric recombinant protein does not comprise the transmembrane domain of the spike protein (S) of the IBV.

10. The method of claim 1, wherein the multimeric recombinant protein does not comprise the cytoplasmic domain of the spike protein (S) of the IBV.

11. The method of claim 1, wherein the multimeric recombinant protein is soluble in aqueous solution.

12. A method for vaccinating chickens against infection by a virulent infectious bronchitis virus (IBV), the method comprising administering to the chickens a composition comprising:
   (a) a viral vector that expresses a multimeric recombinant protein, the multimeric recombinant protein comprising an amino acid sequence represented by $N_{ter}$-S1-Spacer-S2$_{ecto}$-MD-$C_{ter}$, wherein
      (i) S1 is the S1 domain of a spike protein (S) of the IBV or a variant thereof, wherein S1 or the variant thereof comprises an amino acid sequence of SEQ ID NO: 91 or an amino acid sequence having at least about 95% sequence identity to SEQ ID NO: 91;
      (ii) S2$_{ecto}$ is the ectodomain of the S2 domain of the IBV or a variant thereof, wherein S2$_{ecto}$ or the variant thereof comprises an amino acid sequence of SEQ ID NO: 93 or an amino acid sequence having at least about 95% sequence identity to SEQ ID NO:93;
      (iii) MD is a heterologous multimerization domain; and
      (iv) Spacer is a spacer sequence that is glycine rich and comprises >50% glycine residues and the spacer sequence does not comprise the amino acid sequence Arg-X-(Arg/Lys)-Arg; and
   (b) a suitable carrier;
   wherein chickens vaccinated by the method exhibit protection against challenge by the virulent IBV relative to chickens not vaccinated by the method.

13. The method of claim 12, wherein the multimeric recombinant protein that is expressed by the vector further comprises a signal peptide (SP) at the N-terminus of the recombinant protein and the multimeric recombinant protein is represented by the formula $N_{ter}$-SP-S1-Spacer-S2$_{ecto}$-MD-$C_{ter}$.

14. The method of claim 13, wherein the signal peptide of the multimeric recombinant protein that is expressed by the vector is the native signal peptide of the spike protein (S) of the IBV.

15. The method of claim 13, wherein the signal peptide of the multimeric recombinant protein that is expressed by the vector is not the native signal peptide of the spike protein (S) of the IBV.

16. The method of claim 12, wherein the multimeric recombinant protein does not comprise the amino acid sequence Arg-X-(Arg/Lys)-Arg.

17. The method of claim 12, wherein MD of the multimeric recombinant protein comprises a trimerization motif and the multimeric recombinant protein is soluble and forms trimers in aqueous solution.

* * * * *

UNITED STATES PATENT AND TRADEMARK OFFICE
CERTIFICATE OF CORRECTION

| | | |
|---|---|---|
| PATENT NO. | : 10,772,953 B2 | Page 1 of 1 |
| APPLICATION NO. | : 16/059803 | |
| DATED | : September 15, 2020 | |
| INVENTOR(S) | : Vicky L. van Santen, Haroldo E. Toro and Qingzhong Yu | |

It is certified that error appears in the above-identified patent and that said Letters Patent is hereby corrected as shown below:

On the Title Page

The list of inventors:
Please add: Qingzhong Yu Athens, GA

The Applicant:
Please add: The United States of America, as represented by the Secretary of Agriculture Athens, GA Signed and Sealed this
Twenty-second Day of April, 2025

Coke Morgan Stewart
*Acting Director of the United States Patent and Trademark Office*

SEQUENCE LISTING

```
<160> NUMBER OF SEQ ID NOS: 119

<210> SEQ ID NO 1
<211> LENGTH: 1162
<212> TYPE: PRT
<213> ORGANISM: Infectious Bronchitis Virus

<400> SEQUENCE: 1

Met Leu Val Thr Pro Leu Leu Leu Val Thr Leu Leu Cys Ala Leu Cys
1               5                   10                  15

Ser Ala Val Leu Tyr Asp Ser Ser Ser Tyr Val Tyr Tyr Tyr Gln Ser
                20                  25                  30

Ala Phe Arg Pro Pro Ser Gly Trp His Leu Gln Gly Gly Ala Tyr Ala
            35                  40                  45

Val Val Asn Ile Ser Ser Glu Phe Asn Asn Ala Gly Ser Ser Ser Gly
        50                  55                  60

Cys Thr Val Gly Ile Ile His Gly Gly Arg Val Val Asn Ala Ser Ser
65                  70                  75                  80

Ile Ala Met Thr Ala Pro Ser Ser Gly Met Ala Trp Ser Ser Ser Gln
```

```
                    85                  90                  95
Phe Cys Thr Ala His Cys Asn Phe Ser Asp Thr Thr Val Phe Val Thr
                100                 105                 110
His Cys Tyr Lys His Gly Gly Cys Pro Leu Thr Gly Met Leu Gln Gln
                115                 120                 125
Asn Leu Ile Arg Val Ser Ala Met Lys Asn Gly Gln Leu Phe Tyr Asn
            130                 135                 140
Leu Thr Val Ser Val Ala Lys Tyr Pro Thr Phe Arg Ser Phe Gln Cys
145                 150                 155                 160
Val Asn Asn Leu Thr Ser Val Tyr Leu Asn Gly Asp Leu Val Tyr Thr
                165                 170                 175
Ser Asn Glu Thr Ile Asp Val Thr Ser Ala Gly Val Tyr Phe Lys Ala
                180                 185                 190
Gly Gly Pro Ile Thr Tyr Lys Val Met Arg Glu Val Lys Ala Leu Ala
            195                 200                 205
Tyr Phe Val Asn Gly Thr Ala Gln Asp Val Ile Leu Cys Asp Gly Ser
        210                 215                 220
Pro Arg Gly Leu Leu Ala Cys Gln Tyr Asn Thr Gly Asn Phe Ser Asp
225                 230                 235                 240
Gly Phe Tyr Pro Phe Thr Asn Ser Ser Leu Val Lys Gln Lys Phe Ile
                245                 250                 255
Val Tyr Arg Glu Asn Ser Val Asn Thr Thr Cys Thr Leu His Asn Phe
            260                 265                 270
Ile Phe His Asn Glu Thr Gly Ala Asn Pro Asn Pro Ser Gly Val Gln
        275                 280                 285
Asn Ile Gln Thr Tyr Gln Thr Lys Thr Ala Gln Ser Gly Tyr Tyr Asn
        290                 295                 300
Phe Asn Phe Ser Phe Leu Ser Ser Phe Val Tyr Lys Glu Ser Asn Phe
305                 310                 315                 320
Met Tyr Gly Ser Tyr His Pro Ser Cys Lys Phe Arg Leu Glu Thr Ile
                325                 330                 335
Asn Asn Gly Leu Trp Phe Asn Ser Leu Ser Val Ser Ile Ala Tyr Gly
            340                 345                 350
Pro Leu Gln Gly Gly Cys Lys Gln Ser Val Phe Lys Gly Arg Ala Thr
        355                 360                 365
Cys Cys Tyr Ala Tyr Ser Tyr Gly Gly Pro Ser Leu Cys Lys Gly Val
        370                 375                 380
Tyr Ser Gly Glu Leu Asp His Asn Phe Glu Cys Gly Leu Leu Val Tyr
385                 390                 395                 400
Val Thr Lys Ser Gly Gly Ser Arg Ile Gln Thr Ala Thr Glu Pro Pro
                405                 410                 415
Val Ile Thr Gln Asn Asn Tyr Asn Asn Ile Thr Leu Asn Thr Cys Val
            420                 425                 430
Asp Tyr Asn Ile Tyr Gly Arg Thr Gly Gln Gly Phe Ile Thr Asn Val
        435                 440                 445
Thr Asp Ser Ala Val Ser Tyr Asn Tyr Leu Ala Asp Ala Gly Leu Ala
    450                 455                 460
Ile Leu Asp Thr Ser Gly Ser Ile Asp Ile Phe Val Val Gln Gly Glu
465                 470                 475                 480
Tyr Gly Leu Asn Tyr Tyr Lys Val Asn Pro Cys Glu Asp Val Asn Gln
                485                 490                 495
Gln Phe Val Val Ser Gly Gly Lys Leu Val Gly Ile Leu Thr Ser Arg
                500                 505                 510
```

```
Asn Glu Thr Gly Ser Gln Leu Leu Glu Asn Gln Phe Tyr Ile Lys Ile
            515                 520                 525

Thr Asn Gly Thr Arg Arg Phe Arg Arg Ser Ile Thr Glu Asn Val Ala
    530                 535                 540

Asn Cys Pro Tyr Val Ser Tyr Gly Lys Phe Cys Ile Lys Pro Asp Gly
545                 550                 555                 560

Ser Ile Ala Thr Ile Val Pro Lys Gln Leu Glu Gln Phe Val Ala Pro
                565                 570                 575

Leu Phe Asn Val Thr Glu Asn Val Leu Ile Pro Asn Ser Phe Asn Leu
            580                 585                 590

Thr Val Thr Asp Glu Tyr Ile Gln Thr Arg Met Asp Lys Val Gln Ile
        595                 600                 605

Asn Cys Leu Gln Tyr Val Cys Gly Ser Ser Leu Asp Cys Arg Lys Leu
        610                 615                 620

Phe Gln Gln Tyr Gly Pro Val Cys Asp Asn Ile Leu Ser Val Val Asn
625                 630                 635                 640

Ser Val Gly Gln Lys Glu Asp Met Glu Leu Leu Asn Phe Tyr Ser Ser
                645                 650                 655

Thr Lys Pro Ala Gly Phe Asn Thr Pro Val Leu Ser Asn Val Ser Thr
            660                 665                 670

Gly Glu Phe Asn Ile Ser Leu Leu Leu Thr Asn Pro Ser Ser Arg Arg
        675                 680                 685

Lys Arg Ser Leu Ile Glu Asp Leu Leu Phe Thr Ser Val Glu Ser Val
    690                 695                 700

Gly Leu Pro Thr Asn Asp Ala Tyr Lys Asn Cys Thr Ala Gly Pro Leu
705                 710                 715                 720

Gly Phe Phe Lys Asp Leu Ala Cys Ala Arg Glu Tyr Asn Gly Leu Leu
                725                 730                 735

Val Leu Pro Pro Ile Ile Thr Ala Glu Met Gln Ala Leu Tyr Thr Ser
            740                 745                 750

Ser Leu Val Ala Ser Met Ala Phe Gly Gly Ile Thr Ala Ala Gly Ala
        755                 760                 765

Ile Pro Phe Ala Thr Gln Leu Gln Ala Arg Ile Asn His Leu Gly Ile
    770                 775                 780

Thr Gln Ser Leu Leu Leu Lys Asn Gln Glu Lys Ile Ala Ala Ser Phe
785                 790                 795                 800

Asn Lys Ala Ile Gly His Met Gln Glu Gly Phe Arg Ser Thr Ser Leu
                805                 810                 815

Ala Leu Gln Gln Ile Gln Asp Val Val Ser Lys Gln Ser Ala Ile Leu
            820                 825                 830

Thr Glu Thr Met Ala Ser Leu Asn Lys Asn Phe Gly Ala Ile Ser Ser
        835                 840                 845

Val Ile Gln Glu Ile Tyr Gln Gln Phe Asp Ala Ile Gln Ala Asn Ala
    850                 855                 860

Gln Val Asp Arg Leu Ile Thr Gly Arg Leu Ser Ser Leu Ser Val Leu
865                 870                 875                 880

Ala Ser Ala Lys Gln Ala Glu Tyr Ile Arg Val Ser Gln Gln Arg Glu
                885                 890                 895

Leu Ala Thr Gln Lys Ile Asn Glu Cys Val Lys Ser Gln Ser Ile Arg
            900                 905                 910

Tyr Ser Phe Cys Gly Asn Gly Arg His Val Leu Thr Ile Pro Gln Asn
        915                 920                 925
```

Ala Pro Asn Gly Ile Val Phe Ile His Phe Ser Tyr Thr Pro Asp Ser
    930                 935                 940

Phe Val Asn Val Thr Ala Ile Val Gly Phe Cys Val Lys Pro Ala Asn
945                 950                 955                 960

Ala Ser Gln Tyr Ala Ile Val Pro Ala Asn Gly Arg Gly Ile Phe Ile
            965                 970                 975

Gln Val Asn Gly Ser Tyr Tyr Ile Thr Ala Arg Asp Met Tyr Met Pro
        980                 985                 990

Arg Ala Ile Thr Ala Gly Asp Val Val Thr Leu Thr Ser Cys Gln Ala
            995                 1000                1005

Asn Tyr Val Ser Val Asn Lys Thr Val Ile Thr Thr Phe Val Asp
        1010                1015                1020

Asn Asp Asp Phe Asp Phe Asn Asp Glu Leu Ser Lys Trp Trp Asn
    1025                1030                1035

Asp Thr Lys His Glu Leu Pro Asp Phe Asp Lys Phe Asn Tyr Thr
    1040                1045                1050

Val Pro Ile Leu Asp Ile Asp Ser Glu Ile Asp Arg Ile Gln Gly
    1055                1060                1065

Val Ile Gln Gly Leu Asn Asp Ser Leu Ile Asp Leu Glu Lys Leu
    1070                1075                1080

Ser Ile Leu Lys Thr Tyr Ile Lys Trp Pro Trp Tyr Val Trp Leu
    1085                1090                1095

Ala Ile Ala Phe Ala Thr Ile Ile Phe Ile Leu Ile Leu Gly Trp
    1100                1105                1110

Val Phe Phe Met Thr Gly Cys Cys Gly Cys Cys Cys Gly Cys Phe
    1115                1120                1125

Gly Ile Met Pro Leu Met Ser Lys Cys Gly Lys Lys Ser Ser Tyr
    1130                1135                1140

Tyr Thr Thr Phe Asp Asn Asp Val Val Thr Glu Gln Tyr Arg Pro
    1145                1150                1155

Lys Lys Ser Val
    1160

<210> SEQ ID NO 2
<211> LENGTH: 17
<212> TYPE: PRT
<213> ORGANISM: Infectious Bronchitis Virus

<400> SEQUENCE: 2

Met Leu Val Thr Pro Leu Leu Leu Val Thr Leu Leu Cys Ala Leu Cys
1               5                   10                  15

Ser

<210> SEQ ID NO 3
<211> LENGTH: 515
<212> TYPE: PRT
<213> ORGANISM: Infectious Bronchitis Virus

<400> SEQUENCE: 3

Ala Val Leu Tyr Asp Ser Ser Ser Tyr Val Tyr Tyr Tyr Gln Ser Ala
1               5                   10                  15

Phe Arg Pro Pro Ser Gly Trp His Leu Gln Gly Gly Ala Tyr Ala Val
                20                  25                  30

Val Asn Ile Ser Ser Glu Phe Asn Asn Ala Gly Ser Ser Ser Gly Cys
            35                  40                  45

Thr Val Gly Ile Ile His Gly Gly Arg Val Val Asn Ala Ser Ser Ile

```
                    50                  55                  60
Ala Met Thr Ala Pro Ser Ser Gly Met Ala Trp Ser Ser Gln Phe
65                  70                  75                  80

Cys Thr Ala His Cys Asn Phe Ser Asp Thr Thr Val Phe Val Thr His
                    85                  90                  95

Cys Tyr Lys His Gly Gly Cys Pro Leu Thr Gly Met Leu Gln Gln Asn
                100                 105                 110

Leu Ile Arg Val Ser Ala Met Lys Asn Gly Gln Leu Phe Tyr Asn Leu
                115                 120                 125

Thr Val Ser Val Ala Lys Tyr Pro Thr Phe Arg Ser Phe Gln Cys Val
                130                 135                 140

Asn Asn Leu Thr Ser Val Tyr Leu Asn Gly Asp Leu Val Tyr Thr Ser
145                 150                 155                 160

Asn Glu Thr Ile Asp Val Thr Ser Ala Gly Val Tyr Phe Lys Ala Gly
                    165                 170                 175

Gly Pro Ile Thr Tyr Lys Val Met Arg Glu Val Lys Ala Leu Ala Tyr
                180                 185                 190

Phe Val Asn Gly Thr Ala Gln Asp Val Ile Leu Cys Asp Gly Ser Pro
                195                 200                 205

Arg Gly Leu Leu Ala Cys Gln Tyr Asn Thr Gly Asn Phe Ser Asp Gly
210                 215                 220

Phe Tyr Pro Phe Thr Asn Ser Ser Leu Val Lys Gln Lys Phe Ile Val
225                 230                 235                 240

Tyr Arg Glu Asn Ser Val Asn Thr Thr Cys Thr Leu His Asn Phe Ile
                    245                 250                 255

Phe His Asn Glu Thr Gly Ala Asn Pro Asn Pro Ser Gly Val Gln Asn
                260                 265                 270

Ile Gln Thr Tyr Gln Thr Lys Thr Ala Gln Ser Gly Tyr Tyr Asn Phe
                275                 280                 285

Asn Phe Ser Phe Leu Ser Ser Phe Val Tyr Lys Glu Ser Asn Phe Met
                290                 295                 300

Tyr Gly Ser Tyr His Pro Ser Cys Lys Phe Arg Leu Glu Thr Ile Asn
305                 310                 315                 320

Asn Gly Leu Trp Phe Asn Ser Leu Ser Val Ser Ile Ala Tyr Gly Pro
                    325                 330                 335

Leu Gln Gly Gly Cys Lys Gln Ser Val Phe Lys Gly Arg Ala Thr Cys
                340                 345                 350

Cys Tyr Ala Tyr Ser Tyr Gly Gly Pro Ser Leu Cys Lys Gly Val Tyr
                355                 360                 365

Ser Gly Glu Leu Asp His Asn Phe Glu Cys Gly Leu Leu Val Tyr Val
                370                 375                 380

Thr Lys Ser Gly Gly Ser Arg Ile Gln Thr Ala Thr Glu Pro Pro Val
385                 390                 395                 400

Ile Thr Gln Asn Asn Tyr Asn Asn Ile Thr Leu Asn Thr Cys Val Asp
                    405                 410                 415

Tyr Asn Ile Tyr Gly Arg Thr Gly Gln Gly Phe Ile Thr Asn Val Thr
                420                 425                 430

Asp Ser Ala Val Ser Tyr Asn Tyr Leu Ala Asp Ala Gly Leu Ala Ile
                435                 440                 445

Leu Asp Thr Ser Gly Ser Ile Asp Ile Phe Val Val Gln Gly Glu Tyr
                450                 455                 460

Gly Leu Asn Tyr Tyr Lys Val Asn Pro Cys Glu Asp Val Asn Gln Gln
465                 470                 475                 480
```

-continued

```
Phe Val Val Ser Gly Gly Lys Leu Val Gly Ile Leu Thr Ser Arg Asn
                485                 490                 495

Glu Thr Gly Ser Gln Leu Leu Glu Asn Gln Phe Tyr Ile Lys Ile Thr
            500                 505                 510

Asn Gly Thr
        515

<210> SEQ ID NO 4
<211> LENGTH: 5
<212> TYPE: PRT
<213> ORGANISM: Infectious Bronchitits Virus

<400> SEQUENCE: 4

Arg Arg Phe Arg Arg
1               5

<210> SEQ ID NO 5
<211> LENGTH: 554
<212> TYPE: PRT
<213> ORGANISM: Infectious Bronchitits Virus

<400> SEQUENCE: 5

Ser Ile Thr Glu Asn Val Ala Asn Cys Pro Tyr Val Ser Tyr Gly Lys
1               5                   10                  15

Phe Cys Ile Lys Pro Asp Gly Ser Ile Ala Thr Ile Val Pro Lys Gln
            20                  25                  30

Leu Glu Gln Phe Val Ala Pro Leu Phe Asn Val Thr Glu Asn Val Leu
        35                  40                  45

Ile Pro Asn Ser Phe Asn Leu Thr Val Thr Asp Glu Tyr Ile Gln Thr
    50                  55                  60

Arg Met Asp Lys Val Gln Ile Asn Cys Leu Gln Tyr Val Cys Gly Ser
65                  70                  75                  80

Ser Leu Asp Cys Arg Lys Leu Phe Gln Gln Tyr Gly Pro Val Cys Asp
                85                  90                  95

Asn Ile Leu Ser Val Val Asn Ser Val Gly Gln Lys Glu Asp Met Glu
            100                 105                 110

Leu Leu Asn Phe Tyr Ser Ser Thr Lys Pro Ala Gly Phe Asn Thr Pro
        115                 120                 125

Val Leu Ser Asn Val Ser Thr Gly Glu Phe Asn Ile Ser Leu Leu Leu
    130                 135                 140

Thr Asn Pro Ser Ser Arg Arg Lys Arg Ser Leu Ile Glu Asp Leu Leu
145                 150                 155                 160

Phe Thr Ser Val Glu Ser Val Gly Leu Pro Thr Asn Asp Ala Tyr Lys
                165                 170                 175

Asn Cys Thr Ala Gly Pro Leu Gly Phe Phe Lys Asp Leu Ala Cys Ala
            180                 185                 190

Arg Glu Tyr Asn Gly Leu Leu Val Leu Pro Pro Ile Ile Thr Ala Glu
        195                 200                 205

Met Gln Ala Leu Tyr Thr Ser Ser Leu Val Ala Ser Met Ala Phe Gly
    210                 215                 220

Gly Ile Thr Ala Ala Gly Ala Ile Pro Phe Ala Thr Gln Leu Gln Ala
225                 230                 235                 240

Arg Ile Asn His Leu Gly Ile Thr Gln Ser Leu Leu Leu Lys Asn Gln
                245                 250                 255

Glu Lys Ile Ala Ala Ser Phe Asn Lys Ala Ile Gly His Met Gln Glu
            260                 265                 270

```
Gly Phe Arg Ser Thr Ser Leu Ala Leu Gln Gln Ile Gln Asp Val Val
            275                 280                 285

Ser Lys Gln Ser Ala Ile Leu Thr Glu Thr Met Ala Ser Leu Asn Lys
290                 295                 300

Asn Phe Gly Ala Ile Ser Ser Val Ile Gln Glu Ile Tyr Gln Gln Phe
305                 310                 315                 320

Asp Ala Ile Gln Ala Asn Ala Gln Val Asp Arg Leu Ile Thr Gly Arg
                325                 330                 335

Leu Ser Ser Leu Ser Val Leu Ala Ser Ala Lys Gln Ala Glu Tyr Ile
            340                 345                 350

Arg Val Ser Gln Gln Arg Glu Leu Ala Thr Gln Lys Ile Asn Glu Cys
        355                 360                 365

Val Lys Ser Gln Ser Ile Arg Tyr Ser Phe Cys Gly Asn Gly Arg His
    370                 375                 380

Val Leu Thr Ile Pro Gln Asn Ala Pro Asn Gly Ile Val Phe Ile His
385                 390                 395                 400

Phe Ser Tyr Thr Pro Asp Ser Phe Val Asn Val Thr Ala Ile Val Gly
                405                 410                 415

Phe Cys Val Lys Pro Ala Asn Ala Ser Gln Tyr Ala Ile Val Pro Ala
            420                 425                 430

Asn Gly Arg Gly Ile Phe Ile Gln Val Asn Gly Ser Tyr Tyr Ile Thr
        435                 440                 445

Ala Arg Asp Met Tyr Met Pro Arg Ala Ile Thr Ala Gly Asp Val Val
    450                 455                 460

Thr Leu Thr Ser Cys Gln Ala Asn Tyr Val Ser Val Asn Lys Thr Val
465                 470                 475                 480

Ile Thr Thr Phe Val Asp Asn Asp Asp Phe Asp Phe Asn Asp Glu Leu
                485                 490                 495

Ser Lys Trp Trp Asn Asp Thr Lys His Glu Leu Pro Asp Phe Asp Lys
            500                 505                 510

Phe Asn Tyr Thr Val Pro Ile Leu Asp Ile Asp Ser Glu Ile Asp Arg
        515                 520                 525

Ile Gln Gly Val Ile Gln Gly Leu Asn Asp Ser Leu Ile Asp Leu Glu
    530                 535                 540

Lys Leu Ser Ile Leu Lys Thr Tyr Ile Lys
545                 550

<210> SEQ ID NO 6
<211> LENGTH: 67
<212> TYPE: PRT
<213> ORGANISM: Infectious Bronchitis Virus

<400> SEQUENCE: 6

Val Trp Leu Ala Ile Ala Phe Ala Thr Ile Ile Phe Ile Leu Ile Leu
1               5                   10                  15

Gly Trp Val Phe Phe Met Thr Gly Cys Cys Gly Cys Cys Cys Gly Cys
            20                  25                  30

Phe Gly Ile Met Pro Leu Met Ser Lys Cys Gly Lys Lys Ser Ser Tyr
        35                  40                  45

Tyr Thr Thr Phe Asp Asn Asp Val Val Thr Glu Gln Tyr Arg Pro Lys
    50                  55                  60

Lys Ser Val
65
```

```
<210> SEQ ID NO 7
<211> LENGTH: 20
<212> TYPE: PRT
<213> ORGANISM: Infectious Bronchitis Virus

<400> SEQUENCE: 7

Val Trp Leu Ala Ile Ala Phe Ala Thr Ile Ile Phe Ile Leu Ile Leu
1               5                   10                  15

Gly Trp Val Phe
            20

<210> SEQ ID NO 8
<211> LENGTH: 46
<212> TYPE: PRT
<213> ORGANISM: Infectious Bronchitis Virus

<400> SEQUENCE: 8

Met Thr Gly Cys Cys Gly Cys Cys Cys Gly Cys Phe Gly Ile Met Pro
1               5                   10                  15

Leu Met Ser Lys Cys Gly Lys Lys Ser Ser Tyr Tyr Thr Thr Phe Asp
            20                  25                  30

Asn Asp Val Val Thr Glu Gln Tyr Arg Pro Lys Lys Ser Val
        35                  40                  45

<210> SEQ ID NO 9
<211> LENGTH: 1162
<212> TYPE: PRT
<213> ORGANISM: Infectious Bronchitis Virus

<400> SEQUENCE: 9

Met Leu Val Thr Pro Leu Leu Val Thr Leu Leu Cys Ala Leu Cys
1               5                   10                  15

Ser Ala Ala Leu Tyr Asp Ser Ser Ser Tyr Val Tyr Tyr Gln Ser
            20                  25                  30

Ala Phe Arg Pro Pro Asp Gly Trp His Leu His Gly Gly Ala Tyr Ala
        35                  40                  45

Val Val Asn Ile Ser Ser Glu Ser Asn Asn Ala Gly Ser Ser Ser Gly
    50                  55                  60

Cys Thr Val Gly Ile Ile His Gly Gly Arg Val Val Asn Ala Ser Ser
65                  70                  75                  80

Ile Ala Met Thr Ala Pro Ser Ser Gly Met Ala Trp Ser Ser Ser Gln
                85                  90                  95

Phe Cys Thr Ala Tyr Cys Asn Phe Ser Asp Thr Thr Val Phe Val Thr
            100                 105                 110

His Cys Tyr Lys His Val Gly Cys Pro Ile Thr Gly Met Leu Gln Gln
        115                 120                 125

His Ser Ile Arg Val Ser Ala Met Lys Asn Gly Gln Leu Phe Tyr Asn
    130                 135                 140

Leu Thr Val Ser Val Ala Lys Tyr Pro Thr Phe Lys Ser Phe Gln Cys
145                 150                 155                 160

Val Asn Asn Leu Thr Ser Val Tyr Leu Asn Gly Asp Leu Val Tyr Thr
                165                 170                 175

Ser Asn Glu Thr Thr Asp Val Ser Ala Gly Val Tyr Phe Lys Ala
            180                 185                 190

Gly Gly Pro Ile Thr Tyr Lys Val Met Arg Glu Val Arg Ala Leu Ala
        195                 200                 205

Tyr Phe Val Asn Gly Thr Ala Gln Asp Val Ile Leu Cys Asp Gly Ser
    210                 215                 220
```

-continued

```
Pro Arg Gly Leu Leu Ala Cys Gln Tyr Asn Thr Gly Asn Phe Ser Asp
225                 230                 235                 240

Gly Phe Tyr Pro Phe Thr Asn Ser Ser Leu Val Lys Gln Lys Phe Ile
            245                 250                 255

Val Tyr Arg Glu Asn Ser Val Asn Thr Thr Phe Thr Leu His Asn Phe
        260                 265                 270

Thr Phe His Asn Glu Thr Gly Ala Asn Pro Asn Pro Ser Gly Val Gln
    275                 280                 285

Asn Ile Gln Thr Tyr Gln Thr Gln Thr Ala Gln Ser Gly Tyr Tyr Asn
290                 295                 300

Phe Asn Phe Ser Phe Leu Ser Ser Phe Val Tyr Lys Glu Ser Asn Phe
305                 310                 315                 320

Met Tyr Gly Ser Tyr His Pro Ser Cys Asn Phe Arg Leu Glu Thr Ile
            325                 330                 335

Asn Asn Gly Leu Trp Phe Asn Ser Leu Ser Val Ser Ile Ala Tyr Gly
            340                 345                 350

Pro Leu Gln Gly Gly Cys Lys Gln Ser Val Phe Ser Gly Arg Ala Thr
        355                 360                 365

Cys Cys Tyr Ala Tyr Ser Tyr Gly Gly Pro Leu Leu Cys Lys Gly Val
370                 375                 380

Tyr Ser Gly Glu Leu Asp His Asn Phe Glu Cys Gly Leu Leu Val Tyr
385                 390                 395                 400

Val Thr Lys Ser Gly Gly Ser Arg Ile Gln Thr Ala Thr Glu Pro Pro
            405                 410                 415

Val Ile Thr Gln His Asn Tyr Asn Asn Ile Thr Leu Asn Thr Cys Val
        420                 425                 430

Asp Tyr Asn Ile Tyr Gly Arg Thr Gly Gln Gly Phe Ile Thr Asn Val
    435                 440                 445

Thr Asp Ser Ala Val Ser Tyr Asn Tyr Leu Ala Asp Ala Gly Leu Ala
450                 455                 460

Ile Leu Asp Thr Ser Gly Ser Ile Asp Ile Phe Val Val Gln Ser Glu
465                 470                 475                 480

Tyr Gly Leu Asn Tyr Tyr Lys Val Asn Pro Cys Glu Asp Val Asn Gln
            485                 490                 495

Gln Phe Val Val Ser Gly Gly Lys Leu Val Gly Ile Leu Thr Ser Arg
        500                 505                 510

Asn Glu Thr Gly Ser Gln Leu Leu Glu Asn Gln Phe Tyr Ile Lys Ile
    515                 520                 525

Thr Asn Gly Thr Arg Arg Phe Arg Arg Ser Ile Thr Glu Ser Val Glu
530                 535                 540

Asn Cys Pro Tyr Val Ser Tyr Gly Lys Phe Cys Ile Lys Pro Asp Gly
545                 550                 555                 560

Ser Ile Ala Thr Ile Val Pro Lys Gln Leu Glu Gln Phe Val Ala Pro
            565                 570                 575

Leu Leu Asn Val Thr Glu Asn Val Leu Ile Pro Asn Ser Phe Asn Leu
        580                 585                 590

Thr Val Thr Asp Glu Tyr Ile Gln Thr Arg Met Asp Lys Val Gln Ile
    595                 600                 605

Asn Cys Leu Gln Tyr Ile Cys Gly Asn Ser Leu Glu Cys Arg Asn Leu
610                 615                 620

Phe Gln Gln Tyr Gly Pro Val Cys Asp Asn Ile Leu Ser Val Val Asn
625                 630                 635                 640
```

```
Ser Val Gly Gln Lys Glu Asp Met Glu Leu Leu Asn Phe Tyr Ser Ser
                645                 650                 655

Thr Lys Pro Ala Gly Phe Asn Thr Pro Val Leu Ser Asn Val Ser Thr
                660                 665                 670

Gly Glu Phe Asn Ile Ser Leu Phe Leu Thr Thr Pro Ser Ser Pro Arg
                675                 680                 685

Arg Arg Ser Phe Ile Glu Asp Leu Leu Phe Thr Ser Val Glu Ser Val
        690                 695                 700

Gly Leu Pro Thr Asp Asp Ala Tyr Lys Asn Cys Thr Ala Gly Pro Leu
705                 710                 715                 720

Gly Phe Leu Lys Asp Leu Val Cys Ala Arg Glu Tyr Asn Gly Leu Leu
                725                 730                 735

Val Leu Pro Pro Ile Ile Thr Ala Glu Met Gln Thr Leu Tyr Thr Ser
                740                 745                 750

Ser Leu Val Ala Ser Met Ala Phe Gly Gly Ile Thr Ala Ala Gly Ala
                755                 760                 765

Ile Pro Phe Ala Thr Gln Leu Gln Ala Arg Ile Asn His Leu Gly Ile
        770                 775                 780

Thr Gln Ser Leu Leu Leu Lys Asn Gln Glu Lys Ile Ala Ala Ser Phe
785                 790                 795                 800

Asn Lys Ala Ile Gly His Met Gln Glu Gly Phe Arg Ser Thr Ser Leu
                805                 810                 815

Ala Leu Gln Gln Ile Gln Asp Val Val Asn Lys Gln Ser Ala Ile Leu
                820                 825                 830

Thr Glu Thr Met Ala Ser Leu Asn Lys Asn Phe Gly Ala Ile Ser Ser
                835                 840                 845

Val Ile Gln Glu Ile Tyr Gln Gln Leu Asp Ala Ile Gln Ala Asn Ala
850                 855                 860

Gln Val Asp Arg Leu Ile Thr Gly Arg Leu Ser Ser Leu Ser Val Leu
865                 870                 875                 880

Ala Ser Ala Lys Gln Ala Glu Tyr Ile Arg Val Ser Gln Gln Arg Glu
                885                 890                 895

Leu Ala Thr Gln Lys Ile Asn Glu Cys Val Lys Ser Gln Ser Ile Arg
                900                 905                 910

Tyr Ser Phe Cys Gly Asn Gly Arg His Val Leu Thr Ile Pro Gln Asn
            915                 920                 925

Ala Pro Asn Gly Ile Val Phe Ile His Phe Ser Tyr Thr Pro Asp Ser
        930                 935                 940

Phe Val Asn Val Thr Ala Ile Val Gly Phe Cys Val Lys Pro Ala Asn
945                 950                 955                 960

Ala Ser Gln Tyr Ala Ile Val Pro Ala Asn Gly Arg Gly Ile Phe Ile
                965                 970                 975

Gln Val Asn Gly Ser Tyr Tyr Ile Thr Ala Arg Asp Met Tyr Met Pro
                980                 985                 990

Arg Ala Ile Thr Ala Gly Asp Ile Val Thr Leu Thr Ser Cys Gln Val
            995                1000                1005

Asn Tyr Val Ser Val Asn Lys Thr Val Ile Thr Thr Phe Val Asp
        1010                1015                1020

Asn Asp Asp Phe Asp Phe Asn Asp Glu Leu Ser Lys Trp Trp Asn
        1025                1030                1035

Asp Thr Lys His Glu Leu Pro Asp Phe Asp Lys Phe Asn Tyr Thr
        1040                1045                1050

Val Pro Ile Leu Asp Ile Asp Ser Glu Ile Asp Arg Ile Gln Gly
```

```
                    1055                1060                1065

Val Ile Gln Gly Leu Asn Asp Ser Leu Ile Asp Leu Glu Lys Leu
        1070                1075                1080

Ser Ile Leu Lys Thr Tyr Ile Lys Trp Pro Trp Tyr Val Trp Leu
        1085                1090                1095

Ala Ile Ala Phe Ala Thr Ile Ile Phe Ile Leu Ile Leu Gly Trp
        1100                1105                1110

Val Phe Phe Met Thr Gly Cys Cys Gly Cys Cys Cys Gly Cys Phe
        1115                1120                1125

Gly Ile Met Pro Leu Met Ser Lys Cys Gly Lys Lys Ser Ser Tyr
        1130                1135                1140

Tyr Thr Thr Phe Asp Asn Asp Val Val Thr Glu Gln Tyr Arg Pro
        1145                1150                1155

Lys Lys Ser Val
        1160

<210> SEQ ID NO 10
<211> LENGTH: 17
<212> TYPE: PRT
<213> ORGANISM: Infectious Bronchitis Virus

<400> SEQUENCE: 10

Met Leu Val Thr Pro Leu Leu Leu Val Thr Leu Leu Cys Ala Leu Cys
1               5                   10                  15

Ser

<210> SEQ ID NO 11
<211> LENGTH: 515
<212> TYPE: PRT
<213> ORGANISM: Infectious Bronchitis Virus

<400> SEQUENCE: 11

Ala Ala Leu Tyr Asp Ser Ser Ser Tyr Val Tyr Tyr Tyr Gln Ser Ala
1               5                   10                  15

Phe Arg Pro Pro Asp Gly Trp His Leu His Gly Gly Ala Tyr Ala Val
                20                  25                  30

Val Asn Ile Ser Ser Glu Ser Asn Asn Ala Gly Ser Ser Ser Gly Cys
            35                  40                  45

Thr Val Gly Ile Ile His Gly Gly Arg Val Val Asn Ala Ser Ser Ile
        50                  55                  60

Ala Met Thr Ala Pro Ser Ser Gly Met Ala Trp Ser Ser Ser Gln Phe
65                  70                  75                  80

Cys Thr Ala Tyr Cys Asn Phe Ser Asp Thr Thr Val Phe Val Thr His
                85                  90                  95

Cys Tyr Lys His Val Gly Cys Pro Ile Thr Gly Met Leu Gln Gln His
            100                 105                 110

Ser Ile Arg Val Ser Ala Met Lys Asn Gly Gln Leu Phe Tyr Asn Leu
        115                 120                 125

Thr Val Ser Val Ala Lys Tyr Pro Thr Phe Lys Ser Phe Gln Cys Val
    130                 135                 140

Asn Asn Leu Thr Ser Val Tyr Leu Asn Gly Asp Leu Val Tyr Thr Ser
145                 150                 155                 160

Asn Glu Thr Thr Asp Val Thr Ser Ala Gly Val Tyr Phe Lys Ala Gly
                165                 170                 175

Gly Pro Ile Thr Tyr Lys Val Met Arg Glu Val Arg Ala Leu Ala Tyr
            180                 185                 190
```

```
Phe Val Asn Gly Thr Ala Gln Asp Val Ile Leu Cys Asp Gly Ser Pro
            195                 200                 205

Arg Gly Leu Leu Ala Cys Gln Tyr Asn Thr Gly Asn Phe Ser Asp Gly
        210                 215                 220

Phe Tyr Pro Phe Thr Asn Ser Ser Leu Val Lys Gln Lys Phe Ile Val
225                 230                 235                 240

Tyr Arg Glu Asn Ser Val Asn Thr Thr Phe Thr Leu His Asn Phe Thr
                245                 250                 255

Phe His Asn Glu Thr Gly Ala Asn Pro Asn Pro Ser Gly Val Gln Asn
            260                 265                 270

Ile Gln Thr Tyr Gln Thr Gln Thr Ala Gln Ser Gly Tyr Tyr Asn Phe
        275                 280                 285

Asn Phe Ser Phe Leu Ser Ser Phe Val Tyr Lys Glu Ser Asn Phe Met
290                 295                 300

Tyr Gly Ser Tyr His Pro Ser Cys Asn Phe Arg Leu Glu Thr Ile Asn
305                 310                 315                 320

Asn Gly Leu Trp Phe Asn Ser Leu Ser Val Ser Ile Ala Tyr Gly Pro
                325                 330                 335

Leu Gln Gly Gly Cys Lys Gln Ser Val Phe Ser Gly Arg Ala Thr Cys
            340                 345                 350

Cys Tyr Ala Tyr Ser Tyr Gly Gly Pro Leu Leu Cys Lys Gly Val Tyr
        355                 360                 365

Ser Gly Glu Leu Asp His Asn Phe Glu Cys Gly Leu Leu Val Tyr Val
370                 375                 380

Thr Lys Ser Gly Gly Ser Arg Ile Gln Thr Ala Thr Glu Pro Pro Val
385                 390                 395                 400

Ile Thr Gln His Asn Tyr Asn Asn Ile Thr Leu Asn Thr Cys Val Asp
                405                 410                 415

Tyr Asn Ile Tyr Gly Arg Thr Gly Gln Gly Phe Ile Thr Asn Val Thr
            420                 425                 430

Asp Ser Ala Val Ser Tyr Asn Tyr Leu Ala Asp Ala Gly Leu Ala Ile
        435                 440                 445

Leu Asp Thr Ser Gly Ser Ile Asp Ile Phe Val Val Gln Ser Glu Tyr
450                 455                 460

Gly Leu Asn Tyr Tyr Lys Val Asn Pro Cys Glu Asp Val Asn Gln Gln
465                 470                 475                 480

Phe Val Val Ser Gly Gly Lys Leu Val Gly Ile Leu Thr Ser Arg Asn
                485                 490                 495

Glu Thr Gly Ser Gln Leu Leu Glu Asn Gln Phe Tyr Ile Lys Ile Thr
            500                 505                 510

Asn Gly Thr
        515

<210> SEQ ID NO 12
<211> LENGTH: 5
<212> TYPE: PRT
<213> ORGANISM: Infectious Bronchitis Virus

<400> SEQUENCE: 12

Arg Arg Phe Arg Arg
1               5

<210> SEQ ID NO 13
<211> LENGTH: 554
<212> TYPE: PRT
```

<213> ORGANISM: Infectious Bronchitis Virus

<400> SEQUENCE: 13

```
Ser Ile Thr Glu Ser Val Glu Asn Cys Pro Tyr Val Ser Tyr Gly Lys
  1               5                  10                  15

Phe Cys Ile Lys Pro Asp Gly Ser Ile Ala Thr Ile Val Pro Lys Gln
             20                  25                  30

Leu Glu Gln Phe Val Ala Pro Leu Leu Asn Val Thr Glu Asn Val Leu
         35                  40                  45

Ile Pro Asn Ser Phe Asn Leu Thr Val Thr Asp Glu Tyr Ile Gln Thr
 50                  55                  60

Arg Met Asp Lys Val Gln Ile Asn Cys Leu Gln Tyr Ile Cys Gly Asn
 65                  70                  75                  80

Ser Leu Glu Cys Arg Asn Leu Phe Gln Gln Tyr Gly Pro Val Cys Asp
                 85                  90                  95

Asn Ile Leu Ser Val Val Asn Ser Val Gly Gln Lys Glu Asp Met Glu
            100                 105                 110

Leu Leu Asn Phe Tyr Ser Ser Thr Lys Pro Ala Gly Phe Asn Thr Pro
        115                 120                 125

Val Leu Ser Asn Val Ser Thr Gly Glu Phe Asn Ile Ser Leu Phe Leu
130                 135                 140

Thr Thr Pro Ser Ser Pro Arg Arg Arg Ser Phe Ile Glu Asp Leu Leu
145                 150                 155                 160

Phe Thr Ser Val Glu Ser Val Gly Leu Pro Thr Asp Asp Ala Tyr Lys
                165                 170                 175

Asn Cys Thr Ala Gly Pro Leu Gly Phe Leu Lys Asp Leu Val Cys Ala
            180                 185                 190

Arg Glu Tyr Asn Gly Leu Leu Val Leu Pro Pro Ile Ile Thr Ala Glu
        195                 200                 205

Met Gln Thr Leu Tyr Thr Ser Ser Leu Val Ala Ser Met Ala Phe Gly
210                 215                 220

Gly Ile Thr Ala Ala Gly Ala Ile Pro Phe Ala Thr Gln Leu Gln Ala
225                 230                 235                 240

Arg Ile Asn His Leu Gly Ile Thr Gln Ser Leu Leu Leu Lys Asn Gln
                245                 250                 255

Glu Lys Ile Ala Ala Ser Phe Asn Lys Ala Ile Gly His Met Gln Glu
            260                 265                 270

Gly Phe Arg Ser Thr Ser Leu Ala Leu Gln Gln Ile Gln Asp Val Val
        275                 280                 285

Asn Lys Gln Ser Ala Ile Leu Thr Glu Thr Met Ala Ser Leu Asn Lys
290                 295                 300

Asn Phe Gly Ala Ile Ser Ser Val Ile Gln Glu Ile Tyr Gln Gln Leu
305                 310                 315                 320

Asp Ala Ile Gln Ala Asn Ala Gln Val Asp Arg Leu Ile Thr Gly Arg
                325                 330                 335

Leu Ser Ser Leu Ser Val Leu Ala Ser Ala Lys Gln Ala Glu Tyr Ile
            340                 345                 350

Arg Val Ser Gln Gln Arg Glu Leu Ala Thr Gln Lys Ile Asn Glu Cys
        355                 360                 365

Val Lys Ser Gln Ser Ile Arg Tyr Ser Phe Cys Gly Asn Gly Arg His
370                 375                 380

Val Leu Thr Ile Pro Gln Asn Ala Pro Asn Gly Ile Val Phe Ile His
385                 390                 395                 400
```

```
Phe Ser Tyr Thr Pro Asp Ser Phe Val Asn Val Thr Ala Ile Val Gly
                405                 410                 415

Phe Cys Val Lys Pro Ala Asn Ala Ser Gln Tyr Ala Ile Val Pro Ala
            420                 425                 430

Asn Gly Arg Gly Ile Phe Ile Gln Val Asn Gly Ser Tyr Tyr Ile Thr
        435                 440                 445

Ala Arg Asp Met Tyr Met Pro Arg Ala Ile Thr Ala Gly Asp Ile Val
    450                 455                 460

Thr Leu Thr Ser Cys Gln Val Asn Tyr Val Ser Val Asn Lys Thr Val
465                 470                 475                 480

Ile Thr Thr Phe Val Asp Asn Asp Phe Asp Phe Asn Asp Glu Leu
                485                 490                 495

Ser Lys Trp Trp Asn Asp Thr Lys His Glu Leu Pro Asp Phe Asp Lys
            500                 505                 510

Phe Asn Tyr Thr Val Pro Ile Leu Asp Ile Asp Ser Glu Ile Asp Arg
        515                 520                 525

Ile Gln Gly Val Ile Gln Gly Leu Asn Asp Ser Leu Ile Asp Leu Glu
    530                 535                 540

Lys Leu Ser Ile Leu Lys Thr Tyr Ile Lys
545                 550

<210> SEQ ID NO 14
<211> LENGTH: 67
<212> TYPE: PRT
<213> ORGANISM: Infectious Bronchitis Virus

<400> SEQUENCE: 14

Val Trp Leu Ala Ile Ala Phe Ala Thr Ile Ile Phe Ile Leu Ile Leu
1               5                   10                  15

Gly Trp Val Phe Phe Met Thr Gly Cys Cys Gly Cys Cys Cys Gly Cys
            20                  25                  30

Phe Gly Ile Met Pro Leu Met Ser Lys Cys Gly Lys Lys Ser Ser Tyr
        35                  40                  45

Tyr Thr Thr Phe Asp Asn Asp Val Val Thr Glu Gln Tyr Arg Pro Lys
    50                  55                  60

Lys Ser Val
65

<210> SEQ ID NO 15
<211> LENGTH: 20
<212> TYPE: PRT
<213> ORGANISM: Infectious Bronchitis Virus

<400> SEQUENCE: 15

Val Trp Leu Ala Ile Ala Phe Ala Thr Ile Ile Phe Ile Leu Ile Leu
1               5                   10                  15

Gly Trp Val Phe
            20

<210> SEQ ID NO 16
<211> LENGTH: 47
<212> TYPE: PRT
<213> ORGANISM: Infectious Bronchitis Virus

<400> SEQUENCE: 16

Phe Met Thr Gly Cys Cys Gly Cys Cys Cys Gly Cys Phe Gly Ile Met
1               5                   10                  15

Pro Leu Met Ser Lys Cys Gly Lys Lys Ser Ser Tyr Tyr Thr Thr Phe
```

```
                  20                  25                  30
Asp Asn Asp Val Val Thr Glu Gln Tyr Arg Pro Lys Lys Ser Val
            35                  40                  45

<210> SEQ ID NO 17
<211> LENGTH: 1165
<212> TYPE: PRT
<213> ORGANISM: Infectious Bronchititis Virus

<400> SEQUENCE: 17

Met Leu Val Lys Ser Leu Phe Leu Val Thr Ile Leu Cys Ala Leu Cys
1               5                   10                  15

Ser Ala Asn Leu Phe Asp Ser Asp Asn Asn Tyr Val Tyr Tyr Tyr Gln
            20                  25                  30

Ser Ala Phe Arg Pro Pro Asn Gly Trp His Leu Gln Gly Gly Ala Tyr
        35                  40                  45

Ala Val Val Asn Ser Thr Asn Tyr Thr Asn Asn Ala Gly Ser Ala His
    50                  55                  60

Gln Cys Thr Val Gly Val Ile Lys Asp Val Tyr Asn Gln Ser Val Ala
65                  70                  75                  80

Ser Ile Ala Met Lys Ala Pro Leu Gln Gly Met Ala Trp Ser Lys Ser
                85                  90                  95

Gln Phe Cys Ser Ala His Cys Asn Phe Ser Glu Ile Thr Val Phe Val
            100                 105                 110

Thr His Cys Tyr Ser Ser Gly Ser Gly Ser Cys Pro Ile Thr Gly Met
        115                 120                 125

Ile Pro Arg Asp His Ile Arg Ile Ser Ala Met Lys Asn Gly Ser Leu
    130                 135                 140

Phe Tyr Asn Leu Thr Val Ser Val Ser Lys Tyr Pro Asn Phe Lys Ser
145                 150                 155                 160

Phe Gln Cys Val Asn Asn Phe Thr Ser Val Tyr Leu Asn Gly Asp Leu
                165                 170                 175

Val Phe Thr Ser Asn Lys Thr Thr Asp Val Thr Ser Ala Gly Val Tyr
            180                 185                 190

Phe Lys Ala Gly Gly Pro Val Asn Tyr Ser Ile Met Lys Glu Phe Lys
        195                 200                 205

Val Leu Ala Tyr Phe Val Asn Gly Thr Ala Gln Asp Val Val Leu Cys
    210                 215                 220

Asp Asn Ser Pro Lys Gly Leu Leu Ala Cys Gln Tyr Asn Thr Gly Asn
225                 230                 235                 240

Phe Ser Asp Gly Phe Tyr Pro Phe Thr Asn Ser Thr Leu Val Arg Glu
                245                 250                 255

Lys Phe Ile Val Tyr Arg Glu Ser Ser Val Asn Thr Ile Leu Ala Leu
            260                 265                 270

Thr Asn Phe Thr Phe Thr Asn Val Ser Asn Ala Gln Pro Asn Ser Gly
        275                 280                 285

Gly Val Asn Thr Phe His Leu Tyr Gln Thr Gln Thr Ala Gln Ser Gly
    290                 295                 300

Tyr Tyr Asn Phe Asn Leu Ser Phe Leu Ser Gln Phe Val Tyr Lys Ala
305                 310                 315                 320

Ser Asp Phe Met Tyr Gly Ser Tyr His Pro Ser Cys Ser Phe Arg Pro
                325                 330                 335

Glu Thr Ile Asn Ser Gly Leu Trp Phe Asn Ser Leu Ser Val Ser Leu
            340                 345                 350
```

```
Thr Tyr Gly Pro Leu Gln Gly Gly Cys Lys Gln Ser Val Phe Ser Gly
        355                 360                 365

Lys Ala Thr Cys Cys Tyr Ala Tyr Ser Tyr Lys Gly Pro Met Ala Cys
    370                 375                 380

Lys Gly Val Tyr Ser Phe Gln Leu Ser Thr Asn Phe Glu Cys Gly Leu
385                 390                 395                 400

Leu Val Tyr Val Thr Lys Ser Asp Gly Ser Arg Ile Gln Thr Arg Thr
                405                 410                 415

Glu Pro Leu Val Leu Thr Gln Tyr Asn Tyr Asn Asn Ile Thr Leu Asp
                420                 425                 430

Lys Cys Val Ala Tyr Asn Ile Tyr Gly Arg Val Gly Gln Gly Phe Ile
            435                 440                 445

Thr Asn Val Thr Asp Ser Ala Ala Asn Phe Ser Tyr Leu Ala Asp Gly
        450                 455                 460

Gly Leu Ala Ile Leu Asp Thr Ser Gly Ala Ile Asp Val Phe Val Val
465                 470                 475                 480

Gln Gly Ile Tyr Gly Leu Asn Tyr Tyr Lys Val Asn Pro Cys Glu Asp
                485                 490                 495

Val Asn Gln Gln Phe Val Val Ser Gly Gly Asn Ile Val Gly Ile Leu
            500                 505                 510

Thr Ser Arg Asn Glu Thr Gly Ser Glu Gln Val Glu Asn Gln Phe Tyr
        515                 520                 525

Val Lys Leu Thr Asn Ser Ser His Arg Arg Arg Ser Ile Gly Gln
    530                 535                 540

Asn Val Thr Ser Cys Pro Tyr Val Ser Tyr Gly Arg Phe Cys Ile Glu
545                 550                 555                 560

Pro Asp Gly Ser Leu Lys Met Ile Val Pro Glu Glu Leu Lys Gln Phe
                565                 570                 575

Val Ala Pro Leu Leu Asn Ile Thr Glu Ser Val Leu Ile Pro Asn Ser
            580                 585                 590

Phe Asn Leu Thr Val Thr Asp Glu Tyr Ile Gln Thr Arg Met Asp Lys
        595                 600                 605

Val Gln Ile Asn Cys Leu Gln Tyr Val Cys Gly Asn Ser Leu Glu Cys
    610                 615                 620

Arg Lys Leu Phe Gln Gln Tyr Gly Pro Val Cys Asp Asn Ile Leu Ser
625                 630                 635                 640

Val Val Asn Ser Val Ser Gln Lys Glu Asp Met Glu Leu Leu Ser Phe
                645                 650                 655

Tyr Ser Ser Thr Lys Pro Lys Gly Tyr Asp Thr Pro Val Leu Ser Asn
            660                 665                 670

Val Ser Thr Gly Glu Phe Asn Ile Ser Leu Leu Leu Lys Pro Pro Ser
        675                 680                 685

Ser Pro Ser Gly Arg Ser Phe Ile Glu Asp Leu Leu Phe Thr Ser Val
    690                 695                 700

Glu Thr Val Gly Leu Pro Thr Asp Ala Glu Tyr Lys Lys Cys Thr Ala
705                 710                 715                 720

Gly Pro Leu Gly Thr Leu Lys Asp Leu Ile Cys Ala Arg Glu Tyr Asn
                725                 730                 735

Gly Leu Leu Val Leu Pro Pro Ile Ile Thr Ala Asp Met Gln Thr Met
            740                 745                 750

Tyr Thr Ala Ser Leu Val Gly Ala Met Ala Phe Gly Gly Ile Thr Ser
        755                 760                 765

Ala Ala Ala Ile Pro Phe Ala Thr Gln Ile Gln Ala Arg Ile Asn His
```

```
                770             775             780
Leu Gly Ile Thr Gln Ser Leu Leu Met Lys Asn Gln Glu Lys Ile Ala
785                 790                 795                 800

Ala Ser Phe Asn Lys Ala Ile Gly His Met Gln Glu Gly Phe Arg Ser
            805                 810                 815

Thr Ser Leu Ala Leu Gln Gln Ile Gln Asp Val Val Asn Lys Gln Ser
            820                 825                 830

Ala Ile Leu Thr Glu Thr Met Asn Ser Leu Asn Lys Asn Phe Gly Ala
            835                 840                 845

Ile Thr Ser Val Ile Gln Asp Ile Tyr Ala Gln Leu Asp Ala Ile Gln
850                 855                 860

Ala Asp Ala Gln Val Asp Arg Leu Ile Thr Gly Arg Leu Ser Thr Leu
865                 870                 875                 880

Ser Val Leu Ala Phe Ala Lys Gln Ser Glu Tyr Ile Arg Val Ser Gln
                885                 890                 895

Gln Arg Glu Leu Ala Thr Gln Lys Ile Asn Glu Cys Val Lys Ser Gln
                900                 905                 910

Ser Asn Arg Tyr Gly Phe Cys Gly Ser Gly Arg His Val Leu Ser Ile
                915                 920                 925

Pro Gln Asn Ala Pro Asn Gly Ile Val Phe Ile His Phe Thr Tyr Thr
            930                 935                 940

Pro Glu Ser Phe Val Asn Val Thr Ala Ile Val Gly Phe Cys Val Asn
945                 950                 955                 960

Pro Ala Asn Ala Ser Gln Tyr Ala Ile Val Pro Ala Asn Gly Arg Gly
                965                 970                 975

Ile Phe Ile Gln Val Asn Gly Thr Tyr Tyr Ile Thr Ala Arg Asp Met
            980                 985                 990

Tyr Met Pro Arg Asp Ile Thr Ala Gly Asp Ile Val Thr Leu Thr Ser
            995                 1000                1005

Cys Gln Ala Asn Tyr Val Asn Val Asn Lys Thr Val Ile Thr Thr
    1010                1015                1020

Phe Val Glu Asp Asp Asp Phe Asp Phe Asp Asp Glu Leu Ser Lys
    1025                1030                1035

Trp Trp Asn Asp Thr Lys His Gln Leu Pro Asp Phe Asp Asp Phe
    1040                1045                1050

Asn Tyr Thr Val Pro Ile Leu Asn Ile Ser Gly Glu Ile Asp Tyr
    1055                1060                1065

Ile Gln Gly Val Ile Gln Gly Leu Asn Asp Ser Leu Ile Asn Leu
    1070                1075                1080

Glu Glu Leu Ser Ile Ile Lys Thr Tyr Ile Lys Trp Pro Trp Tyr
    1085                1090                1095

Val Trp Leu Ala Ile Gly Phe Ala Ile Ile Ile Phe Ile Leu Ile
    1100                1105                1110

Leu Gly Trp Val Phe Phe Met Thr Gly Cys Cys Gly Cys Cys Cys
    1115                1120                1125

Gly Cys Phe Gly Ile Ile Pro Leu Met Ser Lys Cys Gly Lys Lys
    1130                1135                1140

Ser Ser Tyr Tyr Thr Thr Phe Asp Asn Asp Val Val Thr Glu Gln
    1145                1150                1155

Tyr Arg Pro Lys Lys Ser Val
    1160                1165

<210> SEQ ID NO 18
```

<211> LENGTH: 17
<212> TYPE: PRT
<213> ORGANISM: Infectious Bronchitis Virus

<400> SEQUENCE: 18

Met Leu Val Lys Ser Leu Phe Leu Val Thr Ile Leu Cys Ala Leu Cys
1               5                   10                  15

Ser

<210> SEQ ID NO 19
<211> LENGTH: 519
<212> TYPE: PRT
<213> ORGANISM: Infectious Bronchitis Virus

<400> SEQUENCE: 19

Ala Asn Leu Phe Asp Ser Asp Asn Asn Tyr Val Tyr Tyr Gln Ser
1               5                   10                  15

Ala Phe Arg Pro Pro Asn Gly Trp His Leu Gln Gly Gly Ala Tyr Ala
                20                  25                  30

Val Val Asn Ser Thr Asn Tyr Thr Asn Asn Ala Gly Ser Ala His Gln
            35                  40                  45

Cys Thr Val Gly Val Ile Lys Asp Val Tyr Asn Gln Ser Val Ala Ser
        50                  55                  60

Ile Ala Met Lys Ala Pro Leu Gln Gly Met Ala Trp Ser Lys Ser Gln
65                  70                  75                  80

Phe Cys Ser Ala His Cys Asn Phe Ser Glu Ile Thr Val Phe Val Thr
                85                  90                  95

His Cys Tyr Ser Ser Gly Ser Gly Ser Cys Pro Ile Thr Gly Met Ile
            100                 105                 110

Pro Arg Asp His Ile Arg Ile Ser Ala Met Lys Asn Gly Ser Leu Phe
        115                 120                 125

Tyr Asn Leu Thr Val Ser Val Ser Lys Tyr Pro Asn Phe Lys Ser Phe
130                 135                 140

Gln Cys Val Asn Asn Phe Thr Ser Val Tyr Leu Asn Gly Asp Leu Val
145                 150                 155                 160

Phe Thr Ser Asn Lys Thr Thr Asp Val Thr Ser Ala Gly Val Tyr Phe
                165                 170                 175

Lys Ala Gly Gly Pro Val Asn Tyr Ser Ile Met Lys Glu Phe Lys Val
            180                 185                 190

Leu Ala Tyr Phe Val Asn Gly Thr Ala Gln Asp Val Val Leu Cys Asp
        195                 200                 205

Asn Ser Pro Lys Gly Leu Leu Ala Cys Gln Tyr Asn Thr Gly Asn Phe
    210                 215                 220

Ser Asp Gly Phe Tyr Pro Phe Thr Asn Ser Thr Leu Val Arg Glu Lys
225                 230                 235                 240

Phe Ile Val Tyr Arg Glu Ser Ser Val Asn Thr Ile Leu Ala Leu Thr
                245                 250                 255

Asn Phe Thr Phe Thr Asn Val Ser Asn Ala Gln Pro Asn Ser Gly Gly
            260                 265                 270

Val Asn Thr Phe His Leu Tyr Gln Thr Gln Thr Ala Gln Ser Gly Tyr
        275                 280                 285

Tyr Asn Phe Asn Leu Ser Phe Leu Ser Gln Phe Val Tyr Lys Ala Ser
    290                 295                 300

Asp Phe Met Tyr Gly Ser Tyr His Pro Ser Cys Ser Phe Arg Pro Glu
305                 310                 315                 320

Thr Ile Asn Ser Gly Leu Trp Phe Asn Ser Leu Ser Val Ser Leu Thr
            325                 330                 335

Tyr Gly Pro Leu Gln Gly Gly Cys Lys Gln Ser Val Phe Ser Gly Lys
        340                 345                 350

Ala Thr Cys Cys Tyr Ala Tyr Ser Tyr Lys Gly Pro Met Ala Cys Lys
    355                 360                 365

Gly Val Tyr Ser Phe Gln Leu Ser Thr Asn Phe Glu Cys Gly Leu Leu
370                 375                 380

Val Tyr Val Thr Lys Ser Asp Gly Ser Arg Ile Gln Thr Arg Thr Glu
385                 390                 395                 400

Pro Leu Val Leu Thr Gln Tyr Asn Tyr Asn Asn Ile Thr Leu Asp Lys
                405                 410                 415

Cys Val Ala Tyr Asn Ile Tyr Gly Arg Val Gly Gln Gly Phe Ile Thr
            420                 425                 430

Asn Val Thr Asp Ser Ala Ala Asn Phe Ser Tyr Leu Ala Asp Gly Gly
        435                 440                 445

Leu Ala Ile Leu Asp Thr Ser Gly Ala Ile Asp Val Phe Val Val Gln
    450                 455                 460

Gly Ile Tyr Gly Leu Asn Tyr Tyr Lys Val Asn Pro Cys Glu Asp Val
465                 470                 475                 480

Asn Gln Gln Phe Val Val Ser Gly Gly Asn Ile Val Gly Ile Leu Thr
                485                 490                 495

Ser Arg Asn Glu Thr Gly Ser Glu Gln Val Glu Asn Gln Phe Tyr Val
            500                 505                 510

Lys Leu Thr Asn Ser Ser His
        515

<210> SEQ ID NO 20
<211> LENGTH: 5
<212> TYPE: PRT
<213> ORGANISM: Infectious Bronchitis Virus

<400> SEQUENCE: 20

His Arg Arg Arg Arg
1               5

<210> SEQ ID NO 21
<211> LENGTH: 554
<212> TYPE: PRT
<213> ORGANISM: Infectious Bronchitis Virus

<400> SEQUENCE: 21

Ser Ile Gly Gln Asn Val Thr Ser Cys Pro Tyr Val Ser Tyr Gly Arg
1               5                   10                  15

Phe Cys Ile Glu Pro Asp Gly Ser Leu Lys Met Ile Val Pro Glu Glu
            20                  25                  30

Leu Lys Gln Phe Val Ala Pro Leu Leu Asn Ile Thr Glu Ser Val Leu
        35                  40                  45

Ile Pro Asn Ser Phe Asn Leu Thr Val Thr Asp Glu Tyr Ile Gln Thr
    50                  55                  60

Arg Met Asp Lys Val Gln Ile Asn Cys Leu Gln Tyr Val Cys Gly Asn
65                  70                  75                  80

Ser Leu Glu Cys Arg Lys Leu Phe Gln Gln Tyr Gly Pro Val Cys Asp
                85                  90                  95

Asn Ile Leu Ser Val Val Asn Ser Val Ser Gln Lys Glu Asp Met Glu
            100                 105                 110

-continued

```
Leu Leu Ser Phe Tyr Ser Ser Thr Lys Pro Lys Gly Tyr Asp Thr Pro
            115                 120                 125

Val Leu Ser Asn Val Ser Thr Gly Glu Phe Asn Ile Ser Leu Leu Leu
        130                 135                 140

Lys Pro Pro Ser Ser Pro Ser Gly Arg Ser Phe Ile Glu Asp Leu Leu
145                 150                 155                 160

Phe Thr Ser Val Glu Thr Val Gly Leu Pro Thr Asp Ala Glu Tyr Lys
                165                 170                 175

Lys Cys Thr Ala Gly Pro Leu Gly Thr Leu Lys Asp Leu Ile Cys Ala
            180                 185                 190

Arg Glu Tyr Asn Gly Leu Leu Val Leu Pro Pro Ile Ile Thr Ala Asp
        195                 200                 205

Met Gln Thr Met Tyr Thr Ala Ser Leu Val Gly Ala Met Ala Phe Gly
    210                 215                 220

Gly Ile Thr Ser Ala Ala Ile Pro Phe Ala Thr Gln Ile Gln Ala
225                 230                 235                 240

Arg Ile Asn His Leu Gly Ile Thr Gln Ser Leu Leu Met Lys Asn Gln
                245                 250                 255

Glu Lys Ile Ala Ala Ser Phe Asn Lys Ala Ile Gly His Met Gln Glu
            260                 265                 270

Gly Phe Arg Ser Thr Ser Leu Ala Leu Gln Gln Ile Gln Asp Val Val
        275                 280                 285

Asn Lys Gln Ser Ala Ile Leu Thr Glu Thr Met Asn Ser Leu Asn Lys
    290                 295                 300

Asn Phe Gly Ala Ile Thr Ser Val Ile Gln Asp Ile Tyr Ala Gln Leu
305                 310                 315                 320

Asp Ala Ile Gln Ala Asp Ala Gln Val Asp Arg Leu Ile Thr Gly Arg
                325                 330                 335

Leu Ser Thr Leu Ser Val Leu Ala Phe Ala Lys Gln Ser Glu Tyr Ile
            340                 345                 350

Arg Val Ser Gln Gln Arg Glu Leu Ala Thr Gln Lys Ile Asn Glu Cys
        355                 360                 365

Val Lys Ser Gln Ser Asn Arg Tyr Gly Phe Cys Gly Ser Gly Arg His
    370                 375                 380

Val Leu Ser Ile Pro Gln Asn Ala Pro Asn Gly Ile Val Phe Ile His
385                 390                 395                 400

Phe Thr Tyr Thr Pro Glu Ser Phe Val Asn Val Thr Ala Ile Val Gly
                405                 410                 415

Phe Cys Val Asn Pro Ala Asn Ala Ser Gln Tyr Ala Ile Val Pro Ala
            420                 425                 430

Asn Gly Arg Gly Ile Phe Ile Gln Val Asn Gly Thr Tyr Tyr Ile Thr
        435                 440                 445

Ala Arg Asp Met Tyr Met Pro Arg Asp Ile Thr Ala Gly Asp Ile Val
    450                 455                 460

Thr Leu Thr Ser Cys Gln Ala Asn Tyr Val Asn Val Asn Lys Thr Val
465                 470                 475                 480

Ile Thr Thr Phe Val Glu Asp Asp Phe Asp Phe Asp Asp Glu Leu
                485                 490                 495

Ser Lys Trp Trp Asn Asp Thr Lys His Gln Leu Pro Asp Phe Asp Asp
            500                 505                 510

Phe Asn Tyr Thr Val Pro Ile Leu Asn Ile Ser Gly Glu Ile Asp Tyr
        515                 520                 525

Ile Gln Gly Val Ile Gln Gly Leu Asn Asp Ser Leu Ile Asn Leu Glu
```

```
                530                 535                 540
Glu Leu Ser Ile Ile Lys Thr Tyr Ile Lys
545                 550

<210> SEQ ID NO 22
<211> LENGTH: 67
<212> TYPE: PRT
<213> ORGANISM: Infectious Bronchitis Virus

<400> SEQUENCE: 22

Val Trp Leu Ala Ile Gly Phe Ala Ile Ile Ile Phe Ile Leu Ile Leu
1               5                   10                  15

Gly Trp Val Phe Phe Met Thr Gly Cys Cys Gly Cys Cys Cys Gly Cys
            20                  25                  30

Phe Gly Ile Ile Pro Leu Met Ser Lys Cys Gly Lys Lys Ser Ser Tyr
        35                  40                  45

Tyr Thr Thr Phe Asp Asn Asp Val Val Thr Glu Gln Tyr Arg Pro Lys
    50                  55                  60

Lys Ser Val
65

<210> SEQ ID NO 23
<211> LENGTH: 20
<212> TYPE: PRT
<213> ORGANISM: Infectious Bronchitis Virus

<400> SEQUENCE: 23

Val Trp Leu Ala Ile Gly Phe Ala Ile Ile Phe Ile Leu Ile Leu
1               5                   10                  15

Gly Trp Val Phe
            20

<210> SEQ ID NO 24
<211> LENGTH: 47
<212> TYPE: PRT
<213> ORGANISM: Infectious Bronchitis Virus

<400> SEQUENCE: 24

Phe Met Thr Gly Cys Cys Gly Cys Cys Cys Gly Cys Phe Gly Ile Ile
1               5                   10                  15

Pro Leu Met Ser Lys Cys Gly Lys Lys Ser Ser Tyr Tyr Thr Thr Phe
            20                  25                  30

Asp Asn Asp Val Val Thr Glu Gln Tyr Arg Pro Lys Lys Ser Val
        35                  40                  45

<210> SEQ ID NO 25
<211> LENGTH: 1165
<212> TYPE: PRT
<213> ORGANISM: Infectious Bronchitis Virus

<400> SEQUENCE: 25

Met Leu Val Lys Ser Leu Phe Leu Val Thr Ile Leu Cys Ala Leu Cys
1               5                   10                  15

Ser Ala Asn Leu Phe Asp Ser Asp Asn Asn Tyr Val Tyr Tyr Tyr Gln
            20                  25                  30

Ser Ala Phe Arg Pro Pro Asn Gly Trp His Leu Gln Gly Gly Ala Tyr
        35                  40                  45

Ala Val Val Asn Ser Thr Asn Tyr Thr Asn Asn Ala Gly Ser Ala His
    50                  55                  60
```

```
Glu Cys Thr Val Gly Val Ile Lys Asp Val Tyr Asn Gln Ser Val Ala
 65                  70                  75                  80

Ser Ile Ala Met Thr Ala Pro Leu Gln Gly Met Ala Trp Ser Lys Ser
                 85                  90                  95

Gln Phe Cys Ser Ala His Cys Asn Phe Ser Glu Ile Thr Val Phe Val
            100                 105                 110

Thr His Cys Tyr Ser Ser Gly Ser Gly Ser Cys Pro Ile Thr Gly Met
            115                 120                 125

Ile Pro Arg Asp His Ile Arg Ile Ser Ala Met Lys Asn Gly Ser Leu
        130                 135                 140

Phe Tyr Asn Leu Thr Val Ser Val Ser Lys Tyr Pro Asn Phe Lys Ser
145                 150                 155                 160

Phe Gln Cys Val Asn Asn Phe Thr Ser Val Tyr Leu Asn Gly Asp Leu
            165                 170                 175

Val Phe Thr Ser Asn Lys Thr Thr Asp Val Thr Ser Ala Gly Val Tyr
            180                 185                 190

Phe Lys Ala Gly Gly Pro Val Asn Tyr Ser Ile Met Lys Glu Phe Lys
        195                 200                 205

Val Leu Ala Tyr Phe Val Asn Gly Thr Ala Gln Asp Val Val Leu Cys
210                 215                 220

Asp Asn Ser Pro Lys Gly Leu Leu Ala Cys Gln Tyr Asn Thr Gly Asn
225                 230                 235                 240

Phe Ser Asp Gly Phe Tyr Pro Phe Thr Asn Ser Thr Leu Val Arg Glu
                245                 250                 255

Lys Phe Ile Val Tyr Arg Glu Ser Ser Val Asn Thr Thr Leu Ala Leu
            260                 265                 270

Thr Asn Phe Thr Phe Thr Asn Val Ser Asn Ala Gln Pro Asn Ser Gly
        275                 280                 285

Gly Val Asn Thr Phe His Leu Tyr Gln Thr Gln Thr Ala Gln Ser Gly
        290                 295                 300

Tyr Tyr Asn Phe Asn Leu Ser Phe Leu Ser Gln Phe Val Tyr Lys Ala
305                 310                 315                 320

Ser Asp Phe Met Tyr Gly Ser Tyr His Pro Ser Cys Ser Phe Arg Pro
                325                 330                 335

Glu Thr Ile Asn Ser Gly Leu Trp Phe Asn Ser Leu Ser Val Ser Leu
            340                 345                 350

Thr Tyr Gly Pro Leu Gln Gly Gly Cys Lys Gln Ser Val Phe Ser Gly
        355                 360                 365

Lys Ala Thr Cys Cys Tyr Ala Tyr Ser Tyr Lys Gly Pro Met Ala Cys
370                 375                 380

Lys Gly Val Tyr Ser Gly Glu Leu Ser Thr Asn Phe Glu Cys Gly Leu
385                 390                 395                 400

Leu Val Tyr Val Thr Lys Ser Asp Gly Ser Arg Ile Gln Thr Arg Thr
                405                 410                 415

Glu Pro Leu Val Leu Thr Gln Tyr Asn Tyr Asn Asn Ile Thr Leu Asp
            420                 425                 430

Lys Cys Val Ala Tyr Asn Ile Tyr Gly Arg Val Gly Gln Gly Phe Ile
        435                 440                 445

Thr Asn Val Thr Asp Ser Ala Ala Asn Phe Ser Tyr Leu Ala Asp Gly
        450                 455                 460

Gly Leu Ala Ile Leu Asp Thr Ser Gly Ala Ile Asp Val Phe Val Val
465                 470                 475                 480

Gln Gly Ile Tyr Gly Leu Asn Tyr Tyr Lys Val Asn Pro Cys Glu Asp
```

```
            485                 490                 495
Val Asn Gln Gln Phe Val Val Ser Gly Gly Asn Ile Val Gly Ile Leu
                500                 505                 510

Thr Ser Arg Asn Glu Thr Gly Ser Glu Gln Val Glu Asn Gln Phe Tyr
                515                 520                 525

Val Lys Leu Thr Asn Ser Ser His Arg Arg Arg Ser Ile Gly Gln
                530                 535                 540

Asn Val Thr Ser Cys Pro Tyr Val Ser Tyr Gly Arg Phe Cys Ile Glu
545                 550                 555                 560

Pro Asp Gly Ser Leu Lys Met Ile Val Pro Glu Leu Lys Gln Phe
                565                 570                 575

Val Ala Pro Leu Leu Asn Ile Thr Glu Ser Val Leu Ile Pro Asn Ser
                580                 585                 590

Phe Asn Leu Thr Val Thr Asp Glu Tyr Ile Gln Thr Arg Met Asp Lys
                595                 600                 605

Val Gln Ile Asn Cys Leu Gln Tyr Val Cys Gly Asn Ser Leu Glu Cys
                610                 615                 620

Arg Lys Leu Phe Gln Gln Tyr Gly Pro Val Cys Asp Asn Ile Leu Ser
625                 630                 635                 640

Val Val Asn Ser Val Ser Gln Lys Glu Asp Met Glu Leu Leu Ser Phe
                645                 650                 655

Tyr Ser Ser Thr Lys Pro Lys Gly Tyr Asp Thr Pro Val Leu Ser Asn
                660                 665                 670

Val Ser Thr Gly Glu Phe Asn Ile Ser Leu Leu Leu Lys Pro Pro Ser
                675                 680                 685

Ser Pro Ser Gly Arg Ser Phe Ile Glu Asp Leu Leu Phe Thr Ser Val
                690                 695                 700

Glu Thr Val Gly Leu Pro Thr Asp Ala Glu Tyr Lys Lys Cys Thr Ala
705                 710                 715                 720

Gly Pro Leu Gly Thr Leu Lys Asp Leu Ile Cys Ala Arg Glu Tyr Asn
                725                 730                 735

Gly Leu Leu Val Leu Pro Pro Ile Ile Thr Ala Asp Met Gln Thr Met
                740                 745                 750

Tyr Thr Ala Ser Leu Val Gly Ala Met Ala Phe Gly Gly Ile Thr Ser
                755                 760                 765

Ala Ala Ala Ile Pro Phe Ala Thr Gln Ile Gln Ala Arg Ile Asn His
                770                 775                 780

Leu Gly Ile Thr Gln Ser Leu Leu Met Lys Asn Gln Glu Lys Ile Ala
785                 790                 795                 800

Ala Ser Phe Asn Lys Ala Ile Gly His Met Gln Glu Gly Phe Arg Ser
                805                 810                 815

Thr Ser Leu Ala Leu Gln Gln Ile Gln Asp Val Val Asn Lys Gln Ser
                820                 825                 830

Ala Ile Leu Thr Glu Thr Met Asn Ser Leu Asn Lys Asn Phe Gly Ala
                835                 840                 845

Ile Thr Ser Val Ile Gln Asp Ile Tyr Ala Gln Leu Asp Ala Ile Gln
                850                 855                 860

Ala Asp Ala Gln Val Asp Arg Leu Ile Thr Gly Arg Leu Ser Ser Leu
865                 870                 875                 880

Ser Val Leu Ala Ser Ala Lys Gln Ser Glu Tyr Ile Arg Val Ser Gln
                885                 890                 895

Gln Arg Glu Leu Ala Thr Gln Lys Ile Asn Glu Cys Val Lys Ser Gln
                900                 905                 910
```

Ser Asn Arg Tyr Gly Phe Cys Gly Ser Gly Arg His Val Leu Ser Ile
        915                 920                 925

Pro Gln Asn Ala Pro Asn Gly Ile Val Phe Ile His Phe Thr Tyr Thr
        930                 935                 940

Pro Glu Ser Phe Val Asn Val Thr Ala Ile Val Gly Phe Cys Val Asn
945                 950                 955                 960

Pro Ala Asn Ala Ser Gln Tyr Ala Ile Val Pro Ala Asn Gly Arg Gly
        965                 970                 975

Ile Phe Ile Gln Val Asn Gly Thr Tyr Tyr Ile Thr Ala Arg Asp Met
        980                 985                 990

Tyr Met Pro Arg Asp Ile Thr Ala  Gly Asp Ile Val Thr  Leu Thr Ser
        995                1000               1005

Cys Gln  Ala Asn Tyr Val Asn  Val Asn Lys Thr Val  Ile Thr Thr
    1010                1015               1020

Phe Val  Glu Asp Asp Asp Phe  Asp Phe Asp Glu  Leu Ser Lys
    1025                1030               1035

Trp Trp  Asn Asp Thr Lys His  Gln Leu Pro Asp Phe  Asp Asp Phe
    1040                1045               1050

Asn Tyr  Thr Val Pro Ile Leu  Asn Ile Ser Gly Glu  Ile Asp Tyr
    1055                1060               1065

Ile Gln  Gly Val Ile Gln Gly  Leu Asn Asp Ser Leu  Ile Asn Leu
    1070                1075               1080

Glu Glu  Leu Ser Ile Ile Lys  Thr Tyr Ile Lys Trp  Pro Trp Tyr
    1085                1090               1095

Val Trp  Leu Ala Ile Gly Phe  Ala Ile Ile Ile Phe  Ile Leu Ile
    1100                1105               1110

Leu Gly  Trp Val Phe Phe Met  Thr Gly Cys Cys Gly  Cys Cys Cys
    1115                1120               1125

Gly Cys  Phe Gly Ile Ile Pro  Leu Met Ser Lys Cys  Gly Lys Lys
    1130                1135               1140

Ser Ser  Tyr Tyr Thr Thr Phe  Asp Asn Asp Val  Thr Glu Gln
    1145                1150               1155

Tyr Arg  Pro Lys Lys Ser Val
    1160                1165

<210> SEQ ID NO 26
<211> LENGTH: 17
<212> TYPE: PRT
<213> ORGANISM: Infectious Bronchitis Virus

<400> SEQUENCE: 26

Met Leu Val Lys Ser Leu Phe Leu Val Thr Ile Leu Cys Ala Leu Cys
1               5                 10                15

Ser

<210> SEQ ID NO 27
<211> LENGTH: 518
<212> TYPE: PRT
<213> ORGANISM: Infectious Bronchitis Virus

<400> SEQUENCE: 27

Ala Asn Leu Phe Asp Ser Asp Asn Asn Tyr Val Tyr Tyr Tyr Gln Ser
1               5                 10                15

Ala Phe Arg Pro Pro Asn Gly Trp His Leu Gln Gly Gly Ala Tyr Ala
         20                 25                30

-continued

```
Val Val Asn Ser Thr Asn Tyr Thr Asn Asn Ala Gly Ser Ala His Glu
         35                  40                  45
Cys Thr Val Gly Val Ile Lys Asp Val Tyr Asn Gln Ser Val Ala Ser
 50                  55                  60
Ile Ala Met Thr Ala Pro Leu Gln Gly Met Ala Trp Ser Lys Ser Gln
 65                  70                  75                  80
Phe Cys Ser Ala His Cys Asn Phe Ser Glu Ile Thr Val Phe Val Thr
                 85                  90                  95
His Cys Tyr Ser Ser Gly Ser Gly Ser Cys Pro Ile Thr Gly Met Ile
                100                 105                 110
Pro Arg Asp His Ile Arg Ile Ser Ala Met Lys Asn Gly Ser Leu Phe
                115                 120                 125
Tyr Asn Leu Thr Val Ser Val Ser Lys Tyr Pro Asn Phe Lys Ser Phe
130                 135                 140
Gln Cys Val Asn Asn Phe Thr Ser Val Tyr Leu Asn Gly Asp Leu Val
145                 150                 155                 160
Phe Thr Ser Asn Lys Thr Thr Asp Val Thr Ser Ala Gly Val Tyr Phe
                165                 170                 175
Lys Ala Gly Gly Pro Val Asn Tyr Ser Ile Met Lys Glu Phe Lys Val
                180                 185                 190
Leu Ala Tyr Phe Val Asn Gly Thr Ala Gln Asp Val Val Leu Cys Asp
            195                 200                 205
Asn Ser Pro Lys Gly Leu Leu Ala Cys Gln Tyr Asn Thr Gly Asn Phe
            210                 215                 220
Ser Asp Gly Phe Tyr Pro Phe Thr Asn Ser Thr Leu Val Arg Glu Lys
225                 230                 235                 240
Phe Ile Val Tyr Arg Glu Ser Ser Val Asn Thr Thr Leu Ala Leu Thr
                245                 250                 255
Asn Phe Thr Phe Thr Asn Val Ser Asn Ala Gln Pro Asn Ser Gly Gly
            260                 265                 270
Val Asn Thr Phe His Leu Tyr Gln Thr Gln Thr Ala Gln Ser Gly Tyr
            275                 280                 285
Tyr Asn Phe Asn Leu Ser Phe Leu Ser Gln Phe Val Tyr Lys Ala Ser
            290                 295                 300
Asp Phe Met Tyr Gly Ser Tyr His Pro Ser Cys Ser Phe Arg Pro Glu
305                 310                 315                 320
Thr Ile Asn Ser Gly Leu Trp Phe Asn Ser Leu Ser Val Ser Leu Thr
                325                 330                 335
Tyr Gly Pro Leu Gln Gly Gly Cys Lys Gln Ser Val Phe Ser Gly Lys
            340                 345                 350
Ala Thr Cys Cys Tyr Ala Tyr Ser Tyr Lys Gly Pro Met Ala Cys Lys
            355                 360                 365
Gly Val Tyr Ser Gly Glu Leu Ser Thr Asn Phe Glu Cys Gly Leu Leu
            370                 375                 380
Val Tyr Val Thr Lys Ser Asp Gly Ser Arg Ile Gln Thr Arg Thr Glu
385                 390                 395                 400
Pro Leu Val Leu Thr Gln Tyr Asn Tyr Asn Asn Ile Thr Leu Asp Lys
                405                 410                 415
Cys Val Ala Tyr Asn Ile Tyr Gly Arg Val Gly Gln Gly Phe Ile Thr
            420                 425                 430
Asn Val Thr Asp Ser Ala Ala Asn Phe Ser Tyr Leu Ala Asp Gly Gly
            435                 440                 445
Leu Ala Ile Leu Asp Thr Ser Gly Ala Ile Asp Val Phe Val Val Gln
```

```
            450                 455                 460
Gly Ile Tyr Gly Leu Asn Tyr Tyr Lys Val Asn Pro Cys Glu Asp Val
465                 470                 475                 480

Asn Gln Gln Phe Val Val Ser Gly Gly Asn Ile Val Gly Ile Leu Thr
                485                 490                 495

Ser Arg Asn Glu Thr Gly Ser Glu Gln Val Glu Asn Gln Phe Tyr Val
                500                 505                 510

Lys Leu Thr Asn Ser Ser
            515

<210> SEQ ID NO 28
<211> LENGTH: 5
<212> TYPE: PRT
<213> ORGANISM: Infectious Bronchitis Virus

<400> SEQUENCE: 28

His Arg Arg Arg Arg
1               5

<210> SEQ ID NO 29
<211> LENGTH: 554
<212> TYPE: PRT
<213> ORGANISM: Infectious Bronchitis Virus

<400> SEQUENCE: 29

Ser Ile Gly Gln Asn Val Thr Ser Cys Pro Tyr Val Ser Tyr Gly Arg
1               5                   10                  15

Phe Cys Ile Glu Pro Asp Gly Ser Leu Lys Met Ile Val Pro Glu Glu
                20                  25                  30

Leu Lys Gln Phe Val Ala Pro Leu Leu Asn Ile Thr Glu Ser Val Leu
            35                  40                  45

Ile Pro Asn Ser Phe Asn Leu Thr Val Thr Asp Glu Tyr Ile Gln Thr
        50                  55                  60

Arg Met Asp Lys Val Gln Ile Asn Cys Leu Gln Tyr Val Cys Gly Asn
65                  70                  75                  80

Ser Leu Glu Cys Arg Lys Leu Phe Gln Gln Tyr Gly Pro Val Cys Asp
                85                  90                  95

Asn Ile Leu Ser Val Val Asn Ser Val Ser Gln Lys Glu Asp Met Glu
                100                 105                 110

Leu Leu Ser Phe Tyr Ser Ser Thr Lys Pro Lys Gly Tyr Asp Thr Pro
            115                 120                 125

Val Leu Ser Asn Val Ser Thr Gly Glu Phe Asn Ile Ser Leu Leu Leu
        130                 135                 140

Lys Pro Pro Ser Ser Pro Ser Gly Arg Ser Phe Ile Glu Asp Leu Leu
145                 150                 155                 160

Phe Thr Ser Val Glu Thr Val Gly Leu Pro Thr Asp Ala Glu Tyr Lys
                165                 170                 175

Lys Cys Thr Ala Gly Pro Leu Gly Thr Leu Lys Asp Leu Ile Cys Ala
                180                 185                 190

Arg Glu Tyr Asn Gly Leu Leu Val Leu Pro Pro Ile Ile Thr Ala Asp
            195                 200                 205

Met Gln Thr Met Tyr Thr Ala Ser Leu Val Gly Ala Met Ala Phe Gly
        210                 215                 220

Gly Ile Thr Ser Ala Ala Ala Ile Pro Phe Ala Thr Gln Ile Gln Ala
225                 230                 235                 240

Arg Ile Asn His Leu Gly Ile Thr Gln Ser Leu Leu Met Lys Asn Gln
```

```
            245                 250                 255
Glu Lys Ile Ala Ala Ser Phe Asn Lys Ala Ile Gly His Met Gln Glu
            260                 265                 270

Gly Phe Arg Ser Thr Ser Leu Ala Leu Gln Gln Ile Gln Asp Val Val
        275                 280                 285

Asn Lys Gln Ser Ala Ile Leu Thr Glu Thr Met Asn Ser Leu Asn Lys
    290                 295                 300

Asn Phe Gly Ala Ile Thr Ser Val Ile Gln Asp Ile Tyr Ala Gln Leu
305                 310                 315                 320

Asp Ala Ile Gln Ala Asp Ala Gln Val Asp Arg Leu Ile Thr Gly Arg
                325                 330                 335

Leu Ser Ser Leu Ser Val Leu Ala Ser Ala Lys Gln Ser Glu Tyr Ile
            340                 345                 350

Arg Val Ser Gln Gln Arg Glu Leu Ala Thr Gln Lys Ile Asn Glu Cys
        355                 360                 365

Val Lys Ser Gln Ser Asn Arg Tyr Gly Phe Cys Gly Ser Gly Arg His
    370                 375                 380

Val Leu Ser Ile Pro Gln Asn Ala Pro Asn Gly Ile Val Phe Ile His
385                 390                 395                 400

Phe Thr Tyr Thr Pro Glu Ser Phe Val Asn Val Thr Ala Ile Val Gly
                405                 410                 415

Phe Cys Val Asn Pro Ala Asn Ala Ser Gln Tyr Ala Ile Val Pro Ala
            420                 425                 430

Asn Gly Arg Gly Ile Phe Ile Gln Val Asn Gly Thr Tyr Tyr Ile Thr
        435                 440                 445

Ala Arg Asp Met Tyr Met Pro Arg Asp Ile Thr Ala Gly Asp Ile Val
    450                 455                 460

Thr Leu Thr Ser Cys Gln Ala Asn Tyr Val Asn Val Asn Lys Thr Val
465                 470                 475                 480

Ile Thr Thr Phe Val Glu Asp Asp Phe Asp Phe Asp Asp Glu Leu
                485                 490                 495

Ser Lys Trp Trp Asn Asp Thr Lys His Gln Leu Pro Asp Phe Asp Asp
            500                 505                 510

Phe Asn Tyr Thr Val Pro Ile Leu Asn Ile Ser Gly Glu Ile Asp Tyr
        515                 520                 525

Ile Gln Gly Val Ile Gln Gly Leu Asn Asp Ser Leu Ile Asn Leu Glu
    530                 535                 540

Glu Leu Ser Ile Ile Lys Thr Tyr Ile Lys
545                 550

<210> SEQ ID NO 30
<211> LENGTH: 67
<212> TYPE: PRT
<213> ORGANISM: Infectious Bronchitis Virus

<400> SEQUENCE: 30

Val Trp Leu Ala Ile Gly Phe Ala Ile Ile Phe Ile Leu Ile Leu
1               5                   10                  15

Gly Trp Val Phe Phe Met Thr Gly Cys Cys Gly Cys Cys Cys Gly Cys
            20                  25                  30

Phe Gly Ile Ile Pro Leu Met Ser Lys Cys Gly Lys Lys Ser Ser Tyr
        35                  40                  45

Tyr Thr Thr Phe Asp Asn Asp Val Val Thr Glu Gln Tyr Arg Pro Lys
    50                  55                  60
```

Lys Ser Val
65

<210> SEQ ID NO 31
<211> LENGTH: 20
<212> TYPE: PRT
<213> ORGANISM: Infectious Bronchitis Virus

<400> SEQUENCE: 31

Val Trp Leu Ala Ile Gly Phe Ala Ile Ile Ile Phe Ile Leu Ile Leu
1               5                   10                  15

Gly Trp Val Phe
            20

<210> SEQ ID NO 32
<211> LENGTH: 47
<212> TYPE: PRT
<213> ORGANISM: Infectious Bronchitis Virus

<400> SEQUENCE: 32

Phe Met Thr Gly Cys Cys Gly Cys Cys Cys Gly Cys Phe Gly Ile Ile
1               5                   10                  15

Pro Leu Met Ser Lys Cys Gly Lys Lys Ser Ser Tyr Tyr Thr Thr Phe
            20                  25                  30

Asp Asn Asp Val Val Thr Glu Gln Tyr Arg Pro Lys Lys Ser Val
        35                  40                  45

<210> SEQ ID NO 33
<211> LENGTH: 1165
<212> TYPE: PRT
<213> ORGANISM: Infectious Bronchitis Virus

<400> SEQUENCE: 33

Met Leu Val Lys Pro Leu Phe Ile Val Thr Ala Leu Leu Ser Leu Cys
1               5                   10                  15

Ser Gly Asn Leu Phe Asp Ser Asn Asn Thr Tyr Val Tyr Tyr Tyr Gln
            20                  25                  30

Ser Ala Phe Arg Pro Phe Asp Gly Trp His Val Gln Gly Gly Ala Tyr
        35                  40                  45

Ala Val Ser Ser Val Phe Asn Arg Ser Asn Asn Ala Asn Ser His Thr
    50                  55                  60

Cys Ser Val Gly Thr Leu Gly Pro Ser Tyr Asn Tyr Ser Gly Ala Ala
65                  70                  75                  80

Val Ala Met Thr Ala Pro His Ser Gly Met Asn Trp Ser Lys Asp Gln
                85                  90                  95

Phe Cys Thr Ala His Cys Asn Phe Ser Asp Ile Phe Val Tyr Val Thr
            100                 105                 110

His Cys Tyr Ala Asn Asn Cys Val Leu Val Asn Asn Ile Gly Gln Gly
        115                 120                 125

Asn Ile Tyr Ile Gly Ala Lys Arg Asn Gly Glu Ser Ile Phe Asn Lys
    130                 135                 140

Ile Leu Ser Val Thr Ser Tyr Pro Lys Phe Met Ser Leu His Cys Val
145                 150                 155                 160

Asn Asn Ala Thr Ser Val Tyr Leu Asn Gly Asn Leu Val Phe Thr Ser
                165                 170                 175

Asn Gln Thr Ala Ser Val Thr Gly Ala Gly Val Tyr Phe Lys Ala Gly
            180                 185                 190

Gly Pro Ile Thr Tyr Lys Val Met Lys Asp Phe Pro Val Leu Ala Tyr

```
                195                 200                 205
Phe Lys Asn Gly Thr Val His Asp Val Ile Leu Cys Asp Ser Thr Pro
210                 215                 220

Lys Gly Leu Leu Ala Cys Gln Tyr Asn Thr Gly Asn Phe Thr Asp Gly
225                 230                 235                 240

Leu Tyr Pro Phe Thr Asn Val Thr Glu Ser Lys Glu Lys Phe Ile Val
                245                 250                 255

Tyr Gly Glu Ser Ser Val Thr Thr Leu Leu Thr Leu Thr Asn Tyr Thr
                260                 265                 270

Phe Tyr Asn Val Ser Asn Ala Pro Pro Ala Gly Ala Tyr Val Glu Asn
                275                 280                 285

Phe Val Lys Tyr Gln Thr Gln Thr Ala Gln Glu Gly Phe Tyr Asn Phe
290                 295                 300

Asn Phe Thr Phe Leu Gln Asp Ser Arg Phe Gln Tyr Val Pro Ser Asp
305                 310                 315                 320

Tyr Asp Arg Gly Ser Tyr His Lys Ala Cys Asp Phe Arg Leu Glu Ser
                325                 330                 335

Ile Asn Asn Asn Leu Trp Phe Asn Ser Leu Ser Val Ser Leu Thr Tyr
                340                 345                 350

Gly Pro Ile Gln Gly Gly Cys Lys Gln Ser Val Phe Ser Tyr Lys Thr
                355                 360                 365

Thr Cys Cys Tyr Ala Tyr Ser Tyr Asn Gly Pro Ile Glu Cys Ser Gly
370                 375                 380

Val Tyr Asn Gly Tyr Arg Thr His Lys Tyr Glu Cys Gly Leu Leu Val
385                 390                 395                 400

Tyr Val Ser Met Thr Lys Gly Ser Arg Ile Gln Thr Ser Asn Val Val
                405                 410                 415

Pro Thr Val Thr Gln Tyr Asn Tyr Asn Asn Ile Thr Leu Asp Thr Cys
                420                 425                 430

Val Asp Tyr Ser Ile Tyr Gly Lys Val Gly Gln Gly Phe Ile Thr Asn
                435                 440                 445

Val Thr Asp Gln Leu Ser Ser Asn Asn Tyr Leu Asp Gln Gly Gly Leu
                450                 455                 460

Ala Ile Leu Asp Thr Ser Gly Ala Ile Asp Ile Phe Val Val Asn Gly
465                 470                 475                 480

Ser Ser Gly Arg Asn Tyr Tyr Lys Ile Asn Pro Cys Ser Asp Val Asn
                485                 490                 495

Gln Gln Phe Val Val Ser Gly Gly Asn Ile Val Gly Ile Leu Thr Leu
                500                 505                 510

Leu Asn Lys Thr Gly Ser Gln Gln Val Glu Asp Gln Phe Phe Val Lys
                515                 520                 525

Leu Val Ser Gly Ser His Arg Lys Lys Arg Ser Val Ser Thr Leu Pro
                530                 535                 540

Thr Val Lys Asn Cys Pro Tyr Thr Ala Tyr Gly Lys Phe Cys Phe Asn
545                 550                 555                 560

Pro Asp Gly Glu Phe Tyr Glu Ile Thr Pro Ala Glu Ile Glu Thr Tyr
                565                 570                 575

Ser Ser Pro Leu Leu Asn Val Ser Gly Phe Val Leu Ile Pro Asp Thr
                580                 585                 590

Phe Asn Leu Thr Val Thr Asp Glu Tyr Ile Gln Thr Phe Met Glu Lys
                595                 600                 605

Ile Gln Ile Asn Cys Ile Gln Tyr Val Cys Gly Asn Ser Ile Glu Cys
                610                 615                 620
```

```
Lys Lys Leu Phe Gln Gln Tyr Gly Pro Val Cys Asp Asn Ile Leu Asn
625                 630                 635                 640

Ile Val Tyr Ser Leu Ala Gln Gln Asp Asn Met Glu Phe Leu Gln Phe
            645                 650                 655

Tyr Ser Ala Thr Lys Pro Lys Gly Phe Asp Thr Ile Ile Phe Asn Asn
            660                 665                 670

Val Ser Thr Asp Gly Phe Asn Leu Ser Leu Val Leu Arg Gln Pro Ser
            675                 680                 685

Ser Pro Arg Gly Arg Ser Phe Ile Glu Asp Leu Leu Phe Thr Lys Val
690                 695                 700

Glu Ser Leu Gly Leu Pro Gly Asp Thr Ala Tyr Gln Lys Cys Thr Ala
705                 710                 715                 720

Gly Pro Leu Gly Phe Val Lys Asp Leu Val Cys Ala Gln His Tyr Asn
            725                 730                 735

Gly Leu Leu Val Leu Pro Pro Ile Ile Thr Ala Glu Met Gln Thr Met
            740                 745                 750

Tyr Thr Ala Ser Leu Val Ala Ser Met Ala Phe Gly Gly Ile Thr Ser
            755                 760                 765

Ala Gly Ala Ile Pro Phe Ala Thr Gln Ile Gln Ala Arg Ile Asn His
770                 775                 780

Leu Gly Ile Thr Gln Thr Val Leu Gln Lys Asn Gln Glu Lys Ile Ala
785                 790                 795                 800

Ala Ser Phe Asn Lys Ala Met Ala His Met Gln Asp Gly Phe Arg Ala
            805                 810                 815

Thr Ser Leu Ala Leu Gln Gln Ile Gln Asp Val Leu Asn Arg Gln Gly
            820                 825                 830

Ser Val Leu Gln Asp Ala Met Asn Ser Leu Asn Lys Asn Phe Gly Ala
            835                 840                 845

Ile Ser Ser Val Ile Gln Asp Ile Tyr Ser Arg Leu Asp Thr Leu Glu
850                 855                 860

Ala Asn Thr Gln Val Asp Arg Leu Ile Ser Gly Arg Leu Ser Ser Leu
865                 870                 875                 880

Ser Val Leu Ala Ser Ala Lys Gln Ala Glu Tyr Ala Lys Val Ser Gln
            885                 890                 895

Gln Arg Glu Leu Ala Lys Gln Lys Ile Asn Glu Cys Val Lys Ser Gln
            900                 905                 910

Ser Ser Arg Leu Gly Phe Cys Gly Ala Gly Arg His Val Leu Thr Ile
            915                 920                 925

Pro Gln Asn Ala Pro Asn Gly Ile Leu Leu Leu His Phe Thr Tyr Thr
            930                 935                 940

Pro Glu Thr Phe Lys Asn Val Thr Ala Val Val Gly Phe Cys Val Lys
945                 950                 955                 960

Pro Glu Asn Gly Ser Glu Tyr Ala Ile Val Pro Ala Asn Gly Arg Gly
            965                 970                 975

Ile Phe Ile Gln Val Asn Gly Thr Tyr Tyr Ile Thr Ala Arg Asp Met
            980                 985                 990

Tyr Met Pro Arg Ser Ile Thr Ala Gly Asp Ile Val Thr Leu Thr Ser
            995                 1000                1005

Cys Gln Ala Asn Tyr Val Asn Val Asn Lys Thr Val Ile Thr Thr
        1010                1015                1020

Phe Val Asp Glu Asp Asp Phe Asp Phe Asn Asp Glu Leu Ser Lys
        1025                1030                1035
```

```
Trp Trp Asn Glu Thr Lys His Glu Phe Pro Asp Phe Asp Gln Phe
    1040                1045                1050

Asn Tyr Thr Ile Pro Val Leu Asn Ile Thr Tyr Asp Ile Asp Lys
    1055                1060                1065

Ile Glu Glu Val Ile Lys Gly Leu Asn Asp Ser Leu Ile Asp Leu
    1070                1075                1080

Glu Thr Leu Ser Ile Leu Lys Thr Tyr Ile Lys Trp Pro Trp Tyr
    1085                1090                1095

Val Trp Leu Ala Ile Ala Phe Ala Thr Ile Ile Phe Ile Leu Ile
    1100                1105                1110

Leu Gly Trp Val Phe Phe Met Thr Gly Cys Cys Gly Cys Tyr Cys
    1115                1120                1125

Gly Cys Phe Gly Ile Ile Pro Leu Met Ser Lys Cys Ser Lys Lys
    1130                1135                1140

Ser Ser Tyr Tyr Thr Thr Phe Asp Asn Asp Val Val Thr Glu Gln
    1145                1150                1155

Tyr Arg Pro Lys Lys Ser Val
    1160                1165

<210> SEQ ID NO 34
<211> LENGTH: 17
<212> TYPE: PRT
<213> ORGANISM: Infectious Bronchitis Virus

<400> SEQUENCE: 34

Met Leu Val Lys Pro Leu Phe Ile Val Thr Ala Leu Leu Ser Leu Cys
1               5                   10                  15

Ser

<210> SEQ ID NO 35
<211> LENGTH: 516
<212> TYPE: PRT
<213> ORGANISM: Infectious Bronchitis Virus

<400> SEQUENCE: 35

Gly Asn Leu Phe Asp Ser Asn Asn Thr Tyr Val Tyr Tyr Tyr Gln Ser
1               5                   10                  15

Ala Phe Arg Pro Phe Asp Gly Trp His Val Gln Gly Gly Ala Tyr Ala
                20                  25                  30

Val Ser Ser Val Phe Asn Arg Ser Asn Asn Ala Asn Ser His Thr Cys
            35                  40                  45

Ser Val Gly Thr Leu Gly Pro Ser Tyr Asn Tyr Ser Gly Ala Ala Val
        50                  55                  60

Ala Met Thr Ala Pro His Ser Gly Met Asn Trp Ser Lys Asp Gln Phe
65                  70                  75                  80

Cys Thr Ala His Cys Asn Phe Ser Asp Ile Phe Val Tyr Val Thr His
                85                  90                  95

Cys Tyr Ala Asn Asn Cys Val Leu Val Asn Asn Ile Gly Gln Gly Asn
                100                 105                 110

Ile Tyr Ile Gly Ala Lys Arg Asn Gly Glu Ser Ile Phe Asn Lys Ile
            115                 120                 125

Leu Ser Val Thr Ser Tyr Pro Lys Phe Met Ser Leu His Cys Val Asn
        130                 135                 140

Asn Ala Thr Ser Val Tyr Leu Asn Gly Asn Leu Val Phe Thr Ser Asn
145                 150                 155                 160

Gln Thr Ala Ser Val Thr Gly Ala Gly Val Tyr Phe Lys Ala Gly Gly
```

```
                  165                 170                 175
Pro Ile Thr Tyr Lys Val Met Lys Asp Phe Pro Val Leu Ala Tyr Phe
            180                 185                 190
Lys Asn Gly Thr Val His Asp Val Ile Leu Cys Asp Ser Thr Pro Lys
        195                 200                 205
Gly Leu Leu Ala Cys Gln Tyr Asn Thr Gly Asn Phe Thr Asp Gly Leu
    210                 215                 220
Tyr Pro Phe Thr Asn Val Thr Glu Ser Lys Glu Lys Phe Ile Val Tyr
225                 230                 235                 240
Gly Glu Ser Ser Val Thr Thr Leu Leu Thr Leu Thr Asn Tyr Thr Phe
                245                 250                 255
Tyr Asn Val Ser Asn Ala Pro Pro Ala Gly Ala Tyr Val Glu Asn Phe
            260                 265                 270
Val Lys Tyr Gln Thr Gln Thr Ala Gln Glu Gly Phe Tyr Asn Phe Asn
        275                 280                 285
Phe Thr Phe Leu Gln Asp Ser Arg Phe Gln Tyr Val Pro Ser Asp Tyr
    290                 295                 300
Asp Arg Gly Ser Tyr His Lys Ala Cys Asp Phe Arg Leu Glu Ser Ile
305                 310                 315                 320
Asn Asn Asn Leu Trp Phe Asn Ser Leu Ser Val Ser Leu Thr Tyr Gly
                325                 330                 335
Pro Ile Gln Gly Gly Cys Lys Gln Ser Val Phe Ser Tyr Lys Thr Thr
            340                 345                 350
Cys Cys Tyr Ala Tyr Ser Tyr Asn Gly Pro Ile Glu Cys Ser Gly Val
        355                 360                 365
Tyr Asn Gly Tyr Arg Thr His Lys Tyr Glu Cys Gly Leu Leu Val Tyr
    370                 375                 380
Val Ser Met Thr Lys Gly Ser Arg Ile Gln Thr Ser Asn Val Val Pro
385                 390                 395                 400
Thr Val Thr Gln Tyr Asn Tyr Asn Asn Ile Thr Leu Asp Thr Cys Val
                405                 410                 415
Asp Tyr Ser Ile Tyr Gly Lys Val Gly Gln Gly Phe Ile Thr Asn Val
            420                 425                 430
Thr Asp Gln Leu Ser Ser Asn Asn Tyr Leu Asp Gln Gly Gly Leu Ala
        435                 440                 445
Ile Leu Asp Thr Ser Gly Ala Ile Asp Ile Phe Val Val Asn Gly Ser
    450                 455                 460
Ser Gly Arg Asn Tyr Tyr Lys Ile Asn Pro Cys Ser Asp Val Asn Gln
465                 470                 475                 480
Gln Phe Val Val Ser Gly Gly Asn Ile Val Gly Ile Leu Thr Leu Leu
                485                 490                 495
Asn Lys Thr Gly Ser Gln Gln Val Glu Asp Gln Phe Phe Val Lys Leu
            500                 505                 510
Val Ser Gly Ser
        515

<210> SEQ ID NO 36
<211> LENGTH: 5
<212> TYPE: PRT
<213> ORGANISM: Infectious Bronchitis Virus

<400> SEQUENCE: 36

His Arg Lys Lys Arg
1               5
```

<210> SEQ ID NO 37
<211> LENGTH: 556
<212> TYPE: PRT
<213> ORGANISM: Infectious Brochitis Virus

<400> SEQUENCE: 37

```
Ser Val Ser Thr Leu Pro Thr Val Lys Asn Cys Pro Tyr Thr Ala Tyr
1               5                   10                  15

Gly Lys Phe Cys Phe Asn Pro Asp Gly Glu Phe Tyr Glu Ile Thr Pro
            20                  25                  30

Ala Glu Ile Glu Thr Tyr Ser Ser Pro Leu Leu Asn Val Ser Gly Phe
        35                  40                  45

Val Leu Ile Pro Asp Thr Phe Asn Leu Thr Val Thr Asp Glu Tyr Ile
    50                  55                  60

Gln Thr Phe Met Glu Lys Ile Gln Ile Asn Cys Ile Gln Tyr Val Cys
65                  70                  75                  80

Gly Asn Ser Ile Glu Cys Lys Lys Leu Phe Gln Gln Tyr Gly Pro Val
                85                  90                  95

Cys Asp Asn Ile Leu Asn Ile Val Tyr Ser Leu Ala Gln Gln Asp Asn
            100                 105                 110

Met Glu Phe Leu Gln Phe Tyr Ser Ala Thr Lys Pro Lys Gly Phe Asp
        115                 120                 125

Thr Ile Ile Phe Asn Asn Val Ser Thr Asp Gly Phe Asn Leu Ser Leu
    130                 135                 140

Val Leu Arg Gln Pro Ser Ser Pro Arg Gly Arg Ser Phe Ile Glu Asp
145                 150                 155                 160

Leu Leu Phe Thr Lys Val Glu Ser Leu Gly Leu Pro Gly Asp Thr Ala
                165                 170                 175

Tyr Gln Lys Cys Thr Ala Gly Pro Leu Gly Phe Val Lys Asp Leu Val
            180                 185                 190

Cys Ala Gln His Tyr Asn Gly Leu Leu Val Leu Pro Pro Ile Ile Thr
        195                 200                 205

Ala Glu Met Gln Thr Met Tyr Thr Ala Ser Leu Val Ala Ser Met Ala
    210                 215                 220

Phe Gly Gly Ile Thr Ser Ala Gly Ala Ile Pro Phe Ala Thr Gln Ile
225                 230                 235                 240

Gln Ala Arg Ile Asn His Leu Gly Ile Thr Gln Thr Val Leu Gln Lys
                245                 250                 255

Asn Gln Glu Lys Ile Ala Ala Ser Phe Asn Lys Ala Met Ala His Met
            260                 265                 270

Gln Asp Gly Phe Arg Ala Thr Ser Leu Ala Leu Gln Gln Ile Gln Asp
        275                 280                 285

Val Leu Asn Arg Gln Gly Ser Val Leu Gln Asp Ala Met Asn Ser Leu
    290                 295                 300

Asn Lys Asn Phe Gly Ala Ile Ser Ser Val Ile Gln Asp Ile Tyr Ser
305                 310                 315                 320

Arg Leu Asp Thr Leu Glu Ala Asn Thr Gln Val Asp Arg Leu Ile Ser
                325                 330                 335

Gly Arg Leu Ser Ser Leu Ser Val Leu Ala Ser Ala Lys Gln Ala Glu
            340                 345                 350

Tyr Ala Lys Val Ser Gln Gln Arg Glu Leu Ala Lys Gln Lys Ile Asn
        355                 360                 365

Glu Cys Val Lys Ser Gln Ser Ser Arg Leu Gly Phe Cys Gly Ala Gly
    370                 375                 380
```

```
Arg His Val Leu Thr Ile Pro Gln Asn Ala Pro Asn Gly Ile Leu Leu
385                 390                 395                 400

Leu His Phe Thr Tyr Thr Pro Glu Thr Phe Lys Asn Val Thr Ala Val
            405                 410                 415

Val Gly Phe Cys Val Lys Pro Gly Asn Gly Ser Glu Tyr Ala Ile Val
            420                 425                 430

Pro Ala Asn Gly Arg Gly Ile Phe Ile Gln Val Asn Gly Thr Tyr Tyr
            435                 440                 445

Ile Thr Ala Arg Asp Met Tyr Met Pro Arg Ser Ile Thr Ala Gly Asp
450                 455                 460

Ile Val Thr Leu Thr Ser Cys Gln Ala Asn Tyr Val Asn Val Asn Lys
465                 470                 475                 480

Thr Val Ile Thr Thr Phe Val Asp Glu Asp Asp Phe Asp Phe Asn Asp
                485                 490                 495

Glu Leu Ser Lys Trp Trp Asn Glu Thr Lys His Glu Phe Pro Asp Phe
            500                 505                 510

Asp Gln Phe Asn Tyr Thr Ile Pro Val Leu Asn Ile Thr Tyr Asp Ile
            515                 520                 525

Asp Lys Ile Glu Glu Val Ile Lys Gly Leu Asn Asp Ser Leu Ile Asp
            530                 535                 540

Leu Glu Thr Leu Ser Ile Leu Lys Thr Tyr Ile Lys
545                 550                 555

<210> SEQ ID NO 38
<211> LENGTH: 67
<212> TYPE: PRT
<213> ORGANISM: Infectious Bronchitis Virus

<400> SEQUENCE: 38

Val Trp Leu Ala Ile Ala Phe Ala Thr Ile Ile Phe Ile Leu Ile Leu
1               5                   10                  15

Gly Trp Val Phe Phe Met Thr Gly Cys Cys Gly Cys Tyr Cys Gly Cys
            20                  25                  30

Phe Gly Ile Ile Pro Leu Met Ser Lys Cys Ser Lys Lys Ser Ser Tyr
        35                  40                  45

Tyr Thr Thr Phe Asp Asn Asp Val Val Thr Glu Gln Tyr Arg Pro Lys
    50                  55                  60

Lys Ser Val
65

<210> SEQ ID NO 39
<211> LENGTH: 20
<212> TYPE: PRT
<213> ORGANISM: Infectious Bronchitis Virus

<400> SEQUENCE: 39

Val Trp Leu Ala Ile Ala Phe Ala Thr Ile Ile Phe Ile Leu Ile Leu
1               5                   10                  15

Gly Trp Val Phe
            20

<210> SEQ ID NO 40
<211> LENGTH: 47
<212> TYPE: PRT
<213> ORGANISM: Infectious Bronchitis Virus

<400> SEQUENCE: 40
```

-continued

```
Phe Met Thr Gly Cys Cys Gly Cys Tyr Cys Gly Cys Phe Gly Ile Ile
1               5                   10                  15
Pro Leu Met Ser Lys Cys Ser Lys Ser Ser Tyr Tyr Thr Thr Phe
            20                  25                  30
Asp Asn Asp Val Val Thr Glu Gln Tyr Arg Pro Lys Lys Ser Val
        35                  40                  45
```

<210> SEQ ID NO 41
<211> LENGTH: 1162
<212> TYPE: PRT
<213> ORGANISM: Infectious Bronchitis Virus

<400> SEQUENCE: 41

```
Met Leu Val Thr Pro Leu Leu Val Thr Leu Leu Cys Ala Leu Cys
1               5                   10                  15
Ser Ala Val Leu Tyr Asp Ser Ser Tyr Val Tyr Tyr Gln Ser
            20                  25                  30
Ala Phe Arg Pro Pro Ser Gly Trp His Leu Gln Gly Gly Ala Tyr Ala
            35                  40                  45
Val Val Asn Ile Ser Ser Glu Phe Asn Asn Ala Gly Ser Ser Ser Gly
        50                  55                  60
Cys Thr Val Gly Ile Ile His Gly Gly Arg Val Val Asn Ala Ser Ser
65                  70                  75                  80
Ile Ala Met Thr Ala Pro Ser Ser Gly Met Ala Trp Ser Ser Ser Gln
                85                  90                  95
Phe Cys Thr Ala His Cys Asn Phe Ser Asp Thr Thr Val Phe Val Thr
            100                 105                 110
His Cys Tyr Lys His Gly Gly Cys Pro Ile Thr Gly Met Leu Gln Gln
            115                 120                 125
Asn Phe Ile Arg Val Ser Ala Met Lys Asn Gly Gln Leu Phe Tyr Asn
        130                 135                 140
Leu Thr Val Ser Val Ala Lys Tyr Pro Thr Phe Arg Ser Phe Gln Cys
145                 150                 155                 160
Val Asn Asn Leu Thr Ser Val Tyr Leu Asn Gly Asp Leu Val Tyr Thr
                165                 170                 175
Ser Asn Glu Thr Ile Asp Val Thr Ser Ala Gly Val Tyr Phe Lys Ala
            180                 185                 190
Gly Gly Pro Ile Thr Tyr Lys Val Met Arg Glu Val Lys Ala Leu Ala
            195                 200                 205
Tyr Phe Val Asn Gly Thr Ala Gln Asp Val Ile Leu Cys Asp Gly Ser
        210                 215                 220
Pro Arg Gly Leu Leu Ala Cys Gln Tyr Asn Thr Gly Asn Phe Ser Asp
225                 230                 235                 240
Gly Phe Tyr Pro Phe Thr Asn Ser Ser Leu Val Lys Gln Lys Phe Ile
                245                 250                 255
Val Tyr Arg Glu Asn Ser Val Asn Thr Thr Cys Thr Leu His Asn Phe
            260                 265                 270
Ile Phe His Asn Glu Thr Gly Ala Asn Pro Asn Pro Ser Gly Val Gln
            275                 280                 285
Asn Ile Gln Thr Tyr Gln Thr Lys Thr Ala Gln Ser Gly Tyr Tyr Asn
        290                 295                 300
Phe Asn Phe Ser Phe Leu Ser Ser Phe Val Tyr Lys Glu Ser Asn Phe
305                 310                 315                 320
Met Tyr Gly Ser Tyr His Pro Ser Cys Lys Phe Arg Leu Glu Thr Ile
                325                 330                 335
```

```
Asn Asn Gly Leu Trp Phe Asn Ser Leu Ser Val Ser Ile Ala Tyr Gly
            340                 345                 350

Pro Leu Gln Gly Gly Cys Lys Gln Ser Val Phe Arg Gly Arg Ala Thr
            355                 360                 365

Cys Cys Tyr Ala Tyr Ser Tyr Gly Gly Pro Ser Leu Cys Lys Gly Val
370                 375                 380

Tyr Ser Gly Glu Leu Asp His Asn Phe Glu Cys Gly Leu Leu Val Tyr
385                 390                 395                 400

Val Thr Lys Ser Asp Gly Ser Arg Ile Gln Thr Ala Thr Glu Pro Pro
            405                 410                 415

Val Ile Thr Gln His Asn Tyr Asn Asn Ile Thr Leu Asn Thr Cys Val
            420                 425                 430

Asp Tyr Asn Ile Tyr Gly Arg Thr Gly Gln Gly Phe Ile Thr Asn Val
            435                 440                 445

Thr Asp Ser Ala Val Ser Tyr Asn Tyr Leu Ala Asp Ala Gly Leu Ala
    450                 455                 460

Ile Leu Asp Thr Ser Gly Ser Ile Asp Ile Phe Val Val Gln Gly Glu
465                 470                 475                 480

Tyr Gly Leu Asn Tyr Tyr Lys Val Asn Pro Cys Glu Asp Val Asn Gln
            485                 490                 495

Gln Phe Val Val Ser Gly Gly Lys Leu Val Gly Ile Leu Thr Ser Arg
                500                 505                 510

Asn Glu Thr Gly Ser Gln Leu Leu Glu Asn Gln Phe Tyr Ile Lys Ile
            515                 520                 525

Thr Asn Gly Thr Arg Arg Phe Arg Arg Ser Ile Thr Glu Asn Val Ala
    530                 535                 540

Asn Cys Pro Tyr Val Ser Tyr Gly Lys Phe Cys Ile Lys Pro Asp Gly
545                 550                 555                 560

Ser Ile Ala Thr Ile Val Pro Lys Gln Leu Glu Gln Phe Val Ala Pro
                565                 570                 575

Leu Phe Asn Val Thr Glu Asn Val Leu Ile Pro Asn Ser Phe Asn Leu
            580                 585                 590

Thr Val Thr Asp Glu Tyr Ile Gln Thr Arg Met Asp Lys Val Gln Ile
            595                 600                 605

Asn Cys Leu Gln Tyr Val Cys Gly Ser Ser Leu Asp Cys Arg Asn Leu
610                 615                 620

Phe Gln Gln Tyr Gly Pro Val Cys Asp Asn Ile Leu Ser Val Val Asn
625                 630                 635                 640

Ser Val Gly Gln Lys Glu Asp Met Glu Leu Leu Asn Phe Tyr Ser Ser
            645                 650                 655

Thr Lys Pro Ala Gly Phe Asn Thr Pro Val Leu Ser Asn Val Ser Thr
                660                 665                 670

Gly Glu Phe Asn Ile Ser Leu Leu Leu Thr Thr Pro Ser Ser Arg Arg
            675                 680                 685

Arg Arg Ser Val Ile Glu Asp Leu Leu Phe Thr Ser Val Glu Ser Val
            690                 695                 700

Gly Leu Pro Thr Asp Asp Ala Tyr Lys Asn Cys Thr Ala Gly Pro Leu
705                 710                 715                 720

Gly Phe Leu Lys Asp Leu Ala Cys Ala Arg Glu Tyr Asn Gly Leu Leu
            725                 730                 735

Val Leu Pro Pro Ile Ile Thr Ala Glu Met Gln Ala Leu Tyr Thr Ser
            740                 745                 750
```

-continued

Ser Leu Val Ala Ser Met Ala Phe Gly Gly Ile Thr Ala Gly Ala
        755                 760             765

Ile Pro Phe Ala Thr Gln Leu Gln Ala Arg Ile Asn His Leu Gly Ile
770             775                 780

Thr Gln Ser Leu Leu Lys Asn Gln Glu Lys Ile Ala Ala Ser Phe
785             790                 795                 800

Asn Lys Ala Ile Gly His Met Gln Glu Gly Phe Arg Ser Thr Ser Leu
            805                 810                 815

Ala Leu Gln Gln Ile Gln Asp Val Val Ser Lys Gln Ser Ala Ile Leu
            820                 825                 830

Thr Glu Thr Met Ala Ser Leu Asn Lys Asn Phe Gly Ala Ile Ser Ser
            835                 840                 845

Val Ile Gln Glu Ile Tyr Gln Gln Phe Asp Ala Ile Gln Ala Asn Ala
850                 855                 860

Gln Val Asp Arg Leu Ile Thr Gly Arg Leu Ser Ser Leu Ser Val Leu
865                 870                 875                 880

Ala Ser Ala Lys Gln Ala Glu Tyr Ile Arg Val Ser Gln Gln Arg Glu
            885                 890                 895

Leu Ala Thr Gln Lys Ile Asn Glu Cys Val Lys Ser Gln Ser Ile Arg
            900                 905                 910

Tyr Ser Phe Cys Gly Asn Gly Arg His Val Leu Thr Ile Pro Gln Asn
            915                 920                 925

Ala Pro Asn Gly Ile Val Phe Ile His Phe Ser Tyr Thr Pro Asp Ser
            930                 935                 940

Phe Val Asn Val Thr Ala Ile Val Gly Phe Cys Val Lys Pro Ala Asn
945                 950                 955                 960

Ala Ser Gln Tyr Ala Ile Val Pro Ala Asn Gly Arg Gly Ile Phe Ile
            965                 970                 975

Gln Val Asn Gly Ser Tyr Tyr Ile Thr Ala Arg Asp Met Tyr Met Pro
            980                 985                 990

Arg Ala Ile Thr Ala Gly Asp Val Val Thr Leu Thr Ser Cys Gln Ala
            995                 1000                1005

Asn Tyr Val Ile Val Asn Lys Thr Val Ile Thr Thr Phe Val Asp
    1010                1015                1020

Asn Asp Asp Phe Asp Phe Asn Asp Glu Leu Ser Lys Trp Trp Asn
    1025                1030                1035

Asp Thr Lys His Glu Leu Pro Asp Phe Asp Lys Phe Asn Tyr Thr
    1040                1045                1050

Val Pro Ile Leu Asp Ile Asp Ser Glu Ile Asp Arg Ile Gln Gly
    1055                1060                1065

Val Ile Gln Gly Leu Asn Asp Ser Leu Ile Asp Leu Glu Lys Leu
    1070                1075                1080

Ser Ile Leu Lys Thr Tyr Ile Lys Trp Pro Trp Tyr Val Trp Leu
    1085                1090                1095

Ala Ile Ala Phe Ala Thr Ile Ile Phe Ile Leu Ile Leu Gly Trp
    1100                1105                1110

Val Phe Phe Met Thr Gly Cys Cys Gly Cys Cys Cys Gly Cys Phe
    1115                1120                1125

Gly Ile Met Pro Leu Met Ser Lys Cys Gly Lys Lys Ser Ser Tyr
    1130                1135                1140

Tyr Thr Thr Phe Asp Asn Asp Val Val Thr Glu Gln Tyr Arg Pro
    1145                1150                1155

Lys Lys Ser Val

```
<210> SEQ ID NO 42
<211> LENGTH: 17
<212> TYPE: PRT
<213> ORGANISM: Infectious Bronchitis Virus

<400> SEQUENCE: 42

Met Leu Val Thr Pro Leu Leu Leu Val Thr Leu Leu Cys Ala Leu Cys
1               5                   10                  15

Ser

<210> SEQ ID NO 43
<211> LENGTH: 515
<212> TYPE: PRT
<213> ORGANISM: Infectious Bronchitis Virus

<400> SEQUENCE: 43

Ala Val Leu Tyr Asp Ser Ser Tyr Val Tyr Tyr Gln Ser Ala
1               5                   10                  15

Phe Arg Pro Pro Ser Gly Trp His Leu Gln Gly Gly Ala Tyr Ala Val
                20                  25                  30

Val Asn Ile Ser Ser Glu Phe Asn Asn Ala Gly Ser Ser Gly Cys
            35                  40                  45

Thr Val Gly Ile Ile His Gly Gly Arg Val Val Asn Ala Ser Ser Ile
    50                  55                  60

Ala Met Thr Ala Pro Ser Ser Gly Met Ala Trp Ser Ser Ser Gln Phe
65                  70                  75                  80

Cys Thr Ala His Cys Asn Phe Ser Asp Thr Thr Val Phe Val Thr His
                85                  90                  95

Cys Tyr Lys His Gly Gly Cys Pro Ile Thr Gly Met Leu Gln Gln Asn
            100                 105                 110

Phe Ile Arg Val Ser Ala Met Lys Asn Gly Gln Leu Phe Tyr Asn Leu
        115                 120                 125

Thr Val Ser Val Ala Lys Tyr Pro Thr Phe Arg Ser Phe Gln Cys Val
    130                 135                 140

Asn Asn Leu Thr Ser Val Tyr Leu Asn Gly Asp Leu Val Tyr Thr Ser
145                 150                 155                 160

Asn Glu Thr Ile Asp Val Thr Ser Ala Gly Val Tyr Phe Lys Ala Gly
                165                 170                 175

Gly Pro Ile Thr Tyr Lys Val Met Arg Glu Val Lys Ala Leu Ala Tyr
            180                 185                 190

Phe Val Asn Gly Thr Ala Gln Asp Val Ile Leu Cys Asp Gly Ser Pro
        195                 200                 205

Arg Gly Leu Leu Ala Cys Gln Tyr Asn Thr Gly Asn Phe Ser Asp Gly
    210                 215                 220

Phe Tyr Pro Phe Thr Asn Ser Ser Leu Val Lys Gln Lys Phe Ile Val
225                 230                 235                 240

Tyr Arg Glu Asn Ser Val Asn Thr Thr Cys Thr Leu His Asn Phe Ile
                245                 250                 255

Phe His Asn Glu Thr Gly Ala Asn Pro Asn Pro Ser Gly Val Gln Asn
            260                 265                 270

Ile Gln Thr Tyr Gln Thr Lys Thr Ala Gln Ser Gly Tyr Tyr Asn Phe
        275                 280                 285

Asn Phe Ser Phe Leu Ser Ser Phe Val Tyr Lys Glu Ser Asn Phe Met
    290                 295                 300
```

```
Tyr Gly Ser Tyr His Pro Ser Cys Lys Phe Arg Leu Glu Thr Ile Asn
305                 310                 315                 320

Asn Gly Leu Trp Phe Asn Ser Leu Ser Val Ser Ile Ala Tyr Gly Pro
                325                 330                 335

Leu Gln Gly Gly Cys Lys Gln Ser Val Phe Arg Gly Arg Ala Thr Cys
            340                 345                 350

Cys Tyr Ala Tyr Ser Tyr Gly Gly Pro Ser Leu Cys Lys Gly Val Tyr
        355                 360                 365

Ser Gly Glu Leu Asp His Asn Phe Glu Cys Gly Leu Leu Val Tyr Val
    370                 375                 380

Thr Lys Ser Asp Gly Ser Arg Ile Gln Thr Ala Thr Glu Pro Pro Val
385                 390                 395                 400

Ile Thr Gln His Asn Tyr Asn Asn Ile Thr Leu Asn Thr Cys Val Asp
                405                 410                 415

Tyr Asn Ile Tyr Gly Arg Thr Gly Gln Gly Phe Ile Thr Asn Val Thr
                420                 425                 430

Asp Ser Ala Val Ser Tyr Asn Tyr Leu Ala Asp Ala Gly Leu Ala Ile
            435                 440                 445

Leu Asp Thr Ser Gly Ser Ile Asp Ile Phe Val Val Gln Gly Glu Tyr
        450                 455                 460

Gly Leu Asn Tyr Tyr Lys Val Asn Pro Cys Glu Asp Val Asn Gln Gln
465                 470                 475                 480

Phe Val Val Ser Gly Gly Lys Leu Val Gly Ile Leu Thr Ser Arg Asn
                485                 490                 495

Glu Thr Gly Ser Gln Leu Leu Glu Asn Gln Phe Tyr Ile Lys Ile Thr
            500                 505                 510

Asn Gly Thr
        515

<210> SEQ ID NO 44
<211> LENGTH: 5
<212> TYPE: PRT
<213> ORGANISM: Infectious Bronchitis Virus

<400> SEQUENCE: 44

Arg Arg Phe Arg Arg
1               5

<210> SEQ ID NO 45
<211> LENGTH: 554
<212> TYPE: PRT
<213> ORGANISM: Infectious Bronchitis Virus

<400> SEQUENCE: 45

Ser Ile Thr Glu Asn Val Ala Asn Cys Pro Tyr Val Ser Tyr Gly Lys
1               5                   10                  15

Phe Cys Ile Lys Pro Asp Gly Ser Ile Ala Thr Ile Val Pro Lys Gln
                20                  25                  30

Leu Glu Gln Phe Val Ala Pro Leu Phe Asn Val Thr Glu Asn Val Leu
            35                  40                  45

Ile Pro Asn Ser Phe Asn Leu Thr Val Thr Asp Glu Tyr Ile Gln Thr
        50                  55                  60

Arg Met Asp Lys Val Gln Ile Asn Cys Leu Gln Tyr Val Cys Gly Ser
65                  70                  75                  80

Ser Leu Asp Cys Arg Asn Leu Phe Gln Gln Tyr Gly Pro Val Cys Asp
                85                  90                  95
```

```
Asn Ile Leu Ser Val Val Asn Ser Val Gly Gln Lys Glu Asp Met Glu
            100                 105                 110

Leu Leu Asn Phe Tyr Ser Ser Thr Lys Pro Ala Gly Phe Asn Thr Pro
            115                 120                 125

Val Leu Ser Asn Val Ser Thr Gly Glu Phe Asn Ile Ser Leu Leu Leu
            130                 135                 140

Thr Thr Pro Ser Ser Arg Arg Arg Ser Val Ile Glu Asp Leu Leu
145                 150                 155                 160

Phe Thr Ser Val Glu Ser Val Gly Leu Pro Thr Asp Asp Ala Tyr Lys
                    165                 170                 175

Asn Cys Thr Ala Gly Pro Leu Gly Phe Leu Lys Asp Leu Ala Cys Ala
                    180                 185                 190

Arg Glu Tyr Asn Gly Leu Leu Val Leu Pro Pro Ile Ile Thr Ala Glu
                    195                 200                 205

Met Gln Ala Leu Tyr Thr Ser Ser Leu Val Ala Ser Met Ala Phe Gly
            210                 215                 220

Gly Ile Thr Ala Ala Gly Ala Ile Pro Phe Ala Thr Gln Leu Gln Ala
225                 230                 235                 240

Arg Ile Asn His Leu Gly Ile Thr Gln Ser Leu Leu Leu Lys Asn Gln
                    245                 250                 255

Glu Lys Ile Ala Ala Ser Phe Asn Lys Ala Ile Gly His Met Gln Glu
                    260                 265                 270

Gly Phe Arg Ser Thr Ser Leu Ala Leu Gln Gln Ile Gln Asp Val Val
                    275                 280                 285

Ser Lys Gln Ser Ala Ile Leu Thr Glu Thr Met Ala Ser Leu Asn Lys
            290                 295                 300

Asn Phe Gly Ala Ile Ser Ser Val Ile Gln Glu Ile Tyr Gln Gln Phe
305                 310                 315                 320

Asp Ala Ile Gln Ala Asn Ala Gln Val Asp Arg Leu Ile Thr Gly Arg
                    325                 330                 335

Leu Ser Ser Leu Ser Val Leu Ala Ser Ala Lys Gln Ala Glu Tyr Ile
                    340                 345                 350

Arg Val Ser Gln Gln Arg Glu Leu Ala Thr Gln Lys Ile Asn Glu Cys
                    355                 360                 365

Val Lys Ser Gln Ser Ile Arg Tyr Ser Phe Cys Gly Asn Gly Arg His
            370                 375                 380

Val Leu Thr Ile Pro Gln Asn Ala Pro Asn Gly Ile Val Phe Ile His
385                 390                 395                 400

Phe Ser Tyr Thr Pro Asp Ser Phe Val Asn Val Thr Ala Ile Val Gly
                    405                 410                 415

Phe Cys Val Lys Pro Ala Asn Ala Ser Gln Tyr Ala Ile Val Pro Ala
                    420                 425                 430

Asn Gly Arg Gly Ile Phe Ile Gln Val Asn Gly Ser Tyr Tyr Ile Thr
                    435                 440                 445

Ala Arg Asp Met Tyr Met Pro Arg Ala Ile Thr Ala Gly Asp Val Val
            450                 455                 460

Thr Leu Thr Ser Cys Gln Ala Asn Tyr Val Ile Val Asn Lys Thr Val
465                 470                 475                 480

Ile Thr Thr Phe Val Asp Asn Asp Asp Phe Asp Phe Asn Asp Glu Leu
                    485                 490                 495

Ser Lys Trp Trp Asn Asp Thr Lys His Glu Leu Pro Asp Phe Asp Lys
            500                 505                 510
```

Phe Asn Tyr Thr Val Pro Ile Leu Asp Ile Asp Ser Glu Ile Asp Arg
            515                 520                 525

Ile Gln Gly Val Ile Gln Gly Leu Asn Asp Ser Leu Ile Asp Leu Glu
        530                 535                 540

Lys Leu Ser Ile Leu Lys Thr Tyr Ile Lys
545                 550

<210> SEQ ID NO 46
<211> LENGTH: 67
<212> TYPE: PRT
<213> ORGANISM: Infectious Bronchitis Virus

<400> SEQUENCE: 46

Val Trp Leu Ala Ile Ala Phe Ala Thr Ile Ile Phe Ile Leu Ile Leu
1               5                   10                  15

Gly Trp Val Phe Phe Met Thr Gly Cys Cys Gly Cys Cys Cys Gly Cys
            20                  25                  30

Phe Gly Ile Met Pro Leu Met Ser Lys Cys Gly Lys Lys Ser Ser Tyr
        35                  40                  45

Tyr Thr Thr Phe Asp Asn Asp Val Val Thr Glu Gln Tyr Arg Pro Lys
    50                  55                  60

Lys Ser Val
65

<210> SEQ ID NO 47
<211> LENGTH: 20
<212> TYPE: PRT
<213> ORGANISM: Infectious Bronchitis Virus

<400> SEQUENCE: 47

Val Trp Leu Ala Ile Ala Phe Ala Thr Ile Ile Phe Ile Leu Ile Leu
1               5                   10                  15

Gly Trp Val Phe
            20

<210> SEQ ID NO 48
<211> LENGTH: 47
<212> TYPE: PRT
<213> ORGANISM: Infectious Bronchitis Virus

<400> SEQUENCE: 48

Phe Met Thr Gly Cys Cys Gly Cys Cys Cys Gly Cys Phe Gly Ile Met
1               5                   10                  15

Pro Leu Met Ser Lys Cys Gly Lys Lys Ser Ser Tyr Tyr Thr Thr Phe
            20                  25                  30

Asp Asn Asp Val Val Thr Glu Gln Tyr Arg Pro Lys Lys Ser Val
        35                  40                  45

<210> SEQ ID NO 49
<211> LENGTH: 1162
<212> TYPE: PRT
<213> ORGANISM: Infectious Bronchitis Virus

<400> SEQUENCE: 49

Met Leu Val Thr Pro Leu Leu Leu Val Thr Leu Leu Cys Ala Leu Cys
1               5                   10                  15

Ser Ala Val Leu Tyr Asp Ser Ser Ser Tyr Val Tyr Tyr Tyr Gln Ser
            20                  25                  30

Ala Phe Arg Pro Pro Asn Gly Trp His Leu His Gly Gly Ala Tyr Ala
        35                  40                  45

```
Val Val Asn Ile Ser Ser Glu Ser Asn Asn Ala Gly Ser Ser Pro Gly
 50                  55                  60

Cys Ile Val Gly Thr Ile His Gly Gly Arg Val Asn Ala Ser Ser
 65                  70                  75                  80

Ile Ala Met Thr Ala Pro Ser Ser Gly Met Ala Trp Ser Ser Ser Gln
                     85                  90                  95

Phe Cys Thr Ala His Cys Asn Phe Ser Asp Thr Thr Val Phe Val Thr
                    100                 105                 110

His Cys Tyr Lys Tyr Asp Gly Cys Pro Ile Thr Gly Met Leu Gln Lys
                115                 120                 125

Asn Phe Ile Arg Val Ser Ala Met Lys Asn Gly Gln Leu Phe Tyr Asn
                130                 135                 140

Leu Thr Val Ser Val Ala Lys Tyr Pro Thr Phe Lys Ser Phe Gln Cys
145                 150                 155                 160

Val Asn Asn Leu Thr Ser Val Tyr Leu Asn Gly Asp Leu Val Tyr Thr
                    165                 170                 175

Ser Asn Glu Thr Thr Asp Val Thr Ser Ala Gly Val Tyr Phe Lys Ala
                180                 185                 190

Gly Gly Pro Ile Thr Tyr Lys Val Met Arg Glu Val Lys Ala Leu Ala
                195                 200                 205

Tyr Phe Val Asn Gly Thr Ala Gln Asp Val Ile Leu Cys Asp Gly Ser
210                 215                 220

Pro Arg Gly Leu Leu Ala Cys Gln Tyr Asn Thr Gly Asn Phe Ser Asp
225                 230                 235                 240

Gly Phe Tyr Pro Phe Ile Asn Ser Ser Leu Val Lys Gln Lys Phe Ile
                245                 250                 255

Val Tyr Arg Glu Asn Ser Val Asn Thr Thr Phe Thr Leu His Asn Phe
                260                 265                 270

Thr Phe His Asn Glu Thr Gly Ala Asn Pro Asn Pro Ser Gly Val Gln
                275                 280                 285

Asn Ile Gln Thr Tyr Gln Thr Gln Thr Ala Gln Ser Gly Tyr Tyr Asn
                290                 295                 300

Phe Asn Phe Ser Phe Leu Ser Ser Phe Val Tyr Lys Glu Ser Asn Phe
305                 310                 315                 320

Met Tyr Gly Ser Tyr His Pro Ser Cys Asn Phe Arg Leu Glu Thr Ile
                325                 330                 335

Asn Asn Gly Leu Trp Phe Asn Ser Leu Ser Val Ser Ile Ala Tyr Gly
                340                 345                 350

Pro Leu Gln Gly Gly Cys Lys Gln Ser Val Phe Ser Gly Arg Ala Thr
                355                 360                 365

Cys Cys Tyr Ala Tyr Ser Tyr Gly Gly Pro Ser Leu Cys Lys Gly Val
370                 375                 380

Tyr Ser Gly Glu Leu Asp Leu Asn Phe Glu Cys Gly Leu Leu Val Tyr
385                 390                 395                 400

Val Thr Lys Ser Gly Ser Arg Ile Gln Thr Ala Thr Glu Pro Pro
                405                 410                 415

Val Ile Thr Gln His Asn Tyr Asn Asn Ile Thr Leu Asn Thr Cys Val
                420                 425                 430

Asp Tyr Asn Ile Tyr Gly Arg Thr Gly Gln Gly Phe Ile Thr Asn Val
                435                 440                 445

Thr Asp Ser Ala Val Ser Tyr Asn Tyr Leu Ala Asp Ala Gly Leu Ala
450                 455                 460
```

```
Ile Leu Asp Thr Ser Gly Ser Ile Asp Ile Phe Val Val Gln Gly Glu
465                 470                 475                 480

Tyr Gly Leu Asn Tyr Tyr Lys Val Asn Pro Cys Glu Asp Val Asn Gln
            485                 490                 495

Gln Phe Val Val Ser Gly Gly Lys Leu Val Gly Ile Leu Thr Ser Arg
        500                 505                 510

Asn Glu Thr Gly Ser Gln Leu Leu Glu Asn Gln Phe Tyr Ile Lys Ile
    515                 520                 525

Thr Asn Gly Thr Arg Arg Phe Arg Arg Ser Ile Thr Glu Asn Val Ala
530                 535                 540

Asn Cys Pro Tyr Val Ser Tyr Gly Lys Phe Cys Ile Lys Pro Asp Gly
545                 550                 555                 560

Ser Ile Ala Thr Ile Val Pro Lys Gln Leu Glu Gln Phe Val Ala Pro
            565                 570                 575

Leu Phe Asn Val Thr Glu Asn Val Leu Ile Pro Asn Ser Phe Asn Leu
        580                 585                 590

Thr Val Thr Asp Glu Tyr Ile Gln Thr Arg Met Asp Lys Val Gln Ile
    595                 600                 605

Asn Cys Leu Gln Tyr Val Cys Gly Ser Ser Leu Asp Cys Arg Lys Leu
610                 615                 620

Phe Gln Gln Tyr Gly Pro Val Cys Asp Asn Ile Leu Ser Val Val Asn
625                 630                 635                 640

Ser Val Gly Gln Lys Glu Asp Met Glu Leu Leu Asn Phe Tyr Ser Ser
            645                 650                 655

Thr Lys Pro Ala Gly Phe Asn Thr Pro Val Leu Ser Asn Val Ser Thr
        660                 665                 670

Gly Glu Phe Asn Ile Ser Leu Leu Leu Thr Thr Pro Ser Ser Arg Arg
    675                 680                 685

Arg Arg Ser Phe Ile Glu Asp Leu Leu Phe Thr Ser Val Glu Ser Val
690                 695                 700

Gly Leu Pro Thr Asp Asp Ala Tyr Lys Asn Cys Thr Ala Gly Pro Leu
705                 710                 715                 720

Gly Phe Leu Lys Asp Leu Ala Cys Ala Arg Glu Tyr Asn Gly Leu Leu
            725                 730                 735

Val Leu Pro Pro Ile Ile Thr Ala Glu Met Gln Thr Leu Tyr Thr Ser
        740                 745                 750

Ser Leu Val Ala Ser Met Ala Phe Gly Gly Ile Thr Ala Ala Gly Ala
    755                 760                 765

Ile Pro Phe Ala Thr Gln Leu Gln Ala Arg Ile Asn His Leu Gly Ile
770                 775                 780

Thr Gln Ser Leu Leu Leu Lys Asn Gln Glu Lys Ile Ala Ala Ser Phe
785                 790                 795                 800

Asn Lys Ala Ile Gly His Met Gln Glu Gly Phe Arg Ser Thr Ser Leu
            805                 810                 815

Ala Leu Gln Gln Ile Gln Asp Val Val Asn Lys Gln Ser Ala Ile Leu
        820                 825                 830

Thr Glu Thr Met Ala Ser Leu Asn Lys Asn Phe Gly Ala Ile Ser Ser
    835                 840                 845

Val Ile Gln Glu Ile Tyr Gln Gln Leu Asp Ala Ile Gln Ala Asn Ala
850                 855                 860

Gln Val Asp Arg Leu Ile Thr Gly Arg Leu Ser Ser Leu Ser Val Leu
865                 870                 875                 880

Ala Ser Ala Lys Gln Ala Glu Tyr Ile Arg Val Ser Gln Gln Arg Glu
```

```
                    885                 890                 895

Leu Ala Thr Gln Lys Ile Asn Glu Cys Val Lys Ser Gln Ser Ile Arg
                900                 905                 910

Tyr Ser Phe Cys Gly Asn Gly Arg His Val Leu Thr Ile Pro Gln Asn
            915                 920                 925

Ala Pro Asn Gly Ile Val Phe Ile His Phe Ser Tyr Thr Pro Asp Ser
        930                 935                 940

Phe Val Asn Val Thr Ala Ile Val Gly Phe Cys Val Lys Pro Ala Asn
945                 950                 955                 960

Ala Ser Gln Tyr Ala Ile Val Pro Ser Asn Gly Arg Gly Ile Phe Ile
                965                 970                 975

Gln Val Asn Gly Ser Tyr Tyr Ile Thr Ala Arg Asp Met Tyr Met Pro
            980                 985                 990

Arg Ala Ile Thr Ala Gly Asp Val Val Thr Leu Thr Ser Cys Gln Ala
        995                1000                1005

Asn Tyr Val Ser Val Asn Lys Thr Val Ile Thr Thr Phe Val Asp
    1010                1015                1020

Asn Asp Asp Phe Asp Phe Asn Asp Glu Leu Ser Lys Trp Trp Asn
1025                1030                1035

Asp Thr Lys His Glu Leu Pro Asp Phe Asp Lys Phe Asn Tyr Thr
    1040                1045                1050

Val Pro Ile Leu Asp Ile Asp Ser Glu Ile Asp Arg Ile Gln Gly
    1055                1060                1065

Val Ile Gln Gly Leu Asn Asp Ser Leu Ile Asp Leu Glu Lys Leu
    1070                1075                1080

Ser Ile Leu Lys Thr Tyr Ile Lys Trp Pro Trp Tyr Val Trp Leu
    1085                1090                1095

Ala Ile Ala Phe Ala Thr Ile Ile Phe Ile Leu Ile Leu Gly Trp
    1100                1105                1110

Val Phe Phe Met Thr Gly Cys Cys Gly Cys Cys Cys Gly Cys Phe
    1115                1120                1125

Gly Ile Met Pro Leu Met Ser Lys Cys Gly Lys Lys Ser Ser Tyr
    1130                1135                1140

Tyr Thr Thr Phe Asp Asn Asp Val Val Thr Glu Gln Tyr Arg Pro
    1145                1150                1155

Lys Lys Ser Val
    1160

<210> SEQ ID NO 50
<211> LENGTH: 17
<212> TYPE: PRT
<213> ORGANISM: Infectious Bronchitis Virus

<400> SEQUENCE: 50

Met Leu Val Thr Pro Leu Leu Leu Val Thr Leu Leu Cys Ala Leu Cys
1               5                   10                  15

Ser

<210> SEQ ID NO 51
<211> LENGTH: 515
<212> TYPE: PRT
<213> ORGANISM: Infectious Bronchitis Virus

<400> SEQUENCE: 51

Ala Val Leu Tyr Asp Ser Ser Ser Tyr Val Tyr Tyr Gln Ser Ala
1               5                   10                  15
```

```
Phe Arg Pro Pro Asn Gly Trp His Leu His Gly Gly Ala Tyr Ala Val
         20              25              30

Val Asn Ile Ser Ser Glu Ser Asn Ala Gly Ser Ser Pro Gly Cys
         35              40              45

Ile Val Gly Thr Ile His Gly Gly Arg Val Val Asn Ala Ser Ser Ile
 50              55              60

Ala Met Thr Ala Pro Ser Ser Gly Met Ala Trp Ser Ser Ser Gln Phe
 65              70              75              80

Cys Thr Ala His Cys Asn Phe Ser Asp Thr Thr Val Phe Val Thr His
                 85              90              95

Cys Tyr Lys Tyr Asp Gly Cys Pro Ile Thr Gly Met Leu Gln Lys Asn
             100             105             110

Phe Ile Arg Val Ser Ala Met Lys Asn Gly Gln Leu Phe Tyr Asn Leu
         115             120             125

Thr Val Ser Val Ala Lys Tyr Pro Thr Phe Lys Ser Phe Gln Cys Val
     130             135             140

Asn Asn Leu Thr Ser Val Tyr Leu Asn Gly Asp Leu Val Tyr Thr Ser
145             150             155             160

Asn Glu Thr Thr Asp Val Thr Ser Ala Gly Val Tyr Phe Lys Ala Gly
                 165             170             175

Gly Pro Ile Thr Tyr Lys Val Met Arg Glu Val Lys Ala Leu Ala Tyr
             180             185             190

Phe Val Asn Gly Thr Ala Gln Asp Val Ile Leu Cys Asp Gly Ser Pro
         195             200             205

Arg Gly Leu Leu Ala Cys Gln Tyr Asn Thr Gly Asn Phe Ser Asp Gly
         210             215             220

Phe Tyr Pro Phe Ile Asn Ser Ser Leu Val Lys Gln Lys Phe Ile Val
225             230             235             240

Tyr Arg Glu Asn Ser Val Asn Thr Thr Phe Thr Leu His Asn Phe Thr
                 245             250             255

Phe His Asn Glu Thr Gly Ala Asn Pro Asn Pro Ser Gly Val Gln Asn
             260             265             270

Ile Gln Thr Tyr Gln Thr Gln Thr Ala Gln Ser Gly Tyr Tyr Asn Phe
         275             280             285

Asn Phe Ser Phe Leu Ser Ser Phe Val Tyr Lys Glu Ser Asn Phe Met
         290             295             300

Tyr Gly Ser Tyr His Pro Ser Cys Asn Phe Arg Leu Glu Thr Ile Asn
305             310             315             320

Asn Gly Leu Trp Phe Asn Ser Leu Ser Val Ser Ile Ala Tyr Gly Pro
                 325             330             335

Leu Gln Gly Gly Cys Lys Gln Ser Val Phe Ser Gly Arg Ala Thr Cys
             340             345             350

Cys Tyr Ala Tyr Ser Tyr Gly Gly Pro Ser Leu Cys Lys Gly Val Tyr
         355             360             365

Ser Gly Glu Leu Asp Leu Asn Phe Glu Cys Gly Leu Leu Val Tyr Val
         370             375             380

Thr Lys Ser Gly Gly Ser Arg Ile Gln Thr Ala Thr Glu Pro Pro Val
385             390             395             400

Ile Thr Gln His Asn Tyr Asn Asn Ile Thr Leu Asn Thr Cys Val Asp
                 405             410             415

Tyr Asn Ile Tyr Gly Arg Thr Gly Gln Gly Phe Ile Thr Asn Val Thr
             420             425             430
```

```
Asp Ser Ala Val Ser Tyr Asn Tyr Leu Ala Asp Ala Gly Leu Ala Ile
        435                 440                 445

Leu Asp Thr Ser Gly Ser Ile Asp Ile Phe Val Val Gln Gly Glu Tyr
    450                 455                 460

Gly Leu Asn Tyr Tyr Lys Val Asn Pro Cys Glu Asp Val Asn Gln Gln
465                 470                 475                 480

Phe Val Val Ser Gly Gly Lys Leu Val Gly Ile Leu Thr Ser Arg Asn
                485                 490                 495

Glu Thr Gly Ser Gln Leu Leu Glu Asn Gln Phe Tyr Ile Lys Ile Thr
            500                 505                 510

Asn Gly Thr
        515

<210> SEQ ID NO 52
<211> LENGTH: 5
<212> TYPE: PRT
<213> ORGANISM: Infectious Bronchitis Virus

<400> SEQUENCE: 52

Arg Arg Phe Arg Arg
1               5

<210> SEQ ID NO 53
<211> LENGTH: 554
<212> TYPE: PRT
<213> ORGANISM: Infectious Bronchitis Virus

<400> SEQUENCE: 53

Ser Ile Thr Glu Asn Val Ala Asn Cys Pro Tyr Val Ser Tyr Gly Lys
1               5                   10                  15

Phe Cys Ile Lys Pro Asp Gly Ser Ile Ala Thr Ile Val Pro Lys Gln
            20                  25                  30

Leu Glu Gln Phe Val Ala Pro Leu Phe Asn Val Thr Glu Asn Val Leu
        35                  40                  45

Ile Pro Asn Ser Phe Asn Leu Thr Val Thr Asp Glu Tyr Ile Gln Thr
    50                  55                  60

Arg Met Asp Lys Val Gln Ile Asn Cys Leu Gln Tyr Val Cys Gly Ser
65                  70                  75                  80

Ser Leu Asp Cys Arg Lys Leu Phe Gln Gln Tyr Gly Pro Val Cys Asp
                85                  90                  95

Asn Ile Leu Ser Val Val Asn Ser Val Gly Gln Lys Glu Asp Met Glu
            100                 105                 110

Leu Leu Asn Phe Tyr Ser Ser Thr Lys Pro Ala Gly Phe Asn Thr Pro
        115                 120                 125

Val Leu Ser Asn Val Ser Thr Gly Glu Phe Asn Ile Ser Leu Leu Leu
    130                 135                 140

Thr Thr Pro Ser Ser Arg Arg Arg Ser Phe Ile Glu Asp Leu Leu
145                 150                 155                 160

Phe Thr Ser Val Glu Ser Val Gly Leu Pro Thr Asp Asp Ala Tyr Lys
                165                 170                 175

Asn Cys Thr Ala Gly Pro Leu Gly Phe Leu Lys Asp Leu Ala Cys Ala
            180                 185                 190

Arg Glu Tyr Asn Gly Leu Leu Val Leu Pro Pro Ile Ile Thr Ala Glu
        195                 200                 205

Met Gln Thr Leu Tyr Thr Ser Ser Leu Val Ala Ser Met Ala Phe Gly
    210                 215                 220
```

```
Gly Ile Thr Ala Ala Gly Ala Ile Pro Phe Ala Thr Gln Leu Gln Ala
225                 230                 235                 240

Arg Ile Asn His Leu Gly Ile Thr Gln Ser Leu Leu Leu Lys Asn Gln
            245                 250                 255

Glu Lys Ile Ala Ala Ser Phe Asn Lys Ala Ile Gly His Met Gln Glu
        260                 265                 270

Gly Phe Arg Ser Thr Ser Leu Ala Leu Gln Gln Ile Gln Asp Val Val
    275                 280                 285

Asn Lys Gln Ser Ala Ile Leu Thr Glu Thr Met Ala Ser Leu Asn Lys
290                 295                 300

Asn Phe Gly Ala Ile Ser Ser Val Ile Gln Glu Ile Tyr Gln Gln Leu
305                 310                 315                 320

Asp Ala Ile Gln Ala Asn Ala Gln Val Asp Arg Leu Ile Thr Gly Arg
            325                 330                 335

Leu Ser Ser Leu Ser Val Leu Ala Ser Ala Lys Gln Ala Glu Tyr Ile
        340                 345                 350

Arg Val Ser Gln Gln Arg Glu Leu Ala Thr Gln Lys Ile Asn Glu Cys
    355                 360                 365

Val Lys Ser Gln Ser Ile Arg Tyr Ser Phe Cys Gly Asn Gly Arg His
370                 375                 380

Val Leu Thr Ile Pro Gln Asn Ala Pro Asn Gly Ile Val Phe Ile His
385                 390                 395                 400

Phe Ser Tyr Thr Pro Asp Ser Phe Val Asn Val Thr Ala Ile Val Gly
            405                 410                 415

Phe Cys Val Lys Pro Ala Asn Ala Ser Gln Tyr Ala Ile Val Pro Ser
        420                 425                 430

Asn Gly Arg Gly Ile Phe Ile Gln Val Asn Gly Ser Tyr Tyr Ile Thr
    435                 440                 445

Ala Arg Asp Met Tyr Met Pro Arg Ala Ile Thr Ala Gly Asp Val Val
450                 455                 460

Thr Leu Thr Ser Cys Gln Ala Asn Tyr Val Ser Val Asn Lys Thr Val
465                 470                 475                 480

Ile Thr Thr Phe Val Asp Asn Asp Asp Phe Asp Phe Asn Asp Glu Leu
            485                 490                 495

Ser Lys Trp Trp Asn Asp Thr Lys His Glu Leu Pro Asp Phe Asp Lys
        500                 505                 510

Phe Asn Tyr Thr Val Pro Ile Leu Asp Ile Asp Ser Glu Ile Asp Arg
    515                 520                 525

Ile Gln Gly Val Ile Gln Gly Leu Asn Asp Ser Leu Ile Asp Leu Glu
530                 535                 540

Lys Leu Ser Ile Leu Lys Thr Tyr Ile Lys
545                 550

<210> SEQ ID NO 54
<211> LENGTH: 67
<212> TYPE: PRT
<213> ORGANISM: Infectious Bronchitis Virus

<400> SEQUENCE: 54

Val Trp Leu Ala Ile Ala Phe Ala Thr Ile Ile Phe Ile Leu Ile Leu
1               5                   10                  15

Gly Trp Val Phe Phe Met Thr Gly Cys Cys Gly Cys Cys Cys Gly Cys
                20                  25                  30

Phe Gly Ile Met Pro Leu Met Ser Lys Cys Gly Lys Lys Ser Ser Tyr
            35                  40                  45
```

Tyr Thr Thr Phe Asp Asn Asp Val Val Thr Glu Gln Tyr Arg Pro Lys
            50                  55                  60

Lys Ser Val
65

<210> SEQ ID NO 55
<211> LENGTH: 20
<212> TYPE: PRT
<213> ORGANISM: Infectious Bronchitis Virus

<400> SEQUENCE: 55

Val Trp Leu Ala Ile Ala Phe Ala Thr Ile Ile Phe Ile Leu Ile Leu
1               5                   10                  15

Gly Trp Val Phe
            20

<210> SEQ ID NO 56
<211> LENGTH: 47
<212> TYPE: PRT
<213> ORGANISM: Infectious Bronchitis Virus

<400> SEQUENCE: 56

Phe Met Thr Gly Cys Cys Gly Cys Cys Gly Cys Phe Gly Ile Met
1               5                   10                  15

Pro Leu Met Ser Lys Cys Gly Lys Lys Ser Ser Tyr Tyr Thr Thr Phe
            20                  25                  30

Asp Asn Asp Val Val Thr Glu Gln Tyr Arg Pro Lys Lys Ser Val
            35                  40                  45

<210> SEQ ID NO 57
<211> LENGTH: 1162
<212> TYPE: PRT
<213> ORGANISM: Infectious Bronchitis Virus

<400> SEQUENCE: 57

Met Leu Val Thr Pro Leu Leu Leu Val Thr Leu Leu Cys Ala Leu Cys
1               5                   10                  15

Ser Ala Val Leu Tyr Asp Ser Ser Ser Tyr Val Tyr Tyr Tyr Gln Ser
            20                  25                  30

Ala Phe Arg Pro Pro Ser Gly Trp His Leu Gln Gly Gly Ala Tyr Ala
            35                  40                  45

Val Val Asn Ile Ser Ser Glu Phe Asn Asn Ala Gly Ser Ser Ser Gly
            50                  55                  60

Cys Thr Val Gly Ile Ile His Gly Gly Arg Val Val Asn Ala Ser Ser
65                  70                  75                  80

Ile Ala Met Thr Ala Pro Ser Ser Gly Met Ala Trp Ser Ser Ser Gln
            85                  90                  95

Phe Cys Thr Ala His Cys Asn Phe Ser Asp Thr Thr Val Phe Val Thr
            100                 105                 110

His Cys Tyr Lys His Gly Gly Cys Pro Ile Thr Gly Met Leu Gln Gln
            115                 120                 125

Asn Phe Ile Arg Val Ser Ala Met Lys Asn Gly Gln Leu Phe Tyr Asn
            130                 135                 140

Leu Thr Val Ser Val Ala Lys Tyr Pro Thr Phe Arg Ser Phe Gln Cys
145                 150                 155                 160

Val Asn Asn Leu Thr Ser Val Tyr Leu Asn Gly Asp Leu Val Tyr Thr
            165                 170                 175

-continued

Ser Asn Glu Thr Ile Asp Val Thr Ser Ala Gly Val Tyr Phe Lys Ala
            180                 185                 190

Gly Gly Pro Ile Thr Tyr Lys Val Met Arg Glu Val Lys Ala Leu Ala
        195                 200                 205

Tyr Phe Val Asn Gly Thr Ala Gln Asp Val Ile Leu Cys Asp Gly Ser
    210                 215                 220

Pro Arg Gly Leu Leu Ala Cys Gln Tyr Asn Thr Gly Asn Phe Ser Asp
225                 230                 235                 240

Gly Phe Tyr Pro Phe Thr Asn Ser Ser Leu Val Lys Gln Lys Phe Ile
                245                 250                 255

Val Tyr Arg Glu Asn Ser Val Asn Thr Thr Cys Thr Leu His Asn Phe
            260                 265                 270

Ile Phe His Asn Glu Thr Gly Ala Asn Pro Asn Pro Ser Gly Val Gln
        275                 280                 285

Asn Ile Gln Thr Tyr Gln Thr Lys Thr Ala Gln Ser Gly Tyr Tyr Asn
    290                 295                 300

Phe Asn Phe Ser Phe Leu Ser Ser Phe Val Tyr Lys Glu Ser Asn Phe
305                 310                 315                 320

Met Tyr Gly Ser Tyr His Pro Ser Cys Lys Phe Arg Leu Glu Thr Ile
                325                 330                 335

Asn Asn Gly Leu Trp Phe Asn Ser Leu Ser Val Ser Ile Ala Tyr Gly
            340                 345                 350

Pro Leu Gln Gly Gly Cys Lys Gln Ser Val Phe Arg Gly Arg Ala Thr
        355                 360                 365

Cys Cys Tyr Ala Tyr Ser Tyr Gly Gly Pro Ser Leu Cys Lys Gly Val
370                 375                 380

Tyr Ser Gly Glu Leu Asp His Asn Phe Glu Cys Gly Leu Leu Val Tyr
385                 390                 395                 400

Val Thr Lys Ser Asp Gly Ser Arg Ile Gln Thr Ala Thr Glu Pro Pro
                405                 410                 415

Val Ile Thr Gln His Asn Tyr Asn Asn Ile Thr Leu Asn Thr Cys Val
            420                 425                 430

Asp Tyr Asn Ile Tyr Gly Arg Thr Gly Gln Gly Phe Ile Thr Asn Val
        435                 440                 445

Thr Asp Ser Ala Val Ser Tyr Asn Tyr Leu Ala Asp Ala Gly Leu Ala
    450                 455                 460

Ile Leu Asp Thr Ser Gly Ser Ile Asp Ile Phe Val Val Gln Gly Glu
465                 470                 475                 480

Tyr Gly Leu Asn Tyr Tyr Lys Val Asn Pro Cys Glu Asp Val Asn Gln
                485                 490                 495

Gln Phe Val Val Ser Gly Gly Lys Leu Val Gly Ile Leu Thr Ser Arg
            500                 505                 510

Asn Glu Thr Gly Ser Gln Leu Leu Glu Asn Gln Phe Tyr Ile Lys Ile
        515                 520                 525

Thr Asn Gly Thr Arg Arg Phe Arg Arg Ser Ile Thr Glu Asn Val Ala
    530                 535                 540

Asn Cys Pro Tyr Val Ser Tyr Gly Lys Phe Cys Ile Lys Pro Asp Gly
545                 550                 555                 560

Ser Ile Ala Thr Ile Val Pro Lys Gln Leu Glu Gln Phe Val Ala Pro
                565                 570                 575

Leu Phe Asn Val Thr Glu Asn Val Leu Ile Pro Asn Ser Phe Asn Leu
            580                 585                 590

Thr Val Thr Asp Glu Tyr Ile Gln Thr Arg Met Asp Lys Val Gln Ile

```
              595                 600                 605
Asn Cys Leu Gln Tyr Val Cys Gly Ser Ser Leu Asp Cys Arg Asn Leu
    610                 615                 620

Phe Gln Gln Tyr Gly Pro Val Cys Asp Asn Ile Leu Ser Val Val Asn
625                 630                 635                 640

Ser Val Gly Gln Lys Glu Asp Met Glu Leu Leu Asn Phe Tyr Ser Ser
                645                 650                 655

Thr Lys Pro Ala Gly Phe Asn Thr Pro Val Leu Ser Asn Val Ser Thr
                660                 665                 670

Gly Glu Phe Asn Ile Ser Leu Leu Leu Thr Thr Pro Ser Ser Arg Arg
                675                 680                 685

Arg Arg Ser Val Ile Glu Asp Leu Leu Phe Thr Ser Val Glu Ser Val
                690                 695                 700

Gly Leu Pro Thr Asp Asp Ala Tyr Lys Asn Cys Thr Ala Gly Pro Leu
705                 710                 715                 720

Gly Phe Leu Lys Asp Leu Ala Cys Ala Arg Glu Tyr Asn Gly Leu Leu
                725                 730                 735

Val Leu Pro Pro Ile Ile Thr Ala Glu Met Gln Ala Leu Tyr Thr Ser
                740                 745                 750

Ser Leu Val Ala Ser Met Ala Phe Gly Gly Ile Thr Ala Ala Gly Ala
                755                 760                 765

Ile Pro Phe Ala Thr Gln Leu Gln Ala Arg Ile Asn His Leu Gly Ile
                770                 775                 780

Thr Gln Ser Leu Leu Leu Lys Asn Gln Glu Lys Ile Ala Ala Ser Phe
785                 790                 795                 800

Asn Lys Ala Ile Gly His Met Gln Glu Gly Phe Arg Ser Thr Ser Leu
                805                 810                 815

Ala Leu Gln Gln Ile Gln Asp Val Val Ser Lys Gln Ser Ala Ile Leu
                820                 825                 830

Thr Glu Thr Met Ala Ser Leu Asn Lys Asn Phe Gly Ala Ile Ser Ser
                835                 840                 845

Val Ile Gln Glu Ile Tyr Gln Gln Phe Asp Ala Ile Gln Ala Asn Ala
                850                 855                 860

Gln Val Asp Arg Leu Ile Thr Gly Arg Leu Ser Ser Leu Ser Val Leu
865                 870                 875                 880

Ala Ser Ala Lys Gln Ala Glu Tyr Ile Arg Val Ser Gln Gln Arg Glu
                885                 890                 895

Leu Ala Thr Gln Lys Ile Asn Glu Cys Val Lys Ser Gln Ser Ile Arg
                900                 905                 910

Tyr Ser Phe Cys Gly Asn Gly Arg His Val Leu Thr Ile Pro Gln Asn
                915                 920                 925

Ala Pro Asn Gly Ile Val Phe Ile His Phe Ser Tyr Thr Pro Asp Ser
                930                 935                 940

Phe Val Asn Val Thr Ala Ile Val Gly Phe Cys Val Lys Pro Ala Asn
945                 950                 955                 960

Ala Ser Gln Tyr Ala Ile Val Pro Ala Asn Gly Arg Gly Ile Phe Ile
                965                 970                 975

Gln Val Asn Gly Ser Tyr Tyr Ile Thr Ala Arg Asp Met Tyr Met Pro
                980                 985                 990

Arg Ala Ile Thr Ala Gly Asp Val  Val Thr Leu Thr Ser  Cys Gln Ala
                995                 1000                1005

Asn Tyr  Val Ile Val Asn Lys  Thr Val Ile Thr Thr  Phe Val Asp
    1010                 1015                 1020
```

```
Asn Asp Asp Phe Asp Phe Asn Asp Glu Leu Ser Lys Trp Trp Asn
    1025                1030                1035

Asp Thr Lys His Glu Leu Pro Asp Phe Asp Lys Phe Asn Tyr Thr
    1040                1045                1050

Val Pro Ile Leu Asp Ile Asp Ser Glu Ile Asp Arg Ile Gln Gly
    1055                1060                1065

Val Ile Gln Gly Leu Asn Asp Ser Leu Ile Asp Leu Glu Lys Leu
    1070                1075                1080

Ser Ile Leu Lys Thr Tyr Ile Lys Trp Pro Trp Tyr Val Trp Leu
    1085                1090                1095

Ala Ile Ala Phe Ala Thr Ile Ile Phe Ile Leu Ile Leu Gly Trp
    1100                1105                1110

Val Phe Phe Met Thr Gly Cys Cys Gly Cys Cys Cys Gly Cys Phe
    1115                1120                1125

Gly Ile Met Pro Leu Met Ser Lys Cys Gly Lys Lys Ser Ser Tyr
    1130                1135                1140

Tyr Thr Thr Phe Asp Asn Asp Val Val Thr Glu Gln Tyr Arg Pro
    1145                1150                1155

Lys Lys Ser Val
    1160

<210> SEQ ID NO 58
<211> LENGTH: 17
<212> TYPE: PRT
<213> ORGANISM: Infectious Bronchitis Virus

<400> SEQUENCE: 58

Met Leu Val Thr Pro Leu Leu Leu Val Thr Leu Leu Cys Ala Leu Cys
1               5                   10                  15

Ser

<210> SEQ ID NO 59
<211> LENGTH: 515
<212> TYPE: PRT
<213> ORGANISM: Infectious Bronchitis Virus

<400> SEQUENCE: 59

Ala Val Leu Tyr Asp Ser Ser Ser Tyr Val Tyr Tyr Tyr Gln Ser Ala
1               5                   10                  15

Phe Arg Pro Pro Ser Gly Trp His Leu Gln Gly Gly Ala Tyr Ala Val
                20                  25                  30

Val Asn Ile Ser Ser Glu Phe Asn Asn Ala Gly Ser Ser Ser Gly Cys
            35                  40                  45

Thr Val Gly Ile Ile His Gly Gly Arg Val Val Asn Ala Ser Ser Ile
        50                  55                  60

Ala Met Thr Ala Pro Ser Ser Gly Met Ala Trp Ser Ser Ser Gln Phe
65                  70                  75                  80

Cys Thr Ala His Cys Asn Phe Ser Asp Thr Thr Val Phe Val Thr His
                85                  90                  95

Cys Tyr Lys His Gly Gly Cys Pro Ile Thr Gly Met Leu Gln Gln Asn
                100                 105                 110

Phe Ile Arg Val Ser Ala Met Lys Asn Gly Gln Leu Phe Tyr Asn Leu
            115                 120                 125

Thr Val Ser Val Ala Lys Tyr Pro Thr Phe Arg Ser Phe Gln Cys Val
        130                 135                 140
```

Asn Asn Leu Thr Ser Val Tyr Leu Asn Gly Asp Leu Val Tyr Thr Ser
145                 150                 155                 160

Asn Glu Thr Ile Asp Val Thr Ser Ala Gly Val Tyr Phe Lys Ala Gly
                165                 170                 175

Gly Pro Ile Thr Tyr Lys Val Met Arg Glu Val Lys Ala Leu Ala Tyr
            180                 185                 190

Phe Val Asn Gly Thr Ala Gln Asp Val Ile Leu Cys Asp Gly Ser Pro
        195                 200                 205

Arg Gly Leu Leu Ala Cys Gln Tyr Asn Thr Gly Asn Phe Ser Asp Gly
    210                 215                 220

Phe Tyr Pro Phe Thr Asn Ser Ser Leu Val Lys Gln Lys Phe Ile Val
225                 230                 235                 240

Tyr Arg Glu Asn Ser Val Asn Thr Thr Cys Thr Leu His Asn Phe Ile
                245                 250                 255

Phe His Asn Glu Thr Gly Ala Asn Pro Asn Pro Ser Gly Val Gln Asn
            260                 265                 270

Ile Gln Thr Tyr Gln Thr Lys Thr Ala Gln Ser Gly Tyr Tyr Asn Phe
        275                 280                 285

Asn Phe Ser Phe Leu Ser Ser Phe Val Tyr Lys Glu Ser Asn Phe Met
    290                 295                 300

Tyr Gly Ser Tyr His Pro Ser Cys Lys Phe Arg Leu Glu Thr Ile Asn
305                 310                 315                 320

Asn Gly Leu Trp Phe Asn Ser Leu Ser Val Ser Ile Ala Tyr Gly Pro
                325                 330                 335

Leu Gln Gly Gly Cys Lys Gln Ser Val Phe Arg Gly Arg Ala Thr Cys
            340                 345                 350

Cys Tyr Ala Tyr Ser Tyr Gly Gly Pro Ser Leu Cys Lys Gly Val Tyr
        355                 360                 365

Ser Gly Glu Leu Asp His Asn Phe Glu Cys Gly Leu Leu Val Tyr Val
    370                 375                 380

Thr Lys Ser Asp Gly Ser Arg Ile Gln Thr Ala Thr Glu Pro Pro Val
385                 390                 395                 400

Ile Thr Gln His Asn Tyr Asn Asn Ile Thr Leu Asn Thr Cys Val Asp
                405                 410                 415

Tyr Asn Ile Tyr Gly Arg Thr Gly Gln Gly Phe Ile Thr Asn Val Thr
            420                 425                 430

Asp Ser Ala Val Ser Tyr Asn Tyr Leu Ala Asp Ala Gly Leu Ala Ile
        435                 440                 445

Leu Asp Thr Ser Gly Ser Ile Asp Ile Phe Val Val Gln Gly Glu Tyr
    450                 455                 460

Gly Leu Asn Tyr Tyr Lys Val Asn Pro Cys Glu Asp Val Asn Gln Gln
465                 470                 475                 480

Phe Val Val Ser Gly Gly Lys Leu Val Gly Ile Leu Thr Ser Arg Asn
                485                 490                 495

Glu Thr Gly Ser Gln Leu Leu Glu Asn Gln Phe Tyr Ile Lys Ile Thr
            500                 505                 510

Asn Gly Thr
        515

<210> SEQ ID NO 60
<211> LENGTH: 5
<212> TYPE: PRT
<213> ORGANISM: Infectious Bronchitis Virus

<400> SEQUENCE: 60

```
Arg Arg Phe Arg Arg
1               5
```

<210> SEQ ID NO 61
<211> LENGTH: 554
<212> TYPE: PRT
<213> ORGANISM: Infectious Bronchitis Virus

<400> SEQUENCE: 61

```
Ser Ile Thr Glu Asn Val Ala Asn Cys Pro Tyr Val Ser Tyr Gly Lys
1               5                   10                  15

Phe Cys Ile Lys Pro Asp Gly Ser Ile Ala Thr Ile Val Pro Lys Gln
            20                  25                  30

Leu Glu Gln Phe Val Ala Pro Leu Phe Asn Val Thr Glu Asn Val Leu
        35                  40                  45

Ile Pro Asn Ser Phe Asn Leu Thr Val Thr Asp Glu Tyr Ile Gln Thr
    50                  55                  60

Arg Met Asp Lys Val Gln Ile Asn Cys Leu Gln Tyr Val Cys Gly Ser
65                  70                  75                  80

Ser Leu Asp Cys Arg Asn Leu Phe Gln Gln Tyr Gly Pro Val Cys Asp
                85                  90                  95

Asn Ile Leu Ser Val Val Asn Ser Val Gly Gln Lys Glu Asp Met Glu
            100                 105                 110

Leu Leu Asn Phe Tyr Ser Ser Thr Lys Pro Ala Gly Phe Asn Thr Pro
        115                 120                 125

Val Leu Ser Asn Val Ser Thr Gly Glu Phe Asn Ile Ser Leu Leu Leu
    130                 135                 140

Thr Thr Pro Ser Ser Arg Arg Arg Arg Ser Val Ile Glu Asp Leu Leu
145                 150                 155                 160

Phe Thr Ser Val Glu Ser Val Gly Leu Pro Thr Asp Asp Ala Tyr Lys
                165                 170                 175

Asn Cys Thr Ala Gly Pro Leu Gly Phe Leu Lys Asp Leu Ala Cys Ala
            180                 185                 190

Arg Glu Tyr Asn Gly Leu Leu Val Leu Pro Pro Ile Ile Thr Ala Glu
        195                 200                 205

Met Gln Ala Leu Tyr Thr Ser Ser Leu Val Ala Ser Met Ala Phe Gly
    210                 215                 220

Gly Ile Thr Ala Ala Gly Ala Ile Pro Phe Ala Thr Gln Leu Gln Ala
225                 230                 235                 240

Arg Ile Asn His Leu Gly Ile Thr Gln Ser Leu Leu Leu Lys Asn Gln
                245                 250                 255

Glu Lys Ile Ala Ala Ser Phe Asn Lys Ala Ile Gly His Met Gln Glu
            260                 265                 270

Gly Phe Arg Ser Thr Ser Leu Ala Leu Gln Gln Ile Gln Asp Val Val
        275                 280                 285

Ser Lys Gln Ser Ala Ile Leu Thr Glu Thr Met Ala Ser Leu Asn Lys
    290                 295                 300

Asn Phe Gly Ala Ile Ser Ser Val Ile Gln Glu Ile Tyr Gln Gln Phe
305                 310                 315                 320

Asp Ala Ile Gln Ala Asn Ala Gln Val Asp Arg Leu Ile Thr Gly Arg
                325                 330                 335

Leu Ser Ser Leu Ser Val Leu Ala Ser Ala Lys Gln Ala Glu Tyr Ile
            340                 345                 350

Arg Val Ser Gln Gln Arg Glu Leu Ala Thr Gln Lys Ile Asn Glu Cys
```

```
                355                 360                 365
Val Lys Ser Gln Ser Ile Arg Tyr Ser Phe Cys Gly Asn Gly Arg His
370                 375                 380

Val Leu Thr Ile Pro Gln Asn Ala Pro Asn Gly Ile Val Phe Ile His
385                 390                 395                 400

Phe Ser Tyr Thr Pro Asp Ser Phe Val Asn Val Thr Ala Ile Val Gly
                405                 410                 415

Phe Cys Val Lys Pro Ala Asn Ala Ser Gln Tyr Ala Ile Val Pro Ala
                420                 425                 430

Asn Gly Arg Gly Ile Phe Ile Gln Val Asn Gly Ser Tyr Tyr Ile Thr
                435                 440                 445

Ala Arg Asp Met Tyr Met Pro Arg Ala Ile Thr Ala Gly Asp Val Val
            450                 455                 460

Thr Leu Thr Ser Cys Gln Ala Asn Tyr Val Ile Val Asn Lys Thr Val
465                 470                 475                 480

Ile Thr Thr Phe Val Asp Asn Asp Asp Phe Asp Phe Asn Asp Glu Leu
                485                 490                 495

Ser Lys Trp Trp Asn Asp Thr Lys His Glu Leu Pro Asp Phe Asp Lys
                500                 505                 510

Phe Asn Tyr Thr Val Pro Ile Leu Asp Ile Asp Ser Glu Ile Asp Arg
                515                 520                 525

Ile Gln Gly Val Ile Gln Gly Leu Asn Asp Ser Leu Ile Asp Leu Glu
                530                 535                 540

Lys Leu Ser Ile Leu Lys Thr Tyr Ile Lys
545                 550

<210> SEQ ID NO 62
<211> LENGTH: 67
<212> TYPE: PRT
<213> ORGANISM: Infectious Bronchitis Virus

<400> SEQUENCE: 62

Val Trp Leu Ala Ile Ala Phe Ala Thr Ile Ile Phe Ile Leu Ile Leu
1               5                   10                  15

Gly Trp Val Phe Phe Met Thr Gly Cys Cys Gly Cys Cys Cys Gly Cys
                20                  25                  30

Phe Gly Ile Met Pro Leu Met Ser Lys Cys Gly Lys Lys Ser Ser Tyr
            35                  40                  45

Tyr Thr Thr Phe Asp Asn Asp Val Val Thr Glu Gln Tyr Arg Pro Lys
        50                  55                  60

Lys Ser Val
65

<210> SEQ ID NO 63
<211> LENGTH: 20
<212> TYPE: PRT
<213> ORGANISM: Infectious Bronchitis Virus

<400> SEQUENCE: 63

Val Trp Leu Ala Ile Ala Phe Ala Thr Ile Ile Phe Ile Leu Ile Leu
1               5                   10                  15

Gly Trp Val Phe
                20

<210> SEQ ID NO 64
<211> LENGTH: 47
<212> TYPE: PRT
```

<213> ORGANISM: Infectious Bronchitis Virus

<400> SEQUENCE: 64

Phe Met Thr Gly Cys Cys Gly Cys Cys Gly Cys Phe Gly Ile Met
1               5                   10                  15

Pro Leu Met Ser Lys Cys Gly Lys Lys Ser Ser Tyr Tyr Thr Thr Phe
            20                  25                  30

Asp Asn Asp Val Val Thr Glu Gln Tyr Arg Pro Lys Lys Ser Val
        35                  40                  45

<210> SEQ ID NO 65
<211> LENGTH: 1162
<212> TYPE: PRT
<213> ORGANISM: Infectious Bronchitis Virus

<400> SEQUENCE: 65

Met Leu Val Thr Pro Leu Leu Val Thr Leu Leu Cys Ala Leu Cys
1               5                   10                  15

Ser Ala Val Leu Tyr Asp Ser Ser Tyr Val Tyr Tyr Tyr Gln Ser
            20                  25                  30

Ala Phe Arg Pro Pro Asn Gly Trp His Leu His Gly Gly Ala Tyr Ala
            35                  40                  45

Val Val Asn Ile Ser Ser Glu Ser Asn Asn Ala Gly Ser Ser Pro Gly
        50                  55                  60

Cys Ile Val Gly Thr Ile His Gly Gly Arg Val Val Asn Ala Ser Ser
65                  70                  75                  80

Ile Ala Met Thr Ala Pro Ser Ser Gly Met Ala Trp Ser Ser Ser Gln
                85                  90                  95

Phe Cys Thr Ala His Cys Asn Phe Ser Asp Thr Thr Val Phe Val Thr
            100                 105                 110

His Cys Tyr Lys Tyr Asp Gly Cys Pro Ile Thr Gly Met Leu Gln Lys
        115                 120                 125

Asn Phe Ile Arg Val Ser Ala Met Lys Asn Gly Gln Leu Phe Tyr Asn
    130                 135                 140

Leu Thr Val Ser Val Ala Lys Tyr Pro Thr Phe Lys Ser Phe Gln Cys
145                 150                 155                 160

Val Asn Asn Leu Thr Ser Val Tyr Leu Asn Gly Asp Leu Val Tyr Thr
                165                 170                 175

Ser Asn Glu Thr Thr Asp Val Thr Ser Ala Gly Val Tyr Phe Lys Ala
            180                 185                 190

Gly Gly Pro Ile Thr Tyr Lys Val Met Arg Glu Val Lys Ala Leu Ala
        195                 200                 205

Tyr Phe Val Asn Gly Thr Ala Gln Asp Val Ile Leu Cys Asp Gly Ser
    210                 215                 220

Pro Arg Gly Leu Leu Ala Cys Gln Tyr Asn Thr Gly Asn Phe Ser Asp
225                 230                 235                 240

Gly Phe Tyr Pro Phe Ile Asn Ser Ser Leu Val Lys Gln Lys Phe Ile
                245                 250                 255

Val Tyr Arg Glu Asn Ser Val Asn Thr Thr Phe Thr Leu His Asn Phe
            260                 265                 270

Thr Phe His Asn Glu Thr Gly Ala Asn Pro Asn Pro Ser Gly Val Gln
        275                 280                 285

Asn Ile Gln Thr Tyr Gln Thr Gln Thr Ala Gln Ser Gly Tyr Tyr Asn
    290                 295                 300

Phe Asn Phe Ser Phe Leu Ser Ser Phe Val Tyr Lys Glu Ser Asn Phe

```
        305                 310                 315                 320
Met Tyr Gly Ser Tyr His Pro Ser Cys Asn Phe Arg Leu Glu Thr Ile
                325                 330                 335

Asn Asn Gly Leu Trp Phe Asn Ser Leu Ser Val Ser Ile Ala Tyr Gly
                340                 345                 350

Pro Leu Gln Gly Gly Cys Lys Gln Ser Val Phe Ser Gly Arg Ala Thr
                355                 360                 365

Cys Cys Tyr Ala Tyr Ser Tyr Gly Gly Pro Ser Leu Cys Lys Gly Val
        370                 375                 380

Tyr Ser Gly Glu Leu Asp Leu Asn Phe Glu Cys Gly Leu Leu Val Tyr
385                 390                 395                 400

Val Thr Lys Ser Gly Ser Arg Ile Gln Thr Ala Thr Glu Pro Pro
                405                 410                 415

Val Ile Thr Gln His Asn Tyr Asn Asn Ile Thr Leu Asn Thr Cys Val
                420                 425                 430

Asp Tyr Asn Ile Tyr Gly Arg Thr Gly Gln Gly Phe Ile Thr Asn Val
        435                 440                 445

Thr Asp Ser Ala Val Ser Tyr Asn Tyr Leu Ala Asp Ala Gly Leu Ala
        450                 455                 460

Ile Leu Asp Thr Ser Gly Ser Ile Asp Ile Phe Val Val Gln Gly Glu
465                 470                 475                 480

Tyr Gly Leu Asn Tyr Tyr Lys Val Asn Pro Cys Glu Asp Val Asn Gln
                485                 490                 495

Gln Phe Val Val Ser Gly Gly Lys Leu Val Gly Ile Leu Thr Ser Arg
                500                 505                 510

Asn Glu Thr Gly Ser Gln Leu Leu Glu Asn Gln Phe Tyr Ile Lys Ile
        515                 520                 525

Thr Asn Gly Thr Arg Arg Phe Arg Arg Ser Ile Thr Glu Asn Val Ala
        530                 535                 540

Asn Cys Pro Tyr Val Ser Tyr Gly Lys Phe Cys Ile Lys Pro Asp Gly
545                 550                 555                 560

Ser Ile Ala Thr Ile Val Pro Lys Gln Leu Glu Gln Phe Val Ala Pro
                565                 570                 575

Leu Phe Asn Val Thr Glu Asn Val Leu Ile Pro Asn Ser Phe Asn Leu
                580                 585                 590

Thr Val Thr Asp Glu Tyr Ile Gln Thr Arg Met Asp Lys Val Gln Ile
        595                 600                 605

Asn Cys Leu Gln Tyr Val Cys Gly Ser Ser Leu Asp Cys Arg Lys Leu
        610                 615                 620

Phe Gln Gln Tyr Gly Pro Val Cys Asp Asn Ile Leu Ser Val Val Asn
625                 630                 635                 640

Ser Val Gly Gln Lys Glu Asp Met Glu Leu Leu Asn Phe Tyr Ser Ser
                645                 650                 655

Thr Lys Pro Ala Gly Phe Asn Thr Pro Val Leu Ser Asn Val Ser Thr
                660                 665                 670

Gly Glu Phe Asn Ile Ser Leu Leu Leu Thr Thr Pro Ser Ser Arg Arg
        675                 680                 685

Arg Arg Ser Phe Ile Glu Asp Leu Leu Phe Thr Ser Val Glu Ser Val
        690                 695                 700

Gly Leu Pro Thr Asp Asp Ala Tyr Lys Asn Cys Thr Ala Gly Pro Leu
705                 710                 715                 720

Gly Phe Leu Lys Asp Leu Ala Cys Ala Arg Glu Tyr Asn Gly Leu Leu
                725                 730                 735
```

-continued

Val Leu Pro Pro Ile Ile Thr Ala Glu Met Gln Ala Leu Tyr Thr Ser
            740                 745                 750

Ser Leu Val Ala Ser Met Ala Phe Gly Gly Ile Thr Ala Ala Gly Ala
            755                 760                 765

Met Pro Phe Ala Thr Gln Leu Gln Ala Arg Ile Asn His Leu Gly Ile
            770                 775                 780

Thr Gln Ser Leu Leu Lys Asn Gln Glu Lys Ile Ala Ala Ser Phe
785                 790                 795                 800

Asn Lys Ala Ile Gly His Met Gln Glu Gly Phe Arg Ser Thr Ser Leu
                805                 810                 815

Ala Leu Gln Gln Ile Gln Asp Val Val Ser Lys Gln Ser Ala Ile Leu
            820                 825                 830

Thr Glu Thr Met Ala Ser Leu Asn Lys Asn Phe Gly Ala Ile Ser Ser
            835                 840                 845

Val Ile Gln Glu Ile Tyr Gln Gln Phe Asp Ala Ile Gln Ala Asn Ala
850                 855                 860

Gln Val Asp Arg Leu Ile Thr Gly Arg Leu Ser Ser Leu Ser Val Leu
865                 870                 875                 880

Ala Ser Ala Lys Gln Ala Glu Tyr Ile Arg Val Ser Gln Gln Arg Glu
                885                 890                 895

Leu Ala Thr Gln Lys Ile Asn Glu Cys Val Lys Ser Gln Ser Ile Arg
                900                 905                 910

Tyr Ser Phe Cys Gly Asn Gly Arg His Val Leu Thr Ile Pro Gln Asn
            915                 920                 925

Ala Pro Asn Gly Ile Val Phe Ile His Phe Ser Tyr Thr Pro Asp Ser
            930                 935                 940

Phe Val Asn Val Thr Ala Ile Val Gly Phe Cys Val Lys Pro Ala Asn
945                 950                 955                 960

Ala Ser Gln Tyr Ala Ile Val Pro Ala Asn Gly Arg Gly Ile Phe Ile
                965                 970                 975

Gln Val Asn Gly Ser Tyr Tyr Ile Thr Ala Arg Asp Met Tyr Met Pro
            980                 985                 990

Arg Ala Ile Thr Ala Gly Asp Val Val Thr Leu Thr Ser Cys Gln Ala
            995                 1000                1005

Asn Tyr Val Ile Val Asn Lys Thr Val Ile Thr Thr Phe Val Asp
    1010                1015                1020

Asn Asp Asp Phe Asp Phe Asn Asp Glu Leu Ser Lys Trp Trp Asn
    1025                1030                1035

Asp Thr Lys His Glu Leu Pro Asp Phe Asp Lys Phe Asn Tyr Thr
    1040                1045                1050

Val Pro Ile Leu Asp Ile Asp Ser Glu Ile Asp Arg Ile Gln Gly
    1055                1060                1065

Val Ile Gln Gly Leu Asn Asp Ser Leu Ile Asp Leu Glu Lys Leu
    1070                1075                1080

Ser Ile Leu Lys Thr Tyr Ile Lys Trp Pro Trp Tyr Val Trp Leu
    1085                1090                1095

Ala Ile Ala Phe Ala Thr Ile Ile Phe Ile Leu Ile Leu Gly Trp
    1100                1105                1110

Val Phe Phe Met Thr Gly Cys Cys Gly Cys Cys Cys Gly Cys Phe
    1115                1120                1125

Gly Ile Met Pro Leu Met Ser Lys Cys Gly Lys Lys Ser Ser Tyr
    1130                1135                1140

```
Tyr Thr Thr Phe Asp Asn Asp  Val Val Thr Glu Gln  Tyr Arg Pro
    1145                1150                 1155

Lys Lys Ser Val
    1160

<210> SEQ ID NO 66
<211> LENGTH: 17
<212> TYPE: PRT
<213> ORGANISM: Infectious Bronchitis Virus

<400> SEQUENCE: 66

Met Leu Val Thr Pro Leu Leu Val Thr Leu Leu Cys Ala Leu Cys
1               5                   10                  15

Ser

<210> SEQ ID NO 67
<211> LENGTH: 515
<212> TYPE: PRT
<213> ORGANISM: Infectious Bronchitis Virus

<400> SEQUENCE: 67

Ala Val Leu Tyr Asp Ser Ser Tyr Val Tyr Tyr Gln Ser Ala
1               5                   10                  15

Phe Arg Pro Pro Asn Gly Trp His Leu His Gly Gly Ala Tyr Ala Val
                20                  25                  30

Val Asn Ile Ser Ser Glu Ser Asn Ala Gly Ser Ser Pro Gly Cys
                35                  40                  45

Ile Val Gly Thr Ile His Gly Gly Arg Val Val Asn Ala Ser Ser Ile
        50                  55                  60

Ala Met Thr Ala Pro Ser Ser Gly Met Ala Trp Ser Ser Ser Gln Phe
65              70                  75                      80

Cys Thr Ala His Cys Asn Phe Ser Asp Thr Thr Val Phe Val Thr His
                85                  90                  95

Cys Tyr Lys Tyr Asp Gly Cys Pro Ile Thr Gly Met Leu Gln Lys Asn
                100                 105                 110

Phe Ile Arg Val Ser Ala Met Lys Asn Gly Gln Leu Phe Tyr Asn Leu
                115                 120                 125

Thr Val Ser Val Ala Lys Tyr Pro Thr Phe Lys Ser Phe Gln Cys Val
            130                 135                 140

Asn Asn Leu Thr Ser Val Tyr Leu Asn Gly Asp Leu Val Tyr Thr Ser
145                 150                 155                 160

Asn Glu Thr Thr Asp Val Thr Ser Ala Gly Val Tyr Phe Lys Ala Gly
                165                 170                 175

Gly Pro Ile Thr Tyr Lys Val Met Arg Glu Val Lys Ala Leu Ala Tyr
            180                 185                 190

Phe Val Asn Gly Thr Ala Gln Asp Val Ile Leu Cys Asp Gly Ser Pro
        195                 200                 205

Arg Gly Leu Leu Ala Cys Gln Tyr Asn Thr Gly Asn Phe Ser Asp Gly
    210                 215                 220

Phe Tyr Pro Phe Ile Asn Ser Ser Leu Val Lys Gln Lys Phe Ile Val
225                 230                 235                 240

Tyr Arg Glu Asn Ser Val Asn Thr Thr Phe Thr Leu His Asn Phe Thr
                245                 250                 255

Phe His Asn Glu Thr Gly Ala Asn Pro Asn Pro Ser Gly Val Gln Asn
            260                 265                 270

Ile Gln Thr Tyr Gln Thr Gln Thr Ala Gln Ser Gly Tyr Tyr Asn Phe
```

```
            275                 280                 285
Asn Phe Ser Phe Leu Ser Ser Phe Val Tyr Lys Glu Ser Asn Phe Met
    290                 295                 300

Tyr Gly Ser Tyr His Pro Ser Cys Asn Phe Arg Leu Glu Thr Ile Asn
305                 310                 315                 320

Asn Gly Leu Trp Phe Asn Ser Leu Ser Val Ser Ile Ala Tyr Gly Pro
                325                 330                 335

Leu Gln Gly Gly Cys Lys Gln Ser Val Phe Ser Gly Arg Ala Thr Cys
            340                 345                 350

Cys Tyr Ala Tyr Ser Tyr Gly Gly Pro Ser Leu Cys Lys Gly Val Tyr
        355                 360                 365

Ser Gly Glu Leu Asp Leu Asn Phe Glu Cys Gly Leu Leu Val Tyr Val
    370                 375                 380

Thr Lys Ser Gly Gly Ser Arg Ile Gln Thr Ala Thr Glu Pro Pro Val
385                 390                 395                 400

Ile Thr Gln His Asn Tyr Asn Asn Ile Thr Leu Asn Thr Cys Val Asp
                405                 410                 415

Tyr Asn Ile Tyr Gly Arg Thr Gly Gln Gly Phe Ile Thr Asn Val Thr
            420                 425                 430

Asp Ser Ala Val Ser Tyr Asn Tyr Leu Ala Asp Ala Gly Leu Ala Ile
        435                 440                 445

Leu Asp Thr Ser Gly Ser Ile Asp Ile Phe Val Val Gln Gly Glu Tyr
    450                 455                 460

Gly Leu Asn Tyr Tyr Lys Val Asn Pro Cys Glu Asp Val Asn Gln Gln
465                 470                 475                 480

Phe Val Val Ser Gly Gly Lys Leu Val Gly Ile Leu Thr Ser Arg Asn
                485                 490                 495

Glu Thr Gly Ser Gln Leu Leu Glu Asn Gln Phe Tyr Ile Lys Ile Thr
            500                 505                 510

Asn Gly Thr
        515

<210> SEQ ID NO 68
<211> LENGTH: 5
<212> TYPE: PRT
<213> ORGANISM: Infectious Bronchitis Virus

<400> SEQUENCE: 68

Arg Arg Phe Arg Arg
1               5

<210> SEQ ID NO 69
<211> LENGTH: 554
<212> TYPE: PRT
<213> ORGANISM: Infectious Bronchitis Virus

<400> SEQUENCE: 69

Ser Ile Thr Glu Asn Val Ala Asn Cys Pro Tyr Val Ser Tyr Gly Lys
1               5                   10                  15

Phe Cys Ile Lys Pro Asp Gly Ser Ile Ala Thr Ile Val Pro Lys Gln
            20                  25                  30

Leu Glu Gln Phe Val Ala Pro Leu Phe Asn Val Thr Glu Asn Val Leu
        35                  40                  45

Ile Pro Asn Ser Phe Asn Leu Thr Val Thr Asp Glu Tyr Ile Gln Thr
    50                  55                  60

Arg Met Asp Lys Val Gln Ile Asn Cys Leu Gln Tyr Val Cys Gly Ser
```

-continued

```
                65                  70                  75                  80
Ser Leu Asp Cys Arg Lys Leu Phe Gln Gln Tyr Gly Pro Val Cys Asp
                    85                  90                  95
Asn Ile Leu Ser Val Val Asn Ser Val Gly Gln Lys Glu Asp Met Glu
                100                 105                 110
Leu Leu Asn Phe Tyr Ser Ser Thr Lys Pro Ala Gly Phe Asn Thr Pro
                115                 120                 125
Val Leu Ser Asn Val Ser Thr Gly Glu Phe Asn Ile Ser Leu Leu Leu
            130                 135                 140
Thr Thr Pro Ser Ser Arg Arg Arg Ser Phe Ile Glu Asp Leu Leu
145                 150                 155                 160
Phe Thr Ser Val Glu Ser Val Gly Leu Pro Thr Asp Asp Ala Tyr Lys
                165                 170                 175
Asn Cys Thr Ala Gly Pro Leu Gly Phe Leu Lys Asp Leu Ala Cys Ala
                180                 185                 190
Arg Glu Tyr Asn Gly Leu Leu Val Leu Pro Pro Ile Ile Thr Ala Glu
                195                 200                 205
Met Gln Ala Leu Tyr Thr Ser Ser Leu Val Ala Ser Met Ala Phe Gly
            210                 215                 220
Gly Ile Thr Ala Ala Gly Ala Met Pro Phe Ala Thr Gln Leu Gln Ala
225                 230                 235                 240
Arg Ile Asn His Leu Gly Ile Thr Gln Ser Leu Leu Leu Lys Asn Gln
                245                 250                 255
Glu Lys Ile Ala Ala Ser Phe Asn Lys Ala Ile Gly His Met Gln Glu
                260                 265                 270
Gly Phe Arg Ser Thr Ser Leu Ala Leu Gln Gln Ile Gln Asp Val Val
            275                 280                 285
Ser Lys Gln Ser Ala Ile Leu Thr Glu Thr Met Ala Ser Leu Asn Lys
            290                 295                 300
Asn Phe Gly Ala Ile Ser Ser Val Ile Gln Glu Ile Tyr Gln Gln Phe
305                 310                 315                 320
Asp Ala Ile Gln Ala Asn Ala Gln Val Asp Arg Leu Ile Thr Gly Arg
                325                 330                 335
Leu Ser Ser Leu Ser Val Leu Ala Ser Ala Lys Gln Ala Glu Tyr Ile
            340                 345                 350
Arg Val Ser Gln Gln Arg Glu Leu Ala Thr Gln Lys Ile Asn Glu Cys
            355                 360                 365
Val Lys Ser Gln Ser Ile Arg Tyr Ser Phe Cys Gly Asn Gly Arg His
370                 375                 380
Val Leu Thr Ile Pro Gln Asn Ala Pro Asn Gly Ile Val Phe Ile His
385                 390                 395                 400
Phe Ser Tyr Thr Pro Asp Ser Phe Val Asn Val Thr Ala Ile Val Gly
                405                 410                 415
Phe Cys Val Lys Pro Ala Asn Ala Ser Gln Tyr Ala Ile Val Pro Ala
                420                 425                 430
Asn Gly Arg Gly Ile Phe Ile Gln Val Asn Gly Ser Tyr Tyr Ile Thr
            435                 440                 445
Ala Arg Asp Met Tyr Met Pro Arg Ala Ile Thr Ala Gly Asp Val Val
            450                 455                 460
Thr Leu Thr Ser Cys Gln Ala Asn Tyr Val Ile Val Asn Lys Thr Val
465                 470                 475                 480
Ile Thr Thr Phe Val Asp Asn Asp Asp Phe Asp Phe Asn Asp Glu Leu
                485                 490                 495
```

```
Ser Lys Trp Trp Asn Asp Thr Lys His Glu Leu Pro Asp Phe Asp Lys
            500                 505                 510

Phe Asn Tyr Thr Val Pro Ile Leu Asp Ile Asp Ser Glu Ile Asp Arg
            515                 520                 525

Ile Gln Gly Val Ile Gln Gly Leu Asn Asp Ser Leu Ile Asp Leu Glu
            530                 535                 540

Lys Leu Ser Ile Leu Lys Thr Tyr Ile Lys
545                 550

<210> SEQ ID NO 70
<211> LENGTH: 67
<212> TYPE: PRT
<213> ORGANISM: Infectious Bronchitis Virus

<400> SEQUENCE: 70

Val Trp Leu Ala Ile Ala Phe Ala Thr Ile Ile Phe Ile Leu Ile Leu
1               5                   10                  15

Gly Trp Val Phe Phe Met Thr Gly Cys Cys Gly Cys Cys Cys Gly Cys
            20                  25                  30

Phe Gly Ile Met Pro Leu Met Ser Lys Cys Gly Lys Lys Ser Ser Tyr
            35                  40                  45

Tyr Thr Thr Phe Asp Asn Asp Val Val Thr Glu Gln Tyr Arg Pro Lys
    50                  55                  60

Lys Ser Val
65

<210> SEQ ID NO 71
<211> LENGTH: 20
<212> TYPE: PRT
<213> ORGANISM: Infectious Bronchitis Virus

<400> SEQUENCE: 71

Val Trp Leu Ala Ile Ala Phe Ala Thr Ile Ile Phe Ile Leu Ile Leu
1               5                   10                  15

Gly Trp Val Phe
            20

<210> SEQ ID NO 72
<211> LENGTH: 47
<212> TYPE: PRT
<213> ORGANISM: Infectious Bronchitis Virus

<400> SEQUENCE: 72

Phe Met Thr Gly Cys Cys Gly Cys Cys Cys Gly Cys Phe Gly Ile Met
1               5                   10                  15

Pro Leu Met Ser Lys Cys Gly Lys Lys Ser Ser Tyr Tyr Thr Thr Phe
            20                  25                  30

Asp Asn Asp Val Val Thr Glu Gln Tyr Arg Pro Lys Lys Ser Val
        35                  40                  45

<210> SEQ ID NO 73
<211> LENGTH: 1162
<212> TYPE: PRT
<213> ORGANISM: Infectious Bronchitis Virus

<400> SEQUENCE: 73

Met Leu Val Thr Pro Leu Leu Leu Val Thr Leu Leu Cys Ala Leu Cys
1               5                   10                  15

Ser Ala Val Leu Tyr Asp Ser Ser Ser Tyr Val Tyr Tyr Tyr Gln Ser
```

```
                 20                  25                  30
Ala Phe Arg Pro Pro Asn Gly Trp His Leu His Gly Gly Ala Tyr Ala
             35                  40                  45

Val Val Asn Ile Ser Ser Glu Ser Asn Asn Ala Gly Ser Ser Pro Gly
         50                  55                  60

Cys Ile Val Gly Thr Ile His Gly Gly Arg Val Val Asn Ala Ser Ser
 65                  70                  75                  80

Ile Ala Met Thr Ala Pro Ser Ser Gly Met Ala Trp Ser Ser Ser Gln
                 85                  90                  95

Phe Cys Thr Ala His Cys Asn Phe Ser Asp Thr Thr Val Phe Val Thr
            100                 105                 110

His Cys Tyr Lys Tyr Asp Gly Cys Pro Ile Thr Gly Met Leu Gln Lys
            115                 120                 125

Asn Phe Ile Arg Val Ser Ala Met Lys Asn Gly Gln Leu Phe Tyr Asn
            130                 135                 140

Leu Thr Val Ser Val Ala Lys Tyr Pro Thr Phe Lys Ser Phe Gln Cys
145                 150                 155                 160

Val Asn Asn Leu Thr Ser Val Tyr Leu Asn Gly Asp Leu Val Tyr Thr
                165                 170                 175

Ser Asn Glu Thr Thr Asp Val Thr Ser Ala Gly Val Tyr Phe Lys Ala
            180                 185                 190

Gly Gly Pro Ile Thr Tyr Lys Val Met Arg Glu Val Lys Ala Leu Ala
            195                 200                 205

Tyr Phe Val Asn Gly Thr Ala Gln Asp Val Ile Leu Cys Asp Gly Ser
            210                 215                 220

Pro Arg Gly Leu Leu Ala Cys Gln Tyr Asn Thr Gly Asn Phe Ser Asp
225                 230                 235                 240

Gly Phe Tyr Pro Phe Ile Asn Ser Ser Leu Val Lys Gln Lys Phe Ile
                245                 250                 255

Val Tyr Arg Glu Asn Ser Val Asn Thr Thr Phe Thr Leu His Asn Phe
            260                 265                 270

Thr Phe His Asn Glu Thr Gly Ala Asn Pro Asn Pro Ser Gly Val Gln
            275                 280                 285

Asn Ile Gln Thr Tyr Gln Thr Gln Thr Ala Gln Ser Gly Tyr Tyr Asn
            290                 295                 300

Phe Asn Phe Ser Phe Leu Ser Ser Phe Val Tyr Lys Glu Ser Asn Phe
305                 310                 315                 320

Met Tyr Gly Ser Tyr His Pro Ser Cys Asn Phe Arg Leu Glu Thr Ile
                325                 330                 335

Asn Asn Gly Leu Trp Phe Asn Ser Leu Ser Val Ser Ile Ala Tyr Gly
            340                 345                 350

Pro Leu Gln Gly Gly Cys Lys Gln Ser Val Phe Ser Gly Arg Ala Thr
            355                 360                 365

Cys Cys Tyr Ala Tyr Ser Tyr Gly Gly Pro Ser Leu Cys Lys Gly Val
            370                 375                 380

Tyr Ser Gly Glu Leu Asp Leu Asn Phe Glu Cys Gly Leu Leu Val Tyr
385                 390                 395                 400

Val Thr Lys Ser Gly Gly Ser Arg Ile Gln Thr Ala Thr Glu Pro Pro
                405                 410                 415

Val Ile Thr Gln His Asn Tyr Asn Asn Ile Thr Leu Asn Thr Cys Val
            420                 425                 430

Asp Tyr Asn Ile Tyr Gly Arg Thr Gly Gln Gly Phe Ile Thr Asn Val
            435                 440                 445
```

```
Thr Asp Ser Ala Val Ser Tyr Asn Tyr Leu Ala Asp Ala Gly Leu Ala
    450                 455                 460

Ile Leu Asp Thr Ser Gly Ser Ile Asp Ile Phe Val Val Gln Gly Glu
465                 470                 475                 480

Tyr Gly Leu Asn Tyr Tyr Lys Val Asn Pro Cys Glu Asp Val Asn Gln
                485                 490                 495

Gln Phe Val Val Ser Gly Gly Lys Leu Val Gly Ile Leu Thr Ser Arg
                500                 505                 510

Asn Glu Thr Gly Ser Gln Leu Leu Glu Asn Gln Phe Tyr Ile Lys Ile
            515                 520                 525

Thr Asn Gly Thr Arg Arg Phe Arg Arg Ser Ile Thr Glu Asn Val Ala
530                 535                 540

Asn Cys Pro Tyr Val Ser Tyr Gly Lys Phe Cys Ile Lys Pro Asp Gly
545                 550                 555                 560

Ser Ile Ala Thr Ile Val Pro Lys Gln Leu Glu Gln Phe Val Ala Pro
                565                 570                 575

Leu Phe Asn Val Thr Glu Asn Val Leu Ile Pro Asn Ser Phe Asn Leu
                580                 585                 590

Thr Val Thr Asp Glu Tyr Ile Gln Thr Arg Met Asp Lys Val Gln Ile
            595                 600                 605

Asn Cys Leu Gln Tyr Val Cys Gly Ser Ser Leu Asp Cys Arg Lys Leu
610                 615                 620

Phe Gln Gln Tyr Gly Pro Val Cys Asp Asn Ile Leu Ser Val Val Asn
625                 630                 635                 640

Ser Val Gly Gln Lys Glu Asp Met Glu Leu Leu Asn Phe Tyr Ser Ser
                645                 650                 655

Thr Lys Pro Ala Gly Phe Asn Thr Pro Val Leu Ser Asn Val Ser Thr
                660                 665                 670

Gly Glu Phe Asn Ile Ser Leu Leu Leu Thr Thr Pro Ser Ser Arg Arg
            675                 680                 685

Arg Arg Ser Phe Ile Glu Asp Leu Leu Phe Thr Ser Val Glu Ser Val
690                 695                 700

Gly Leu Pro Thr Asp Asp Ala Tyr Lys Asn Cys Thr Ala Gly Pro Leu
705                 710                 715                 720

Gly Phe Leu Lys Asp Leu Ala Cys Ala Arg Glu Tyr Asn Gly Leu Leu
                725                 730                 735

Val Leu Pro Pro Ile Ile Thr Ala Glu Met Gln Ala Leu Tyr Thr Ser
                740                 745                 750

Ser Leu Val Ala Ser Met Ala Phe Gly Gly Ile Thr Ala Ala Gly Ala
            755                 760                 765

Ile Pro Phe Ala Thr Gln Leu Gln Ala Arg Ile Asn His Leu Gly Ile
770                 775                 780

Thr Gln Ser Leu Leu Leu Lys Asn Gln Glu Lys Ile Ala Ala Ser Phe
785                 790                 795                 800

Asn Lys Ala Ile Gly His Met Gln Glu Gly Phe Arg Ser Thr Ser Leu
                805                 810                 815

Ala Leu Gln Gln Ile Gln Asp Val Val Ser Lys Gln Ser Ala Ile Leu
                820                 825                 830

Thr Glu Thr Met Ala Ser Leu Asn Lys Asn Phe Gly Ala Ile Ser Ser
            835                 840                 845

Val Ile Gln Glu Ile Tyr Gln Gln Phe Asp Ala Ile Gln Ala Asn Ala
        850                 855                 860
```

```
Gln Val Asp Arg Leu Ile Thr Gly Arg Leu Ser Ser Leu Ser Val Leu
865                 870                 875                 880

Ala Ser Ala Lys Gln Ala Glu Tyr Ile Arg Val Ser Gln Gln Arg Glu
                885                 890                 895

Leu Ala Thr Gln Lys Ile Asn Glu Cys Val Lys Ser Gln Ser Ile Arg
            900                 905                 910

Tyr Ser Phe Cys Gly Asn Gly Arg His Val Leu Thr Ile Pro Gln Asn
        915                 920                 925

Ala Pro Asn Gly Ile Val Phe Ile His Phe Ser Tyr Thr Pro Asp Ser
    930                 935                 940

Phe Val Asn Val Thr Ala Ile Val Gly Phe Cys Val Lys Pro Ala Asn
945                 950                 955                 960

Ala Ser Gln Tyr Ala Ile Val Pro Ala Asn Gly Arg Gly Ile Phe Ile
                965                 970                 975

Gln Val Asn Gly Ser Tyr Tyr Ile Thr Ala Arg Asp Met Tyr Met Pro
            980                 985                 990

Arg Ala Ile Thr Ala Gly Asp Val Val Thr Leu Thr Ser Cys Gln Ala
        995                 1000                1005

Asn Tyr Val Ile Val Asn Lys Thr Val Ile Thr Thr Phe Val Asp
    1010                1015                1020

Asn Asp Asp Phe Asp Phe Asn Asp Glu Leu Ser Lys Trp Trp Asn
    1025                1030                1035

Asp Thr Lys His Glu Leu Pro Asp Phe Asp Lys Phe Asn Tyr Thr
    1040                1045                1050

Val Pro Ile Leu Asp Ile Asp Ser Glu Ile Asp Arg Ile Gln Gly
    1055                1060                1065

Val Ile Gln Gly Leu Asn Asp Ser Leu Ile Asp Leu Glu Lys Leu
    1070                1075                1080

Ser Ile Leu Lys Thr Tyr Ile Lys Trp Pro Trp Tyr Val Trp Leu
    1085                1090                1095

Ala Ile Ala Phe Ala Thr Ile Ile Phe Ile Leu Ile Leu Gly Trp
    1100                1105                1110

Val Phe Phe Met Thr Gly Cys Cys Gly Cys Cys Cys Gly Cys Phe
    1115                1120                1125

Gly Ile Met Pro Leu Met Ser Lys Cys Gly Lys Lys Ser Ser Tyr
    1130                1135                1140

Tyr Thr Thr Phe Asp Asn Asp Val Val Thr Glu Gln Tyr Arg Pro
    1145                1150                1155

Lys Lys Ser Val
    1160

<210> SEQ ID NO 74
<211> LENGTH: 17
<212> TYPE: PRT
<213> ORGANISM: Infectious Bronchitis Virus

<400> SEQUENCE: 74

Met Leu Val Thr Pro Leu Leu Val Thr Leu Leu Cys Ala Leu Cys
1               5                   10                  15

Ser

<210> SEQ ID NO 75
<211> LENGTH: 515
<212> TYPE: PRT
<213> ORGANISM: Infectious Bronchitis Virus
```

<400> SEQUENCE: 75

```
Ala Val Leu Tyr Asp Ser Ser Tyr Val Tyr Tyr Gln Ser Ala
1               5                   10                  15
Phe Arg Pro Pro Asn Gly Trp His Leu His Gly Gly Ala Tyr Ala Val
                20                  25                  30
Val Asn Ile Ser Ser Glu Ser Asn Ala Gly Ser Ser Pro Gly Cys
            35                  40                  45
Ile Val Gly Thr Ile His Gly Gly Arg Val Val Asn Ala Ser Ser Ile
    50                  55                  60
Ala Met Thr Ala Pro Ser Ser Gly Met Ala Trp Ser Ser Ser Gln Phe
65                  70                  75                  80
Cys Thr Ala His Cys Asn Phe Ser Asp Thr Thr Val Phe Val Thr His
                85                  90                  95
Cys Tyr Lys Tyr Asp Gly Cys Pro Ile Thr Gly Met Leu Gln Lys Asn
                100                 105                 110
Phe Ile Arg Val Ser Ala Met Lys Asn Gly Gln Leu Phe Tyr Asn Leu
            115                 120                 125
Thr Val Ser Val Ala Lys Tyr Pro Thr Phe Lys Ser Phe Gln Cys Val
    130                 135                 140
Asn Asn Leu Thr Ser Val Tyr Leu Asn Gly Asp Leu Val Tyr Thr Ser
145                 150                 155                 160
Asn Glu Thr Thr Asp Val Thr Ser Ala Gly Val Tyr Phe Lys Ala Gly
                165                 170                 175
Gly Pro Ile Thr Tyr Lys Val Met Arg Glu Val Lys Ala Leu Ala Tyr
            180                 185                 190
Phe Val Asn Gly Thr Ala Gln Asp Val Ile Leu Cys Asp Gly Ser Pro
    195                 200                 205
Arg Gly Leu Leu Ala Cys Gln Tyr Asn Thr Gly Asn Phe Ser Asp Gly
            210                 215                 220
Phe Tyr Pro Phe Ile Asn Ser Ser Leu Val Lys Gln Lys Phe Ile Val
225                 230                 235                 240
Tyr Arg Glu Asn Ser Val Asn Thr Thr Phe Thr Leu His Asn Phe Thr
                245                 250                 255
Phe His Asn Glu Thr Gly Ala Asn Pro Asn Pro Ser Gly Val Gln Asn
            260                 265                 270
Ile Gln Thr Tyr Gln Thr Gln Thr Ala Gln Ser Gly Tyr Tyr Asn Phe
    275                 280                 285
Asn Phe Ser Phe Leu Ser Ser Phe Val Tyr Lys Glu Ser Asn Phe Met
        290                 295                 300
Tyr Gly Ser Tyr His Pro Ser Cys Asn Phe Arg Leu Glu Thr Ile Asn
305                 310                 315                 320
Asn Gly Leu Trp Phe Asn Ser Leu Ser Val Ser Ile Ala Tyr Gly Pro
                325                 330                 335
Leu Gln Gly Gly Cys Lys Gln Ser Val Phe Ser Gly Arg Ala Thr Cys
            340                 345                 350
Cys Tyr Ala Tyr Ser Tyr Gly Gly Pro Ser Leu Cys Lys Gly Val Tyr
    355                 360                 365
Ser Gly Glu Leu Asp Leu Asn Phe Glu Cys Gly Leu Leu Val Tyr Val
        370                 375                 380
Thr Lys Ser Gly Gly Ser Arg Ile Gln Thr Ala Thr Glu Pro Pro Val
385                 390                 395                 400
Ile Thr Gln His Asn Tyr Asn Asn Ile Thr Leu Asn Thr Cys Val Asp
                405                 410                 415
```

```
Tyr Asn Ile Tyr Gly Arg Thr Gly Gln Gly Phe Ile Thr Asn Val Thr
            420                 425                 430

Asp Ser Ala Val Ser Tyr Asn Tyr Leu Ala Asp Ala Gly Leu Ala Ile
            435                 440                 445

Leu Asp Thr Ser Gly Ser Ile Asp Ile Phe Val Val Gln Gly Glu Tyr
450                 455                 460

Gly Leu Asn Tyr Tyr Lys Val Asn Pro Cys Glu Asp Val Asn Gln Gln
465                 470                 475                 480

Phe Val Val Ser Gly Gly Lys Leu Val Gly Ile Leu Thr Ser Arg Asn
                485                 490                 495

Glu Thr Gly Ser Gln Leu Leu Glu Asn Gln Phe Tyr Ile Lys Ile Thr
            500                 505                 510

Asn Gly Thr
        515

<210> SEQ ID NO 76
<211> LENGTH: 5
<212> TYPE: PRT
<213> ORGANISM: Infectious Bronchitis Virus

<400> SEQUENCE: 76

Phe Phe Arg Phe Phe
1               5

<210> SEQ ID NO 77
<211> LENGTH: 554
<212> TYPE: PRT
<213> ORGANISM: Infectious Bronchitis Virus

<400> SEQUENCE: 77

Ser Ile Thr Glu Asn Val Ala Asn Cys Pro Tyr Val Ser Tyr Gly Lys
1               5                   10                  15

Phe Cys Ile Lys Pro Asp Gly Ser Ile Ala Thr Ile Val Pro Lys Gln
                20                  25                  30

Leu Glu Gln Phe Val Ala Pro Leu Phe Asn Val Thr Glu Asn Val Leu
            35                  40                  45

Ile Pro Asn Ser Phe Asn Leu Thr Val Thr Asp Glu Tyr Ile Gln Thr
        50                  55                  60

Arg Met Asp Lys Val Gln Ile Asn Cys Leu Gln Tyr Val Cys Gly Ser
65                  70                  75                  80

Ser Leu Asp Cys Arg Lys Leu Phe Gln Gln Tyr Gly Pro Val Cys Asp
                85                  90                  95

Asn Ile Leu Ser Val Val Asn Ser Val Gly Gln Lys Glu Asp Met Glu
            100                 105                 110

Leu Leu Asn Phe Tyr Ser Ser Thr Lys Pro Ala Gly Phe Asn Thr Pro
        115                 120                 125

Val Leu Ser Asn Val Ser Thr Gly Glu Phe Asn Ile Ser Leu Leu Leu
    130                 135                 140

Thr Thr Pro Ser Ser Arg Arg Arg Ser Phe Ile Glu Asp Leu Leu
145                 150                 155                 160

Phe Thr Ser Val Glu Ser Val Gly Leu Pro Thr Asp Asp Ala Tyr Lys
                165                 170                 175

Asn Cys Thr Ala Gly Pro Leu Gly Phe Leu Lys Asp Leu Ala Cys Ala
            180                 185                 190

Arg Glu Tyr Asn Gly Leu Leu Val Leu Pro Pro Ile Ile Thr Ala Glu
        195                 200                 205
```

```
Met Gln Ala Leu Tyr Thr Ser Ser Leu Val Ala Ser Met Ala Phe Gly
    210                 215                 220

Gly Ile Thr Ala Ala Gly Ala Ile Pro Phe Ala Thr Gln Leu Gln Ala
225                 230                 235                 240

Arg Ile Asn His Leu Gly Ile Thr Gln Ser Leu Leu Leu Lys Asn Gln
                245                 250                 255

Glu Lys Ile Ala Ala Ser Phe Asn Lys Ala Ile Gly His Met Gln Glu
            260                 265                 270

Gly Phe Arg Ser Thr Ser Leu Ala Leu Gln Gln Ile Gln Asp Val Val
        275                 280                 285

Ser Lys Gln Ser Ala Ile Leu Thr Glu Thr Met Ala Ser Leu Asn Lys
290                 295                 300

Asn Phe Gly Ala Ile Ser Ser Val Ile Gln Glu Ile Tyr Gln Gln Phe
305                 310                 315                 320

Asp Ala Ile Gln Ala Asn Ala Gln Val Asp Arg Leu Ile Thr Gly Arg
                325                 330                 335

Leu Ser Ser Leu Ser Val Leu Ala Ser Ala Lys Gln Ala Glu Tyr Ile
            340                 345                 350

Arg Val Ser Gln Gln Arg Glu Leu Ala Thr Gln Lys Ile Asn Glu Cys
        355                 360                 365

Val Lys Ser Gln Ser Ile Arg Tyr Ser Phe Cys Gly Asn Gly Arg His
370                 375                 380

Val Leu Thr Ile Pro Gln Asn Ala Pro Asn Gly Ile Val Phe Ile His
385                 390                 395                 400

Phe Ser Tyr Thr Pro Asp Ser Phe Val Asn Val Thr Ala Ile Val Gly
                405                 410                 415

Phe Cys Val Lys Pro Ala Asn Ala Ser Gln Tyr Ala Ile Val Pro Ala
            420                 425                 430

Asn Gly Arg Gly Ile Phe Ile Gln Val Asn Gly Ser Tyr Tyr Ile Thr
        435                 440                 445

Ala Arg Asp Met Tyr Met Pro Arg Ala Ile Thr Ala Gly Asp Val Val
450                 455                 460

Thr Leu Thr Ser Cys Gln Ala Asn Tyr Val Ile Val Asn Lys Thr Val
465                 470                 475                 480

Ile Thr Thr Phe Val Asp Asn Asp Asp Phe Asp Phe Asn Asp Glu Leu
                485                 490                 495

Ser Lys Trp Trp Asn Asp Thr Lys His Glu Leu Pro Asp Phe Asp Lys
            500                 505                 510

Phe Asn Tyr Thr Val Pro Ile Leu Asp Ile Asp Ser Glu Ile Asp Arg
        515                 520                 525

Ile Gln Gly Val Ile Gln Gly Leu Asn Asp Ser Leu Ile Asp Leu Glu
530                 535                 540

Lys Leu Ser Ile Leu Lys Thr Tyr Ile Lys
545                 550

<210> SEQ ID NO 78
<211> LENGTH: 67
<212> TYPE: PRT
<213> ORGANISM: Infectious Bronchitis Virus

<400> SEQUENCE: 78

Val Trp Leu Ala Ile Ala Phe Ala Thr Ile Ile Phe Ile Leu Ile Leu
1               5                   10                  15

Gly Trp Val Phe Phe Met Thr Gly Cys Cys Gly Cys Cys Cys Gly Cys
```

```
                20                  25                  30

Phe Gly Ile Met Pro Leu Met Ser Lys Cys Gly Lys Lys Ser Ser Tyr
            35                  40                  45

Tyr Thr Thr Phe Asp Asn Asp Val Val Thr Glu Gln Tyr Arg Pro Lys
        50                  55                  60

Lys Ser Val
65

<210> SEQ ID NO 79
<211> LENGTH: 20
<212> TYPE: PRT
<213> ORGANISM: Infectoius Bronchitis Virus

<400> SEQUENCE: 79

Val Trp Leu Ala Ile Ala Phe Ala Thr Ile Ile Phe Ile Leu Ile Leu
1               5                   10                  15

Gly Trp Val Phe
            20

<210> SEQ ID NO 80
<211> LENGTH: 47
<212> TYPE: PRT
<213> ORGANISM: Infectious Bronchitis Virus

<400> SEQUENCE: 80

Phe Met Thr Gly Cys Cys Gly Cys Cys Gly Cys Phe Gly Ile Met
1               5                   10                  15

Pro Leu Met Ser Lys Cys Gly Lys Lys Ser Ser Tyr Tyr Thr Thr Phe
            20                  25                  30

Asp Asn Asp Val Val Thr Glu Gln Tyr Arg Pro Lys Lys Ser Val
            35                  40                  45

<210> SEQ ID NO 81
<211> LENGTH: 1169
<212> TYPE: PRT
<213> ORGANISM: Infectious Bronchitis Virus

<400> SEQUENCE: 81

Met Leu Val Lys Ser Leu Phe Leu Val Thr Ile Leu Phe Ala Leu Cys
1               5                   10                  15

Ser Ala Asn Leu Tyr Asp Asn Glu Ser Phe Val Tyr Tyr Tyr Gln Ser
            20                  25                  30

Ala Phe Arg Pro Gly His Gly Trp His Leu His Gly Gly Ala Tyr Ala
        35                  40                  45

Val Val Asn Val Ser Ser Glu Asn Asn Asn Ala Gly Thr Ala Pro Ser
    50                  55                  60

Cys Thr Ala Gly Ala Ile Gly Tyr Ser Lys Asn Leu Ser Ala Ala Ser
65                  70                  75                  80

Val Ala Met Thr Ala Pro Leu Ser Gly Met Ser Trp Ser Ala Asn Ser
                85                  90                  95

Phe Cys Thr Ala His Cys Asn Phe Thr Ser Tyr Ile Val Phe Val Thr
            100                 105                 110

His Cys Tyr Lys Ser Gly Ser Asn Ser Cys Pro Leu Thr Gly Leu Ile
        115                 120                 125

Pro Ser Gly Tyr Ile Arg Ile Ala Ala Met Lys His Gly Ser Ala Met
    130                 135                 140

Pro Gly His Leu Phe Tyr Asn Leu Thr Val Ser Val Thr Lys Tyr Pro
145                 150                 155                 160
```

Lys Phe Arg Ser Leu Gln Cys Val Asn Asn His Thr Ser Val Tyr Leu
                165                 170                 175

Asn Gly Asp Leu Val Phe Thr Ser Asn Tyr Thr Glu Asp Val Val Ala
            180                 185                 190

Ala Gly Val His Phe Lys Ser Gly Gly Pro Ile Thr Tyr Lys Val Met
        195                 200                 205

Arg Glu Val Lys Ala Leu Ala Tyr Phe Val Asn Gly Thr Ala His Asp
    210                 215                 220

Val Ile Leu Cys Asp Asp Thr Pro Arg Gly Leu Leu Ala Cys Gln Tyr
225                 230                 235                 240

Asn Thr Gly Asn Phe Ser Asp Gly Phe Tyr Pro Phe Thr Asn Thr Ser
                245                 250                 255

Ile Val Lys Asp Lys Phe Ile Val Tyr Arg Glu Ser Ser Val Asn Thr
            260                 265                 270

Thr Leu Thr Leu Thr Asn Phe Thr Phe Ser Asn Glu Ser Gly Ala Pro
        275                 280                 285

Pro Asn Thr Gly Gly Val Asp Ser Phe Ile Leu Tyr Gln Thr Gln Thr
    290                 295                 300

Ala Gln Ser Gly Tyr Tyr Asn Phe Asn Phe Ser Phe Leu Ser Ser Phe
305                 310                 315                 320

Val Tyr Arg Glu Ser Tyr Tyr Met Tyr Gly Ser Tyr His Pro Arg Cys
                325                 330                 335

Ser Phe Arg Pro Glu Thr Leu Asn Asn Gly Leu Trp Phe Asn Ser Leu
            340                 345                 350

Ser Val Ser Leu Thr Tyr Gly Pro Ile Gln Gly Gly Cys Lys Gln Ser
        355                 360                 365

Val Phe Asn Gly Lys Ala Thr Cys Cys Tyr Ala Tyr Ser Tyr Gly Gly
    370                 375                 380

Pro Arg Gly Cys Lys Gly Val Tyr Arg Gly Glu Leu Thr Gln His Phe
385                 390                 395                 400

Glu Cys Gly Leu Leu Val Tyr Val Thr Lys Ser Asp Gly Ser Arg Ile
                405                 410                 415

Gln Thr Ala Thr Gln Pro Pro Val Leu Thr Gln Asn Phe Tyr Asn Asn
            420                 425                 430

Ile Asn Leu Gly Lys Cys Val Asp Tyr Asn Ile Tyr Gly Arg Ile Gly
        435                 440                 445

Gln Gly Leu Ile Thr Asn Val Thr Asp Leu Ala Val Ser Tyr Asn Tyr
    450                 455                 460

Leu Ser Asp Ala Gly Leu Ala Ile Leu Asp Thr Ser Gly Ala Ile Asp
465                 470                 475                 480

Ile Phe Val Val Gln Gly Glu Tyr Gly Pro Asn Tyr Tyr Lys Val Asn
                485                 490                 495

Pro Cys Glu Asp Val Asn Gln Gln Phe Val Val Ser Gly Gly Lys Leu
            500                 505                 510

Val Gly Ile Leu Thr Ser Arg Asn Glu Thr Gly Ser Gln Leu Leu Glu
        515                 520                 525

Asn Gln Phe Tyr Ile Lys Ile Thr Asn Gly Thr Arg Arg Ser Arg Arg
    530                 535                 540

Ser Val Thr Glu Asn Val Thr Asn Cys Pro Tyr Val Ser Tyr Gly Lys
545                 550                 555                 560

Phe Cys Ile Lys Pro Asp Gly Ser Ile Ser Val Ile Val Pro Lys Glu
                565                 570                 575

-continued

Leu Asp Gln Phe Val Ala Pro Leu Leu Asn Val Thr Glu Tyr Val Leu
            580                 585                 590

Ile Pro Asn Ser Phe Asn Leu Thr Val Thr Asp Glu Tyr Ile Gln Thr
        595                 600                 605

Arg Met Asp Lys Ile Gln Ile Asn Cys Leu Gln Tyr Val Cys Gly Asn
    610                 615                 620

Ser Leu Ala Cys Arg Lys Leu Phe Gln Gln Tyr Gly Pro Val Cys Asp
625                 630                 635                 640

Asn Ile Leu Ser Val Val Asn Ser Val Gly Gln Lys Glu Asp Met Glu
                645                 650                 655

Leu Leu Asn Phe Tyr Ser Ser Thr Lys Pro Ala Arg Phe Asn Thr Pro
            660                 665                 670

Val Phe Ser Asn Leu Ser Thr Gly Glu Phe Asn Ile Ser Leu Leu Leu
        675                 680                 685

Thr Pro Pro Ser Ser Pro Arg Arg Ser Phe Ile Glu Asp Leu Leu
    690                 695                 700

Phe Thr Ser Val Glu Ser Val Gly Leu Pro Thr Asp Asp Ala Tyr Lys
705                 710                 715                 720

Lys Cys Thr Ala Gly Pro Leu Gly Phe Leu Lys Asp Leu Ala Cys Ala
                725                 730                 735

Arg Glu Tyr Asn Gly Leu Leu Val Leu Pro Pro Ile Ile Thr Ala Glu
            740                 745                 750

Met Gln Thr Leu Tyr Thr Ser Ser Leu Val Ala Ser Met Ala Phe Gly
        755                 760                 765

Gly Ile Thr Ala Ala Gly Ala Ile Pro Phe Ala Thr Gln Leu Gln Ala
    770                 775                 780

Arg Ile Asn His Leu Gly Ile Thr Gln Ser Leu Leu Leu Lys Asn Gln
785                 790                 795                 800

Glu Lys Ile Ala Ala Ser Phe Asn Lys Ala Ile Gly His Met Gln Glu
                805                 810                 815

Gly Phe Arg Ser Thr Ser Leu Ala Leu Gln Gln Ile Gln Asp Val Val
            820                 825                 830

Asn Lys Gln Ser Ala Ile Leu Thr Glu Thr Met Ala Ala Leu Asn Lys
        835                 840                 845

Asn Phe Gly Ala Ile Ser Ser Val Ile Gln Asp Ile Tyr Gln Gln Leu
    850                 855                 860

Asp Ser Ile Gln Ala Asp Ala Gln Val Asp Arg Leu Ile Thr Gly Arg
865                 870                 875                 880

Leu Ser Ser Leu Ser Val Leu Ala Ser Ala Lys Gln Ser Glu Tyr Ile
                885                 890                 895

Arg Val Ser Gln Gln Arg Glu Leu Ala Thr Gln Lys Ile Asn Glu Cys
            900                 905                 910

Val Lys Ser Gln Ser Ile Arg Tyr Ser Phe Cys Gly Asn Gly Arg His
        915                 920                 925

Val Leu Thr Ile Pro Gln Asn Ala Pro Asn Gly Ile Val Phe Ile His
    930                 935                 940

Phe Thr Tyr Thr Pro Glu Ser Phe Ile Asn Val Thr Ala Ile Val Gly
945                 950                 955                 960

Phe Cys Val Ser Pro Ala Asn Ala Ser Gln Tyr Ala Ile Val Pro Ala
                965                 970                 975

Asn Gly Arg Gly Ile Phe Ile Gln Val Asn Gly Ser Tyr Tyr Ile Thr
            980                 985                 990

Ala Arg Asp Met Tyr Met Pro Arg Asp Ile Thr Ala Gly Asp Ile Val

-continued

```
                    995                 1000                1005
Thr Leu Thr Ser Cys Gln Ala Asn Tyr Val Ser Val Asn Lys Thr
        1010                1015                1020

Val Ile Thr Thr Phe Val Asp Asn Asp Phe Asp Phe Asp Asp
        1025                1030                1035

Glu Leu Ser Lys Trp Trp Asn Asp Thr Lys His Glu Leu Pro Asp
        1040                1045                1050

Phe Asp Lys Phe Asn Tyr Thr Val Pro Ile Leu Asp Ile Asp Ser
        1055                1060                1065

Glu Ile Asp Arg Ile Gln Gly Val Ile Gln Gly Leu Asn Asp Ser
        1070                1075                1080

Leu Ile Asp Leu Glu Thr Leu Ser Ile Leu Lys Thr Tyr Ile Lys
        1085                1090                1095

Trp Pro Trp Tyr Val Trp Leu Ala Ile Ala Phe Ala Thr Ile Ile
        1100                1105                1110

Phe Ile Leu Ile Leu Gly Trp Leu Phe Phe Met Thr Gly Cys Cys
        1115                1120                1125

Gly Cys Cys Cys Gly Cys Phe Gly Ile Ile Pro Leu Met Ser Lys
        1130                1135                1140

Cys Gly Lys Lys Ser Ser Tyr Tyr Thr Thr Phe Asp Asn Asp Val
        1145                1150                1155

Val Thr Glu Gln Tyr Arg Pro Lys Lys Ser Val
        1160                1165

<210> SEQ ID NO 82
<211> LENGTH: 17
<212> TYPE: PRT
<213> ORGANISM: Infectious Bronchitis Virus

<400> SEQUENCE: 82

Met Leu Val Lys Ser Leu Phe Leu Val Thr Ile Leu Phe Ala Leu Cys
1               5                   10                  15

Ser

<210> SEQ ID NO 83
<211> LENGTH: 522
<212> TYPE: PRT
<213> ORGANISM: Infectious Bronchitis Virus

<400> SEQUENCE: 83

Ala Asn Leu Tyr Asp Asn Glu Ser Phe Val Tyr Tyr Gln Ser Ala
1               5                   10                  15

Phe Arg Pro Gly His Gly Trp His Leu His Gly Gly Ala Tyr Ala Val
                20                  25                  30

Val Asn Val Ser Ser Glu Asn Asn Asn Ala Gly Thr Ala Pro Ser Cys
            35                  40                  45

Thr Ala Gly Ala Ile Gly Tyr Ser Lys Asn Leu Ser Ala Ala Ser Val
        50                  55                  60

Ala Met Thr Ala Pro Leu Ser Gly Met Ser Trp Ser Ala Asn Ser Phe
65                  70                  75                  80

Cys Thr Ala His Cys Asn Phe Ser Tyr Ile Val Phe Val Thr His
                85                  90                  95

Cys Tyr Lys Ser Gly Ser Asn Ser Cys Pro Leu Thr Gly Leu Ile Pro
            100                 105                 110

Ser Gly Tyr Ile Arg Ile Ala Ala Met Lys His Gly Ser Ala Met Pro
        115                 120                 125
```

```
Gly His Leu Phe Tyr Asn Leu Thr Val Ser Val Thr Lys Tyr Pro Lys
    130                 135                 140

Phe Arg Ser Leu Gln Cys Val Asn Asn His Thr Ser Val Tyr Leu Asn
145                 150                 155                 160

Gly Asp Leu Val Phe Thr Ser Asn Tyr Thr Glu Asp Val Val Ala Ala
                    165                 170                 175

Gly Val His Phe Lys Ser Gly Gly Pro Ile Thr Tyr Lys Val Met Arg
                180                 185                 190

Glu Val Lys Ala Leu Ala Tyr Phe Val Asn Gly Thr Ala His Asp Val
            195                 200                 205

Ile Leu Cys Asp Asp Thr Pro Arg Gly Leu Leu Ala Cys Gln Tyr Asn
    210                 215                 220

Thr Gly Asn Phe Ser Asp Gly Phe Tyr Pro Phe Thr Asn Thr Ser Ile
225                 230                 235                 240

Val Lys Asp Lys Phe Ile Val Tyr Arg Glu Ser Ser Val Asn Thr Thr
                    245                 250                 255

Leu Thr Leu Thr Asn Phe Thr Phe Ser Asn Glu Ser Gly Ala Pro Pro
                260                 265                 270

Asn Thr Gly Gly Val Asp Ser Phe Ile Leu Tyr Gln Thr Gln Thr Ala
            275                 280                 285

Gln Ser Gly Tyr Tyr Asn Phe Asn Phe Ser Phe Leu Ser Ser Phe Val
    290                 295                 300

Tyr Arg Glu Ser Tyr Tyr Met Tyr Gly Ser Tyr His Pro Arg Cys Ser
305                 310                 315                 320

Phe Arg Pro Glu Thr Leu Asn Asn Gly Leu Trp Phe Asn Ser Leu Ser
                    325                 330                 335

Val Ser Leu Thr Tyr Gly Pro Ile Gln Gly Gly Cys Lys Gln Ser Val
                340                 345                 350

Phe Asn Gly Lys Ala Thr Cys Cys Tyr Ala Tyr Ser Tyr Gly Gly Pro
            355                 360                 365

Arg Gly Cys Lys Gly Val Tyr Arg Gly Glu Leu Thr Gln His Phe Glu
    370                 375                 380

Cys Gly Leu Leu Val Tyr Val Thr Lys Ser Asp Gly Ser Arg Ile Gln
385                 390                 395                 400

Thr Ala Thr Gln Pro Pro Val Leu Thr Gln Asn Phe Tyr Asn Asn Ile
                    405                 410                 415

Asn Leu Gly Lys Cys Val Asp Tyr Asn Ile Tyr Gly Arg Ile Gly Gln
                420                 425                 430

Gly Leu Ile Thr Asn Val Thr Asp Leu Ala Val Ser Tyr Asn Tyr Leu
            435                 440                 445

Ser Asp Ala Gly Leu Ala Ile Leu Asp Thr Ser Gly Ala Ile Asp Ile
    450                 455                 460

Phe Val Val Gln Gly Glu Tyr Gly Pro Asn Tyr Tyr Lys Val Asn Pro
465                 470                 475                 480

Cys Glu Asp Val Asn Gln Gln Phe Val Val Ser Gly Gly Lys Leu Val
                    485                 490                 495

Gly Ile Leu Thr Ser Arg Asn Glu Thr Gly Ser Gln Leu Leu Glu Asn
                500                 505                 510

Gln Phe Tyr Ile Lys Ile Thr Asn Gly Thr
            515                 520

<210> SEQ ID NO 84
<211> LENGTH: 5
```

<212> TYPE: PRT
<213> ORGANISM: Infectious Bronchitis Virus

<400> SEQUENCE: 84

Arg Arg Ser Arg Arg
1               5

<210> SEQ ID NO 85
<211> LENGTH: 554
<212> TYPE: PRT
<213> ORGANISM: Infectious Bronchitis Virus

<400> SEQUENCE: 85

Ser Val Thr Glu Asn Val Thr Asn Cys Pro Tyr Val Ser Tyr Gly Lys
1               5                   10                  15

Phe Cys Ile Lys Pro Asp Gly Ser Ile Ser Val Ile Val Pro Lys Glu
                20                  25                  30

Leu Asp Gln Phe Val Ala Pro Leu Leu Asn Val Thr Glu Tyr Val Leu
            35                  40                  45

Ile Pro Asn Ser Phe Asn Leu Thr Val Thr Asp Glu Tyr Ile Gln Thr
        50                  55                  60

Arg Met Asp Lys Ile Gln Ile Asn Cys Leu Gln Tyr Val Cys Gly Asn
65                  70                  75                  80

Ser Leu Ala Cys Arg Lys Leu Phe Gln Gln Tyr Gly Pro Val Cys Asp
                85                  90                  95

Asn Ile Leu Ser Val Val Asn Ser Val Gly Gln Lys Glu Asp Met Glu
                100                 105                 110

Leu Leu Asn Phe Tyr Ser Ser Thr Lys Pro Ala Arg Phe Asn Thr Pro
            115                 120                 125

Val Phe Ser Asn Leu Ser Thr Gly Glu Phe Asn Ile Ser Leu Leu Leu
        130                 135                 140

Thr Pro Pro Ser Ser Pro Arg Arg Arg Ser Phe Ile Glu Asp Leu Leu
145                 150                 155                 160

Phe Thr Ser Val Glu Ser Val Gly Leu Pro Thr Asp Asp Ala Tyr Lys
                165                 170                 175

Lys Cys Thr Ala Gly Pro Leu Gly Phe Leu Lys Asp Leu Ala Cys Ala
                180                 185                 190

Arg Glu Tyr Asn Gly Leu Leu Val Leu Pro Pro Ile Ile Thr Ala Glu
            195                 200                 205

Met Gln Thr Leu Tyr Thr Ser Ser Leu Val Ala Ser Met Ala Phe Gly
        210                 215                 220

Gly Ile Thr Ala Ala Gly Ala Ile Pro Phe Ala Thr Gln Leu Gln Ala
225                 230                 235                 240

Arg Ile Asn His Leu Gly Ile Thr Gln Ser Leu Leu Leu Lys Asn Gln
                245                 250                 255

Glu Lys Ile Ala Ala Ser Phe Asn Lys Ala Ile Gly His Met Gln Glu
                260                 265                 270

Gly Phe Arg Ser Thr Ser Leu Ala Leu Gln Gln Ile Gln Asp Val Val
            275                 280                 285

Asn Lys Gln Ser Ala Ile Leu Thr Glu Thr Met Ala Ala Leu Asn Lys
        290                 295                 300

Asn Phe Gly Ala Ile Ser Ser Val Ile Gln Asp Ile Tyr Gln Gln Leu
305                 310                 315                 320

Asp Ser Ile Gln Ala Asp Ala Gln Val Asp Arg Leu Ile Thr Gly Arg
                325                 330                 335

```
Leu Ser Ser Leu Ser Val Leu Ala Ser Ala Lys Gln Ser Glu Tyr Ile
                340                 345                 350

Arg Val Ser Gln Gln Arg Glu Leu Ala Thr Gln Lys Ile Asn Glu Cys
            355                 360                 365

Val Lys Ser Gln Ser Ile Arg Tyr Ser Phe Cys Gly Asn Gly Arg His
        370                 375                 380

Val Leu Thr Ile Pro Gln Asn Ala Pro Asn Gly Ile Val Phe Ile His
385                 390                 395                 400

Phe Thr Tyr Thr Pro Glu Ser Phe Ile Asn Val Thr Ala Ile Val Gly
                405                 410                 415

Phe Cys Val Ser Pro Ala Asn Ala Ser Gln Tyr Ala Ile Val Pro Ala
            420                 425                 430

Asn Gly Arg Gly Ile Phe Ile Gln Val Asn Gly Ser Tyr Tyr Ile Thr
        435                 440                 445

Ala Arg Asp Met Tyr Met Pro Arg Asp Ile Thr Ala Gly Asp Ile Val
    450                 455                 460

Thr Leu Thr Ser Cys Gln Ala Asn Tyr Val Ser Val Asn Lys Thr Val
465                 470                 475                 480

Ile Thr Thr Phe Val Asp Asn Asp Asp Phe Asp Phe Asp Asp Glu Leu
                485                 490                 495

Ser Lys Trp Trp Asn Asp Thr Lys His Glu Leu Pro Asp Phe Asp Lys
            500                 505                 510

Phe Asn Tyr Thr Val Pro Ile Leu Asp Ile Asp Ser Glu Ile Asp Arg
        515                 520                 525

Ile Gln Gly Val Ile Gln Gly Leu Asn Asp Ser Leu Ile Asp Leu Glu
    530                 535                 540

Thr Leu Ser Ile Leu Lys Thr Tyr Ile Lys
545                 550

<210> SEQ ID NO 86
<211> LENGTH: 67
<212> TYPE: PRT
<213> ORGANISM: Infectious Bronchitis Virus

<400> SEQUENCE: 86

Val Trp Leu Ala Ile Ala Phe Ala Thr Ile Ile Phe Ile Leu Ile Leu
1               5                   10                  15

Gly Trp Leu Phe Phe Met Thr Gly Cys Cys Gly Cys Cys Cys Gly Cys
            20                  25                  30

Phe Gly Ile Ile Pro Leu Met Ser Lys Cys Gly Lys Lys Ser Ser Tyr
        35                  40                  45

Tyr Thr Thr Phe Asp Asn Asp Val Val Thr Glu Gln Tyr Arg Pro Lys
    50                  55                  60

Lys Ser Val
65

<210> SEQ ID NO 87
<211> LENGTH: 20
<212> TYPE: PRT
<213> ORGANISM: Infectious Bronchitis Virus

<400> SEQUENCE: 87

Val Trp Leu Ala Ile Ala Phe Ala Thr Ile Ile Phe Ile Leu Ile Leu
1               5                   10                  15

Gly Trp Leu Phe
            20
```

<210> SEQ ID NO 88
<211> LENGTH: 47
<212> TYPE: PRT
<213> ORGANISM: Infectious Bronchitis Virus

<400> SEQUENCE: 88

Phe Met Thr Gly Cys Cys Gly Cys Cys Cys Gly Cys Phe Gly Ile Ile
1               5                   10                  15

Pro Leu Met Ser Lys Cys Gly Lys Lys Ser Ser Tyr Tyr Thr Thr Phe
            20                  25                  30

Asp Asn Asp Val Val Thr Glu Gln Tyr Arg Pro Lys Lys Ser Val
        35                  40                  45

<210> SEQ ID NO 89
<211> LENGTH: 1168
<212> TYPE: PRT
<213> ORGANISM: Infectious Bronchitis Virus

<400> SEQUENCE: 89

Met Leu Val Lys Ser Leu Phe Leu Val Thr Ile Leu Phe Ala Leu Cys
1               5                   10                  15

Ser Ala Asn Leu Tyr Asp Asn Glu Ser Phe Val Tyr Tyr Tyr Gln Ser
            20                  25                  30

Ala Phe Arg Pro Gly His Gly Trp His Leu His Gly Gly Ala Tyr Ala
        35                  40                  45

Val Val Asn Val Ser Ser Glu Asn Asn Asn Ala Gly Thr Ala Pro Ser
    50                  55                  60

Cys Thr Ala Gly Ala Ile Gly Tyr Ser Lys Asn Leu Ser Ala Ala Ser
65                  70                  75                  80

Val Ala Met Thr Ala Pro Leu Ser Gly Met Ser Trp Ser Ala Asn Ser
                85                  90                  95

Phe Cys Thr Ala His Cys Asn Phe Thr Ser Tyr Ile Val Phe Val Thr
            100                 105                 110

His Cys Tyr Lys Ser Gly Ser Asn Ser Cys Pro Leu Thr Gly Leu Ile
        115                 120                 125

Pro Ser Gly Tyr Ile Arg Ile Ala Ala Met Lys His Gly Ser Ala Met
    130                 135                 140

Pro Gly His Leu Phe Tyr Asn Leu Thr Val Ser Val Thr Lys Tyr Pro
145                 150                 155                 160

Lys Phe Arg Ser Leu Gln Cys Val Asn Asn Tyr Thr Ser Val Tyr Leu
                165                 170                 175

Asn Gly Asp Leu Val Phe Thr Ser Asn Tyr Thr Glu Asp Val Val Ala
            180                 185                 190

Ala Gly Val His Phe Lys Ser Gly Gly Pro Ile Thr Tyr Lys Val Met
        195                 200                 205

Arg Glu Val Lys Ala Leu Ala Tyr Phe Val Asn Gly Thr Ala His Asp
    210                 215                 220

Val Ile Leu Cys Asp Asp Thr Pro Arg Gly Leu Leu Ala Cys Gln Tyr
225                 230                 235                 240

Asn Thr Gly Asn Phe Ser Asp Gly Phe Tyr Pro Phe Thr Asn Thr Ser
                245                 250                 255

Ile Val Lys Asp Lys Phe Ile Val Tyr Arg Glu Ser Ser Val Asn Thr
            260                 265                 270

Thr Leu Thr Leu Thr Asn Phe Thr Phe Ser Asn Glu Ser Gly Ala Pro
        275                 280                 285

-continued

```
Pro Asn Thr Gly Gly Val Asp Ser Phe Ile Leu Tyr Gln Thr Gln Thr
    290                 295                 300

Ala Gln Ser Gly Tyr Tyr Asn Phe Asn Phe Ser Phe Leu Ser Ser Phe
305                 310                 315                 320

Val Tyr Arg Glu Ser Asn Tyr Met Tyr Gly Ser Tyr His Pro Arg Cys
                325                 330                 335

Ser Phe Arg Pro Glu Thr Leu Asn Gly Leu Trp Phe Asn Ser Leu Ser
            340                 345                 350

Val Ser Leu Thr Tyr Gly Pro Ile Gln Gly Gly Cys Lys Gln Ser Val
        355                 360                 365

Phe Asn Gly Lys Ala Thr Cys Cys Tyr Ala Tyr Ser Tyr Gly Gly Pro
370                 375                 380

Arg Gly Cys Lys Gly Val Tyr Arg Gly Glu Leu Thr Gln His Phe Glu
385                 390                 395                 400

Cys Gly Leu Leu Val Tyr Val Thr Lys Ser Asp Gly Ser Arg Ile Gln
                405                 410                 415

Thr Ala Thr Gln Pro Pro Val Leu Thr Gln Asn Phe Tyr Asn Asn Ile
            420                 425                 430

Asn Leu Gly Lys Cys Val Asp Tyr Asn Ile Tyr Gly Arg Ile Gly Gln
        435                 440                 445

Gly Leu Ile Thr Asn Val Thr Asp Leu Ala Val Ser Tyr Asn Tyr Leu
    450                 455                 460

Ser Asp Ala Gly Leu Ala Ile Leu Asp Thr Ser Gly Ala Ile Asp Ile
465                 470                 475                 480

Phe Val Val Gln Gly Glu Tyr Gly Pro Asn Tyr Tyr Lys Val Asn Pro
                485                 490                 495

Cys Glu Asp Val Asn Gln Gln Phe Val Val Ser Gly Gly Lys Leu Val
            500                 505                 510

Gly Ile Leu Thr Ser Arg Asn Glu Thr Gly Ser Gln Leu Leu Glu Asn
        515                 520                 525

Gln Phe Tyr Ile Lys Ile Thr Asn Gly Thr Arg Arg Ser Arg Arg Ser
    530                 535                 540

Val Thr Glu Asn Val Thr Asn Cys Pro Tyr Val Ser Tyr Gly Lys Phe
545                 550                 555                 560

Cys Ile Lys Pro Asp Gly Ser Ile Ser Val Ile Val Pro Lys Glu Leu
                565                 570                 575

Asp Gln Phe Val Ala Pro Leu Leu Asn Val Thr Glu Tyr Val Leu Ile
            580                 585                 590

Pro Asn Ser Phe Asn Leu Thr Val Thr Asp Glu Tyr Ile Gln Thr Arg
        595                 600                 605

Met Asp Lys Ile Gln Ile Asn Cys Leu Gln Tyr Val Cys Gly Asn Ser
    610                 615                 620

Leu Ala Cys Arg Lys Leu Phe Gln Gln Tyr Gly Pro Val Cys Asp Asn
625                 630                 635                 640

Ile Leu Ser Val Val Asn Ser Val Gly Gln Lys Glu Asp Met Glu Leu
                645                 650                 655

Leu Asn Phe Tyr Ser Ser Thr Lys Pro Ala Arg Phe Asn Thr Pro Val
            660                 665                 670

Phe Ser Asn Leu Ser Thr Gly Glu Phe Asn Ile Ser Leu Leu Leu Thr
        675                 680                 685

Ser Pro Ser Ser Pro Arg Arg Arg Ser Phe Ile Glu Asp Leu Leu Phe
690                 695                 700

Thr Ser Val Glu Ser Val Gly Leu Pro Thr Asp Asp Ala Tyr Lys Lys
```

-continued

```
            705                 710                 715                 720
        Cys Thr Ala Gly Pro Leu Gly Phe Phe Lys Asp Leu Ala Cys Ala Arg
                        725                 730                 735
        Glu Tyr Asn Gly Leu Leu Val Leu Pro Pro Ile Ile Thr Ala Glu Met
                        740                 745                 750
        Gln Thr Leu Tyr Thr Ser Ser Leu Val Ala Ser Met Ala Phe Gly Gly
                        755                 760                 765
        Ile Thr Ala Ala Gly Ala Ile Pro Phe Ala Thr Gln Leu Gln Ala Arg
                        770                 775                 780
        Ile Asn His Leu Gly Ile Thr Gln Ser Leu Leu Leu Lys Asn Gln Glu
        785                 790                 795                 800
        Lys Ile Ala Ala Ser Phe Asn Lys Ala Ile Gly His Met Gln Glu Gly
                        805                 810                 815
        Phe Arg Ser Thr Ser Leu Ala Leu Gln Gln Ile Gln Asp Val Val Asn
                        820                 825                 830
        Lys Gln Ser Ala Ile Leu Thr Glu Thr Met Ala Ala Leu Asn Lys Asn
                        835                 840                 845
        Phe Gly Ala Ile Ser Ser Val Ile Gln Asp Ile Tyr Gln Gln Leu Asp
                        850                 855                 860
        Ser Ile Gln Ala Asp Ala Gln Val Asp Arg Leu Ile Thr Gly Arg Leu
        865                 870                 875                 880
        Ser Ser Leu Ser Val Leu Ala Ser Ala Lys Gln Ser Glu Tyr Ile Arg
                        885                 890                 895
        Val Ser Gln Gln Arg Glu Leu Ala Thr Gln Lys Ile Asn Glu Cys Val
                        900                 905                 910
        Lys Ser Gln Ser Ile Arg Tyr Ser Phe Cys Gly Asn Gly Arg His Val
                        915                 920                 925
        Leu Thr Ile Pro Gln Asn Ala Pro Asn Gly Ile Val Phe Ile His Phe
                        930                 935                 940
        Thr Tyr Thr Pro Glu Ser Phe Ile Asn Val Thr Ala Ile Val Gly Phe
        945                 950                 955                 960
        Cys Val Ser Pro Ala Asn Ala Ser Gln Tyr Ala Ile Val Pro Ala Asn
                        965                 970                 975
        Gly Arg Gly Ile Phe Ile Gln Val Asn Gly Ser Tyr Tyr Ile Thr Ala
                        980                 985                 990
        Arg Asp Met Tyr Met Pro Arg Asp Ile Thr Ala Gly Asp Ile Val Thr
                        995                 1000                1005
        Leu Thr Ser Cys Gln Ala Asn Tyr Val Ser Val Asn Lys Thr Val
                        1010                1015                1020
        Ile Thr Thr Phe Val Asp Asn Asp Asp Phe Asp Phe Asp Asp Glu
                        1025                1030                1035
        Leu Ser Lys Trp Trp Asn Asp Thr Lys His Glu Leu Pro Asp Phe
                        1040                1045                1050
        Asp Lys Phe Asn Tyr Thr Val Pro Ile Leu Asp Ile Asp Ser Glu
                        1055                1060                1065
        Ile Asp Arg Ile Gln Gly Val Ile Gln Gly Leu Asn Asp Ser Leu
                        1070                1075                1080
        Ile Asp Leu Glu Thr Leu Ser Ile Leu Lys Thr Tyr Ile Lys Trp
                        1085                1090                1095
        Pro Trp Tyr Val Trp Leu Ala Ile Ala Phe Ala Thr Ile Ile Phe
                        1100                1105                1110
        Ile Leu Ile Leu Gly Trp Leu Phe Phe Met Thr Gly Cys Cys Gly
                        1115                1120                1125
```

```
Cys Cys Cys Gly Cys Phe Gly Ile Ile Pro Leu Met Ser Lys Cys
    1130            1135             1140

Gly Lys Lys Ser Ser Tyr Tyr Thr Thr Phe Asp Asn Asp Val Val
    1145            1150             1155

Thr Glu Gln Tyr Arg Pro Lys Lys Ser Val
    1160            1165

<210> SEQ ID NO 90
<211> LENGTH: 17
<212> TYPE: PRT
<213> ORGANISM: Infectious Bronchitis Virus

<400> SEQUENCE: 90

Met Leu Val Lys Ser Leu Phe Leu Val Thr Ile Leu Phe Ala Leu Cys
1               5                   10                  15

Ser

<210> SEQ ID NO 91
<211> LENGTH: 521
<212> TYPE: PRT
<213> ORGANISM: Infectious Bronchitis Virus

<400> SEQUENCE: 91

Ala Asn Leu Tyr Asp Asn Glu Ser Phe Val Tyr Tyr Gln Ser Ala
1               5                   10                  15

Phe Arg Pro Gly His Gly Trp His Leu His Gly Gly Ala Tyr Ala Val
                20                  25                  30

Val Asn Val Ser Ser Glu Asn Asn Ala Gly Thr Ala Pro Ser Cys
            35                  40                  45

Thr Ala Gly Ala Ile Gly Tyr Ser Lys Asn Leu Ser Ala Ala Ser Val
    50                  55                  60

Ala Met Thr Ala Pro Leu Ser Gly Met Ser Trp Ser Ala Asn Ser Phe
65                  70                  75                  80

Cys Thr Ala His Cys Asn Phe Thr Ser Tyr Ile Val Phe Val Thr His
                85                  90                  95

Cys Tyr Lys Ser Gly Ser Asn Ser Cys Pro Leu Thr Gly Leu Ile Pro
                100                 105                 110

Ser Gly Tyr Ile Arg Ile Ala Ala Met Lys His Gly Ser Ala Met Pro
                115                 120                 125

Gly His Leu Phe Tyr Asn Leu Thr Val Ser Val Thr Lys Tyr Pro Lys
    130                 135                 140

Phe Arg Ser Leu Gln Cys Val Asn Asn Tyr Thr Ser Val Tyr Leu Asn
145                 150                 155                 160

Gly Asp Leu Val Phe Thr Ser Asn Tyr Thr Glu Asp Val Val Ala Ala
                165                 170                 175

Gly Val His Phe Lys Ser Gly Gly Pro Ile Thr Tyr Lys Val Met Arg
                180                 185                 190

Glu Val Lys Ala Leu Ala Tyr Phe Val Asn Gly Thr Ala His Asp Val
                195                 200                 205

Ile Leu Cys Asp Asp Thr Pro Arg Gly Leu Leu Ala Cys Gln Tyr Asn
    210                 215                 220

Thr Gly Asn Phe Ser Asp Gly Phe Tyr Pro Phe Thr Asn Thr Ser Ile
225                 230                 235                 240

Val Lys Asp Lys Phe Ile Val Tyr Arg Glu Ser Ser Val Asn Thr Thr
                245                 250                 255
```

```
Leu Thr Leu Thr Asn Phe Thr Phe Ser Asn Glu Ser Gly Ala Pro Pro
            260                 265                 270

Asn Thr Gly Gly Val Asp Ser Phe Ile Leu Tyr Gln Thr Gln Thr Ala
            275                 280                 285

Gln Ser Gly Tyr Tyr Asn Phe Asn Phe Ser Phe Leu Ser Ser Phe Val
        290                 295                 300

Tyr Arg Glu Ser Asn Tyr Met Tyr Gly Ser Tyr His Pro Arg Cys Ser
305                 310                 315                 320

Phe Arg Pro Glu Thr Leu Asn Gly Leu Trp Phe Asn Ser Leu Ser Val
                325                 330                 335

Ser Leu Thr Tyr Gly Pro Ile Gln Gly Gly Cys Lys Gln Ser Val Phe
            340                 345                 350

Asn Gly Lys Ala Thr Cys Cys Tyr Ala Tyr Ser Tyr Gly Gly Pro Arg
            355                 360                 365

Gly Cys Lys Gly Val Tyr Arg Gly Glu Leu Thr Gln His Phe Glu Cys
370                 375                 380

Gly Leu Leu Val Tyr Val Thr Lys Ser Asp Gly Ser Arg Ile Gln Thr
385                 390                 395                 400

Ala Thr Gln Pro Pro Val Leu Thr Gln Asn Phe Tyr Asn Asn Ile Asn
                405                 410                 415

Leu Gly Lys Cys Val Asp Tyr Asn Ile Tyr Gly Arg Ile Gly Gln Gly
            420                 425                 430

Leu Ile Thr Asn Val Thr Asp Leu Ala Val Ser Tyr Asn Tyr Leu Ser
            435                 440                 445

Asp Ala Gly Leu Ala Ile Leu Asp Thr Ser Gly Ala Ile Asp Ile Phe
        450                 455                 460

Val Val Gln Gly Glu Tyr Gly Pro Asn Tyr Tyr Lys Val Asn Pro Cys
465                 470                 475                 480

Glu Asp Val Asn Gln Gln Phe Val Val Ser Gly Gly Lys Leu Val Gly
                485                 490                 495

Ile Leu Thr Ser Arg Asn Glu Thr Gly Ser Gln Leu Leu Glu Asn Gln
            500                 505                 510

Phe Tyr Ile Lys Ile Thr Asn Gly Thr
        515                 520

<210> SEQ ID NO 92
<211> LENGTH: 5
<212> TYPE: PRT
<213> ORGANISM: Infectious Bronchitis Virus

<400> SEQUENCE: 92

Arg Arg Ser Arg Arg
1               5

<210> SEQ ID NO 93
<211> LENGTH: 554
<212> TYPE: PRT
<213> ORGANISM: Infectious Bronchitis Virus

<400> SEQUENCE: 93

Ser Val Thr Glu Asn Val Thr Asn Cys Pro Tyr Val Ser Tyr Gly Lys
1               5                   10                  15

Phe Cys Ile Lys Pro Asp Gly Ser Ile Ser Val Ile Val Pro Lys Glu
            20                  25                  30

Leu Asp Gln Phe Val Ala Pro Leu Leu Asn Val Thr Glu Tyr Val Leu
        35                  40                  45
```

-continued

```
Ile Pro Asn Ser Phe Asn Leu Thr Val Thr Asp Glu Tyr Ile Gln Thr
 50                  55                  60

Arg Met Asp Lys Ile Gln Ile Asn Cys Leu Gln Tyr Val Cys Gly Asn
 65                  70                  75                  80

Ser Leu Ala Cys Arg Lys Leu Phe Gln Gln Tyr Gly Pro Val Cys Asp
                 85                  90                  95

Asn Ile Leu Ser Val Val Asn Ser Val Gly Gln Lys Glu Asp Met Glu
                100                 105                 110

Leu Leu Asn Phe Tyr Ser Ser Thr Lys Pro Ala Arg Phe Asn Thr Pro
                115                 120                 125

Val Phe Ser Asn Leu Ser Thr Gly Glu Phe Asn Ile Ser Leu Leu Leu
130                 135                 140

Thr Ser Pro Ser Pro Arg Arg Ser Phe Ile Glu Asp Leu Leu
145                 150                 155                 160

Phe Thr Ser Val Glu Ser Val Gly Leu Pro Thr Asp Ala Tyr Lys
                165                 170                 175

Lys Cys Thr Ala Gly Pro Leu Gly Phe Phe Lys Asp Leu Ala Cys Ala
                180                 185                 190

Arg Glu Tyr Asn Gly Leu Leu Val Leu Pro Pro Ile Ile Thr Ala Glu
                195                 200                 205

Met Gln Thr Leu Tyr Thr Ser Ser Leu Val Ala Ser Met Ala Phe Gly
        210                 215                 220

Gly Ile Thr Ala Ala Gly Ala Ile Pro Phe Ala Thr Gln Leu Gln Ala
225                 230                 235                 240

Arg Ile Asn His Leu Gly Ile Thr Gln Ser Leu Leu Leu Lys Asn Gln
                245                 250                 255

Glu Lys Ile Ala Ala Ser Phe Asn Lys Ala Ile Gly His Met Gln Glu
                260                 265                 270

Gly Phe Arg Ser Thr Ser Leu Ala Leu Gln Gln Ile Gln Asp Val Val
                275                 280                 285

Asn Lys Gln Ser Ala Ile Leu Thr Glu Thr Met Ala Ala Leu Asn Lys
                290                 295                 300

Asn Phe Gly Ala Ile Ser Ser Val Ile Gln Asp Ile Tyr Gln Gln Leu
305                 310                 315                 320

Asp Ser Ile Gln Ala Asp Ala Gln Val Asp Arg Leu Ile Thr Gly Arg
                325                 330                 335

Leu Ser Ser Leu Ser Val Leu Ala Ser Ala Lys Gln Ser Glu Tyr Ile
                340                 345                 350

Arg Val Ser Gln Gln Arg Glu Leu Ala Thr Gln Lys Ile Asn Glu Cys
                355                 360                 365

Val Lys Ser Gln Ser Ile Arg Tyr Ser Phe Cys Gly Asn Gly Arg His
                370                 375                 380

Val Leu Thr Ile Pro Gln Asn Ala Pro Asn Gly Ile Val Phe Ile His
385                 390                 395                 400

Phe Thr Tyr Thr Pro Glu Ser Phe Ile Asn Val Thr Ala Ile Val Gly
                405                 410                 415

Phe Cys Val Ser Pro Ala Asn Ala Ser Gln Tyr Ala Ile Val Pro Ala
                420                 425                 430

Asn Gly Arg Gly Ile Phe Ile Gln Val Asn Gly Ser Tyr Tyr Ile Thr
                435                 440                 445

Ala Arg Asp Met Tyr Met Pro Arg Asp Ile Thr Ala Gly Asp Ile Val
450                 455                 460

Thr Leu Thr Ser Cys Gln Ala Asn Tyr Val Ser Val Asn Lys Thr Val
```

```
                465                 470                 475                 480
Ile Thr Thr Phe Val Asp Asn Asp Asp Phe Asp Phe Asp Asp Glu Leu
                        485                 490                 495

Ser Lys Trp Trp Asn Asp Thr Lys His Glu Leu Pro Asp Phe Asp Lys
                500                 505                 510

Phe Asn Tyr Thr Val Pro Ile Leu Asp Ile Asp Ser Glu Ile Asp Arg
                515                 520                 525

Ile Gln Gly Val Ile Gln Gly Leu Asn Asp Ser Leu Ile Asp Leu Glu
            530                 535                 540

Thr Leu Ser Ile Leu Lys Thr Tyr Ile Lys
545                 550
```

<210> SEQ ID NO 94
<211> LENGTH: 67
<212> TYPE: PRT
<213> ORGANISM: Infectious Bronchitis Virus

<400> SEQUENCE: 94

```
Val Trp Leu Ala Ile Ala Phe Ala Thr Ile Ile Phe Ile Leu Ile Leu
1               5                   10                  15

Gly Trp Leu Phe Phe Met Thr Gly Cys Cys Gly Cys Cys Cys Gly Cys
            20                  25                  30

Phe Gly Ile Ile Pro Leu Met Ser Lys Cys Gly Lys Lys Ser Ser Tyr
        35                  40                  45

Tyr Thr Thr Phe Asp Asn Asp Val Val Thr Glu Gln Tyr Arg Pro Lys
    50                  55                  60

Lys Ser Val
65
```

<210> SEQ ID NO 95
<211> LENGTH: 20
<212> TYPE: PRT
<213> ORGANISM: Infectious Bronchitis Virus

<400> SEQUENCE: 95

```
Val Trp Leu Ala Ile Ala Phe Ala Thr Ile Ile Phe Ile Leu Ile Leu
1               5                   10                  15

Gly Trp Leu Phe
            20
```

<210> SEQ ID NO 96
<211> LENGTH: 47
<212> TYPE: PRT
<213> ORGANISM: Infectious Bronchitis Virus

<400> SEQUENCE: 96

```
Phe Met Thr Gly Cys Cys Gly Cys Cys Cys Gly Cys Phe Gly Ile Ile
1               5                   10                  15

Pro Leu Met Ser Lys Cys Gly Lys Lys Ser Ser Tyr Tyr Thr Thr Phe
            20                  25                  30

Asp Asn Asp Val Val Thr Glu Gln Tyr Arg Pro Lys Lys Ser Val
        35                  40                  45
```

<210> SEQ ID NO 97
<211> LENGTH: 1152
<212> TYPE: PRT
<213> ORGANISM: Artificial
<220> FEATURE:
<223> OTHER INFORMATION: Recombinant Spike Ectodomain of Infectious
      Bronchitis Virus

<400> SEQUENCE: 97

Met Pro Met Gly Ser Leu Gln Pro Leu Ala Thr Leu Tyr Leu Leu Gly
1               5                   10                  15

Met Leu Val Ala Ser Val Leu Ala Asn Leu Tyr Asp Asn Glu Ser Phe
            20                  25                  30

Val Tyr Tyr Tyr Gln Ser Ala Phe Arg Pro Gly His Gly Trp His Leu
        35                  40                  45

His Gly Gly Ala Tyr Ala Val Val Asn Val Ser Glu Asn Asn Asn
    50                  55                  60

Ala Gly Thr Ala Pro Ser Cys Thr Ala Gly Ala Ile Gly Tyr Ser Lys
65                  70                  75                  80

Asn Leu Ser Ala Ala Ser Val Ala Met Thr Ala Pro Leu Ser Gly Met
                85                  90                  95

Ser Trp Ser Ala Asn Ser Phe Cys Thr Ala His Cys Asn Phe Thr Ser
            100                 105                 110

Tyr Ile Val Phe Val Thr His Cys Tyr Lys Ser Gly Ser Asn Ser Cys
        115                 120                 125

Pro Leu Thr Gly Leu Ile Pro Ser Gly Tyr Ile Arg Ile Ala Ala Met
    130                 135                 140

Lys His Gly Ser Ala Met Pro Gly His Leu Phe Tyr Asn Leu Thr Val
145                 150                 155                 160

Ser Val Thr Lys Tyr Pro Lys Phe Arg Ser Leu Gln Cys Val Asn Asn
                165                 170                 175

Tyr Thr Ser Val Tyr Leu Asn Gly Asp Leu Val Phe Thr Ser Asn Tyr
            180                 185                 190

Thr Glu Asp Val Val Ala Ala Gly Val His Phe Lys Ser Gly Gly Pro
        195                 200                 205

Ile Thr Tyr Lys Val Met Arg Glu Val Lys Ala Leu Ala Tyr Phe Val
    210                 215                 220

Asn Gly Thr Ala His Asp Val Ile Leu Cys Asp Asp Thr Pro Arg Gly
225                 230                 235                 240

Leu Leu Ala Cys Gln Tyr Asn Thr Gly Asn Phe Ser Asp Gly Phe Tyr
                245                 250                 255

Pro Phe Thr Asn Thr Ser Ile Val Lys Asp Lys Phe Ile Val Tyr Arg
            260                 265                 270

Glu Ser Ser Val Asn Thr Thr Leu Thr Leu Thr Asn Phe Thr Phe Ser
        275                 280                 285

Asn Glu Ser Gly Ala Pro Pro Asn Thr Gly Gly Val Asp Ser Phe Ile
    290                 295                 300

Leu Tyr Gln Thr Gln Thr Ala Gln Ser Gly Tyr Tyr Asn Phe Asn Phe
305                 310                 315                 320

Ser Phe Leu Ser Ser Phe Val Tyr Arg Glu Ser Asn Tyr Met Tyr Gly
                325                 330                 335

Ser Tyr His Pro Arg Cys Ser Phe Arg Pro Glu Thr Leu Asn Gly Leu
            340                 345                 350

Trp Phe Asn Ser Leu Ser Val Ser Leu Thr Tyr Gly Pro Ile Gln Gly
        355                 360                 365

Gly Cys Lys Gln Ser Val Phe Asn Gly Lys Ala Thr Cys Cys Tyr Ala
    370                 375                 380

Tyr Ser Tyr Gly Gly Pro Arg Gly Cys Lys Gly Val Tyr Arg Gly Glu
385                 390                 395                 400

Leu Thr Gln His Phe Glu Cys Gly Leu Leu Val Tyr Val Thr Lys Ser

-continued

```
                405                 410                 415
Asp Gly Ser Arg Ile Gln Thr Ala Thr Gln Pro Pro Val Leu Thr Gln
                420                 425                 430

Asn Phe Tyr Asn Asn Ile Asn Leu Gly Lys Cys Val Asp Tyr Asn Ile
                435                 440                 445

Tyr Gly Arg Ile Gly Gln Gly Leu Ile Thr Asn Val Thr Asp Leu Ala
                450                 455                 460

Val Ser Tyr Asn Tyr Leu Ser Asp Ala Gly Leu Ala Ile Leu Asp Thr
465                 470                 475                 480

Ser Gly Ala Ile Asp Ile Phe Val Val Gln Gly Glu Tyr Gly Pro Asn
                485                 490                 495

Tyr Tyr Lys Val Asn Pro Cys Glu Asp Val Asn Gln Gln Phe Val Val
                500                 505                 510

Ser Gly Gly Lys Leu Val Gly Ile Leu Thr Ser Arg Asn Glu Thr Gly
                515                 520                 525

Ser Gln Leu Leu Glu Asn Gln Phe Tyr Ile Lys Ile Thr Asn Gly Thr
                530                 535                 540

Gly Gly Gly Val Pro Ser Val Thr Glu Asn Val Thr Asn Cys Pro Tyr
545                 550                 555                 560

Val Ser Tyr Gly Lys Phe Cys Ile Lys Pro Asp Gly Ser Ile Ser Val
                565                 570                 575

Ile Val Pro Lys Glu Leu Asp Gln Phe Val Ala Pro Leu Leu Asn Val
                580                 585                 590

Thr Glu Tyr Val Leu Ile Pro Asn Ser Phe Asn Leu Thr Val Thr Asp
                595                 600                 605

Glu Tyr Ile Gln Thr Arg Met Asp Lys Ile Gln Ile Asn Cys Leu Gln
                610                 615                 620

Tyr Val Cys Gly Asn Ser Leu Ala Cys Arg Lys Leu Phe Gln Gln Tyr
625                 630                 635                 640

Gly Pro Val Cys Asp Asn Ile Leu Ser Val Val Asn Ser Val Gly Gln
                645                 650                 655

Lys Glu Asp Met Glu Leu Leu Asn Phe Tyr Ser Ser Thr Lys Pro Ala
                660                 665                 670

Arg Phe Asn Thr Pro Val Phe Ser Asn Leu Ser Thr Gly Glu Phe Asn
                675                 680                 685

Ile Ser Leu Leu Leu Thr Ser Pro Ser Pro Arg Arg Arg Ser Phe
                690                 695                 700

Ile Glu Asp Leu Leu Phe Thr Ser Val Glu Ser Val Gly Leu Pro Thr
705                 710                 715                 720

Asp Asp Ala Tyr Lys Lys Cys Thr Ala Gly Pro Leu Gly Phe Phe Lys
                725                 730                 735

Asp Leu Ala Cys Ala Arg Glu Tyr Asn Gly Leu Leu Val Leu Pro Pro
                740                 745                 750

Ile Ile Thr Ala Glu Met Gln Thr Leu Tyr Thr Ser Ser Leu Val Ala
                755                 760                 765

Ser Met Ala Phe Gly Gly Ile Thr Ala Ala Gly Ala Ile Pro Phe Ala
                770                 775                 780

Thr Gln Leu Gln Ala Arg Ile Asn His Leu Gly Ile Thr Gln Ser Leu
785                 790                 795                 800

Leu Leu Lys Asn Gln Glu Lys Ile Ala Ala Ser Phe Asn Lys Ala Ile
                805                 810                 815

Gly His Met Gln Glu Gly Phe Arg Ser Thr Ser Leu Ala Leu Gln Gln
                820                 825                 830
```

```
Ile Gln Asp Val Val Asn Lys Gln Ser Ala Ile Leu Thr Glu Thr Met
        835                 840                 845

Ala Ala Leu Asn Lys Asn Phe Gly Ala Ile Ser Ser Val Ile Gln Asp
    850                 855                 860

Ile Tyr Gln Gln Leu Asp Ser Ile Gln Ala Asp Ala Gln Val Asp Arg
865                 870                 875                 880

Leu Ile Thr Gly Arg Leu Ser Ser Leu Ser Val Leu Ala Ser Ala Lys
                885                 890                 895

Gln Ser Glu Tyr Ile Arg Val Ser Gln Gln Arg Glu Leu Ala Thr Gln
                900                 905                 910

Lys Ile Asn Glu Cys Val Lys Ser Gln Ser Ile Arg Tyr Ser Phe Cys
            915                 920                 925

Gly Asn Gly Arg His Val Leu Thr Ile Pro Gln Asn Ala Pro Asn Gly
        930                 935                 940

Ile Val Phe Ile His Phe Thr Tyr Thr Pro Glu Ser Phe Ile Asn Val
945                 950                 955                 960

Thr Ala Ile Val Gly Phe Cys Val Ser Pro Ala Asn Ala Ser Gln Tyr
                965                 970                 975

Ala Ile Val Pro Ala Asn Gly Arg Gly Ile Phe Ile Gln Val Asn Gly
                980                 985                 990

Ser Tyr Tyr Ile Thr Ala Arg Asp Met Tyr Met Pro Arg Asp Ile Thr
            995                 1000                1005

Ala Gly Asp Ile Val Thr Leu Thr Ser Cys Gln Ala Asn Tyr Val
    1010                1015                1020

Ser Val Asn Lys Thr Val Ile Thr Thr Phe Val Asp Asn Asp Asp
    1025                1030                1035

Phe Asp Phe Asp Asp Glu Leu Ser Lys Trp Trp Asn Asp Thr Lys
    1040                1045                1050

His Glu Leu Pro Asp Phe Asp Lys Phe Asn Tyr Thr Val Pro Ile
    1055                1060                1065

Leu Asp Ile Asp Ser Glu Ile Asp Arg Ile Gln Gly Val Ile Gln
    1070                1075                1080

Gly Leu Asn Asp Ser Leu Ile Asp Leu Glu Thr Leu Ser Ile Leu
    1085                1090                1095

Lys Thr Tyr Ile Lys Leu Ile Lys Arg Met Lys Gln Ile Glu Asp
    1100                1105                1110

Lys Ile Glu Glu Ile Glu Ser Lys Gln Lys Lys Ile Glu Asn Glu
    1115                1120                1125

Ile Ala Arg Ile Lys Lys Ile Lys Leu Val Pro Arg Gly Ser Leu
    1130                1135                1140

Glu Trp Ser His Pro Gln Phe Glu Lys
    1145                1150
```

<210> SEQ ID NO 98
<211> LENGTH: 23
<212> TYPE: PRT
<213> ORGANISM: Homo sapiens

<400> SEQUENCE: 98

```
Met Pro Met Gly Ser Leu Gln Pro Leu Ala Thr Leu Tyr Leu Leu Gly
1               5                   10                  15

Met Leu Val Ala Ser Val Leu
            20
```

<210> SEQ ID NO 99
<211> LENGTH: 521
<212> TYPE: PRT
<213> ORGANISM: Infectious Bronchitis Virus

<400> SEQUENCE: 99

| Ala | Asn | Leu | Tyr | Asp | Asn | Glu | Ser | Phe | Val | Tyr | Tyr | Gln | Ser | Ala |
|-----|-----|-----|-----|-----|-----|-----|-----|-----|-----|-----|-----|-----|-----|-----|
| 1   |     |     |     | 5   |     |     |     |     | 10  |     |     |     |     | 15  |

Phe Arg Pro Gly His Gly Trp His Leu His Gly Gly Ala Tyr Ala Val
              20                  25                  30

Val Asn Val Ser Ser Glu Asn Asn Ala Gly Thr Ala Pro Ser Cys
         35                  40                  45

Thr Ala Gly Ala Ile Gly Tyr Ser Lys Asn Leu Ser Ala Ser Val
     50                  55                  60

Ala Met Thr Ala Pro Leu Ser Gly Met Ser Trp Ser Ala Asn Ser Phe
65                  70                  75                  80

Cys Thr Ala His Cys Asn Phe Thr Ser Tyr Ile Val Phe Val Thr His
                 85                  90                  95

Cys Tyr Lys Ser Gly Ser Asn Ser Cys Pro Leu Thr Gly Leu Ile Pro
                100                 105                 110

Ser Gly Tyr Ile Arg Ile Ala Ala Met Lys His Gly Ser Ala Met Pro
            115                 120                 125

Gly His Leu Phe Tyr Asn Leu Thr Val Ser Val Thr Lys Tyr Pro Lys
        130                 135                 140

Phe Arg Ser Leu Gln Cys Val Asn Asn Tyr Thr Ser Val Tyr Leu Asn
145                 150                 155                 160

Gly Asp Leu Val Phe Thr Ser Asn Tyr Thr Glu Asp Val Val Ala Ala
                165                 170                 175

Gly Val His Phe Lys Ser Gly Gly Pro Ile Thr Tyr Lys Val Met Arg
            180                 185                 190

Glu Val Lys Ala Leu Ala Tyr Phe Val Asn Gly Thr Ala His Asp Val
        195                 200                 205

Ile Leu Cys Asp Asp Thr Pro Arg Gly Leu Leu Ala Cys Gln Tyr Asn
210                 215                 220

Thr Gly Asn Phe Ser Asp Gly Phe Tyr Pro Phe Thr Asn Thr Ser Ile
225                 230                 235                 240

Val Lys Asp Lys Phe Ile Val Tyr Arg Glu Ser Ser Val Asn Thr Thr
                245                 250                 255

Leu Thr Leu Thr Asn Phe Thr Phe Ser Asn Glu Ser Gly Ala Pro Pro
            260                 265                 270

Asn Thr Gly Gly Val Asp Ser Phe Ile Leu Tyr Gln Thr Gln Thr Ala
        275                 280                 285

Gln Ser Gly Tyr Tyr Asn Phe Asn Phe Ser Leu Ser Ser Phe Val
290                 295                 300

Tyr Arg Glu Ser Asn Tyr Met Tyr Gly Ser Tyr His Pro Arg Cys Ser
305                 310                 315                 320

Phe Arg Pro Glu Thr Leu Asn Gly Leu Trp Phe Asn Ser Leu Ser Val
                325                 330                 335

Ser Leu Thr Tyr Gly Pro Ile Gln Gly Gly Cys Lys Gln Ser Val Phe
            340                 345                 350

Asn Gly Lys Ala Thr Cys Cys Tyr Ala Tyr Ser Tyr Gly Gly Pro Arg
        355                 360                 365

Gly Cys Lys Gly Val Tyr Arg Gly Glu Leu Thr Gln His Phe Glu Cys
370                 375                 380

-continued

Gly Leu Leu Val Tyr Val Thr Lys Ser Asp Gly Ser Arg Ile Gln Thr
385                 390                 395                 400

Ala Thr Gln Pro Pro Val Leu Thr Gln Asn Phe Tyr Asn Asn Ile Asn
            405                 410                 415

Leu Gly Lys Cys Val Asp Tyr Asn Ile Tyr Gly Arg Ile Gly Gln Gly
            420                 425                 430

Leu Ile Thr Asn Val Thr Asp Leu Ala Val Ser Tyr Asn Tyr Leu Ser
            435                 440                 445

Asp Ala Gly Leu Ala Ile Leu Asp Thr Ser Gly Ala Ile Asp Ile Phe
            450                 455                 460

Val Val Gln Gly Glu Tyr Gly Pro Asn Tyr Tyr Lys Val Asn Pro Cys
465                 470                 475                 480

Glu Asp Val Asn Gln Gln Phe Val Val Ser Gly Gly Lys Leu Val Gly
            485                 490                 495

Ile Leu Thr Ser Arg Asn Glu Thr Gly Ser Gln Leu Leu Glu Asn Gln
            500                 505                 510

Phe Tyr Ile Lys Ile Thr Asn Gly Thr
            515                 520

<210> SEQ ID NO 100
<211> LENGTH: 5
<212> TYPE: PRT
<213> ORGANISM: Artificial
<220> FEATURE:
<223> OTHER INFORMATION: Glycine-rich spacer sequence

<400> SEQUENCE: 100

Gly Gly Gly Val Pro
1               5

<210> SEQ ID NO 101
<211> LENGTH: 554
<212> TYPE: PRT
<213> ORGANISM: Infectious Bronchitis Virus

<400> SEQUENCE: 101

Ser Val Thr Glu Asn Val Thr Asn Cys Pro Tyr Val Ser Tyr Gly Lys
1               5                   10                  15

Phe Cys Ile Lys Pro Asp Gly Ser Ile Ser Val Ile Val Pro Lys Glu
            20                  25                  30

Leu Asp Gln Phe Val Ala Pro Leu Leu Asn Val Thr Glu Tyr Val Leu
        35                  40                  45

Ile Pro Asn Ser Phe Asn Leu Thr Val Thr Asp Glu Tyr Ile Gln Thr
    50                  55                  60

Arg Met Asp Lys Ile Gln Ile Asn Cys Leu Gln Tyr Val Cys Gly Asn
65                  70                  75                  80

Ser Leu Ala Cys Arg Lys Leu Phe Gln Gln Tyr Gly Pro Val Cys Asp
            85                  90                  95

Asn Ile Leu Ser Val Val Asn Ser Val Gly Gln Lys Glu Asp Met Glu
            100                 105                 110

Leu Leu Asn Phe Tyr Ser Ser Thr Lys Pro Ala Arg Phe Asn Thr Pro
        115                 120                 125

Val Phe Ser Asn Leu Ser Thr Gly Glu Phe Asn Ile Ser Leu Leu Leu
    130                 135                 140

Thr Ser Pro Ser Ser Pro Arg Arg Arg Ser Phe Ile Glu Asp Leu Leu
145                 150                 155                 160

Phe Thr Ser Val Glu Ser Val Gly Leu Pro Thr Asp Asp Ala Tyr Lys

```
                165                 170                 175
Lys Cys Thr Ala Gly Pro Leu Gly Phe Phe Lys Asp Leu Ala Cys Ala
            180                 185                 190

Arg Glu Tyr Asn Gly Leu Leu Val Leu Pro Pro Ile Ile Thr Ala Glu
        195                 200                 205

Met Gln Thr Leu Tyr Thr Ser Ser Leu Val Ala Ser Met Ala Phe Gly
    210                 215                 220

Gly Ile Thr Ala Ala Gly Ala Ile Pro Phe Ala Thr Gln Leu Gln Ala
225                 230                 235                 240

Arg Ile Asn His Leu Gly Ile Thr Gln Ser Leu Leu Leu Lys Asn Gln
            245                 250                 255

Glu Lys Ile Ala Ala Ser Phe Asn Lys Ala Ile Gly His Met Gln Glu
        260                 265                 270

Gly Phe Arg Ser Thr Ser Leu Ala Leu Gln Gln Ile Gln Asp Val Val
    275                 280                 285

Asn Lys Gln Ser Ala Ile Leu Thr Glu Thr Met Ala Ala Leu Asn Lys
290                 295                 300

Asn Phe Gly Ala Ile Ser Ser Val Ile Gln Asp Ile Tyr Gln Gln Leu
305                 310                 315                 320

Asp Ser Ile Gln Ala Asp Ala Gln Val Asp Arg Leu Ile Thr Gly Arg
            325                 330                 335

Leu Ser Ser Leu Ser Val Leu Ala Ser Ala Lys Gln Ser Glu Tyr Ile
        340                 345                 350

Arg Val Ser Gln Gln Arg Glu Leu Ala Thr Gln Lys Ile Asn Glu Cys
    355                 360                 365

Val Lys Ser Gln Ser Ile Arg Tyr Ser Phe Cys Gly Asn Gly Arg His
370                 375                 380

Val Leu Thr Ile Pro Gln Asn Ala Pro Asn Gly Ile Val Phe Ile His
385                 390                 395                 400

Phe Thr Tyr Thr Pro Glu Ser Phe Ile Asn Val Thr Ala Ile Val Gly
            405                 410                 415

Phe Cys Val Ser Pro Ala Asn Ala Ser Gln Tyr Ala Ile Val Pro Ala
        420                 425                 430

Asn Gly Arg Gly Ile Phe Ile Gln Val Asn Gly Ser Tyr Tyr Ile Thr
    435                 440                 445

Ala Arg Asp Met Tyr Met Pro Arg Asp Ile Thr Ala Gly Asp Ile Val
    450                 455                 460

Thr Leu Thr Ser Cys Gln Ala Asn Tyr Val Ser Val Asn Lys Thr Val
465                 470                 475                 480

Ile Thr Thr Phe Val Asp Asn Asp Asp Phe Asp Phe Asp Asp Glu Leu
            485                 490                 495

Ser Lys Trp Trp Asn Asp Thr Lys His Glu Leu Pro Asp Phe Asp Lys
        500                 505                 510

Phe Asn Tyr Thr Val Pro Ile Leu Asp Ile Asp Ser Glu Ile Asp Arg
    515                 520                 525

Ile Gln Gly Val Ile Gln Gly Leu Asn Asp Ser Leu Ile Asp Leu Glu
    530                 535                 540

Thr Leu Ser Ile Leu Lys Thr Tyr Ile Lys
545                 550

<210> SEQ ID NO 102
<211> LENGTH: 38
<212> TYPE: PRT
<213> ORGANISM: Artificial
```

```
<220> FEATURE:
<223> OTHER INFORMATION: Modified trimerization domain of Saccharomyces
      cerevisiae GCN4

<400> SEQUENCE: 102

Arg Met Lys Gln Ile Glu Asp Lys Ile Glu Glu Ile Glu Ser Lys Gln
1               5                   10                  15

Lys Lys Ile Glu Asn Glu Ile Ala Arg Ile Lys Lys Ile Lys Leu Val
            20                  25                  30

Pro Arg Gly Ser Leu Glu
        35

<210> SEQ ID NO 103
<211> LENGTH: 8
<212> TYPE: PRT
<213> ORGANISM: Streptococcus pyogenes

<400> SEQUENCE: 103

Trp Ser His Pro Gln Phe Glu Lys
1               5

<210> SEQ ID NO 104
<211> LENGTH: 539
<212> TYPE: PRT
<213> ORGANISM: Infectious Bronchitis Virus

<400> SEQUENCE: 104

Met Ser Val Thr Pro Leu Leu Val Thr Leu Leu Phe Ala Leu Cys
1               5                   10                  15

Ser Ala Ala Pro Tyr Asp Asn Asn Ser Phe Val Tyr Tyr Tyr Gln Ser
            20                  25                  30

Ala Phe Arg Pro Phe Asp Gly Trp His Leu His Gly Gly Ala Tyr Glu
        35                  40                  45

Val Ile Asn Thr Thr Gln Glu Phe Asn Asn Ala Gly Ser Asn Ser Glu
    50                  55                  60

Cys Thr Ala Gly Ala Ile Ser Trp Ser Lys His Phe Ser Ala Ala Ser
65                  70                  75                  80

Val Ala Met Thr Ala Pro Tyr Asn Gly Met Ser Trp Ser Ala Gln Gln
                85                  90                  95

Phe Cys Thr Ala His Cys Asn Phe Thr Tyr Phe Thr Val Phe Val Thr
            100                 105                 110

His Cys Tyr Lys Ser Gly Val Gly Met Cys Pro Leu Thr Gly Met Ile
        115                 120                 125

Pro Lys Lys Gln Ile Arg Ile Ser Ala Met Arg Ser Gly Ser Gly Pro
    130                 135                 140

Pro Asp Leu Phe Tyr Asn Leu Thr Val Pro Val Thr Lys Tyr Pro Ser
145                 150                 155                 160

Phe Lys Ser Leu Gln Cys Val Asn Asn Gln Thr Ser Val Tyr Leu Asn
                165                 170                 175

Gly Asp Leu Val Phe Ser Ser Asn Glu Thr Ile Asp Val Ser Gly Ala
            180                 185                 190

Gly Val His Phe Lys Ala Gly Gly Pro Ile Thr Tyr Lys Val Met Arg
        195                 200                 205

Glu Val Lys Ala Leu Ala Tyr Phe Val Asn Gly Thr Ala His Asp Val
    210                 215                 220

Ile Leu Cys Asp Gly Thr Pro Arg Gly Leu Leu Ala Cys Gln Tyr Asn
225                 230                 235                 240
```

Thr Gly Asn Phe Thr Asp Gly Phe Tyr Pro Phe Thr Asn Ser Ser Leu
                    245                 250                 255

Val Lys Glu Lys Phe Ile Val Tyr Arg Glu Asn Ser Val Asn Thr Thr
            260                 265                 270

Leu Val Leu His Asn Ile Thr Phe Ser Asn Val Thr Ser Ala Pro Pro
        275                 280                 285

Ala Gly Gly Asp Ile Ser Ala Ile Phe Pro Thr Tyr Gln Met Val Thr
    290                 295                 300

Ala Gln Ser Gly Tyr Tyr Asn Phe Asn Phe Ser Phe Leu Ser Gly Phe
305                 310                 315                 320

Val Tyr Lys Val Ser Asp Phe Met Tyr Gly Ser Tyr His Pro Lys Cys
                325                 330                 335

Asn Phe Arg Pro Glu Asn Leu Asn Asn Asp Leu Trp Phe Asn Ser Leu
            340                 345                 350

Ser Ile Ser Leu Ala Tyr Gly Pro Leu Gln Gly Gly Cys Lys Gln Ser
        355                 360                 365

Val Phe Asn Gly Arg Ala Thr Cys Cys Tyr Ala Tyr Ser Tyr Asn Gly
    370                 375                 380

Pro His Ala Cys Lys Gly Val Tyr Arg Gly Gln Leu Gln Gln Tyr Phe
385                 390                 395                 400

Glu Cys Gly Leu Leu Val Tyr Ile Thr Lys Ser Asp Gly Ser Arg Ile
                405                 410                 415

Gln Thr Ala Thr Lys Ala Pro Val Val Thr Thr Asn Phe Tyr Asn Asn
            420                 425                 430

Ile Thr Leu Asp Arg Cys Val Asp Tyr Asn Ile Tyr Gly Arg Val Gly
        435                 440                 445

Gln Gly Phe Ile Thr Asn Val Thr Asp Ser Thr Ala Asp Tyr Asn Tyr
    450                 455                 460

Leu Ala Asp Gly Gly Leu Ala Ile Leu Asp Thr Ser Gly Ala Ile Asp
465                 470                 475                 480

Ile Phe Val Val Gln Gly Glu Tyr Gly Leu Asn Phe Tyr Lys Val Asn
                485                 490                 495

Pro Cys Glu Asp Val Asn Gln Gln Phe Val Val Ser Gly Gly Lys Leu
            500                 505                 510

Val Gly Val Leu Thr Ser Arg Asn Glu Thr Gly Ser Gln Phe Leu Glu
        515                 520                 525

Asn Gln Phe Tyr Ile Lys Leu Thr Asn Glu Thr
    530                 535

<210> SEQ ID NO 105
<211> LENGTH: 17
<212> TYPE: PRT
<213> ORGANISM: Infectious Bronchitis Virus

<400> SEQUENCE: 105

Met Ser Val Thr Pro Leu Leu Leu Val Thr Leu Leu Phe Ala Leu Cys
1               5                   10                  15

Ser

<210> SEQ ID NO 106
<211> LENGTH: 522
<212> TYPE: PRT
<213> ORGANISM: Infectious Bronchitis Virus

<400> SEQUENCE: 106

Ala Ala Pro Tyr Asp Asn Asn Ser Phe Val Tyr Tyr Gln Ser Ala

```
              1               5              10              15
            Phe Arg Pro Phe Asp Gly Trp His Leu His Gly Gly Ala Tyr Glu Val
                             20                  25                  30
            Ile Asn Thr Thr Gln Glu Phe Asn Asn Ala Gly Ser Asn Ser Glu Cys
                             35                  40                  45
            Thr Ala Gly Ala Ile Ser Trp Ser Lys His Phe Ser Ala Ala Ser Val
                 50                  55                  60
            Ala Met Thr Ala Pro Tyr Asn Gly Met Ser Trp Ser Ala Gln Gln Phe
             65                  70                  75                  80
            Cys Thr Ala His Cys Asn Phe Thr Tyr Phe Thr Val Phe Val Thr His
                             85                  90                  95
            Cys Tyr Lys Ser Gly Val Gly Met Cys Pro Leu Thr Gly Met Ile Pro
                            100                 105                 110
            Lys Lys Gln Ile Arg Ile Ser Ala Met Arg Ser Gly Ser Gly Pro Pro
                            115                 120                 125
            Asp Leu Phe Tyr Asn Leu Thr Val Pro Val Thr Lys Tyr Pro Ser Phe
                            130                 135                 140
            Lys Ser Leu Gln Cys Val Asn Asn Gln Thr Ser Val Tyr Leu Asn Gly
            145                 150                 155                 160
            Asp Leu Val Phe Ser Ser Asn Glu Thr Ile Asp Val Ser Gly Ala Gly
                                165                 170                 175
            Val His Phe Lys Ala Gly Gly Pro Ile Thr Tyr Lys Val Met Arg Glu
                            180                 185                 190
            Val Lys Ala Leu Ala Tyr Phe Val Asn Gly Thr Ala His Asp Val Ile
                            195                 200                 205
            Leu Cys Asp Gly Thr Pro Arg Gly Leu Leu Ala Cys Gln Tyr Asn Thr
                            210                 215                 220
            Gly Asn Phe Thr Asp Gly Phe Tyr Pro Phe Thr Asn Ser Ser Leu Val
            225                 230                 235                 240
            Lys Glu Lys Phe Ile Val Tyr Arg Glu Asn Ser Val Asn Thr Thr Leu
                            245                 250                 255
            Val Leu His Asn Ile Thr Phe Ser Asn Val Thr Ser Ala Pro Pro Ala
                            260                 265                 270
            Gly Gly Asp Ile Ser Ala Ile Phe Pro Thr Tyr Gln Met Val Thr Ala
                            275                 280                 285
            Gln Ser Gly Tyr Tyr Asn Phe Asn Phe Ser Phe Leu Ser Gly Phe Val
                            290                 295                 300
            Tyr Lys Val Ser Asp Phe Met Tyr Gly Ser Tyr His Pro Lys Cys Asn
            305                 310                 315                 320
            Phe Arg Pro Glu Asn Leu Asn Asn Asp Leu Trp Phe Asn Ser Leu Ser
                            325                 330                 335
            Ile Ser Leu Ala Tyr Gly Pro Leu Gln Gly Gly Cys Lys Gln Ser Val
                            340                 345                 350
            Phe Asn Gly Arg Ala Thr Cys Cys Tyr Ala Tyr Ser Tyr Asn Gly Pro
                            355                 360                 365
            His Ala Cys Lys Gly Val Tyr Arg Gly Gln Leu Gln Gln Tyr Phe Glu
                            370                 375                 380
            Cys Gly Leu Leu Val Tyr Ile Thr Lys Ser Asp Gly Ser Arg Ile Gln
            385                 390                 395                 400
            Thr Ala Thr Lys Ala Pro Val Val Thr Thr Asn Phe Tyr Asn Asn Ile
                            405                 410                 415
            Thr Leu Asp Arg Cys Val Asp Tyr Asn Ile Tyr Gly Arg Val Gly Gln
                            420                 425                 430
```

```
Gly Phe Ile Thr Asn Val Thr Asp Ser Thr Ala Asp Tyr Asn Tyr Leu
            435                 440                 445

Ala Asp Gly Gly Leu Ala Ile Leu Asp Thr Ser Gly Ala Ile Asp Ile
    450                 455                 460

Phe Val Gln Gly Glu Tyr Gly Leu Asn Phe Tyr Lys Val Asn Pro
465                 470                 475                 480

Cys Glu Asp Val Asn Gln Gln Phe Val Ser Gly Gly Lys Leu Val
                485                 490                 495

Gly Val Leu Thr Ser Arg Asn Glu Thr Gly Ser Gln Phe Leu Glu Asn
                500                 505                 510

Gln Phe Tyr Ile Lys Leu Thr Asn Glu Thr
            515                 520

<210> SEQ ID NO 107
<211> LENGTH: 554
<212> TYPE: PRT
<213> ORGANISM: Infectious Bronchitis Virus

<400> SEQUENCE: 107

Ser Val Ser Glu Asn Val Thr Ser Cys Pro Tyr Val Ser Tyr Gly Asn
1               5                   10                  15

Tyr Cys Ile Lys Pro Asp Gly Ser Val Ser Leu Ile Val Pro Gln Glu
                20                  25                  30

Leu Glu Gln Phe Val Ala Pro Leu Leu Asn Val Thr Glu His Val Leu
            35                  40                  45

Leu Pro Asp Ser Phe Asn Leu Thr Val Thr Asp Glu Tyr Ile Gln Thr
        50                  55                  60

Arg Met Asp Lys Val Gln Ile Asn Cys Leu Gln Tyr Val Cys Gly Asn
65                  70                  75                  80

Ser Leu Glu Cys Arg Lys Leu Phe Gln Gln Tyr Gly Pro Val Cys Asp
                85                  90                  95

Asn Ile Leu Ser Val Val Asn Ser Val Gly Gln Lys Glu Asp Met Glu
            100                 105                 110

Leu Leu Ser Phe Tyr Ser Ser Thr Lys Pro Thr Gly Tyr Asn Thr Pro
        115                 120                 125

Ile Phe Asn Asn Leu Thr Thr Gly Ala Phe Asn Val Ser Leu Leu Leu
    130                 135                 140

Pro Gln Leu Asp Ser Pro Arg Gly Arg Ser Phe Leu Glu Asp Leu Leu
145                 150                 155                 160

Phe Thr Ser Val Glu Thr Val Gly Leu Pro Thr Asp Ala Glu Tyr Lys
                165                 170                 175

Lys Cys Thr Ala Gly Pro Leu Gly Thr Leu Lys Asp Leu Ile Cys Ala
            180                 185                 190

Arg Glu Tyr Asn Gly Leu Leu Val Leu Pro Pro Ile Ile Thr Ala Asp
        195                 200                 205

Met Gln Thr Met Tyr Thr Ala Ser Leu Val Gly Ala Met Ala Phe Gly
    210                 215                 220

Gly Ile Thr Ser Ala Ala Ile Pro Phe Ala Thr Gln Ile Gln Ala
225                 230                 235                 240

Arg Ile Asn His Leu Gly Ile Thr Gln Ser Leu Leu Met Lys Asn Gln
                245                 250                 255

Glu Lys Ile Ala Ala Ser Phe Asn Lys Ala Ile Gly His Met Gln Glu
            260                 265                 270

Gly Phe Arg Ser Thr Ser Leu Ala Leu Gln Gln Ile Gln Asp Val Val
```

```
            275                 280                 285
Asn Lys Gln Ser Ala Ile Leu Thr Glu Thr Met Gln Ser Leu Asn Lys
    290                 295                 300

Asn Phe Gly Ala Ile Ser Ser Val Ile Gln Glu Ile Tyr Gln Gln Leu
305                 310                 315                 320

Asp Thr Ile Gln Ala Asn Ala Gln Val Asp Arg Leu Ile Thr Gly Arg
                325                 330                 335

Leu Ser Ser Leu Ser Val Leu Ala Ser Ala Lys Gln Ala Glu Tyr Ile
                340                 345                 350

Arg Val Ser Gln Gln Arg Glu Leu Ala Thr Gln Lys Ile Asn Glu Cys
            355                 360                 365

Val Lys Ser Gln Ser Ile Arg Tyr Ser Phe Cys Gly Asn Gly Arg His
    370                 375                 380

Val Leu Thr Ile Pro Gln Asn Ala Pro Asn Gly Ile Val Phe Ile His
385                 390                 395                 400

Phe Thr Tyr Thr Pro Glu Ser Phe Val Asn Val Thr Ala Ile Val Gly
                405                 410                 415

Phe Cys Val Asn Pro Ala Asn Ala Ser Gln Tyr Ala Ile Val Pro Ala
                420                 425                 430

Asn Gly Arg Gly Ile Phe Ile Gln Val Asn Gly Ser Tyr Tyr Ile Thr
            435                 440                 445

Ala Arg Asp Met Tyr Met Pro Arg Ala Ile Thr Ala Gly Asp Ile Val
    450                 455                 460

Met Leu Thr Ser Cys Gln Ala Asn Tyr Val Ser Val Asn Lys Thr Val
465                 470                 475                 480

Ile Thr Thr Phe Val Glu Asp Asp Phe Asp Phe Asn Asp Glu Leu
                485                 490                 495

Ser Lys Trp Trp Asn Glu Thr Lys His Glu Phe Pro Asp Phe Asp Gln
                500                 505                 510

Phe Asn Tyr Thr Ile Pro Val Leu Asn Ile Thr Tyr Asp Ile Asp Lys
            515                 520                 525

Ile Glu Glu Val Ile Lys Gly Leu Asn Asp Ser Leu Ile Asp Leu Glu
    530                 535                 540

Thr Leu Ser Ile Leu Lys Thr Tyr Ile Lys
545                 550

<210> SEQ ID NO 108
<211> LENGTH: 539
<212> TYPE: PRT
<213> ORGANISM: Infectious Bronchitis Virus

<400> SEQUENCE: 108

Met Ser Val Leu Leu Pro Leu Leu Val Thr Leu Leu Cys Ala Leu Cys
1               5                   10                  15

Ser Ala Val Leu Tyr Asp Ile Asn Ser Tyr Val Tyr Tyr Tyr Gln Ser
                20                  25                  30

Ala Phe Arg Pro Ser Asn Gly Trp His Leu Tyr Gly Gly Ala Tyr Ala
            35                  40                  45

Val Val Asn Val Ser Asn Glu Asn Asn Asn Ala Gly Ser Ala Ser Thr
    50                  55                  60

Cys Thr Ala Gly Ala Ile Gly Tyr Ser Lys Asn Phe Ser Ala Ala Ser
65                  70                  75                  80

Ile Ala Met Thr Ala Pro Pro Ser Gly Met Ala Trp Ser Thr Ala Ala
                85                  90                  95
```

```
Phe Cys Thr Ala His Cys Asn Phe Thr Asn Ile Val Val Phe Val Thr
            100                 105                 110

His Cys Tyr Lys Ser Gly Ser Gly Ser Cys Pro Leu Thr Gly Phe Ile
        115                 120                 125

Gln Ser Gly Tyr Ile Arg Ile Ser Ala Met Lys Lys Glu Cys Ser Gly
    130                 135                 140

Pro Ser Cys Leu Phe Tyr Asn Leu Thr Glu Ser Val Ser Lys Tyr Pro
145                 150                 155                 160

Thr Phe Arg Ser Leu Gln Cys Val Asn Asn Tyr Thr Ser Val Tyr Leu
                165                 170                 175

Asn Gly Asp Leu Val Phe Thr Ser Asn Tyr Thr Gln Asp Val Val Ala
            180                 185                 190

Ala Gly Val His Phe Lys Ser Gly Gly Pro Ile Thr Tyr Lys Val Met
        195                 200                 205

Arg Glu Val Lys Ala Leu Ala Tyr Phe Val Asn Gly Thr Ala Gln Asp
    210                 215                 220

Val Ile Leu Cys Asp Asp Thr Pro Arg Gly Leu Leu Ala Cys Gln Tyr
225                 230                 235                 240

Asn Thr Gly Asn Phe Ser Asp Gly Phe Tyr Pro Phe Thr Asn Thr Ser
                245                 250                 255

Ile Val Lys Asp Lys Phe Ile Val Tyr Arg Glu Ser Ser Val Asn Thr
            260                 265                 270

Thr Leu Thr Leu Thr Asn Phe Thr Phe Ser Asn Glu Ser Gly Ala Pro
        275                 280                 285

Pro Asn Thr Gly Gly Val Asn Ser Phe Ile Leu Tyr Gln Thr Gln Thr
    290                 295                 300

Ala Gln Ser Gly Tyr Tyr Asn Phe Asn Phe Ser Phe Leu Ser Gly Phe
305                 310                 315                 320

Val Tyr Glu Glu Ser Asn Tyr Met Tyr Gly Ser Tyr His Pro Leu Cys
                325                 330                 335

Ser Phe Arg Pro Glu Asn Ile Asn Asn Gly Leu Trp Phe Asn Ser Leu
            340                 345                 350

Ser Val Ser Ile Thr Tyr Gly Pro Leu Gln Gly Gly Cys Lys Gln Ser
        355                 360                 365

Phe Phe Gln Gly Arg Ala Thr Cys Cys Tyr Ala Tyr Ser Tyr Asn Gly
    370                 375                 380

Pro Arg Ala Cys Lys Gly Val Tyr Ser Gly Glu Leu Thr Gln Ser Phe
385                 390                 395                 400

Glu Cys Gly Leu Leu Val Tyr Ile Thr Lys Ser Asp Gly Ser Arg Ile
                405                 410                 415

Gln Thr Ala Thr Lys Ala Pro Val Val Thr Thr Asn Phe Tyr Asn Asn
            420                 425                 430

Ile Thr Leu Asp Lys Cys Val Glu Tyr Asn Ile Tyr Gly Arg Val Gly
        435                 440                 445

Gln Gly Phe Ile Thr Asn Val Thr Asp Ser Ala Phe Gly Tyr Asn Tyr
    450                 455                 460

Leu Gln Asp Gly Gly Leu Ala Ile Leu Asp Thr Ser Gly Ala Ile Asp
465                 470                 475                 480

Ile Phe Val Val Lys Gly Val Tyr Gly Leu Asn Tyr Tyr Lys Val Asn
                485                 490                 495

Pro Cys Glu Asp Val Asn Gln Gln Phe Val Val Ser Gly Gly Thr Leu
            500                 505                 510

Val Gly Val Leu Thr Ser Arg Asn Glu Thr Gly Ser Gln Phe Leu Glu
```

```
                515                 520                 525

Asn Gln Phe Tyr Ile Lys Leu Thr Asn Gly Thr
    530                 535

<210> SEQ ID NO 109
<211> LENGTH: 17
<212> TYPE: PRT
<213> ORGANISM: Infectious Bronchitis Virus

<400> SEQUENCE: 109

Met Ser Val Leu Leu Pro Leu Val Thr Leu Leu Cys Ala Leu Cys
1               5                   10                  15

Ser

<210> SEQ ID NO 110
<211> LENGTH: 522
<212> TYPE: PRT
<213> ORGANISM: Infectious Bronchitis Virus

<400> SEQUENCE: 110

Ala Val Leu Tyr Asp Ile Asn Ser Tyr Val Tyr Tyr Tyr Gln Ser Ala
1               5                   10                  15

Phe Arg Pro Ser Asn Gly Trp His Leu Tyr Gly Gly Ala Tyr Ala Val
                20                  25                  30

Val Asn Val Ser Asn Glu Asn Asn Ala Gly Ser Ala Ser Thr Cys
            35                  40                  45

Thr Ala Gly Ala Ile Gly Tyr Ser Lys Asn Phe Ser Ala Ala Ser Ile
        50                  55                  60

Ala Met Thr Ala Pro Pro Ser Gly Met Ala Trp Ser Thr Ala Ala Phe
65                  70                  75                  80

Cys Thr Ala His Cys Asn Phe Thr Asn Ile Val Val Phe Val Thr His
                    85                  90                  95

Cys Tyr Lys Ser Gly Ser Gly Ser Cys Pro Leu Thr Gly Phe Ile Gln
                100                 105                 110

Ser Gly Tyr Ile Arg Ile Ser Ala Met Lys Lys Glu Cys Ser Gly Pro
            115                 120                 125

Ser Cys Leu Phe Tyr Asn Leu Thr Glu Ser Val Ser Lys Tyr Pro Thr
        130                 135                 140

Phe Arg Ser Leu Gln Cys Val Asn Asn Tyr Thr Ser Val Tyr Leu Asn
145                 150                 155                 160

Gly Asp Leu Val Phe Thr Ser Asn Tyr Thr Gln Asp Val Val Ala Ala
                    165                 170                 175

Gly Val His Phe Lys Ser Gly Gly Pro Ile Thr Tyr Lys Val Met Arg
                180                 185                 190

Glu Val Lys Ala Leu Ala Tyr Phe Val Asn Gly Thr Ala Gln Asp Val
            195                 200                 205

Ile Leu Cys Asp Asp Thr Pro Arg Gly Leu Leu Ala Cys Gln Tyr Asn
        210                 215                 220

Thr Gly Asn Phe Ser Asp Gly Phe Tyr Pro Phe Thr Asn Thr Ser Ile
225                 230                 235                 240

Val Lys Asp Lys Phe Ile Val Tyr Arg Glu Ser Ser Val Asn Thr Thr
                    245                 250                 255

Leu Thr Leu Thr Asn Phe Thr Phe Ser Asn Glu Ser Gly Ala Pro Pro
                260                 265                 270

Asn Thr Gly Gly Val Asn Ser Phe Ile Leu Tyr Gln Thr Gln Thr Ala
            275                 280                 285
```

-continued

```
Gln Ser Gly Tyr Tyr Asn Phe Asn Phe Ser Phe Leu Ser Gly Phe Val
            290                 295                 300

Tyr Glu Glu Ser Asn Tyr Met Tyr Gly Ser Tyr His Pro Leu Cys Ser
305                 310                 315                 320

Phe Arg Pro Glu Asn Ile Asn Asn Gly Leu Trp Phe Asn Ser Leu Ser
                325                 330                 335

Val Ser Ile Thr Tyr Gly Pro Leu Gln Gly Gly Cys Lys Gln Ser Phe
            340                 345                 350

Phe Gln Gly Arg Ala Thr Cys Cys Tyr Ala Tyr Ser Tyr Asn Gly Pro
        355                 360                 365

Arg Ala Cys Lys Gly Val Tyr Ser Gly Glu Leu Thr Gln Ser Phe Glu
    370                 375                 380

Cys Gly Leu Leu Val Tyr Ile Thr Lys Ser Asp Gly Ser Arg Ile Gln
385                 390                 395                 400

Thr Ala Thr Lys Ala Pro Val Val Thr Thr Asn Phe Tyr Asn Asn Ile
                405                 410                 415

Thr Leu Asp Lys Cys Val Glu Tyr Asn Ile Tyr Gly Arg Val Gly Gln
            420                 425                 430

Gly Phe Ile Thr Asn Val Thr Asp Ser Ala Phe Gly Tyr Asn Tyr Leu
        435                 440                 445

Gln Asp Gly Gly Leu Ala Ile Leu Asp Thr Ser Gly Ala Ile Asp Ile
    450                 455                 460

Phe Val Val Lys Gly Val Tyr Gly Leu Asn Tyr Tyr Lys Val Asn Pro
465                 470                 475                 480

Cys Glu Asp Val Asn Gln Gln Phe Val Val Ser Gly Gly Thr Leu Val
                485                 490                 495

Gly Val Leu Thr Ser Arg Asn Glu Thr Gly Ser Gln Phe Leu Glu Asn
            500                 505                 510

Gln Phe Tyr Ile Lys Leu Thr Asn Gly Thr
        515                 520

<210> SEQ ID NO 111
<211> LENGTH: 554
<212> TYPE: PRT
<213> ORGANISM: Infectious Bronchitis Virus

<400> SEQUENCE: 111

Ser Val Asn Glu Asn Val Thr Ser Cys Pro Tyr Val Ser Tyr Gly Lys
1               5                   10                  15

Phe Cys Ile Lys Pro Asp Gly Ser Thr Ser Val Ile Val Pro Lys Glu
            20                  25                  30

Leu Glu Gln Phe Val Thr Pro Leu Leu Asn Ala Thr Glu Tyr Val Pro
        35                  40                  45

Ile Pro Asp Ser Phe Asn Leu Thr Val Thr Asp Glu Tyr Ile Gln Thr
    50                  55                  60

Arg Met Asp Lys Val Gln Ile Asn Cys Leu Gln Tyr Val Cys Gly Asn
65                  70                  75                  80

Ser Phe Glu Cys Arg Asn Leu Phe Gln Gln Tyr Gly Pro Val Cys Asp
                85                  90                  95

Asn Ile Leu Ser Ile Val Asn Ser Val Ser Gln Lys Glu Asp Met Glu
            100                 105                 110

Leu Leu Thr Phe Tyr Ser Ser Thr Lys Pro Phe Gly Phe Asn Thr Pro
        115                 120                 125

Ile Leu Ser Asn Leu Ser Thr Gly Asp Phe Asn Ile Ser Leu Leu Leu
```

```
              130                 135                 140
Thr Pro Pro Ser Ser Thr Thr Gly Arg Ser Phe Ile Glu Asp Leu Leu
145                 150                 155                 160

Phe Thr Ser Val Glu Ser Val Gly Leu Pro Thr Asp Asp Ala Tyr Lys
                    165                 170                 175

Lys Cys Thr Ala Gly Pro Leu Gly Phe Leu Lys Asp Leu Ala Cys Ala
                180                 185                 190

Arg Glu Tyr Asn Gly Leu Leu Val Leu Pro Pro Ile Ile Thr Ala Glu
            195                 200                 205

Met Gln Thr Met Tyr Thr Ser Ser Leu Val Ala Ser Met Ala Leu Gly
        210                 215                 220

Gly Ile Thr Ala Ala Gly Ala Ile Pro Phe Ala Thr Gln Leu Gln Ala
225                 230                 235                 240

Arg Ile Asn His Leu Gly Ile Thr Gln Ala Val Leu Leu Lys Asn Gln
                    245                 250                 255

Glu Lys Ile Ala Ala Ser Phe Asn Lys Ala Ile Gly Gln Met Gln Glu
                260                 265                 270

Gly Phe Arg Ser Thr Ser Leu Ala Leu Gln Gln Ile Gln Asp Val Val
            275                 280                 285

Asn Lys Gln Ser Ala Ile Leu Thr Glu Thr Met Ala Ser Leu Asn Lys
        290                 295                 300

Asn Phe Gly Ala Ile Ser Ser Val Ile Gln Asp Ile Tyr Gln Gln Leu
305                 310                 315                 320

Asp Val Ile Gln Ala Asp Ala Gln Val Asp Arg Leu Ile Thr Gly Arg
                    325                 330                 335

Leu Ser Ser Leu Ser Val Leu Ala Ser Ala Lys Gln Ser Glu His Ile
                340                 345                 350

Ile Ala Ser Gln Gln Arg Glu Leu Ala Thr Gln Lys Ile Asn Glu Cys
            355                 360                 365

Val Lys Ser Gln Ser Thr Arg Tyr Ser Phe Cys Gly Asn Gly Arg His
        370                 375                 380

Val Leu Thr Ile Pro Gln Asn Ala Pro Asn Gly Ile Val Phe Ile His
385                 390                 395                 400

Phe Thr Tyr Thr Pro Glu Ser Phe Val Asn Val Thr Ala Ile Val Gly
                    405                 410                 415

Phe Cys Val Lys Pro Ala Asn Ala Ser Gln Tyr Ala Ile Val Pro Ala
                420                 425                 430

Asn Gly Arg Gly Ile Phe Ile Gln Phe Asn Gly Ser Tyr Tyr Ile Thr
            435                 440                 445

Ala Arg Asp Met Tyr Met Pro Arg Asn Ile Thr Ala Gly Asp Ile Val
        450                 455                 460

Thr Leu Thr Ser Cys Gln Ser Asn Tyr Val Ser Val Asn Lys Thr Val
465                 470                 475                 480

Ile Thr Thr Phe Val Asp Asn Asp Asp Phe Asp Phe Asp Asp Glu Leu
                    485                 490                 495

Ser Lys Trp Trp Asn Asp Thr Lys His Glu Leu Pro Asp Phe Asp Glu
                500                 505                 510

Phe Asn Tyr Thr Ala Pro Ile Leu Asp Ile Asp Ser Glu Ile Asp Arg
            515                 520                 525

Ile Gln Gly Val Ile Gln Gly Leu Asn Asp Ser Leu Ile Asp Leu Glu
        530                 535                 540

Thr Leu Ser Ile Leu Lys Thr Tyr Ile Lys
545                 550
```

<210> SEQ ID NO 112
<211> LENGTH: 534
<212> TYPE: PRT
<213> ORGANISM: Infectious Bronchitis Virus

<400> SEQUENCE: 112

Met Leu Gly Lys Ser Leu Phe Leu Val Thr Ile Leu Cys Ala Leu Cys
1               5                   10                  15

Ser Ala Asn Leu Phe Asp Pro Ala Asn Tyr Val Tyr Tyr Gln Ser
            20                  25                  30

Ala Phe Arg Pro Ser Asn Gly Trp His Leu Gln Gly Gly Ala Tyr Ala
        35                  40                  45

Val Val Asn Ser Ser Asn Tyr Ala Asn Ala Gly Ser Ala Ser Glu
    50                  55                  60

Cys Thr Val Gly Val Ile Lys Asp Val Tyr Asn Gln Ser Ala Ala Ser
65                  70                  75                  80

Ile Ala Met Thr Ala Pro Leu Gln Gly Met Ala Trp Ser Lys Ser Gln
                85                  90                  95

Phe Cys Ser Ala His Cys Asp Phe Ser Glu Ile Thr Val Phe Val Thr
            100                 105                 110

His Cys Tyr Ser Ser Gly Ser Gly Ser Cys Pro Ile Thr Gly Met Ile
        115                 120                 125

Ala Arg Gly His Ile Arg Ile Ser Ala Met Lys Asn Gly Ser Leu Phe
    130                 135                 140

Tyr Asn Leu Thr Val Ser Val Ser Lys Tyr Pro Asn Phe Lys Ser Phe
145                 150                 155                 160

Gln Cys Val Asn Asn Phe Thr Ser Val Tyr Leu Asn Gly Asp Leu Val
                165                 170                 175

Phe Thr Ser Asn Lys Thr Thr Asp Val Thr Ser Ala Gly Val Tyr Phe
            180                 185                 190

Lys Ala Gly Gly Pro Val Asn Tyr Ser Ile Met Lys Glu Phe Lys Val
        195                 200                 205

Leu Ala Tyr Phe Val Asn Gly Thr Ala Gln Asp Val Ile Leu Cys Asp
    210                 215                 220

Asn Ser Pro Lys Gly Leu Leu Ala Cys Gln Tyr Asn Thr Gly Asn Phe
225                 230                 235                 240

Ser Asp Gly Phe Tyr Pro Phe Thr Asn Ser Thr Leu Val Arg Glu Lys
                245                 250                 255

Phe Ile Val Tyr Arg Glu Ser Ser Val Asn Thr Thr Leu Ala Leu Thr
            260                 265                 270

Asn Phe Thr Phe Thr Asn Val Ser Asn Ala Gln Pro Asn Ser Gly Gly
        275                 280                 285

Val His Thr Phe His Leu Tyr Gln Thr Gln Thr Ala Gln Ser Gly Tyr
    290                 295                 300

Tyr Asn Phe Asn Leu Ser Phe Leu Ser Gln Phe Val Tyr Lys Ala Ser
305                 310                 315                 320

Asp Tyr Met Tyr Gly Ser Tyr His Pro Ile Cys Ala Phe Arg Pro Glu
                325                 330                 335

Thr Ile Asn Ser Gly Leu Trp Phe Asn Ser Leu Ser Val Ser Leu Thr
            340                 345                 350

Tyr Gly Pro Leu Gln Gly Gly Tyr Lys Gln Ser Val Phe Ser Gly Lys
        355                 360                 365

Ala Thr Cys Cys Tyr Ala Tyr Ser Tyr Asn Gly Pro Arg Ala Cys Lys

```
                  370                 375                 380
Gly Val Tyr Ser Gly Glu Leu Ser Arg Asp Phe Glu Cys Gly Leu Leu
385                 390                 395                 400

Val Tyr Val Thr Lys Ser Asp Gly Ser Arg Ile Gln Thr Arg Thr Glu
                405                 410                 415

Pro Leu Val Leu Thr Gln His Asn Tyr Asn Asn Ile Thr Leu Asp Lys
                420                 425                 430

Cys Val Ala Tyr Asn Ile Tyr Gly Arg Val Gly Gln Gly Phe Ile Thr
                435                 440                 445

Asn Val Thr Asp Ser Val Ala Asn Phe Ser Tyr Leu Ala Asp Gly Gly
                450                 455                 460

Leu Ala Ile Leu Asp Thr Ser Gly Ala Ile Asp Val Phe Val Val Gln
465                 470                 475                 480

Gly Ser Tyr Gly Leu Asn Tyr Tyr Lys Val Asn Pro Cys Glu Asp Val
                485                 490                 495

Asn Gln Gln Phe Val Val Ser Gly Gly Asn Ile Val Gly Ile Leu Thr
                500                 505                 510

Ser Arg Asn Glu Thr Gly Ser Glu Gln Val Glu Asn Gln Phe Tyr Val
                515                 520                 525

Lys Leu Thr Asn Ser Ser
                530
```

<210> SEQ ID NO 113
<211> LENGTH: 17
<212> TYPE: PRT
<213> ORGANISM: Infectious Bronchitis Virus

<400> SEQUENCE: 113

```
Met Leu Gly Lys Ser Leu Phe Leu

Cys Val Asn Asn Phe Thr Ser Val Tyr Leu Asn Gly Asp Leu Val Phe
145                 150                 155                 160

Thr Ser Asn Lys Thr Thr Asp Val Thr Ser Ala Gly Val Tyr Phe Lys
            165                 170                 175

Ala Gly Gly Pro Val Asn Tyr Ser Ile Met Lys Glu Phe Lys Val Leu
        180                 185                 190

Ala Tyr Phe Val Asn Gly Thr Ala Gln Asp Val Ile Leu Cys Asp Asn
    195                 200                 205

Ser Pro Lys Gly Leu Leu Ala Cys Gln Tyr Asn Thr Gly Asn Phe Ser
210                 215                 220

Asp Gly Phe Tyr Pro Phe Thr Asn Ser Thr Leu Val Arg Glu Lys Phe
225                 230                 235                 240

Ile Val Tyr Arg Glu Ser Ser Val Asn Thr Thr Leu Ala Leu Thr Asn
                245                 250                 255

Phe Thr Phe Thr Asn Val Ser Asn Ala Gln Pro Asn Ser Gly Gly Val
                260                 265                 270

His Thr Phe His Leu Tyr Gln Thr Gln Thr Ala Gln Ser Gly Tyr Tyr
            275                 280                 285

Asn Phe Asn Leu Ser Phe Leu Ser Gln Phe Val Tyr Lys Ala Ser Asp
290                 295                 300

Tyr Met Tyr Gly Ser Tyr His Pro Ile Cys Ala Phe Arg Pro Glu Thr
305                 310                 315                 320

Ile Asn Ser Gly Leu Trp Phe Asn Ser Leu Ser Val Ser Leu Thr Tyr
                325                 330                 335

Gly Pro Leu Gln Gly Gly Tyr Lys Gln Ser Val Phe Ser Gly Lys Ala
            340                 345                 350

Thr Cys Cys Tyr Ala Tyr Ser Tyr Asn Gly Pro Arg Ala Cys Lys Gly
        355                 360                 365

Val Tyr Ser Gly Glu Leu Ser Arg Asp Phe Glu Cys Gly Leu Leu Val
    370                 375                 380

Tyr Val Thr Lys Ser Asp Gly Ser Arg Ile Gln Thr Arg Thr Glu Pro
385                 390                 395                 400

Leu Val Leu Thr Gln His Asn Tyr Asn Asn Ile Thr Leu Asp Lys Cys
                405                 410                 415

Val Ala Tyr Asn Ile Tyr Gly Arg Val Gly Gln Gly Phe Ile Thr Asn
            420                 425                 430

Val Thr Asp Ser Val Ala Asn Phe Ser Tyr Leu Ala Asp Gly Gly Leu
        435                 440                 445

Ala Ile Leu Asp Thr Ser Gly Ala Ile Asp Val Phe Val Val Gln Gly
    450                 455                 460

Ser Tyr Gly Leu Asn Tyr Tyr Lys Val Asn Pro Cys Glu Asp Val Asn
465                 470                 475                 480

Gln Gln Phe Val Val Ser Gly Gly Asn Ile Val Gly Ile Leu Thr Ser
                485                 490                 495

Arg Asn Glu Thr Gly Ser Glu Gln Val Glu Asn Gln Phe Tyr Val Lys
            500                 505                 510

Leu Thr Asn Ser Ser
        515

<210> SEQ ID NO 115
<211> LENGTH: 554
<212> TYPE: PRT
<213> ORGANISM: Infectious Bronchitis Virus

<400> SEQUENCE: 115

```
Ser Ile Gly Gln Asn Val Thr Ser Cys Pro Tyr Val Ser Tyr Gly Arg
1               5                   10                  15
Phe Cys Ile Glu Pro Asp Gly Ser Leu Lys Met Ile Val Pro Glu Glu
            20                  25                  30
Leu Lys Gln Phe Val Ala Pro Leu Leu Asn Ile Thr Glu Ser Val Leu
        35                  40                  45
Ile Pro Asn Ser Phe Asn Leu Thr Val Thr Asp Glu Tyr Ile Gln Thr
    50                  55                  60
Arg Met Asp Lys Val Gln Ile Asn Cys Leu Gln Tyr Val Cys Gly Asn
65                  70                  75                  80
Ser Leu Glu Cys Arg Lys Leu Phe Gln Gln Tyr Gly Pro Val Cys Asp
                85                  90                  95
Asn Ile Leu Ser Val Val Asn Ser Val Ser Gln Lys Glu Asp Met Glu
            100                 105                 110
Leu Leu Ser Phe Tyr Ser Ser Thr Lys Pro Lys Gly Tyr Asp Thr Pro
        115                 120                 125
Val Leu Ser Asn Val Ser Thr Gly Glu Phe Asn Ile Ser Leu Leu Leu
    130                 135                 140
Thr Pro Pro Ser Ser Pro Ser Gly Arg Ser Phe Val Glu Asp Leu Leu
145                 150                 155                 160
Phe Thr Ser Val Glu Thr Val Gly Leu Pro Thr Asp Ala Glu Tyr Lys
                165                 170                 175
Lys Cys Thr Ala Gly Pro Leu Gly Thr Leu Lys Asp Leu Ile Cys Ala
            180                 185                 190
Arg Glu Tyr Asn Gly Leu Leu Val Leu Pro Pro Ile Ile Thr Ala Asp
        195                 200                 205
Met Gln Thr Met Tyr Thr Ala Ser Leu Val Gly Ala Met Ala Phe Gly
    210                 215                 220
Gly Ile Thr Ser Ala Ala Ile Pro Phe Ala Thr Gln Ile Gln Ala
225                 230                 235                 240
Arg Ile Asn His Leu Gly Ile Ala Gln Ser Leu Leu Met Lys Asn Gln
                245                 250                 255
Glu Lys Ile Ala Ala Ser Phe Asn Lys Ala Ile Gly His Met Gln Glu
            260                 265                 270
Gly Phe Arg Ser Thr Ser Leu Ala Leu Gln Gln Val Gln Asp Val Val
        275                 280                 285
Asn Lys Gln Ser Ala Ile Leu Thr Glu Thr Met Asn Ser Leu Asn Lys
    290                 295                 300
Asn Phe Gly Ala Ile Ser Ser Val Ile Gln Asp Ile Tyr Ala Gln Leu
305                 310                 315                 320
Asp Ala Ile Gln Ala Asp Ala Gln Val Asp Arg Leu Ile Thr Gly Arg
                325                 330                 335
Leu Ser Ser Leu Ser Val Leu Ala Ser Ala Lys Gln Ser Glu Tyr Ile
            340                 345                 350
Arg Val Ser Gln Gln Arg Glu Leu Ala Thr Gln Lys Ile Asn Glu Cys
        355                 360                 365
Val Lys Ser Gln Ser Asn Arg Tyr Gly Phe Cys Gly Ser Gly Arg His
    370                 375                 380
Val Leu Ser Ile Pro Gln Asn Ala Pro Asn Gly Ile Val Phe Ile His
385                 390                 395                 400
Phe Thr Tyr Thr Pro Glu Thr Phe Val Asn Val Thr Ala Ile Val Gly
                405                 410                 415
```

```
Phe Cys Val Asn Pro Leu Asn Ala Ser Gln Tyr Ala Ile Val Pro Ala
                420                 425                 430

Asn Gly Arg Gly Ile Phe Ile Gln Val Asn Gly Thr Tyr Tyr Ile Thr
            435                 440                 445

Ser Arg Asp Met Tyr Met Pro Arg Asp Ile Thr Ala Gly Asp Ile Val
450                 455                 460

Thr Leu Thr Ser Cys Gln Ala Asn Tyr Val Asn Val Asn Lys Thr Val
465                 470                 475                 480

Ile Thr Thr Phe Val Glu Asp Asp Phe Asn Phe Asp Glu Leu
                485                 490                 495

Ser Lys Trp Trp Asn Asp Thr Lys His Gly Leu Pro Asp Phe Asp Asp
            500                 505                 510

Phe Asn Tyr Thr Val Pro Ile Leu Asn Ile Ser Gly Glu Ile Asp Asn
            515                 520                 525

Ile Gln Gly Val Ile Gln Gly Leu Asn Asp Ser Leu Ile Asn Leu Glu
            530                 535                 540

Glu Leu Ser Ile Ile Lys Thr Tyr Ile Lys
545                 550

<210> SEQ ID NO 116
<211> LENGTH: 529
<212> TYPE: PRT
<213> ORGANISM: Infectious Bronchitis Virus

<400> SEQUENCE: 116

Met Leu Val Lys Ser Leu Phe Ile Val Thr Leu Leu Ala Leu Cys
1               5                   10                  15

Glu Gly Gly Leu Val Gly Val Asn Tyr Thr Tyr Tyr Gln Ser Gly
                20                  25                  30

Tyr Arg Pro Pro Asn Gly Trp His Met Gln Gly Gly Ala Tyr Lys Val
            35                  40                  45

Val Asn Lys Thr Thr Ile Ser Tyr Thr Asn Gln Gly Cys Thr Ile Gly
 50                  55                  60

Val Ile Arg Gly Gly Val Thr Ile Asn Gln Ser Ala Ile Ala Phe Thr
 65                  70                  75                  80

Ser Ala Thr Gly Ser Ser Trp Ser Lys Gln Gly Val Cys Thr Val Tyr
                85                  90                  95

Cys Asn Tyr Thr Ser Phe Tyr Val Phe Val Thr His Cys Gly Gly Thr
                100                 105                 110

Gly His Asn Cys Ile Val Asn Thr Lys Gln Leu Gly Val Leu Val Phe
            115                 120                 125

Gly Val Lys Asn Tyr Asn Asp Gln Phe Ile Tyr Asn Arg Thr Leu Gly
 130                 135                 140

Ala Ala Gly Pro Tyr Ala Asn Phe Lys Ala Trp Gln Cys Leu Ser Asn
 145                 150                 155                 160

Tyr Thr Ser Val Phe Leu Asn Gly Asn Leu Leu Tyr Thr Ser Asn Tyr
                165                 170                 175

Thr Glu Asp Val Lys Ala Ala Gly Val Tyr Ala Lys Gln Val Asn Gly
            180                 185                 190

Leu Glu Arg Arg Val Met Arg Asp Thr Pro Val Met Ala Tyr Phe Val
            195                 200                 205

Asn Gly Thr Val Gln Asp Val Ile Leu Cys Asp Asp Ser Pro Lys Gly
 210                 215                 220

Arg Leu Ala Cys Gln Tyr Asn Thr Gly Asn Phe Ser Asp Gly Leu Tyr
```

```
            225                 230                 235                 240
        Pro Val Tyr Glu Glu Pro Val Ala Ser Asn Phe Thr Phe Val Pro Leu
                        245                 250                 255

Asp Thr Ser Ser Thr Ser Tyr Gly Val Leu His Asn Phe Thr Phe Asn
                        260                 265                 270

Asn Val Thr Gly Val Ala Pro Asn Gln Asn His Ile Ala Arg Phe Asn
                        275                 280                 285

Ile Ser Thr Ile Ser Glu Gly Tyr Val Asn Phe Lys Phe Asn Phe Leu
                        290                 295                 300

Asn Ser Phe Thr Tyr Val Glu Ser Asp Phe Asp Arg Gly Ser Tyr Tyr
        305                 310                 315                 320

Gly Lys Pro Gly Ser Arg Cys Asn Phe Arg Leu Glu Ser Ile Asn Arg
                        325                 330                 335

Gly Leu Ser Phe Asn Ser Leu Thr Val Ser Ile Gly Tyr Gly Pro Ile
                        340                 345                 350

Ser Gly Gly Cys Lys Gln Ser Val Trp Lys Asn Glu Ala Thr Cys Cys
                        355                 360                 365

Phe Ala Tyr Lys Tyr Asn Gly Gly Ser Arg Asn Cys Lys Gly Leu Tyr
        370                 375                 380

Thr Phe Asp Ser Asp Val Asn Tyr Glu Cys Val Leu Leu Val Phe Ile
        385                 390                 395                 400

Ser Lys Thr Asp Gly Ser Arg Ile Arg Thr Ala Thr Ser Pro Pro Val
                        405                 410                 415

Tyr Ser Asn Asn Asn Val Asn Ile Asn Leu Gly Leu Cys Val Asp Tyr
                        420                 425                 430

Asn Val Tyr Gly Ile Thr Gly Arg Gly Leu Ile Thr Asn Ile Thr Glu
                        435                 440                 445

Ser Val His Pro Gly Tyr Leu Asp His Gly Gly Leu Val Leu Leu Asp
                        450                 455                 460

Ala Thr Gly Ser Ile Asp Thr Phe Val Leu His Ser Asp Asn Leu Thr
        465                 470                 475                 480

Ser Tyr Tyr Lys Val Asn Pro Cys Ser Asp Ile Asn Glu Gln Tyr Val
                        485                 490                 495

Val Ser Gly Gly Asn Leu Val Gly Lys Leu Thr Ser Asn Asn Gln Thr
                        500                 505                 510

Val Ala Gln Gln Leu Gly Asp Met Phe Tyr Val Lys Phe Ser Thr Ser
                        515                 520                 525

Gly

<210> SEQ ID NO 117
<211> LENGTH: 17
<212> TYPE: PRT
<213> ORGANISM: Infectious Bronchitis Virus

<400> SEQUENCE: 117

Met Leu Val Lys Ser Leu Phe Ile Val Thr Leu Leu Ala Leu Cys
        1               5                   10                  15

Glu

<210> SEQ ID NO 118
<211> LENGTH: 512
<212> TYPE: PRT
<213> ORGANISM: Infectious Bronchitis Virus

<400> SEQUENCE: 118
```

-continued

```
Gly Gly Leu Val Gly Val Asn Tyr Thr Tyr Tyr Gln Ser Gly Tyr
1               5                   10                  15
Arg Pro Pro Asn Gly Trp His Met Gln Gly Ala Tyr Lys Val Val
            20                  25                  30
Asn Lys Thr Thr Ile Ser Tyr Thr Asn Gln Gly Cys Thr Ile Gly Val
            35                  40                  45
Ile Arg Gly Gly Val Thr Ile Asn Gln Ser Ala Ile Ala Phe Thr Ser
50                  55                  60
Ala Thr Gly Ser Ser Trp Ser Lys Gln Gly Val Cys Thr Val Tyr Cys
65                  70                  75                  80
Asn Tyr Thr Ser Phe Tyr Val Phe Val Thr His Cys Gly Gly Thr Gly
                85                  90                  95
His Asn Cys Ile Val Asn Thr Lys Gln Leu Gly Val Leu Val Phe Gly
            100                 105                 110
Val Lys Asn Tyr Asn Asp Gln Phe Ile Tyr Asn Arg Thr Leu Gly Ala
            115                 120                 125
Ala Gly Pro Tyr Ala Asn Phe Lys Ala Trp Gln Cys Leu Ser Asn Tyr
130                 135                 140
Thr Ser Val Phe Leu Asn Gly Asn Leu Leu Tyr Thr Ser Asn Tyr Thr
145                 150                 155                 160
Glu Asp Val Lys Ala Ala Gly Val Tyr Ala Lys Gln Val Asn Gly Leu
            165                 170                 175
Glu Arg Arg Val Met Arg Asp Thr Pro Val Met Ala Tyr Phe Val Asn
            180                 185                 190
Gly Thr Val Gln Asp Val Ile Leu Cys Asp Asp Ser Pro Lys Gly Arg
            195                 200                 205
Leu Ala Cys Gln Tyr Asn Thr Gly Asn Phe Ser Asp Gly Leu Tyr Pro
210                 215                 220
Val Tyr Glu Glu Pro Val Ala Ser Asn Phe Thr Phe Val Pro Leu Asp
225                 230                 235                 240
Thr Ser Ser Thr Ser Tyr Gly Val Leu His Asn Phe Thr Phe Asn Asn
            245                 250                 255
Val Thr Gly Val Ala Pro Asn Gln Asn His Ile Ala Arg Phe Asn Ile
            260                 265                 270
Ser Thr Ile Ser Glu Gly Tyr Val Asn Phe Lys Phe Asn Phe Leu Asn
            275                 280                 285
Ser Phe Thr Tyr Val Glu Ser Asp Phe Asp Arg Gly Ser Tyr Tyr Gly
            290                 295                 300
Lys Pro Gly Ser Arg Cys Asn Phe Arg Leu Glu Ser Ile Asn Arg Gly
305                 310                 315                 320
Leu Ser Phe Asn Ser Leu Thr Val Ser Ile Gly Tyr Gly Pro Ile Ser
            325                 330                 335
Gly Gly Cys Lys Gln Ser Val Trp Lys Asn Glu Ala Thr Cys Cys Phe
            340                 345                 350
Ala Tyr Lys Tyr Asn Gly Gly Ser Arg Asn Cys Lys Gly Leu Tyr Thr
            355                 360                 365
Phe Asp Ser Asp Val Asn Tyr Glu Cys Val Leu Leu Val Phe Ile Ser
370                 375                 380
Lys Thr Asp Gly Ser Arg Ile Arg Thr Ala Thr Ser Pro Pro Val Tyr
385                 390                 395                 400
Ser Asn Asn Asn Val Asn Ile Asn Leu Gly Leu Cys Val Asp Tyr Asn
            405                 410                 415
Val Tyr Gly Ile Thr Gly Arg Gly Leu Ile Thr Asn Ile Thr Glu Ser
```

```
                    420                 425                 430
Val His Pro Gly Tyr Leu Asp His Gly Gly Leu Val Leu Leu Asp Ala
                435                 440                 445

Thr Gly Ser Ile Asp Thr Phe Val Leu His Ser Asp Asn Leu Thr Ser
        450                 455                 460

Tyr Tyr Lys Val Asn Pro Cys Ser Asp Ile Asn Glu Gln Tyr Val Val
465                 470                 475                 480

Ser Gly Gly Asn Leu Val Gly Lys Leu Thr Ser Asn Asn Gln Thr Val
                485                 490                 495

Ala Gln Gln Leu Gly Asp Met Phe Tyr Val Lys Phe Ser Thr Ser Gly
                500                 505                 510

<210> SEQ ID NO 119
<211> LENGTH: 554
<212> TYPE: PRT
<213> ORGANISM: Infectious Bronchitis Virus

<400> SEQUENCE: 119

Ala Thr Ser Glu Asn Val Ile Ser Cys Pro Tyr Val Thr Tyr Gly Lys
1               5                   10                  15

Phe Cys Ile Lys Pro Asp Gly Gly Ile Ser Asn Ile Val Pro Glu Glu
                20                  25                  30

Val Lys Asp Tyr Thr Ser Leu Leu Leu Asn Arg Thr Asp Tyr Val Leu
            35                  40                  45

Ile Pro Asn Ser Phe Asn Leu Thr Val Thr Asp Glu Phe Ile Gln Thr
        50                  55                  60

Gln Phe Gln Lys Ile Gln Ile Asn Cys Ile Gln Tyr Val Cys Gly Ser
65                  70                  75                  80

Ser Ile Gln Cys Lys Gln Leu Phe Gln Gln Tyr Gly Ser Val Cys Asp
                85                  90                  95

Ser Ile Leu Ser Ile Val Asn Gly Ile Ala Leu Gln Asp Asn Ala Glu
                100                 105                 110

Met Leu His Phe Tyr Ser Ser Thr Lys Pro Arg Gly Phe Asp Thr Asn
            115                 120                 125

Ser Phe Val Asn Phe Thr Ala Gly Glu Phe Asn Ile Ser Leu Val Leu
        130                 135                 140

Pro Lys Asn Gly Gln Pro Thr Gly Arg Ser Phe Ile Glu Asp Leu Leu
145                 150                 155                 160

Phe Asp Lys Val Glu Ser Leu Gly Leu Pro Gly Asp Ser Ala Tyr Gln
                165                 170                 175

Lys Cys Thr Ser Gly Pro Leu Gly Phe Val Lys Asp Leu Val Cys Ala
                180                 185                 190

Gln Asn Tyr Asn Gly Leu Leu Val Leu Pro Pro Ile Ile Thr Ala Glu
            195                 200                 205

Met Gln Ala Met Tyr Thr Ser Ser Leu Val Ala Ser Met Ala Phe Gly
        210                 215                 220

Gly Ile Thr Ser Ala Gly Ala Ile Pro Phe Ala Thr Gln Ile Gln Ala
225                 230                 235                 240

Arg Ile Asn His Leu Gly Ile Thr Gln Thr Val Leu Gln Lys Asn Gln
                245                 250                 255

Glu Lys Ile Ala Ala Ser Phe Asn Lys Ala Met Lys His Met Gln Asp
                260                 265                 270

Gly Phe Ser Ala Thr Ser Leu Ala Leu Gln Gln Val Gln Asp Val Val
            275                 280                 285
```

-continued

```
Asn Glu Gln Gly Ala Ile Leu Gln Gln Thr Met His Ser Leu Asn Lys
    290                 295                 300
Asn Phe Gly Ala Ile Ser His Val Ile Gln Asp Ile Tyr Lys Gln Leu
305                 310                 315                 320
Asp Ala Leu Glu Ala Asn Ala Gln Val Asp Arg Ile Ile Thr Gly Arg
                325                 330                 335
Leu Ser Ser Leu Ser Val Leu Ala Ser Ala Lys Gln Leu Glu Tyr Thr
            340                 345                 350
Lys Val Ser Gln Gln Arg Glu Leu Ala Lys Glu Lys Ile Asn Glu Cys
        355                 360                 365
Val Lys Ser Gln Ser Asn Arg His Gly Phe Cys Gly Glu Gly Met His
    370                 375                 380
Ile Met Ser Ile Pro Gln Asn Ala Pro Asn Gly Ile Val Phe Leu His
385                 390                 395                 400
Phe Thr Tyr Thr Pro Glu Thr Tyr Ala Asn Val Thr Ala Val Val Gly
                405                 410                 415
Phe Cys Val Lys Pro Gly Asn Gly Thr Glu Tyr Gly Leu Val Pro Val
            420                 425                 430
Val Gly Arg Gly Ile Phe Ile Glu Val Asn Gly Thr Tyr Tyr Ile Thr
        435                 440                 445
Gly Arg Asp Met Tyr Ser Pro Arg Ala Ile Thr Ala Gly Asp Val Val
    450                 455                 460
Lys Leu Thr Ser Cys Gln Ala Asn Tyr Gln Ser Ile Asn Arg Thr Val
465                 470                 475                 480
Ile Thr Thr Phe Val Asp Glu Asp Phe Asp Phe Asp His Glu Leu
                485                 490                 495
Ser Lys Trp Trp Asn Glu Thr Ser Arg Asp Phe Pro Asn Leu Asp Glu
            500                 505                 510
Phe Asn Tyr Thr Ile Pro Val Leu Asn Ile Ser Asn Glu Ile Asp Lys
        515                 520                 525
Ile Gln Glu Val Ile Gln Gly Leu Asn Asp Ser Ile Ile Asp Leu Glu
    530                 535                 540
Thr Leu Ser Ile Leu Lys Thr Tyr Ile Lys
545                 550
```